US012435139B2

(12) United States Patent
Raum et al.

(10) Patent No.: US 12,435,139 B2
(45) Date of Patent: Oct. 7, 2025

(54) ANTIBODY CONSTRUCTS FOR DLL3 AND CD3

(71) Applicant: AMGEN RESEARCH (MUNICH) GMBH, Munich (DE)

(72) Inventors: Tobias Raum, Munich (DE); Claudia Blümel, Munich (DE); Christoph Dahlhoff, Munich (DE); Patrick Hoffmann, Munich (DE); Peter Kufer, Munich (DE); Ralf Lutterbüse, Munich (DE); Elisabeth Nahrwold, Munich (DE); Jochen Pendzialek, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 0 days.

(21) Appl. No.: 18/069,704

(22) Filed: Dec. 21, 2022

(65) Prior Publication Data

US 2023/0312717 A1 Oct. 5, 2023

Related U.S. Application Data

(60) Continuation of application No. 16/868,257, filed on May 6, 2020, now Pat. No. 11,591,396, which is a division of application No. 16/291,826, filed on Mar. 4, 2019, now Pat. No. 10,683,351, which is a division of application No. 15/225,107, filed on Aug. 1, 2016, now Pat. No. 10,294,300.

(60) Provisional application No. 62/290,896, filed on Feb. 3, 2016, provisional application No. 62/199,930, filed on Jul. 31, 2015.

(51) Int. Cl.

| | |
|---|---|
| ***C07K 16/18*** | (2006.01) |
| ***A61K 39/395*** | (2006.01) |
| ***A61K 40/11*** | (2025.01) |
| ***A61K 40/42*** | (2025.01) |
| ***C07K 16/22*** | (2006.01) |
| ***C07K 16/28*** | (2006.01) |
| ***C07K 16/30*** | (2006.01) |
| ***C12N 5/07*** | (2010.01) |
| ***C12N 15/63*** | (2006.01) |
| *A61K 39/00* | (2006.01) |
| *C07K 14/475* | (2006.01) |
| *C07K 14/725* | (2006.01) |

(52) U.S. Cl.

CPC ...... *C07K 16/2809* (2013.01); *A61K 39/3955* (2013.01); *A61K 39/39558* (2013.01); *A61K 40/11* (2025.01); *A61K 40/4225* (2025.01); *C07K 16/18* (2013.01); *C07K 16/28* (2013.01); *C12N 5/06* (2013.01); *C12N 15/63* (2013.01); *A61K 2039/505* (2013.01); *A61K 2239/31* (2023.05); *A61K 2239/38* (2023.05); *A61K 2239/55* (2023.05); *A61K 2239/57* (2023.05); *C07K 16/22* (2013.01); *C07K 16/30* (2013.01); *C07K 2317/31* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/622* (2013.01); *C07K 2317/73* (2013.01); *C07K 2317/76* (2013.01); *C07K 2317/77* (2013.01); *C07K 2317/92* (2013.01); *C07K 2317/94* (2013.01)

(58) Field of Classification Search

CPC ........ C07K 16/18; C07K 16/22; C07K 16/24; C07K 16/2809; C07K 2317/31; C07K 2317/33; C07K 2317/73; C07K 2317/76; C07K 2317/92; C07K 16/468; C07K 2317/56; C07K 2317/565; A61K 39/3955; A61K 39/39558; A61K 2039/505

See application file for complete search history.

(56) References Cited

U.S. PATENT DOCUMENTS

| | | | |
|---|---|---|---|
| 3,691,016 | A | 9/1972 | Patel |
| 3,773,919 | A | 11/1973 | Boswell et al. |
| 3,969,287 | A | 7/1976 | Jaworek et al. |
| 4,179,337 | A | 12/1979 | Davis et al. |
| 4,195,128 | A | 3/1980 | Gribnau et al. |
| 4,229,537 | A | 10/1980 | Hodgins et al. |
| 4,247,642 | A | 1/1981 | Hirohara et al. |

(Continued)

FOREIGN PATENT DOCUMENTS

| | | |
|---|---|---|
| CN | 104592392 B | 8/2018 |
| EP | 0088046 A2 | 9/1983 |

(Continued)

OTHER PUBLICATIONS

Paul, William E., Fundamental Immunology, 3rd Edition, Raven Press, New York, Chapt. 8, pp. 292-295 (1993).*

(Continued)

*Primary Examiner* — Bridget E Bunner

(74) *Attorney, Agent, or Firm* — MARSHALL, GERSTEIN & BORUN LLP

(57) ABSTRACT

The present invention relates to a bispecific antibody construct comprising a first binding domain which binds to human DLL3 on the surface of a target cell and a second binding domain which binds to human CD3 on the surface of a T cell. Moreover, the invention provides a polynucleotide encoding the antibody construct, a vector comprising the polynucleotide and a host cell transformed or transfected with the polynucleotide or vector. Furthermore, the invention provides a process for the production of the antibody construct of the invention, a medical use of the antibody construct and a kit comprising the antibody construct.

12 Claims, 12 Drawing Sheets

Specification includes a Sequence Listing.

(56) References Cited

U.S. PATENT DOCUMENTS

| | | | |
|---|---|---|---|
| 4,301,144 | A | 11/1981 | Iwashita et al. |
| 4,330,440 | A | 5/1982 | Ayers et al. |
| 4,439,196 | A | 3/1984 | Higuchi |
| 4,447,224 | A | 5/1984 | Decant et al. |
| 4,447,233 | A | 5/1984 | Mayfield |
| 4,475,196 | A | 10/1984 | La Zor |
| 4,485,045 | A | 11/1984 | Regen |
| 4,486,194 | A | 12/1984 | Ferrara |
| 4,487,603 | A | 12/1984 | Harris |
| 4,496,689 | A | 1/1985 | Mitra |
| 4,544,545 | A | 10/1985 | Ryan et al. |
| 4,596,556 | A | 6/1986 | Morrow et al. |
| 4,640,835 | A | 2/1987 | Shimizu et al. |
| 4,670,417 | A | 6/1987 | Iwasaki et al. |
| 4,751,180 | A | 6/1988 | Cousens et al. |
| 4,790,824 | A | 12/1988 | Morrow et al. |
| 4,791,192 | A | 12/1988 | Nakagawa et al. |
| 4,816,397 | A | 3/1989 | Boss et al. |
| 4,816,567 | A | 3/1989 | Cabilly et al. |
| 4,935,233 | A | 6/1990 | Bell et al. |
| 4,941,880 | A | 7/1990 | Burns |
| 4,946,778 | A | 8/1990 | Ladner et al. |
| 5,013,556 | A | 5/1991 | Woodle et al. |
| 5,064,413 | A | 11/1991 | Mckinnon et al. |
| 5,223,409 | A | 6/1993 | Ladner et al. |
| 5,225,539 | A | 7/1993 | Winter |
| 5,292,658 | A | 3/1994 | Cormier et al. |
| 5,312,335 | A | 5/1994 | Mckinnon et al. |
| 5,383,851 | A | 1/1995 | Mckinnon et al. |
| 5,399,163 | A | 3/1995 | Peterson et al. |
| 5,418,155 | A | 5/1995 | Cormier et al. |
| 5,476,996 | A | 12/1995 | Wilson et al. |
| 5,545,806 | A | 8/1996 | Lonberg et al. |
| 5,545,807 | A | 8/1996 | Surani et al. |
| 5,565,332 | A | 10/1996 | Hoogenboom et al. |
| 5,569,825 | A | 10/1996 | Lonberg et al. |
| 5,585,089 | A | 12/1996 | Queen et al. |
| 5,591,669 | A | 1/1997 | Krimpenfort et al. |
| 5,612,205 | A | 3/1997 | Kay et al. |
| 5,625,126 | A | 4/1997 | Lonberg et al. |
| 5,625,825 | A | 4/1997 | Rostoker et al. |
| 5,633,425 | A | 5/1997 | Lonberg et al. |
| 5,643,763 | A | 7/1997 | Dunn et al. |
| 5,648,260 | A | 7/1997 | Winter et al. |
| 5,661,016 | A | 8/1997 | Lonberg et al. |
| 5,683,888 | A | 11/1997 | Campbell |
| 5,693,761 | A | 12/1997 | Queen et al. |
| 5,693,762 | A | 12/1997 | Queen et al. |
| 5,698,767 | A | 12/1997 | Wilson et al. |
| 5,721,367 | A | 2/1998 | Kay et al. |
| 5,741,668 | A | 4/1998 | Ward et al. |
| 5,770,429 | A | 6/1998 | Lonberg et al. |
| 5,777,079 | A | 7/1998 | Tsien et al. |
| 5,789,215 | A | 8/1998 | Berns et al. |
| 5,789,650 | A | 8/1998 | Lonberg et al. |
| 5,804,387 | A | 9/1998 | Cormack et al. |
| 5,814,318 | A | 9/1998 | Lonberg et al. |
| 5,859,205 | A | 1/1999 | Adair et al. |
| 5,874,299 | A | 2/1999 | Lonberg et al. |
| 5,874,304 | A | 2/1999 | Zolotukhin et al. |
| 5,876,995 | A | 3/1999 | Bryan |
| 5,877,397 | A | 3/1999 | Lonberg et al. |
| 5,925,558 | A | 7/1999 | Tsien et al. |
| 5,939,598 | A | 8/1999 | Kucherlapati et al. |
| 5,958,765 | A | 9/1999 | Brams et al. |
| 5,981,175 | A | 11/1999 | Loring et al. |
| 6,023,010 | A | 2/2000 | Krimpenfort et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,255,458 | B1 | 7/2001 | Lonberg et al. |
| 6,300,064 | B1 | 10/2001 | Knappik et al. |
| 6,407,213 | B1 | 6/2002 | Carter et al. |
| 6,673,986 | B1 | 1/2004 | Kucherlapati et al. |
| 9,089,615 | B2 | 7/2015 | Stull et al. |
| 9,243,058 | B2 | 1/2016 | Armitage et al. |
| 9,765,157 | B2 | 9/2017 | Xiao et al. |
| 10,059,766 | B2 | 8/2018 | Xiao et al. |
| 10,220,090 | B2 | 3/2019 | Armitage et al. |
| 10,294,300 | B2 * | 5/2019 | Raum ..................... A61P 35/00 |
| 10,301,391 | B2 | 5/2019 | Raum et al. |
| 10,519,241 | B2 | 12/2019 | Raum et al. |
| 11,591,396 | B2 * | 2/2023 | Raum ................ A61K 39/3955 |
| 2002/0160004 | A1 | 10/2002 | Lyman et al. |
| 2003/0070185 | A1 | 4/2003 | Jakobovits et al. |
| 2005/0076395 | A1 | 4/2005 | Kucherlapati et al. |
| 2010/0150918 | A1 * | 6/2010 | Kufer ..................... C07K 16/28 536/23.53 |
| 2012/0328624 | A1 | 12/2012 | Yoshida et al. |
| 2014/0302037 | A1 | 10/2014 | Borges et al. |
| 2014/0308285 | A1 | 10/2014 | Yan et al. |
| 2014/0363455 | A1 | 12/2014 | Stull et al. |
| 2014/0364590 | A1 | 12/2014 | Stull et al. |
| 2016/0176973 | A1 | 6/2016 | Kufer et al. |
| 2017/0029502 | A1 | 2/2017 | Raum et al. |
| 2017/0029512 | A1 | 2/2017 | Raum et al. |
| 2017/0037149 | A1 | 2/2017 | Raum et al. |
| 2017/0129961 | A1 | 5/2017 | Raum et al. |
| 2017/0218078 | A1 | 8/2017 | Raum et al. |
| 2017/0218079 | A1 | 8/2017 | Raum et al. |
| 2017/0349668 | A1 | 12/2017 | Rattel et al. |
| 2020/0048357 | A1 | 2/2020 | Raum et al. |

FOREIGN PATENT DOCUMENTS

| | | | |
|---|---|---|---|
| EP | 0133988 | A2 | 3/1985 |
| EP | 0171496 | A2 | 2/1986 |
| EP | 0173494 | A2 | 3/1986 |
| EP | 0058481 | B1 | 10/1986 |
| EP | 0143949 | B1 | 10/1988 |
| EP | 0036676 | B2 | 9/1990 |
| EP | 0239400 | B1 | 8/1994 |
| EP | 0463151 | B1 | 6/1996 |
| EP | 0773288 | A2 | 5/1997 |
| EP | 0546073 | B1 | 9/1997 |
| EP | 0843961 | A1 | 5/1998 |
| GB | 2177096 | B | 5/1989 |
| JP | 3068180 | B2 | 7/2000 |
| JP | 3068507 | B2 | 7/2000 |
| WO | 87/05330 | A1 | 9/1987 |
| WO | 88/09344 | A1 | 12/1988 |
| WO | 91/10741 | A1 | 7/1991 |
| WO | 92/03918 | A1 | 3/1992 |
| WO | 92/15673 | A1 | 9/1992 |
| WO | 92/22645 | A1 | 12/1992 |
| WO | 92/22647 | A1 | 12/1992 |
| WO | 92/22670 | A1 | 12/1992 |
| WO | 93/12227 | A1 | 6/1993 |
| WO | 93/15722 | A1 | 8/1993 |
| WO | 94/00569 | A1 | 1/1994 |
| WO | 94/02602 | A1 | 2/1994 |
| WO | 94/10308 | A1 | 5/1994 |
| WO | 94/25585 | A1 | 11/1994 |
| WO | 95/07463 | A1 | 3/1995 |
| WO | 96/14436 | A1 | 5/1996 |
| WO | 96/33735 | A1 | 10/1996 |
| WO | 96/34096 | A1 | 10/1996 |
| WO | 97/13852 | A1 | 4/1997 |
| WO | 97/38731 | A1 | 10/1997 |
| WO | 98/14605 | A1 | 4/1998 |
| WO | 98/24884 | A1 | 6/1998 |
| WO | 98/24893 | A2 | 6/1998 |
| WO | 98/26277 | A2 | 6/1998 |
| WO | 98/52976 | A1 | 11/1998 |
| WO | 99/49019 | A2 | 9/1999 |
| WO | 99/54440 | A1 | 10/1999 |
| WO | 00/06605 | A2 | 2/2000 |
| WO | 00/34317 | A2 | 6/2000 |
| WO | 00/76310 | A1 | 12/2000 |
| WO | 03/47336 | A2 | 6/2003 |
| WO | 2004/003019 | A2 | 1/2004 |
| WO | 2005/040220 | A1 | 5/2005 |
| WO | 2006/138181 | A2 | 12/2006 |

(56) References Cited

FOREIGN PATENT DOCUMENTS

| | | | |
|---|---|---|---|
| WO | 2007/042261 | A2 | 4/2007 |
| WO | 2007/098420 | A2 | 8/2007 |
| WO | 2008/119567 | A2 | 10/2008 |
| WO | 2009/127691 | A1 | 10/2009 |
| WO | 2010/037838 | A2 | 4/2010 |
| WO | 2011/051489 | A2 | 5/2011 |
| WO | 2011/093097 | A1 | 8/2011 |
| WO | 2012/059486 | A1 | 5/2012 |
| WO | 2012/150319 | A1 | 11/2012 |
| WO | 2013/026833 | A1 | 2/2013 |
| WO | 2013/026837 | A1 | 2/2013 |
| WO | 2013/075066 | A2 | 5/2013 |
| WO | 2013/126746 | A2 | 8/2013 |
| WO | 2013/135896 | A1 | 9/2013 |
| WO | 2014/072481 | A1 | 5/2014 |
| WO | 2014/125273 | A1 | 8/2014 |
| WO | 2014/144722 | A2 | 9/2014 |
| WO | 2014/151910 | A1 | 9/2014 |
| WO | 2015/048272 | A1 | 4/2015 |
| WO | 2016/016859 | A1 | 2/2016 |
| WO | 2017/134140 | A1 | 8/2017 |

OTHER PUBLICATIONS

Edwards et al. The remarkable flexibility of the human antibody repertoire; isolation of over one thousand different antibodies to a single protein, BLyS. J Mol Biol 334: 103-118, 2003.

Lipman et al. Monoclonal Versus Polyclonal Antibodies: Distinguishing Characteristics, Applications, and Information Resources. ILAR J 46(3): 258-268, 2005.

Lloyd et al. Modelling the human immune response: performance of a 10"11 human antibody repertoire against a broad panel of therapeutically relevant antigens. Protein Eng Design Selection 22(3): 159-168, 2009.

Dickopf et al., Format and geometries matter: Structure-based design defines the functionality of bispecific antibodies, Comput Struct Biotechnol J, 18:1221-7 (May 2020).

Roda-Navarro et al., Understanding the Spatial Topology of Artificial Immunological Synapses Assembled in T Cell-Redirecting Strategies: A Major Issue in Cancer Immunotherapy, Front Cell Dev Biol., 7:370 (Jan. 2020).

Giffin et al., AMG 757, a Half-Life Extended, DLL3-Targeted Bispecific T-Cell Engager, Shows High Potency and Sensitivity in Preclinical Models of Small-Cell Lung Cancer, Clin Cancer Res., 27(5):1526-37 (Mar. 2021).

Bhattacharya et al., Impact of genetic variation on three dimensional structure and function of proteins, PLoS One, 12(3):e0171355 (2017).

Bork et al., Powers and pitfalls in sequence analysis: the 70% hurdle, Genome Res., 10(4):398-400 (2000).

Bork, Go hunting in sequence databases but watch out for the traps, Trends in Genetics, 12(10):425-7 (1996).

Brenner, Errors in genome annotation, Trends Genet., 15(4):132-3 (1999).

Brorson et al., Mutational analysis of avidity and fine specificity of anti-levan antibodies, J. Immunol., 163(12):6694-701 (1999).

Brummel et al., Probing the combining site of an anti-carbohydrate antibody by saturation-mutagenesis: role of the heavy-chain CDR3 residues, Biochem., 32(4):1180-7 (1993).

Burks et al., In vitro scanning saturation mutagenesis of an antibody binding pocket, Proc. Natl. Acad. Sci. USA, 94(2):412-7 (1997).

Casset et al., A peptide mimetic of an anti-CD4 monoclonal antibody by rational design, Biochem. Biophys. Res. Commun., 307(1):198-205 (2003).

Chen et al., Selection and analysis of an optimized anti-VEGF antibody: crystal structure of an affinity-matured Fab in complex with antigen, J. Mol. Biol., 293(4):865-81 (1999).

Colman, Effects of amino acid sequence changes on antibody-antigen interactions, Res. Immunol., 145(1):33-6 (1994).

Doerks et al., Protein annotation: detective work for function prediction, Trends Genet., 14(6):248-50 (1998).

Fenton et al., Rheostat positions: A new classification of protein positions relevant to pharmacogenomic, Med. Chem. Res., 29(7):1133-46 (Jul. 2020).

Guo et al., Protein tolerance to random amino acid change, Proc Natl Acad Sci USA 101(25): 9205-9210 (2004).

Holm et al., Functional mapping and single chain construction of the anti-cytokeratin 8 monoclonal antibody TS1. Mol Immunol 44: 1075-1084 (2007).

Ikeuchi et al., Delicate balance among thermal stability, binding affinity, and conformational space explored by single-domain VHH antibodies. Sci Reports, 11: 20624 (2021).

Jang et al., The structural basis for DNA binding by an anti-DNA autobody. Mol Immunol, 35: 1207-1217(1998).

Kobayashi et al. Tryptophan H33 plays an important role in pyrimidine (6-4) pyrimidone photoproduct binding by a high-affinity antibody. Protein Engineering 12(10): 879-884 (1999).

Rudikoff et al. Single amino acid substitution altering antigen-binding specificity. Proc Natl Acad Sci USA 79: 1979-1983 (1982).

Skolnick et al. From genes to protein structure and function: novel applications of computational approaches in the genomic era. Trends Biotechnol 18(1):34-39 (2000).

Smith et al. The challenges of genome sequence annotation or "the devil is in the details". Nature Biotechnol 15: 1222-1223 (1997).

Tokuriki et al. Stability effects of mutations and protein evolvability. Curr Opin Structural Biol 19: 596-604 (2009).

Vasudevan et al. A single amino acid change in the binding pocket alters specificity of an anti-integrin antibody AP7.4 as revealed by its crystal structure. Blood Cells Mol Diseases 32: 176-181 (2004).

Zhang et al. Comprehensize optimization of a single-chain variable domain antibody fragment as a targeting ligand for a cytotoxic nanoparticle. mAbs 7(1): 42-52 (2015).

D'Angelo et al. Many routes to an antibody heavy-chain CDR3: Necessary, yet insufficient, for specific binding. Front Immunol 9: 305 (2018).

Altschul et al., Basic local alignment search tool. J. Mol. Biol. 215:403-10 (1990).

Altschul et al., Gapped BLAST and PSI-BLAST: a new generation of protein database search programs. Nucl. Acids Res. 25(17): 3389-402 (1997).

Altschul et al., Local alignment statistics. Methods in Enzymology, 266:460-80 (1996).

Aplin et al., Preparation, properties, and applications of carbohydrate conjugates of proteins and lipids. CRC Crit. Rev. Biochem. 259-306 (1981).

Arakawa et al., Solvent interactions in pharmaceutical formulations. Pharm Res. 8(3): 285-91 (1991).

Artsaenko et al., The expression of a single-chain Fv antibody against abscisic acid creates a wilty phenotype in transgenic tobacco. The Plant J. 8: 745-50 (1995).

Bitelman et al., IGF1R-directed targeted therapy enhances the cytotoxic effect of chemotherapy in endometrial cancer, Cancer Letters, 335:153-159 (2013).

Bruhl et al., Depletion of CCR5-expressing cells with bispecific antibodies and chemokine toxins: a new strategy in the treatment of chronic inflammatory diseases and HIV. Immunol. 166: 2420-6 (2001).

Carter et al., High level *Escherichia coli* expression and production of a bivalent humanized antibody fragment. Biotechnology 10: 163-7 (1992).

Chalfie et al., Green fluorescent protein as a marker for gene expression. Science. 263: 802-5 (1994).

Cheadle et al., Cloning and expression of the variable regions of mouse myeloma protein MOPC315 in *E. coli*: recovery of active FV fragments. Mol. Immunol. 29: 21-30 (1992).

Cheson et al., Report of an international workshop to standardize response criteria for non-Hodgkin's lymphomas. NCI Sponsored International Working Group. J. Clin. Oncol. 17(4) : 1244-53 (1999).

Chothia et al., Canonical structures for the hypervariable regions of immunoglobulins. J. Mol. Biol. 196: 901-17 (1987).

(56) References Cited

OTHER PUBLICATIONS

Chothia et al., Conformation of immunoglobulin hypervariable regions. Nature 342: 877-83 (1989).
Clackson et al., Making antibody fragments using phage display libraries. Lett. Nature 352: 624-8 (1991).
Cook et al., The human immunoglobulin VH repertoire. Immunol. Today 16(5): 237-42 (1995).
Cunningham et al., High-resolution epitope mapping of hGH-receptor interactions by alanine-scanning mutagenesis. Science. 244: 1081-5 (1989).
Dall'Acqua et al., Contribution of domain interface residues to the stability of antibody CH3 domain homodimers. Biochemistry. 37: 9266-73 (1998).
Devereux et al., A comprehensive set of sequence analysis programs for the VAX. Nucl. Acid. Res. 12: 387-95 (1984).
Duskin et al., Relationship of the structure and biological activity of the natural homologues of tunicamycin. J. Biol. Chem., 257:3105-9 (1982).
Edge et al., Deglycosylation of glycoproteins by trifluoromethanesulfonic acid. Anal. Biochem. 118:131-7 (1981).
Eppstein et al., Biological activity of liposome-encapsulated murine interferon y is mediated by a cell membrane receptor. Proc. Natl. Acad. Sci. USA. 82: 3688-92 (1985).
Fecker et al., Expression of single-chain antibody fragments (scFv) specific for beet necrotic yellow vein virus coat protein or 25 kDa protein in *Escherichia coli* and Nicotiana benthamiana. Plant Mol. Biol. 32: 979-86 (1996).
Feng et al., Progressive sequence alignment as a prerequisite to correct phylogenetic trees. J. Mol. Evol., 35: 351-60 (1987).
Gabizon et al., Pharmacokinetics and tissue distribution of doxorubicin encapsulated in stable liposomes with long circulation times. J. National Cancer Inst. 81(19): 1484-8 (1989).
Graham et al., Characteristics of a human cell line transformed by DNA from human adenovirus type 5. J. Gen Virol. 36: 59-74 (1977).
Green et al., Antigen-specific human monoclonal antibodies from mice engineered with human lg heavy and light chain YACs. Nature Genetics 7:13-21 (1994).
Green et al., Regulation of B cell development by variable gene complexity in mice reconstituted with human immunoglobulin yeast artificial chromosomes. J. Exp. Med. 188:483-95 (1998).
Hakimuddin et al., A chemical method for the deglycosylation of proteins. Arch. Biochem. Biophys. 259:52-7 (1987).
Hawkins et al., Selection of phaae antibodies by bindina affinity. J. Mol. Biol. 254: 889-96 (1992).
Heim et al., Engineering green fluorescent protein for improved brightness, longer wavelengths and fluorescence resonating energy transfer. Curr. Biol. 6:178-82 (1996).
Hiatt et al., Production of antibodies in transgenic plants. Nature 342: 76-8 (1989).
Higgins et al., Fast and sensitive multiple sequence alignments on a microcomputer. CABIOS 5: 151-3 (1989).
Holliger et al., "Diabodies": small bivalent and bispecific antibody fragments. Proc. Natl. Acad. Sci. USA 90(14): 6444-8 (1993).
Hoppe et al., A parallel three stranded alpha-helical bundle at the nucleation site of collagen triple-helix formation. FEBS Lett. 344: 191-5 (1994).
Huston et al., Protein engineering of antibody binding sites: recovery of specific activity in an anti-digoxin single-chain Fv analogue produced in *Escherichia coli*. Proc. Natl. Acad. Sci. USA. 85: 5879-83 (1988).
Hwang et al., Hepatic uptake and degradation of unilamellar sphingomyelin/cholecterol liposomes: A kinetic study. Proc. Natl. Acad. Sci. USA. 77: 4030-4 (1980).
Ichiki et al., Regulation of the expression of human C epsilon germline transcript. Identification of a novel IL-4 responsive element. J. Immunol. 150: 5408-17 (1993).
International Search Report, PCT/EP2016/068285, dated Nov. 25, 2016.
Jones et al., Replacing the complementarity-determine regions in a human antibody with those from a mouse. Nature, 321: 522-5 (1986).
Karlin et al., Applications and statistics for multiple high-scoring segments in molecular sequences. Proc. Natl. Acad. Sci. USA 90: 5873-7 (1993).
Kaufman, Selection and coamplification of heterologous genes in mammalian cells. Meth. Enzvmol. 185: 537-66 (1990).
Kipriyanov et al., Bispecific tandem diabody for tumor therapy with improved antigen binding and pharmacokinetics. J. Mol. Biol. 293: 41-56 (1999).
Kohler et al., Continuous cultures of fused cells secreting antibody of predefined specificity. Nature. 256:495-7 (1975).
Kozbor et al., The production of monoclonal antibodies from human lymphocytes. Immunol. Today. 4(3): 72-9 (1983).
Kufer et al., A revival of bispecific antibodies. Trends Biotechnol. 22(5): 238-44 (2004).
Kufer et al., Construction and biological activity of a recombinant bispecific single-chain antibody designed for therapy of minimal residual colorectal cancer. Cancer Immunol. Immunother. 45: 193-7 (1997).
Kumar et al., Molecular cloning and expression of the Fabs of human autoantibodies in *Escherichia coli*, Determination of the heavy or light chain contribution to the anti-DNA/-cardiolipin activity of the Fab, J. Biol. Chem., 275: 35129-36 (2000).
Langer et al., Biocompatibility of polymeric delivery systems for macromolecules. J. Biomed. Mater. Res. 15(2): 267-77 (1981).
Langer, Controlled release of macromolecules, Chem. Tech. 12: 98-105 (1982).
U.S. Appl. No. 08/486,853, Kucherlapati et al.
U.S. Appl. No. 08/486,859, Kucherlapati et al.
U.S. Appl. No. 08/759,620, Jakobovits et al.
Ward et al., Binding activities of a repertoire of single immunoglobulin variable domains secreted from *Escherichia coli*, Nature, 341:544-546 (1989).
Xiu et al., The role of DLLs in cancer: a novel therapeutic target, Oncotargets Therapy, 13:3881-3901 (2020).
Lowman et al., Selecting high-affinity binding proteins by monovalent phage display. Biochemistry 30: 10832-7 (1991).
Maccallum et al., Antibody-antigen interactions: Contact analysis and binding site topography. J. Mol. Biol. 262:732-45 (1996).
Mack et al., Biologic properties of a bispecific single-chain antibody directed against 17-1A (EpCAM) and CD3: tumor cell-dependent T cell stimulation and cytotoxic activity. J. Immunol. 158: 3965-70 (1997).
Marks et al., By-passing immunization. Human antibodies from V-gene libraries displayed on phage. J. Mol. Biol. 222:581-97 (1991).
Martin et al., Irreversible coupling of immunoglobulin fragments to preformed vesicles. An improved method for liposome targeting. J. Biol. Chem. 257:286-8 (1982).
Martin et al., Structural families in loops of homologous proteins: automatic classification, modelling and application to antibodies. J. Mol. Biol. 263: 800-15 (1996).
Mather et al., Culture of testicular cells in hormone-supplemented serum-free medium. Ann. N.Y. Acad. Sci. 383: 44-68 (1982).
Mather, Establishment and characterization of two distinct mouse testicular epithelial cell lines. Biol. Reprod. 23: 243-51 (1980).
Mendez et al., Functional transplant of megabase human immunoglobulin loci recapitulates human antibody response in mice. Nature Genetics 15:146-56 (1997).
Morrison et al., Chimeric human antibody molecules: mouse antigen-binding domains with human constant reaion domains. Proc. Natl. Acad. Sci. USA 81: 6851-5 (1984).
Needleman et al., A general method applicable to the search for similarities in the amino acid sequence of two proteins. J. Mol. Biol. 48: 443-53 (1970).
Nolan et al., Fluorescence-activated cell analysis and sorting of viable mammalian cells based on beta-D-galactosidase activity after transduction of *Escherichia coli* lacZ. Proc. Natl. Acad. Sci. USA. 85: 2603-7 (1988).
Office Action corresponding to Colombian Application No. NC2018/0000877, dated May 27, 2019.

(56) References Cited

OTHER PUBLICATIONS

Ohtani et al. Mechanisms of antibody-mediated insulin-like growth factor I receptor (IFG-IR) down-regulation in MCF-7 breast cancer cells, BioScience Trends, 3(4): 131-138 (2009).
Olsson et al., Human-human monoclonal antibody-producing hybridomas: Technical aspects. Meth. Enzymol. 92: 3-16 (1982).
Owen et al., Synthesis of a functional anti-phytochrome single-chain Fv protein in transgenic tobacco. Bio/Technology. 10: 790-4 (1992).
Pearson et al., Improved tools for biological sequence comparison. Proc. Natl. Acad. Sci. USA. 85:2444-8 (1988).
Presta, Antibody engineering. Curr. Op. Struct. Biol. 2: 593-6 (1992).
Randolph et al., Surfactant-protein interactions. Pharm Biotechnol. 13: 159-75 (2002).
Raum et al., Anti-self antibodies selected from a human IgD heavy chain repertoire: a novel approach to generate therapeutic human antibodies against tumor-associated differentiation antiqens. Cancer Immunol. Immunother. 50: 141-50 (2001).
Riechmann et al., Reshaping human antibodies for therapy. Nature 332: 323-9 (1988).
Schier et al., Efficient in vitro affinity maturation of phage antibodies using BIAcore guided selections. Hum. Antibodies Hybridomas. 7(3): 97-105 (1996).
Schlereth et al., T-cell activation and B-cell depletion in chimpanzees treated with a bispecific anti-CD19/anti-CD3 sinale-chain antibody construct. Cancer Immunol. Immunother. 55: 503-14 (2006).
Sidman et al., Controlled release of macromolecules and pharmaceuticals from synthetic polypeptides based on glutamic acid. Biopolymers 2: 547-56 (1983).
Smith et al., Comparison of Biosequences. Adv. Appl. Math. 2:482-9 (1981).
Smith-Gill et al., Contributions of immunoglobulin heavy and light chains to antibody specificity for lysozyme and two haptens, J. Immunol., 139: 4135-4144 (1987).
Song et al. Light chain of natural antibody plays a dominant role in protein antigen binding, Biochem. Biophys. Res. Comm., 268: 390-394 (2000).
Stauber et al., Development and applications of enhanced green fluorescent protein mutants. Biotechniques. 24: 462-71 (1998).
Takeda et al., Construction of chimaeric processed immunoglobulin genes containing mouse variable and human constant region sequences. Nature, 314: 452-4 (1985).
Thotakura et al., Enzymatic deglycosylation of glycoproteins. Meth. Enzymol. 138:350-9 (1987).
Tomlinson et al., The repertoire of human germline VH sequences reveals about fifty groups of VH segments with different hypervariable loops. J. Mol. Biol. 227: 776-98 (1992).
Tomlinson et al., The structural repertoire of the human V kappa domain. EMBO J. 14:4628-38 (1995).
Topp et al., Long-term follow-up of hematologic relapse-free survival in a phase 2 study of blinatumomab in patients with MRD in B-lineage ALL. Blood, 120(26): 5185-7 (2012).
U.S. Appl. No. 07/466,008, Kucherlapati et al.
U.S. Appl. No. 07/574,748, Kay et al.
U.S. Appl. No. 07/575,962, Lonberg et al.
U.S. Appl. No. 07/610,515, Kucherlapati et al.
U.S. Appl. No. 07/904,068, Lonberg et al.
U.S. Appl. No. 07/919,297, Kucherlapati et al.
U.S. Appl. No. 08/112,848, Kucherlapati et al.
U.S. Appl. No. 08/155,301, Lonberg et al.
U.S. Appl. No. 08/161,739, Lonberg et al.
U.S. Appl. No. 08/165,699, Lonberg et al.
U.S. Appl. No. 08/209,741, Kay et al.
U.S. Appl. No. 08/234,145, Kucherlapati et al.
U.S. Appl. No. 08/376,279, Kucherlapati et al.
U.S. Appl. No. 08/430,938, Kucherlapati et al.
U.S. Appl. No. 08/462,837, Kucherlapati et al.
U.S. Appl. No. 08/463,191, Kucherlapati et al.
U.S. Appl. No. 08/464,584, Kucherlapati et al.
Bluemel et al., Epitope distance to the target cell membrane and antigen size determine the potency of T cell-mediated lysis by BiTE antibodies specific for a large melanoma surface antigen, Cancer Immunology Immunotherapy, 59:1197-1209 (Mar. 23, 2010).

* cited by examiner

ANTIBODY CONSTRUCTS FOR DLL3 AND CD3

This application includes a sequence listing submitted electronically by the file name 49895_Seqlisting.XML; Size: 844,366 bytes; Created: Dec. 21, 2022, and is incorporated herein by reference.

The present invention relates to a bispecific antibody construct comprising a first binding domain which binds to human DLL3 on the surface of a target cell and a second binding domain which binds to human CD3 on the surface of a T cell. Moreover, the invention provides a polynucleotide encoding the antibody construct, a vector comprising said polynucleotide and a host cell transformed or transfected with said polynucleotide or vector. Furthermore, the invention provides a process for the production of the antibody construct of the invention, a medical use of said antibody construct and a kit comprising said antibody construct.

Small cell lung cancer (SCLC) is an aggressive form of lung cancer with a poor prognosis and limited therapeutic options, representing about 15% of all newly diagnosed lung cancers and equal to about 25,000 new cases in the US and 180,000 new cases worldwide per year. Survival rates have remained low for several decades, with only 5% of SCLC patients surviving five years, in a large part due to the lack of new therapies to combat this form of lung cancer. Most patients present with extensive-stage disease, while about a third of patients present with limited stage disease, defined by the presence of tumors in only one side of the chest and that fit in a single radiation field. These stages impact available therapeutic regiments, with limited stage disease treated with chemotherapy and radiation and extensive stage disease treated with chemotherapy alone. Disseminated, metastatic tumors with lymphoma-like characteristics are a hallmark of SCLC. The first known diagnosis of SCLC patients described it as a disease of the lymphatic system, not being recognized as lung cancer until 1926, which highlights some of the unique nature of SCLC tumors as compared to other solid tumors.

Patients typically respond well to the current front-line therapy, which includes etoposide and cisplatin, but invariably quickly relapse with chemoresistant disease, for which no therapeutic options are currently available. Prognosis in the relapsed refractory setting is extremely poor, with rapid disease progression and short median survival of less than six months. Furthermore, SCLC patients have high rates of comorbidities, including hypertension, cardiac disease, diabetes and paraneoplastic syndromes. These, coupled with the typically advanced age of SCLC patients, impact the ability of patients to endure harsh chemo regimens, further limiting treatment options.

A bispecific antibody modality, comprising an scFv that recognizes CD3 expressed on T cells and another scFv that recognizes a tumor-associated antigen, has shown promising efficacy in the clinic, with high response rates in hematological malignancies such as refractory B-ALL (Topp, M. S. et al. Blood, 2012. 120(26): p. 5185-5187), resulting in the approval of Blincyto. While efficacy with T cell-engaging therapies has yet to be demonstrated in a solid tumor indication, SCLC may represent a promising solid tumor indication for the CD3×tumor target bispecific antibody modality, given the disseminated nature of the disease. Therefore, a bispecific T cell engager that directs T cells against a specific tumor antigen presents a new opportunity as a new therapeutic option in the treatment of SCLC.

DLL3 was presently identified as an SCLC-specific tumor antigen by next-generation sequencing, comparing the prevalence of DLL3 mRNA in a panel of primary patient tumors and a large collection of normal tissues. The level of DLL3 expression in SCLC tumors was moderate, but highly prevalent, with approximately 90% of the tumors analyzed showing evidence of DLL3 expression by RNA-seq. In contrast to SCLC tumors, normal tissues showed very low expression of DLL3 transcript, with small levels detected in testis, optic nerve and cerebellum. Comparison of SCLC cell lines and tumors by RNA-seq showed similar expression levels, while cell surface quantitation of DLL3 expression on SCLC cell lines indicated expression levels below 5000 DLL3 per cell, with typical expression levels below 2000 DLL3/cell. Expression of DLL3 protein was confirmed by IHC, where 86% of SCLC tumors showed positive staining for DLL3, with a homogeneous and membranous staining pattern. Aside from very faint staining in cerebellum, all other normal tissues were negative for DLL3 staining.

DLL3 is a non-canonical Notch ligand, functioning in a cell autonomous manner to inhibit Notch signaling, binding to Notch in cis, thus blocking cell to cell interactions and internalization of Notch in the target cell, a hallmark of canonical Notch signaling. The primary role for DLL3 is in somitogenesis during embryonic development. Mice with DLL3 knockouts show segmental defects in the axial skeleton and cranial and neuronal development. Somitic patterning defects are also seen in humans with certain germline DLL3 mutations, resulting in a condition called spondylocostal dysostosis.

DLL3 has been proposed previously in methods to diagnose and treat glioma, in addition to SCLC, using an antibody-drug conjugate (ADC) (WO 2013/126746). Using an ADC-based approach for DLL3 may have limitations, given the low expression levels of the protein on the cell surface and the reduced performance of ADCs against targets with low expression. Furthermore, ADC molecules often demonstrate toxicity related to free warhead, likely a result of linker degradation, resulting in maximum tolerated dose limitations and potential impacts on efficacy unrelated to the target chosen for the antibody. This is less likely to be an issue for a T cell-engaging bispecific molecule, engineered to engage DLL3 and CD3 simultaneously, given the required sensitivity of T cells for their targets, and highly potent in vitro cytotoxicity has been demonstrated on cell lines expressing several hundred target proteins per cell. Additionally, the usually smaller size of a bispecific T cell engaging antibody construct relative to a normal antibody (full-length IgG) may improve tissue penetration and increase potency due to more efficient engagement of the DLL3 and CD3 targets, resulting in improved synapse formation between the T cell and target tumor cell.

SCLC remains a significant unmet medical need, and new therapeutic options are required to improve the outlook for this sizable patient population. The above discussed bispecific antibody modality is clinically validated, and as such an antibody construct targeting DLL3 and CD3 represents a promising new possibility for the treatment of SCLC and an opportunity to improve the survival of patients suffering with this indication. As there is still a need for having available further options for the treatment of tumor or cancer diseases related to the overexpression of DLL3, there are provided herewith means and methods for the solution of this problem in the form of a bispecific antibody construct with one binding domain directed to DLL3 and a second binding domain directed to CD3 on T cells.

Thus, in a first aspect, the present invention provides a bispecific antibody construct comprising a first binding domain which binds to human DLL3 on the surface of a target cell and a second binding domain which binds to human CD3 on the surface of a T cell, wherein the first binding domain binds to an epitope of DLL3 which is comprised within the region as depicted in SEQ ID NO: 260.

It must be noted that as used herein, the singular forms "a", "an", and "the" include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

The term "antibody construct" refers to a molecule in which the structure and/or function is/are based on the structure and/or function of an antibody, e.g., of a full-length or whole immunoglobulin molecule. An antibody construct is hence capable of binding to its specific target or antigen. Furthermore, an antibody construct according to the invention comprises the minimum structural requirements of an antibody which allow for the target binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region), preferably of all six CDRs. The antibodies on which the constructs according to the invention are based include for example monoclonal, recombinant, chimeric, deimmunized, humanized and human antibodies.

Within the definition of "antibody constructs" according to the invention are full-length or whole antibodies also including camelid antibodies and other immunoglobulin antibodies generated by biotechnological or protein engineering methods or processes. These full-length antibodies may be for example monoclonal, recombinant, chimeric, deimmunized, humanized and human antibodies. Also within the definition of "antibody constructs" are fragments of full-length antibodies, such as VH, VHH, VL, (s)dAb, Fv, Fd, Fab, Fab', F(ab')2 or "r IgG" ("half antibody"). Antibody constructs according to the invention may also be modified fragments of antibodies, also called antibody variants, such as scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, "minibodies" exemplified by a structure which is as follows: (VH-VL-CH3)2, (scFv-CH3)2, ((scFv)2-CH3+CH3), ((scFv)2-CH3) or (scFv-CH3-scFv)2, multibodies such as triabodies or tetrabodies, and single domain antibodies such as nanobodies or single variable domain antibodies comprising merely one variable domain, which might be VHH, VH or VL, that specifically bind an antigen or epitope independently of other V regions or domains. Further preferred formats of the antibody constructs according to the invention are cross bodies, maxi bodies, hetero Fc constructs and mono Fc constructs. Examples for those formats will be described herein below.

A binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Additional examples for the format of antibody fragments, antibody variants or binding domains include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv), the latter being preferred (for example, derived from an scFv-library). Examples for embodiments of antibody constructs according to the invention are e.g. described in WO 00/006605, WO 2005/040220, WO 2008/119567, WO 2010/037838, WO 2013/026837, WO 2013/026833, US 2014/0308285, US 2014/0302037, WO2014/144722, WO 2014/151910, and WO 2015/048272.

Furthermore, the definition of the term "antibody construct" includes monovalent, bivalent and polyvalent/multivalent constructs and, thus, monospecific constructs, specifically binding to only one antigenic structure, as well as bispecific and polyspecific/multispecific constructs, which specifically bind more than one antigenic structure, e.g. two, three or more, through distinct binding domains. Moreover, the definition of the term "antibody construct" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter alia in Harlow and Lane, Antibodies a laboratory manual, CSHL Press (1988) and Using Antibodies: a laboratory manual, CSHL Press (1999), Kontermann and Dubel, Antibody Engineering, Springer, 2nd ed. 2010 and Little, Recombinant Antibodies for Immunotherapy, Cambridge University Press 2009.

The antibody constructs of the present invention are preferably "in vitro generated antibody constructs". This term refers to an antibody construct according to the above definition where all or part of the variable region (e.g., at least one CDR) is generated in a non-immune cell selection, e.g., an in vitro phage display, protein chip or any other method in which candidate sequences can be tested for their ability to bind to an antigen. This term thus preferably excludes sequences generated solely by genomic rearrangement in an immune cell in an animal. A "recombinant antibody" is an antibody made through the use of recombinant DNA technology or genetic engineering.

The term "monoclonal antibody" (mAb) or monoclonal antibody construct as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site or determinant on the antigen, in contrast to conventional (polyclonal) antibody preparations which typically include different antibodies directed against different determinants (or epitopes). In addition to their specificity, the monoclonal antibodies are advantageous in that they are synthesized by the hybridoma culture, hence uncontaminated by other immunoglobulins. The modifier "monoclonal" indicates the character of the antibody as being obtained from a substantially homogeneous population of antibodies, and is not to be construed as requiring production of the antibody by any particular method.

For the preparation of monoclonal antibodies, any technique providing antibodies produced by continuous cell line cultures can be used. For example, monoclonal antibodies to be used may be made by the hybridoma method first described by Koehler et al., Nature, 256: 495 (1975), or may be made by recombinant DNA methods (see, e.g., U.S. Pat. No. 4,816,567). Examples for further techniques to produce human monoclonal antibodies include the trioma technique, the human B-cell hybridoma technique (Kozbor, Immunology Today 4 (1983), 72) and the EBV-hybridoma technique (Cole et al., Monoclonal Antibodies and Cancer Therapy, Alan R. Liss, Inc. (1985), 77-96).

Hybridomas can then be screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the relevant antigen may be used as the immunogen, e.g., recombinant antigen, naturally occurring forms, any variants or fragments thereof, as well as an antigenic peptide thereof. Surface plasmon resonance as employed in the BIAcore system can be used to increase the efficiency of phage antibodies which bind to an epitope of a target antigen, such as DLL3 or CD3 epsilon (Schier, Human Antibodies Hybridomas 7 (1996), 97-105; Malmborg, J. Immunol. Methods 183 (1995), 7-13).

Another exemplary method of making monoclonal antibodies includes screening protein expression libraries, e.g., phage display or ribosome display libraries. Phage display is described, for example, in Ladner et al., U.S. Pat. No. 5,223,409; Smith (1985) Science 228:1315-1317, Clackson et al., Nature, 352: 624-628 (1991) and Marks et al., J. Mol. Biol., 222: 581-597 (1991).

In addition to the use of display libraries, the relevant antigen can be used to immunize a non-human animal, e.g., a rodent (such as a mouse, hamster, rabbit or rat). In one embodiment, the non-human animal includes at least a part of a human immunoglobulin gene. For example, it is possible to engineer mouse strains deficient in mouse antibody production with large fragments of the human Ig (immunoglobulin) loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, and WO 96/33735.

A monoclonal antibody can also be obtained from a non-human animal, and then modified, e.g., humanized, deimmunized, rendered chimeric etc., using recombinant DNA techniques known in the art. Examples of modified antibody constructs include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dubel (2010), loc. cit. and Little (2009), loc. cit.).

In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. The in vitro affinity maturation has successfully been used to optimize antibodies, antibody constructs, and antibody fragments. Random mutations inside the CDRs are introduced using radiation, chemical mutagens or error-prone PCR. In addition, the genetical diversity can be increased by chain shuffling. Two or three rounds of mutation and selection using display methods like phage display usually results in antibody fragments with affinities in the low nanomolar range.

A preferred type of an amino acid substitutional varianation of the antibody constructs involves substituting one or more hypervariable region residues of a parent antibody (e. g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e. g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e. g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domain and, e.g., human DLL3. Such contact residues and neighbouring residues are candidates for substitution according to the techniques elaborated herein. Once such variants are generated, the panel of variants is subjected to screening as described herein and antibodies with superior properties in one or more relevant assays may be selected for further development.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human constant region sequences. A variety of approaches for making chimeric antibodies have been described. See e.g., Morrison et al., Proc. Natl. Acad. ScL U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 0171496; EP 0173494; and GB 2177096.

An antibody, antibody construct, antibody fragment or antibody variant may also be modified by specific deletion of human T cell epitopes (a method called "deimmunization") by the methods disclosed for example in WO 98/52976 or WO 00/34317. Briefly, the heavy and light chain variable domains of an antibody can be analyzed for peptides that bind to MHC class II; these peptides represent potential T cell epitopes (as defined in WO 98/52976 and WO 00/34317). For detection of potential T cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences are disclosed e.g. in Tomlinson, et al. (1992) J. Mol. Biol. 227:776-798; Cook, G. P. et al. (1995) Immunol. Today Vol. 16 (5): 237-242; and Tomlinson et al. (1995) EMBO J. 14: 14:4628-4638. The V BASE directory provides a comprehensive directory of human immunoglobulin variable region sequences (compiled by Tomlinson, LA. et al. MRC Centre for Protein Engineering, Cambridge, UK). These sequences can be used as a source of human sequence, e.g., for framework regions and CDRs. Consensus human framework regions can also be used, for example as described in U.S. Pat. No. 6,300,064.

"Humanized" antibodies, antibody constructs, variants or fragments thereof (such as Fv, Fab, Fab', F(ab')2 or other antigen-binding subsequences of antibodies) are antibodies or immunoglobulins of mostly human sequences, which contain (a) minimal sequence(s) derived from non-human immunoglobulin. For the most part, humanized antibodies are human immunoglobulins (recipient antibody) in which residues from a hypervariable region (also CDR) of the recipient are replaced by residues from a hypervariable region of a non-human (e.g., rodent) species (donor antibody) such as mouse, rat, hamster or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody may also comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

Humanized antibodies may also be produced using transgenic animals such as mice that express human heavy and light chain genes, but are incapable of expressing the endogenous mouse immunoglobulin heavy and light chain genes. Winter describes an exemplary CDR grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

A humanized antibody can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982, and EP 239 400).

The term "human antibody", "human antibody construct" and "human binding domain" includes antibodies, antibody constructs and binding domains having antibody regions such as variable and constant regions or domains which correspond substantially to human germline immunoglobulin sequences known in the art, including, for example, those described by Kabat et al. (1991) (loc. cit.). The human antibodies, antibody constructs or binding domains of the invention may include amino acid residues not encoded by human germline immunoglobulin sequences (e.g., mutations introduced by random or site-specific mutagenesis in vitro or by somatic mutation in vivo), for example in the CDRs, and in particular, in CDR3. The human antibodies, antibody constructs or binding domains can have at least one, two, three, four, five, or more positions replaced with an amino acid residue that is not encoded by the human germline immunoglobulin sequence. The definition of human antibodies, antibody constructs and binding domains as used herein also contemplates fully human antibodies, which include only non-artificially and/or genetically altered human sequences of antibodies as those can be derived by using technologies or systems such as the Xenomouse.

In some embodiments, the antibody constructs of the invention are "isolated" or "substantially pure" antibody constructs. "Isolated" or "substantially pure", when used to describe the antibody constructs disclosed herein, means an antibody construct that has been identified, separated and/or recovered from a component of its production environment. Preferably, the antibody construct is free or substantially free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. The antibody constructs may e.g constitute at least about 5%, or at least about 50% by weight of the total protein in a given sample. It is understood that the isolated protein may constitute from 5% to 99.9% by weight of the total protein content, depending on the circumstances. The polypeptide may be made at a significantly higher concentration through the use of an inducible promoter or high expression promoter, such that it is made at increased concentration levels. The definition includes the production of an antibody construct in a wide variety of organisms and/or host cells that are known in the art. In preferred embodiments, the antibody construct will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody construct will be prepared by at least one purification step.

The term "binding domain" characterizes in connection with the present invention a domain which (specifically) binds to/interacts with/recognizes a given target epitope or a given target site on the target molecules (antigens), here: DLL3 and CD3, respectively. The structure and function of the first binding domain (recognizing DLL3), and preferably also the structure and/or function of the second binding domain (recognizing CD3), is/are based on the structure and/or function of an antibody, e.g. of a full-length or whole immunoglobulin molecule. According to the invention, the first binding domain is characterized by the presence of three light chain CDRs (i.e. CDR1, CDR2 and CDR3 of the VL region) and/or three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold.

According to the present invention, binding domains are in the form of one or more polypeptides. Such polypeptides may include proteinaceous parts and non-proteinaceous parts (e.g. chemical linkers or chemical cross-linking agents such as glutaraldehyde). Proteins (including fragments thereof, preferably biologically active fragments, and peptides, usually having less than 30 amino acids) comprise two or more amino acids coupled to each other via a covalent peptide bond (resulting in a chain of amino acids). The term "polypeptide" as used herein describes a group of molecules, which usually consist of more than 30 amino acids. Polypeptides may further form multimers such as dimers, trimers and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a hereteromultimer is an antibody molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is effected e.g. by post-translational modifications like glycosylation, acetylation, phosphorylation and the like. A "peptide", "polypeptide" or "protein" when referred to herein may also be chemically modified such as pegylated. Such modifications are well known in the art and described herein below.

Preferably the binding domain which binds to DLL3 and/or the binding domain which binds to CD3 is/are human binding domains. Antibodies and antibody constructs comprising at least one human binding domain avoid some of the problems associated with antibodies or antibody constructs that possess non-human such as rodent (e.g. murine, rat, hamster or rabbit) variable and/or constant regions. The presence of such rodent derived proteins can lead to the rapid clearance of the antibodies or antibody constructs or can lead to the generation of an immune response against the antibody or antibody construct by a patient. In order to avoid the use of rodent derived antibodies or antibody constructs, human or fully human antibodies/antibody constructs can be generated through the introduction of human antibody function into a rodent so that the rodent produces fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the use of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies or antibody constructs are expected to minimize the immunogenic and allergic responses intrinsic to mouse or mouse-derivatized mAbs and thus to increase the efficacy and safety of the administered antibodies/antibody constructs. The use of fully human antibodies or antibody constructs can be expected to provide a substantial advantage in the treatment of chronic and recurring human diseases, such as inflammation, autoimmunity, and cancer, which require repeated compound administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with the generation of the first XenoMouse mouse strains (see Green et al. Nature Genetics 7:13-21 (1994)). The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. The human Ig containing YACs proved to be compatible with the mouse system for both rearrangement and expression of antibodies and were capable of substituting for the inactivated mouse Ig genes. This was demonstrated by their ability to induce B cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620.

The production of the XenoMouse mice is further discussed and delineated in U.S. patent application Ser. No. 07/466,008, Ser. No. 07/610,515, Ser. No. 07/919,297, Ser. No. 07/922,649, Ser. No. 08/031,801, Ser. No. 08/112,848, Ser. No. 08/234,145, Ser. No. 08/376,279, Ser. No. 08/430,938, Ser. No. 08/464,584, Ser. No. 08/464,582, Ser. No. 08/463,191, Ser. No. 08/462,837, Ser. No. 08/486,853, Ser. No. 08/486,857, Ser. No. 08/486,859, Ser. No. 08/462,513, Ser. No. 08/724,752, and Ser. No. 08/759,620; and U.S. Pat. Nos. 6,162,963; 6,150,584; 6,114,598; 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998), EP 0 463 151 B1, WO 94/02602, WO 96/34096, WO 98/24893, WO 00/76310, and WO 03/47336.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806; 5,625,825; 5,625,126; 5,633,425; 5,661,016; 5,770,429; 5,789,650; 5,814,318; 5,877,397; 5,874,299; and 6,255,458 each to Lonberg and Kay, U.S. Pat. Nos. 5,591,669 and 6,023,010 to Krimpenfort and Berns, U.S. Pat. Nos. 5,612,205; 5,721,367; and U.S. Pat. No. 5,789,215 to Berns et al., and U.S. Pat. No. 5,643,763 to Choi and Dunn, and GenPharm International U.S. patent application Ser. No. 07/574,748, Ser. No. 07/575,962, Ser. No. 07/810,279, Ser. No. 07/853,408, Ser. No. 07/904,068, Ser. No. 07/990,860, Ser. No. 08/053,131, Ser. No. 08/096,762, Ser. No. 08/155,301, Ser. No. 08/161,739, Ser. No. 08/165,699, Ser. No. 08/209,741. See also EP 0 546 073 B1, WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175. See further Taylor et al. (1992), Chen et al. (1993), Tuaillon et al. (1993), Choi et al. (1993), Lonberg et al. (1994), Taylor et al. (1994), and Tuaillon et al. (1995), Fishwild et al. (1996).

Kirin has also demonstrated the generation of human antibodies from mice in which, through microcell fusion, large pieces of chromosomes, or entire chromosomes, have been introduced. See European Patent Application Nos. 773 288 and 843 961. Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996; 5,698,767; and 5,958,765.

Human anti-mouse antibody (HAMA) responses have led the industry to prepare chimeric or otherwise humanized antibodies. It is however expected that certain human anti-chimeric antibody (HACA) responses will be observed, particularly in chronic or multi-dose utilizations of the antibody. Thus, it would be desirable to provide antibody constructs comprising a human binding domain against DLL3 and/or a human binding domain against CD3 in order to vitiate concerns and/or effects of HAMA or HACA response.

The terms "(specifically) binds to", (specifically) recognizes", "is (specifically) directed to", and "(specifically) reacts with" mean in accordance with this invention that a binding domain interacts or specifically interacts with a given epitope or a given target site on the target molecules (antigens), here: DLL3 and CD3, respectively.

The term "epitope" refers to a site on an antigen to which a binding domain, an antibody or immunoglobulin, or a derivative, fragment or variant of an antibody or an immunoglobulin, specifically binds. An "epitope" is antigenic and thus the term epitope is sometimes also referred to herein as "antigenic structure" or "antigenic determinant". Thus, the binding domain is an "antigen interaction site". Said binding/interaction is also understood to define a "specific recognition".

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically a conformational epitope comprises an increased number of amino acids relative to a linear epitope. With regard to recognition of conformational epitopes, the binding domain recognizes a three-dimensional structure of the antigen, preferably a peptide or protein or fragment thereof (in the context of the present invention, the antigenic structure for the first binding domain is comprised within the DLL3 protein). For example, when a protein molecule folds to form a three-dimensional structure, certain amino acids and/or the polypeptide backbone forming the conformational epitope become juxtaposed enabling the antibody to recognize the epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

A method for epitope mapping is described in the following: When a region (a contiguous amino acid stretch) in the human DLL3 protein is exchanged/replaced with its corresponding region of a non-human and non-primate DLL3 antigen (e.g., mouse DLL3, but others like chicken, rat, hamster, rabbit etc. might also be conceivable), a decrease in the binding of the binding domain is expected to occur, unless the binding domain is cross-reactive for the non-human, non-primate DLL3 used. Said decrease is preferably at least 10%, 20%, 30%, 40%, or 50%; more preferably at least 60%, 70%, or 80%, and most preferably 90%, 95% or even 100% in comparison to the binding to the respective region in the human DLL3 protein, whereby binding to the respective region in the human DLL3 protein is set to be 100%. It is envisaged that the aforementioned human DLL3/non-human DLL3 chimeras are expressed in CHO cells. It is also envisaged that the human DLL3/non-human DLL3 chimeras are fused with a transmembrane domain and/or cytoplasmic domain of a different membrane-bound protein such as EpCAM.

In an alternative or additional method for epitope mapping, several truncated versions of the human DLL3 extracellular domain can be generated in order to determine a specific region that is recognized by a binding domain. In these truncated versions, the different extracellular DLL3 domains/sub-domains or regions are stepwise deleted, starting from the N-terminus. The truncated DLL3 versions that were generated and used in the context of the present invention are depicted in FIG. 1. It is envisaged that the truncated DLL3 versions are expressed in CHO cells. It is also envisaged that the truncated DLL3 versions are fused with a transmembrane domain and/or cytoplasmic domain of a different membrane-bound protein such as EpCAM. It is also envisaged that the truncated DLL3 versions encompass a signal peptide domain at their N-terminus, for example a signal peptide derived from mouse IgG heavy chain signal peptide. It is furthermore envisaged that the truncated DLL3 versions encompass a v5 domain at their N-terminus (following the signal peptide) which allows verifying their correct expression on the cell surface. A decrease or a loss of binding is expected to occur with those truncated DLL3 versions which do not encompass any more the DLL3 region that is recognized by the binding domain. The decrease of binding is preferably at least 10%, 20%, 30%, 40%, 50%; more preferably at least 60%, 70%, 80%, and most preferably 90%, 95% or even 100%, whereby binding to the entire human DLL3 protein (or its extracellular region or domain) is set to be 100%. A method to test this loss of binding is described in Example 2.

A further method to determine the contribution of a specific residue of a target antigen to the recognition by a antibody construct or binding domain is alanine scanning (see e.g. Morrison K L & Weiss G A. Cur Opin Chem Biol. 2001 June; 5(3):302-7), where each residue to be analyzed is replaced by alanine, e.g. via site-directed mutagenesis. Alanine is used because of its non-bulky, chemically inert, methyl functional group that nevertheless mimics the secondary structure references that many of the other amino acids possess. Sometimes bulky amino acids such as valine or leucine can be used in cases where conservation of the size of mutated residues is desired. Alanine scanning is a mature technology which has been used for a long period of time.

The interaction between the binding domain and the epitope or the region comprising the epitope implies that a binding domain exhibits appreciable affinity for the epitope/the region comprising the epitope on a particular protein or antigen (here: DLL3 and CD3, respectively) and, generally, does not exhibit significant reactivity with proteins or antigens other than DLL3 or CD3. "Appreciable affinity" includes binding with an affinity of about $10^{-6}$ M (KD) or stronger. Preferably, binding is considered specific when the binding affinity is about $10^{-12}$ to $10^{-8}$ M, $10^{-12}$ to $10^{-9}$ M, $10^{-12}$ to $10^{-10}$ M, $10^{-11}$ to $10^{-8}$ M, preferably of about $10^{-11}$ to $10^{-9}$ M. Whether a binding domain specifically reacts with or binds to a target can be tested readily by, inter alia, comparing the reaction of said binding domain with a target protein or antigen with the reaction of said binding domain with proteins or antigens other than DLL3 or CD3. Preferably, a binding domain of the invention does not essentially or substantially bind to proteins or antigens other than DLL3 or CD3 (i.e., the first binding domain is not capable of binding to proteins other than DLL3 and the second binding domain is not capable of binding to proteins other than CD3).

The term "does not essentially/substantially bind" or "is not capable of binding" means that a binding domain of the present invention does not bind a protein or antigen other than DLL3 or CD3, i.e., does not show reactivity of more than 30%, preferably not more than 20%, more preferably not more than 10%, particularly preferably not more than 9%, 8%, 7%, 6% or 5% with proteins or antigens other than DLL3 or CD3, whereby binding to DLL3 or CD3, respectively, is set to be 100%.

It is also envisaged that the antibody constructs of the present invention bind to a human DLL3 isoform having one or both of the following DLL3 point mutations: F172C and L218P. See Example 5.

Specific binding is believed to be effected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-site with its specific antigen may result in a simple binding of said site to the antigen. Moreover, the specific interaction of the antigen-interaction-site with its specific antigen may alternatively or additionally result in the initiation of a signal, e.g. due to the induction of a change of the conformation of the antigen, an oligomerization of the antigen, etc.

The antibody constructs according to the invention bind to an epitope of DLL3 which is comprised within the region as depicted in SEQ ID NO: 260, corresponding to an amino acid stretch encompassing the regions EGF-3 and EGF-4. Other groups of anti-DLL3 binders were also generated and their DLL3 binding specificities were identified during epitope mapping (see Example 2).

The largest group of generated binders recognized an epitope within the DSL domain. However, none of those antibody constructs fulfilled the criteria for sufficient cytotoxic activity in an initial 18-hour $^{51}Cr$-based cytotoxicity assay with stimulated human CD8+ T cells as effector cells and hu DLL3 transfected CHO cells as target cells.

In a further initial 48 hour FACS-based cytotoxicity assay (using unstimulated human PBMC as effector cells and hu DLL3 transfected CHO cells as target cells), those binders that recognized a DLL3 epitope within the N-terminus of the protein had EC50 values between 1455 and 1580 pM. In the present context, these values are not considered adequate for bispecific antibodies that are provided for a therapeutic use in directing a patient's immune system, more specifically the T cells' cytotoxic activity, against cancer cells.

Finally, another group of binders was generated and characterized for its cytotoxic activity in a variety of assays. The epitope mapping of these binders revealed a specificity for a DLL3 epitope comprised within the EGF-5 region, and to some extend also within the EGF-6 region (for details, see Example 2). An overall view of the data generated in the different cytotoxicity assays (see Examples 8.3, 8.5, 8.6 and 8.7) for these binders denominated DLL3-18, DLL3-19, DLL3-20 and DLL3-21 revealed the following: While not all of the binders fail in all of the assays in terms of favorable EC50 values, the entire group clearly underperforms if compared with the antibody constructs according to the invention. This observation is highlighted with a darker shadowing of the results shown in Tables 6-9.

In summary, it can clearly be stated that the antibody constructs according to the invention (which bind to an epitope of DLL3 comprised within the region as depicted in SEQ ID NO: 260) show by far the best activity performance compared to a variety of other groups of DLL3 binders having different epitope specificities. In other words, the antibody constructs according to the invention present with a favorable epitope-activity relationship, hence supporting potent bispecific antibody construct mediated cytotoxic activity.

In another aspect, the present invention provides a bispecific antibody construct comprising a first binding domain which binds to human DLL3 on the surface of a target cell and a second binding domain which binds to human CD3 on the surface of a T cell, wherein the first binding domain binds to an epitope of DLL3 which is comprised within the region as depicted in SEQ ID NO: 258.

Preferably, the first binding domain of the bispecific antibody construct of the invention comprises a VH region comprising CDR-H1, CDR-H2 and CDR-H3 and a VL region comprising CDR-L1, CDR-L2 and CDR-L3 selected from the group consisting of:

a) CDR-H1 as depicted in SEQ ID NO: 31, CDR-H2 as depicted in SEQ ID NO: 32, CDR-H3 as depicted in SEQ ID NO: 33, CDR-L1 as depicted in SEQ ID NO: 34, CDR-L2 as depicted in SEQ ID NO: 35 and CDR-L3 as depicted in SEQ ID NO: 36;
b) CDR-H1 as depicted in SEQ ID NO: 41, CDR-H2 as depicted in SEQ ID NO: 42, CDR-H3 as depicted in SEQ ID NO: 43, CDR-L1 as depicted in SEQ ID NO: 44, CDR-L2 as depicted in SEQ ID NO: 45 and CDR-L3 as depicted in SEQ ID NO: 46;
c) CDR-H1 as depicted in SEQ ID NO: 51, CDR-H2 as depicted in SEQ ID NO: 52, CDR-H3 as depicted in SEQ ID NO: 53, CDR-L1 as depicted in SEQ ID NO: 54, CDR-L2 as depicted in SEQ ID NO: 55 and CDR-L3 as depicted in SEQ ID NO: 56;
d) CDR-H1 as depicted in SEQ ID NO: 61, CDR-H2 as depicted in SEQ ID NO: 62, CDR-H3 as depicted in SEQ ID NO: 63, CDR-L1 as depicted in SEQ ID NO: 64, CDR-L2 as depicted in SEQ ID NO: 65 and CDR-L3 as depicted in SEQ ID NO: 66;
e) CDR-H1 as depicted in SEQ ID NO: 71, CDR-H2 as depicted in SEQ ID NO: 72, CDR-H3 as depicted in SEQ ID NO: 73, CDR-L1 as depicted in SEQ ID NO: 74, CDR-L2 as depicted in SEQ ID NO: 75 and CDR-L3 as depicted in SEQ ID NO: 76;
f) CDR-H1 as depicted in SEQ ID NO: 81, CDR-H2 as depicted in SEQ ID NO: 82, CDR-H3 as depicted in SEQ ID NO: 83, CDR-L1 as depicted in SEQ ID NO: 84, CDR-L2 as depicted in SEQ ID NO: 85 and CDR-L3 as depicted in SEQ ID NO: 86;
g) CDR-H1 as depicted in SEQ ID NO: 91, CDR-H2 as depicted in SEQ ID NO: 92, CDR-H3 as depicted in SEQ ID NO: 93, CDR-L1 as depicted in SEQ ID NO: 94, CDR-L2 as depicted in SEQ ID NO: 95 and CDR-L3 as depicted in SEQ ID NO: 96;
h) CDR-H1 as depicted in SEQ ID NO: 101, CDR-H2 as depicted in SEQ ID NO: 102, CDR-H3 as depicted in SEQ ID NO: 103, CDR-L1 as depicted in SEQ ID NO: 104, CDR-L2 as depicted in SEQ ID NO: 105 and CDR-L3 as depicted in SEQ ID NO: 106; and
i) CDR-H1 as depicted in SEQ ID NO: 111, CDR-H2 as depicted in SEQ ID NO: 112, CDR-H3 as depicted in SEQ ID NO: 113, CDR-L1 as depicted in SEQ ID NO: 114, CDR-L2 as depicted in SEQ ID NO: 115 and CDR-L3 as depicted in SEQ ID NO: 116.

The term "variable" refers to the portions of the antibody or immunoglobulin domains that exhibit variability in their sequence and that are involved in determining the specificity and binding affinity of a particular antibody (i.e., the "variable domain(s)"). The pairing of a variable heavy chain (VH) and a variable light chain (VL) together forms a single antigen-binding site.

Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a p-sheet configuration, connected by three hypervariable regions, which form loops connecting, and in some cases forming part of, the p-sheet structure. The hypervariable regions in each chain are held together in close proximity by the FRM and, with the hypervariable regions from the other chain, contribute to the formation of the antigen-binding site (see Kabat et al., loc. cit.).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding site is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding site. H3, for example, can be as short as two amino acid residues or greater than 26 amino acids.

In a classical full-length antibody or immunoglobulin, each light (L) chain is linked to a heavy (H) chain by one covalent disulfide bond, while the two H chains are linked to each other by one or more disulfide bonds depending on the H chain isotype. The CH domain most proximal to VH is usually designated as CH1. The constant ("C") domains are not directly involved in antigen binding, but exhibit various effector functions, such as antibody-dependent, cell-mediated cytotoxicity and complement activation. The Fc region of an antibody is comprised within the heavy chain constant domains and is for example able to interact with cell surface located Fc receptors.

The sequence of antibody genes after assembly and somatic mutation is highly varied, and these varied genes are estimated to encode $10^{10}$ different antibody molecules (Immunoglobulin Genes, 2nd ed., eds. Jonio et al., Academic Press, San Diego, CA, 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

A preferred antibody construct according to the invention can also be defined as a bispecific antibody construct comprising a first (preferably human) binding domain which binds to human DLL3 on the surface of a target cell and a second binding domain which binds to human CD3 on the surface of a T cell, wherein the first binding domain binds to the same epitope of DLL3 as an antibody selected from the group consisting of DLL3-4, DLL3-5, DLL3-6, DLL3-7, DLL3-8, DLL3-9, and DLL3-10, i.e., an antibody comprising a VH region comprising CDR-H1, CDR-H2 and CDR-H3 and a VL region comprising CDR-L1, CDR-L2 and CDR-L3 selected from the group consisting of:

a) CDR-H1 as depicted in SEQ ID NO: 31, CDR-H2 as depicted in SEQ ID NO: 32, CDR-H3 as depicted in SEQ ID NO: 33, CDR-L1 as depicted in SEQ ID NO: 34, CDR-L2 as depicted in SEQ ID NO: 35 and CDR-L3 as depicted in SEQ ID NO: 36;
b) CDR-H1 as depicted in SEQ ID NO: 41, CDR-H2 as depicted in SEQ ID NO: 42, CDR-H3 as depicted in SEQ ID NO: 43, CDR-L1 as depicted in SEQ ID NO: 44, CDR-L2 as depicted in SEQ ID NO: 45 and CDR-L3 as depicted in SEQ ID NO: 46;
c) CDR-H1 as depicted in SEQ ID NO: 51, CDR-H2 as depicted in SEQ ID NO: 52, CDR-H3 as depicted in SEQ ID NO: 53, CDR-L1 as depicted in SEQ ID NO: 54, CDR-L2 as depicted in SEQ ID NO: 55 and CDR-L3 as depicted in SEQ ID NO: 56;
d) CDR-H1 as depicted in SEQ ID NO: 61, CDR-H2 as depicted in SEQ ID NO: 62, CDR-H3 as depicted in SEQ ID NO: 63, CDR-L1 as depicted in SEQ ID NO: 64, CDR-L2 as depicted in SEQ ID NO: 65 and CDR-L3 as depicted in SEQ ID NO: 66;
e) CDR-H1 as depicted in SEQ ID NO: 71, CDR-H2 as depicted in SEQ ID NO: 72, CDR-H3 as depicted in SEQ ID NO: 73, CDR-L1 as depicted in SEQ ID NO: 74, CDR-L2 as depicted in SEQ ID NO: 75 and CDR-L3 as depicted in SEQ ID NO: 76;
f) CDR-H1 as depicted in SEQ ID NO: 81, CDR-H2 as depicted in SEQ ID NO: 82, CDR-H3 as depicted in SEQ ID NO: 83, CDR-L1 as depicted in SEQ ID NO: 84, CDR-L2 as depicted in SEQ ID NO: 85 and CDR-L3 as depicted in SEQ ID NO: 86; and
g) CDR-H1 as depicted in SEQ ID NO: 91, CDR-H2 as depicted in SEQ ID NO: 92, CDR-H3 as depicted in SEQ ID NO: 93, CDR-L1 as depicted in SEQ ID NO: 94, CDR-L2 as depicted in SEQ ID NO: 95 and CDR-L3 as depicted in SEQ ID NO: 96.

Whether or not an antibody construct binds to the same epitope of DLL3 as another given antibody construct can be measured e.g. by epitope mapping with chimeric or truncated target molecules, e.g. as described herein above and in Example 2.

A preferred antibody construct according to the invention can also be defined as a bispecific antibody construct comprising a first (preferably human) binding domain which binds to human DLL3 on the surface of a target cell and a second binding domain which binds to human CD3 on the surface of a T cell, wherein the first binding domain competes for binding with an antibody selected from the group consisting of DLL3-4, DLL3-5, DLL3-6, DLL3-7, DLL3-8, DLL3-9, and DLL3-10, i.e., an antibody comprising a VH region comprising CDR-H1, CDR-H2 and CDR-H3 and a VL region comprising CDR-L1, CDR-L2 and CDR-L3 selected from the group consisting of those described above.

Whether or not an antibody construct competes for binding with another given antibody construct can be measured in a competition assay such as a competitive ELISA or a cell-based competition assay. Avidin-coupled microparticles (beads) can also be used. Similar to an avidin-coated ELISA plate, when reacted with a biotinylated protein, each of these beads can be used as a substrate on which an assay can be performed. Antigen is coated onto a bead and then precoated with the first antibody. The second antibody is added and any additional binding is determined. Read-out occurs via flow cytometry.

In one embodiment of the invention, the first binding domain of the antibody construct of the invention comprises a VH region selected from the group consisting of those depicted in SEQ ID NO: 37, SEQ ID NO: 47, SEQ ID NO: 57, SEQ ID NO: 67, SEQ ID NO: 77, SEQ ID NO: 87, SEQ ID NO: 97, SEQ ID NO: 107, SEQ ID NO: 117, SEQ ID NO: 435 and SEQ ID NO: 529.

In a further embodiment, the first binding domain of the antibody construct of the invention comprises a VL region selected from the group consisting of those depicted in SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 436 and SEQ ID NO: 530.

In another embodiment, the first binding domain of the antibody construct of the invention comprises a VH region and a VL region selected from the group consisting of pairs of a VH region and a VL region as depicted in SEQ ID NOs: 37+38; SEQ ID NOs: 47+48; SEQ ID NOs: 57+58; SEQ ID NOs: 67+68; SEQ ID NOs: 77+78; SEQ ID NOs: 87+88; SEQ ID NOs: 97+98; SEQ ID NOs: 107+108; SEQ ID NOs: 117+118; SEQ ID NOs: 435+436; and SEQ ID Nos: 529+530.

In yet a further embodiment, the first binding domain of the antibody construct of the invention comprises a polypeptide selected from the group consisting of those depicted in SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 437 and SEQ ID NO: 531.

The above first binding domains (which are specified by their CDRs, VH region and VL region and combinations thereof) characterize as binding domains which bind to a DLL3 epitope comprised within the region as depicted in SEQ ID NO: 258.

The term “bispecific” as used herein refers to an antibody construct which is “at least bispecific”, i.e., it comprises at least a first binding domain and a second binding domain, wherein the first binding domain binds to one antigen or target (here: DLL3), and the second binding domain binds to another antigen or target (here: CD3). Accordingly, antibody constructs according to the invention comprise specificities for at least two different antigens or targets. The term “bispecific antibody construct” of the invention also encompasses multispecific antibody constructs such as trispecific antibody constructs, the latter ones including three binding domains, or constructs having more than three (e.g. four, five . . . ) specificites.

Given that the antibody constructs according to the invention are (at least) bispecific, they do not occur naturally and they are markedly different from naturally occurring products. A “bispecific” antibody construct or immunoglobulin is hence an artificial hybrid antibody or immunoglobulin having at least two distinct binding sites with different specificities. Bispecific antibody constructs can be produced by a variety of methods including fusion of hybridomas or linking of Fab' fragments. See, e.g., Songsivilai & Lachmann, Clin. Exp. Immunol. 79:315-321 (1990).

The at least two binding domains and the variable domains of the antibody construct of the present invention may or may not comprise peptide linkers (spacer peptides). The term “peptide linker” comprises in accordance with the present invention an amino acid sequence by which the amino acid sequences of one (variable and/or binding) domain and another (variable and/or binding) domain of the antibody construct of the invention are linked with each other. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody construct of the invention.

In the event that a linker is used, this linker is preferably of a length and sequence sufficient to ensure that each of the first and second domains can, independently from one another, retain their differential binding specificities. For peptide linkers which connect the at least two binding domains (or two variable domains) in the antibody construct of the invention, those peptide linkers are preferred which comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or one amino acid(s), wherein Gly-rich linkers are preferred. A particularly preferred "single" amino acid in the context of said "peptide linker" is Gly. Accordingly, said peptide linker may consist of the single amino acid Gly. Another preferred embodiment of a peptide linker is characterized by the amino acid sequence Gly-Gly-Gly-Gly-Ser, i.e. Gly4Ser (SEQ ID NO: 286), or polymers thereof, i.e. (Gly4Ser)x, where x is an integer of 1 or greater (e.g. 2 or 3). Preferred linkers are depicted in SEQ ID NOs: 285-293. The characteristics of said peptide linker, which comprise the absence of the promotion of secondary structures, are known in the art and are described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which furthermore do not promote any secondary structures are preferred. The linkage of said domains to each other can be provided, e.g., by genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, New York, 2001).

As described herein above, the invention provides a preferred embodiment wherein the antibody construct is in a format selected from the group consisting of (scFv)2, scFv-single domain mAb, diabodies and oligomers of any of the afermentioned formats. The term "is in a format" does not exclude that the construct can be further modified, e.g. by attachment or fusion to other moieties, as described herein.

According to a particularly preferred embodiment, and as documented in the appended examples, the antibody construct of the invention is a "bispecific single chain antibody construct", more preferably a bispecific "single chain Fv" (scFv). Although the two domains of the Fv fragment, VL and VH, are coded for by separate genes, they can be joined, using recombinant methods, by a synthetic linker—as described hereinbefore—that enables them to be made as a single protein chain in which the VL and VH regions pair to form a monovalent molecule; see e.g., Huston et al. (1988) Proc. Natl. Acad. Sci USA 85:5879-5883). These antibody fragments are obtained using conventional techniques known to those with skill in the art, and the fragments are evaluated for function in the same manner as are whole or full-length antibodies. A single-chain variable fragment (scFv) is hence a fusion protein of the variable region of the heavy chain (VH) and of the light chain (VL) of immunoglobulins, usually connected with a short linker peptide of about ten to about 25 amino acids, preferably about 15 to 20 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and introduction of the linker.

Bispecific single chain molecules are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Loffler, Blood, (2000), 95, 6, 2098-2103, Brühl, Immunol., (2001), 166, 2420-2426, Kipriyanov, J. Mol. Biol., (1999), 293, 41-56. Techniques described for the production of single chain antibodies (see, inter alia, U.S. Pat. No. 4,946, 778, Kontermann and Dubel (2010), loc. cit. and Little (2009), loc. cit.) can be adapted to produce single chain antibody constructs specifically recognizing (an) elected target(s).

Bivalent (also called divalent) or bispecific single-chain variable fragments (bi-scFvs or di-scFvs having the format (scFv)2 can be engineered by linking two scFv molecules (e.g. with linkers as described hereinbefore). If these two scFv molecules have the same binding specificity, the resulting (scFv)2 molecule will preferably be called bivalent (i.e. it has two valences for the same target epitope). If the two scFv molecules have different binding specificities, the resulting (scFv)2 molecule will preferably be called bispecific. The linking can be done by producing a single peptide chain with two VH regions and two VL regions, yielding tandem scFvs (see e.g. Kufer P. et al., (2004) Trends in Biotechnology 22(5):238-244). Another possibility is the creation of scFv molecules with linker peptides that are too short for the two variable regions to fold together (e.g. about five amino acids), forcing the scFvs to dimerize. This type is known as diabodies (see e.g. Hollinger, Philipp et al., (July 1993) Proceedings of the National Academy of Sciences of the United States of America 90 (14): 6444-8.).

According to a further preferred embodiment of the antibody construct of the invention the heavy chain (VH) and the light chain (VL) of a binding domain (binding either to the target antigen DLL3 or to CD3) are not directly connected via a peptide linker as described above, but the binding domains are formed as described for the diabody. Thus, the VH of the CD3 binding domain may be fused to the VL of the DLL3 binding domain via a peptide linker, and the VH of the DLL3 binding domain is fused to the VL of the CD3 binding domain via such peptide linker.

Single domain antibodies comprise merely one (monomeric) antibody variable domain which is able to bind selectively to a specific antigen, independently of other V regions or domains. The first single domain antibodies were engineered from heavy chain antibodies found in camelids, and these are called VHH fragments. Cartilaginous fishes also have heavy chain antibodies (IgNAR) from which single domain antibodies called VNAR fragments can be obtained. An alternative approach is to split the dimeric variable domains from common immunoglobulins e.g. from humans or rodents into monomers, hence obtaining VH or VL as a single domain Ab. Although most research into single domain antibodies is currently based on heavy chain variable domains, nanobodies derived from light chains have also been shown to bind specifically to target epitopes. Examples of single domain antibodies are called sdAb, nanobodies or single variable domain antibodies.

A (single domain mAb)2 is hence a monoclonal antibody construct composed of (at least) two single domain monoclonal antibodies, which are individually selected from the group comprising VH, VL, VHH and VNAR. The linker is preferably in the form of a peptide linker. Similarly, an "scFv-single domain mAb" is a monoclonal antibody construct composed of at least one single domain antibody as described above and one scFv molecule as described above. Again, the linker is preferably in the form of a peptide linker.

It is furthermore envisaged that the present invention provides a bispecific antibody construct comprising a first binding domain which binds to human DLL3 on the surface of a target cell and a second binding domain which binds to human CD3 on the surface of a T cell, wherein the first binding domain binds to an epitope of DLL3 which is comprised within the region as depicted in SEQ ID NO: 259.

Accordingly, in a further aspect of the invention, the first binding domain of the bispecific antibody construct comprises a VH region comprising CDR-H1, CDR-H2 and CDR-H3 and a VL region comprising CDR-L1, CDR-L2 and CDR-L3 selected from the group consisting of:

a) CDR-H1 as depicted in SEQ ID NO: 121, CDR-H2 as depicted in SEQ ID NO: 122, CDR-H3 as depicted in SEQ ID NO: 123, CDR-L1 as depicted in SEQ ID NO: 124, CDR-L2 as depicted in SEQ ID NO: 125 and CDR-L3 as depicted in SEQ ID NO: 126;
b) CDR-H1 as depicted in SEQ ID NO: 131, CDR-H2 as depicted in SEQ ID NO: 132, CDR-H3 as depicted in SEQ ID NO: 133, CDR-L1 as depicted in SEQ ID NO: 134, CDR-L2 as depicted in SEQ ID NO: 135 and CDR-L3 as depicted in SEQ ID NO: 136;
c) CDR-H1 as depicted in SEQ ID NO: 141, CDR-H2 as depicted in SEQ ID NO: 142, CDR-H3 as depicted in SEQ ID NO: 143, CDR-L1 as depicted in SEQ ID NO: 144, CDR-L2 as depicted in SEQ ID NO: 145 and CDR-L3 as depicted in SEQ ID NO: 146;
d) CDR-H1 as depicted in SEQ ID NO: 151, CDR-H2 as depicted in SEQ ID NO: 152, CDR-H3 as depicted in SEQ ID NO: 153, CDR-L1 as depicted in SEQ ID NO: 154, CDR-L2 as depicted in SEQ ID NO: 155 and CDR-L3 as depicted in SEQ ID NO: 156; and
e) CDR-H1 as depicted in SEQ ID NO: 161, CDR-H2 as depicted in SEQ ID NO: 162, CDR-H3 as depicted in SEQ ID NO: 163, CDR-L1 as depicted in SEQ ID NO: 164, CDR-L2 as depicted in SEQ ID NO: 165 and CDR-L3 as depicted in SEQ ID NO: 166;
f) CDR-H1 as depicted in SEQ ID NO: 131, CDR-H2 as depicted in SEQ ID NO: 439, CDR-H3 as depicted in SEQ ID NO: 133, CDR-L1 as depicted in SEQ ID NO: 134, CDR-L2 as depicted in SEQ ID NO: 135 and CDR-L3 as depicted in SEQ ID NO: 136;
g) CDR-H1 as depicted in SEQ ID NO: 131, CDR-H2 as depicted in SEQ ID NO: 440, CDR-H3 as depicted in SEQ ID NO: 133, CDR-L1 as depicted in SEQ ID NO: 134, CDR-L2 as depicted in SEQ ID NO: 135 and CDR-L3 as depicted in SEQ ID NO: 136;
h) CDR-H1 as depicted in SEQ ID NO: 131, CDR-H2 as depicted in SEQ ID NO: 132, CDR-H3 as depicted in SEQ ID NO: 133, CDR-L1 as depicted in SEQ ID NO: 441, CDR-L2 as depicted in SEQ ID NO: 135 and CDR-L3 as depicted in SEQ ID NO: 136;
i) CDR-H1 as depicted in SEQ ID NO: 131, CDR-H2 as depicted in SEQ ID NO: 132, CDR-H3 as depicted in SEQ ID NO: 133, CDR-L1 as depicted in SEQ ID NO: 442, CDR-L2 as depicted in SEQ ID NO: 135 and CDR-L3 as depicted in SEQ ID NO: 136;
j) CDR-H1 as depicted in SEQ ID NO: 131, CDR-H2 as depicted in SEQ ID NO: 132, CDR-H3 as depicted in SEQ ID NO: 133, CDR-L1 as depicted in SEQ ID NO: 443, CDR-L2 as depicted in SEQ ID NO: 135 and CDR-L3 as depicted in SEQ ID NO: 136;
k) CDR-H1 as depicted in SEQ ID NO: 131, CDR-H2 as depicted in SEQ ID NO: 132, CDR-H3 as depicted in SEQ ID NO: 133, CDR-L1 as depicted in SEQ ID NO: 444, CDR-L2 as depicted in SEQ ID NO: 135 and CDR-L3 as depicted in SEQ ID NO: 136;
l) CDR-H1 as depicted in SEQ ID NO: 131, CDR-H2 as depicted in SEQ ID NO: 439, CDR-H3 as depicted in SEQ ID NO: 133, CDR-L1 as depicted in SEQ ID NO: 441, CDR-L2 as depicted in SEQ ID NO: 135 and CDR-L3 as depicted in SEQ ID NO: 136; and
m) CDR-H1 as depicted in SEQ ID NO: 131, CDR-H2 as depicted in SEQ ID NO: 440, CDR-H3 as depicted in SEQ ID NO: 133, CDR-L1 as depicted in SEQ ID NO: 442, CDR-L2 as depicted in SEQ ID NO: 135 and CDR-L3 as depicted in SEQ ID NO: 136.

In one embodiment, the first binding domain of the antibody construct of the invention comprises a VH region selected from the group consisting of those depicted in SEQ ID NO: 127, SEQ ID NO: 137, SEQ ID NO: 147, SEQ ID NO: 157, SEQ ID NO: 167, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, and SEQ ID NO: 455.

In a further embodiment, the first binding domain of the antibody construct of the invention comprises a VL region selected from the group consisting of those depicted in SEQ ID NO: 128, SEQ ID NO: 138, SEQ ID NO: 148, SEQ ID NO: 158, SEQ ID NO: 168, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, and SEQ ID NO: 470.

In another embodiment, the first binding domain of the antibody construct of the invention comprises a VH region and a VL region selected from the group consisting of pairs of a VH region and a VL region as depicted in SEQ ID NOs: 127+128; SEQ ID NOs: 137+138; SEQ ID NOs: 147+148; SEQ ID NOs: 157+158; SEQ ID NOs: 167+168; SEQ ID NOs 137+456; SEQ ID NOs 137+457; SEQ ID NOs 137+458; SEQ ID NOs 137+459; SEQ ID NOs 137+460; SEQ ID NOs 445+138; SEQ ID NOs 446+138; SEQ ID NOs 447+138; SEQ ID NOs 445+460; SEQ ID NOs 448+461; SEQ ID NOs 449+462; SEQ ID NOs 450+463; SEQ ID NOs 450+464; SEQ ID NOs 450+465; SEQ ID NOs 450+466; SEQ ID NOs 450+467; SEQ ID NOs 450+468; SEQ ID NOs 451+463; SEQ ID NOs 452+463; SEQ ID NOs 453+463; SEQ ID NOs 451+468; SEQ ID NOs 454+469; and SEQ ID NOs 455+470.

In a further embodiment, the first binding domain of the antibody construct of the invention comprises a polypeptide selected from the group consisting of those depicted in SEQ ID NO: 129, SEQ ID NO: 139, SEQ ID NO: 149, SEQ ID NO: 159, SEQ ID NO: 169, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, and SEQ ID NO: 493.

The above first binding domains (which are specified by their CDRs, VH region and VL region and combinations thereof) characterize as binding domains which bind to a DLL3 epitope comprised within the region as depicted in SEQ ID NO: 259.

Another preferred antibody construct according to the invention can also be defined as a bispecific antibody construct comprising a first (preferably human) binding domain which binds to human DLL3 on the surface of a target cell and a second binding domain which binds to human CD3 on the surface of a T cell, wherein the first binding domain binds to the same epitope of DLL3 as an antibody selected from the group consisting of DLL3-13, DLL3-14, and DLL3-15, i.e., an antibody comprising a VH region comprising CDR-H1, CDR-H2 and CDR-H3 and a VL region comprising CDR-L1, CDR-L2 and CDR-L3 selected from the group consisting of:

a) CDR-H1 as depicted in SEQ ID NO: 121, CDR-H2 as depicted in SEQ ID NO: 122, CDR-H3 as depicted in SEQ ID NO: 123, CDR-L1 as depicted in SEQ ID NO: 124, CDR-L2 as depicted in SEQ ID NO: 125 and CDR-L3 as depicted in SEQ ID NO: 126;

b) CDR-H1 as depicted in SEQ ID NO: 131, CDR-H2 as depicted in SEQ ID NO: 132, CDR-H3 as depicted in SEQ ID NO: 133, CDR-L1 as depicted in SEQ ID NO: 134, CDR-L2 as depicted in SEQ ID NO: 135 and CDR-L3 as depicted in SEQ ID NO: 136; and c) CDR-H1 as depicted in SEQ ID NO: 141, CDR-H2 as depicted in SEQ ID NO: 142, CDR-H3 as depicted in SEQ ID NO: 143, CDR-L1 as depicted in SEQ ID NO: 144, CDR-L2 as depicted in SEQ ID NO: 145 and CDR-L3 as depicted in SEQ ID NO: 146.

Another preferred antibody construct according to the invention can also be defined as a bispecific antibody construct comprising a first (preferably human) binding domain which binds to human DLL3 on the surface of a target cell and a second binding domain which binds to human CD3 on the surface of a T cell, wherein the first binding domain competes for binding with an antibody selected from the group consisting of DLL3-13, DLL3-14, and DLL3-15, i.e., an antibody comprising a VH region comprising CDR-H1, CDR-H2 and CDR-H3 and a VL region comprising CDR-L1, CDR-L2 and CDR-L3 selected from the group consisting of those described above.

It is also envisaged that the antibody construct of the invention has, in addition to its function to bind to the target molecules DLL3 and CD3, a further function. In this format, the antibody construct is a trifunctional or multifunctional antibody construct by targeting target cells through binding to DLL3, mediating cytotoxic T cell activity through CD3 binding and providing a further function such as a fully functional Fc constant domain mediating antibody-dependent cellular cytotoxicity through recruitment of effector cells like NK cells, a label (fluorescent etc.), a therapeutic agent such as a toxin or radionuclide, and/or means to enhance serum half-life, etc.

Examples for means to extend serum half-life of the antibody constructs of the invention include peptides, proteins or domains of proteins, which are fused or otherwise attached to the antibody constructs. The group of peptides, proteins or protein domains includes peptides binding to other proteins with preferred pharmacokinetic profile in the human body such as serum albumin (see WO 2009/127691). An alternative concept of such half-life extending peptides includes peptides binding to the neonatal Fc receptor (FcRn, see WO 2007/098420), which can also be used in the constructs of the present invention. The concept of attaching larger domains of proteins or complete proteins includes e.g. the fusion of human serum albumin, variants or mutants of human serum albumin (see WO 2011/051489, WO 2012/059486, WO 2012/150319, WO 2013/135896, WO 2014/072481, WO 2013/075066) or domains thereof as well as the fusion of constant region of immunoglobulins (Fc domains) and variants thereof. Such variants of Fc domains may be optimized/modified in order to allow the desired pairing of dimers or multimers, to abolish Fc receptor binding (e.g. the Fcγ receptor) or for other reasons. A further concept known in the art to extend the half-life of small protein compounds in the human body is the pegylation of those compounds such as the antibody construct of the present invention.

In a preferred embodiment, the bispecific antibody constructs according to the invention may be linked (e.g. via peptide bond) with a fusion partner (such as a protein or polypeptide or peptide), e.g. for the purpose of extending the construct's serum half-life. These fusion partners can be selected from human serum albumin ("HSA" or "HALB") as wells as sequence variants thereof, peptides binding to HSA, peptides binding to FcRn ("FcRn BP"), or constructs comprising an (antibody derived) Fc region. Exemplary sequences of these fusion partners are depicted in SEQ ID NOs: 295-341. In general, the fusion partners may be linked to the N-terminus or to the C-terminus of the bispecific antibody constructs according to the invention, either directly (e.g. via peptide bond) or through a peptide linker such as (GGGGS)n (wherein "n" is an integer of 2 or greater, e.g. 2 or 3 or 4). Suitable peptide linkers are depicted in SEQ ID NOs: 285-293.

Hence, a preferred antibody construct according to the present invention comprises:

(a) a polypeptide comprising in the following order starting from the N-terminus:
  - a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531;
  - a peptide linker having an amino acid sequence selected from the group consisting of SEQ ID NOs: 285-293; and
  - a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434; and
  - optionally a His-tag, such as the one depicted in SEQ ID NO: 294;

(b) a polypeptide comprising in the following order starting from the N-terminus:
  - a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531;

a peptide linker having an amino acid sequence selected from the group consisting of SEQ ID NOs: 285-293;

a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434;

optionally a peptide linker having an amino acid sequence selected from the group consisting of SEQ ID NOs: 285-293;

a polypeptide having an amino acid sequence selected from the group consisting of SEQ ID NOs: 295 and 301-330; and optionally a His-tag, such as the one depicted in SEQ ID NO: 294;

(c) a polypeptide comprising in the following order starting from the N-terminus:

a polypeptide having the amino acid sequence QRFVTGHFGGLX1 PANG (SEQ ID NO: 296) wherein X1 is Y or H; and a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531;

a peptide linker having an amino acid sequence selected from the group consisting of SEQ ID NOs: 285-293;

a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434;

a polypeptide having the amino acid sequence QRFVTGHFGGLHPANG (SEQ ID NO: 298) or QRFCTGHFGGLHPCNG (SEQ ID NO: 300); and optionally a His-tag, such as the one depicted in SEQ ID NO: 294;

(d) a polypeptide comprising in the following order starting from the N-terminus a polypeptide having an amino acid sequence selected from the group consisting of SEQ ID NO: 348, SEQ ID NO: 357, SEQ ID NO: 366, SEQ ID NO: 375, SEQ ID NO: 384, SEQ ID NO: 393, SEQ ID NO: 402, SEQ ID NO: 411, SEQ ID NO: 420, SEQ ID NO: 429, and SEQ ID NO: 432;

a peptide linker having the amino acid sequence depicted in SEQ ID NO: 292;

a polypeptide having an amino acid sequence selected from the group consisting of SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 128, SEQ ID NO: 138, SEQ ID NO: 148, SEQ ID NO: 158, SEQ ID NO: 168, SEQ ID NO: 436, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, and SEQ ID NO: 530, followed by a serine residue at the C-terminus;

a polypeptide having the amino acid sequence depicted in SEQ ID NO: 331; and a polypeptide comprising in the following order starting from the N-terminus:

a polypeptide having an amino acid sequence selected from the group consisting of SEQ ID NO: 37, SEQ ID NO: 47, SEQ ID NO: 57, SEQ ID NO: 67, SEQ ID NO: 77, SEQ ID NO: 87, SEQ ID NO: 97, SEQ ID NO: 107, SEQ ID NO: 117, SEQ ID NO: 127, SEQ ID NO: 137, SEQ ID NO: 147, SEQ ID NO: 157, SEQ ID NO: 167, SEQ ID NO: 435, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, and SEQ ID NO: 455, and SEQ ID NO: 529;

a peptide linker having the amino acid sequence depicted in SEQ ID NO: 292;

a polypeptide having an amino acid sequence selected from the group consisting of SEQ ID NO: 349, SEQ ID NO: 358, SEQ ID NO: 367, SEQ ID NO: 376, SEQ ID NO: 385, SEQ ID NO: 394, SEQ ID NO: 403, SEQ ID NO: 412, SEQ ID NO: 421, SEQ ID NO: 430, and SEQ ID NO: 433 followed by a serine residue at the C-terminus; and a polypeptide having the amino acid sequence depicted in SEQ ID NO: 332;

(e) a polypeptide comprising in the following order starting from the N-terminus:

a polypeptide having an amino acid sequence selected from the group consisting of SEQ ID NO: 348, SEQ ID NO: 357, SEQ ID NO: 366, SEQ ID NO: 375, SEQ ID NO: 384, SEQ ID NO: 393, SEQ ID NO: 402, SEQ ID NO: 411, SEQ ID NO: 420, SEQ ID NO: 429, and SEQ ID NO: 432;

a peptide linker having the amino acid sequence depicted in SEQ ID NO: 292;

a polypeptide having an amino acid sequence selected from the group consisting of SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 128, SEQ ID NO: 138, SEQ ID NO: 148, SEQ ID NO: 158, SEQ ID NO: 168, SEQ ID NO: 436, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, and SEQ ID NO: 530; and a polypeptide having the amino acid sequence depicted in SEQ ID NO: 333; and a polypeptide comprising in the following order starting from the N-terminus:

a polypeptide having an amino acid sequence selected from the group consisting of SEQ ID NO: 37, SEQ ID NO: 47, SEQ ID NO: 57, SEQ ID NO: 67, SEQ ID NO: 77, SEQ ID NO: 87, SEQ ID NO: 97, SEQ ID NO: 107, SEQ ID NO: 117, SEQ ID NO: 127, SEQ ID NO: 137, SEQ ID NO: 147, SEQ ID NO: 157, and SEQ ID NO: 167, SEQ ID NO: 435, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, and SEQ ID NO: 529;

a peptide linker having the amino acid sequence depicted in SEQ ID NO: 292;

a polypeptide having an amino acid sequence selected from the group consisting of SEQ ID NO: 349, SEQ ID NO: 358, SEQ ID NO: 367, SEQ ID NO: 376, SEQ ID NO: 385, SEQ ID NO: 394, SEQ ID NO: 403, SEQ ID NO: 412, SEQ ID NO: 421, SEQ ID NO: 430, and SEQ ID NO: 433 followed by a serine residue at the C-terminus; and a polypeptide having the amino acid sequence depicted in SEQ ID NO: 334;

(f) a polypeptide comprising in the following order starting from the N-terminus:

a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531;

a peptide linker having an amino acid sequence selected from the group consisting of SEQ ID NOs: 285-293;

a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434;

a polypeptide having the amino acid sequence depicted in SEQ ID NO: 335; and a polypeptide having the amino acid sequence depicted in SEQ ID NO: 336;

(g) a polypeptide comprising in the following order starting from the N-terminus:

a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531; and a polypeptide having the amino acid sequence depicted in SEQ ID NO: 337; and a polypeptide comprising in the following order starting from the N-terminus:

a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434; and a polypeptide having the amino acid sequence depicted in SEQ ID NO: 338;

(h) a polypeptide comprising in the following order starting from the N-terminus:

a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531; and a polypeptide having the amino acid sequence depicted in SEQ ID NO: 339; and a polypeptide comprising in the following order starting from the N-terminus:

a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434; and a polypeptide having the amino acid sequence depicted in SEQ ID NO: 340; or (i) a polypeptide comprising in the following order starting from the N-terminus:

a polypeptide having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531;

a peptide linker having an amino acid sequence selected from the group consisting of SEQ ID NOs: 285-293;

a polypeptide having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434; and a polypeptide having the amino acid sequence depicted in SEQ ID NO: 341.

For example, a preferred bispecific antibody construct of the present invention comprises or consists of a polypeptide selected from the group consisting of those depicted in: SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237; SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, and SEQ ID NO: 251.

As described above, several preferred antibody constructs of the invention are modified by fusion with another moiety such as albumin or albumin variants. If these fusion constructs are characterized for their properties, such as in particular their target affinity or cytotoxic activity, the skilled person will be aware that similar fusion constructs or unmodified bispecific antibody constructs can be expected to have similar (or possibly even better) properties. For example, if a bispecific antibody construct fused with albumin has an appreciable or desirable cytotoxic activity or target affinity, it can be expected that the same/similar or even a higher cytotoxic activity/target affinity will be observed for the same construct w/o albumin.

According to another preferred embodiment, the bispecific antibody construct of the invention comprises (in addition to the two binding domains) a third domain which comprises two polypeptide monomers, each comprising a hinge, a CH2 and a CH3 domain, wherein said two polypeptides (or polypeptide monomers) are fused to each other via a peptide linker. Preferably, said third domain comprises in an N- to C-terminal order: hinge-CH2-CH3-linker-hinge-CH2-CH3. Preferred amino acid sequences for said third domain are depicted in SEQ ID NOs: 541-548. Each of said polypeptide monomers preferably has an amino acid sequence that is selected from the group consisting of SEQ ID NOs: 533-540, or that is at least 90% identical to those sequences. In another preferred embodiment, the first and second binding domains of the bispecific antibody construct of the invention are fused to the third domain via a peptide linker which is for example selected from the group consisting of SEQ ID NOs: 285, 286, 288, 289, 290, 292 and 293.

In line with the present invention, a "hinge" is an IgG hinge region. This region can be identified by analogy using the Kabat numbering, see Kabat positions 223-243. In line with the above, the minimal requirement for a "hinge" are the amino acid residues corresponding to the IgG1 sequence stretch of D231 to P243 according to the Kabat numbering. The terms CH2 and CH3 refer to the immunoglobulin heavy chain constant regions 2 and 3. These regions can as well be identified by analogy using the Kabat numbering, see Kabat positions 244-360 for CH2 and Kabat positions 361-478 for CH3. Is is understood that there is some variation between the immunoglobulins in terms of their IgG1 Fc region, IgG2 Fc region, IgG3 Fc region, IgG4 Fc region, IgM Fc region, IgA Fc region, IgD Fc region and IgE Fc region (see, e.g., Padlan, Molecular Immunology, 31(3), 169-217 (1993)). The term Fc monomer refers to the last two heavy chain constant regions of IgA, IgD, and IgG, and the last three heavy chain constant regions of IgE and IgM. The Fc monomer can also include the flexible hinge N-terminal to these domains. For IgA and IgM, the Fc monomer may include the J chain. For IgG, the Fc portion comprises immunoglobulin domains CH2 and CH3 and the hinge between the first two domains and CH2. Although the boundaries of the Fc portion of an immunoglobulin may vary, an example for a human IgG heavy chain Fc portion comprising a functional hinge, CH2 and CH3 domain can be defined e.g. to comprise residues D231 (of the hinge domain) to P476 (of the C-terminus of the CH3 domain), or D231 to L476, respectively, for IgG4, wherein the numbering is according to Kabat.

The antibody construct of the invention may hence comprise in an N- to C-terminal order:

(a) the first binding domain;

(b) a peptide linker having an amino acid sequence selected from the group consisting of SEQ ID NOs: 286, 292 and 293;

(c) the second binding domain;

(d) a peptide linker having an amino acid sequence selected from the group consisting of SEQ ID NOs: 285, 286, 288, 289, 290, 292 and 293;

(e) the first polypeptide monomer of the third domain (comprising a hinge, a CH2 and a CH3 domain);

(f) a peptide linker having an amino acid sequence selected from the group consisting of SEQ ID NOs: 550, 551, 552 and 553; and (g) the second polypeptide monomer of the third domain (comprising a hinge, a CH2 and a CH3 domain).

It is also preferred that the antibody construct of the invention comprises in an N- to C-terminal order:

the first binding domain having an amino acid sequence selected from the group consisting of SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 139, SEQ ID NO: 149, SEQ ID NO: 159, SEQ ID NO: 169, SEQ ID NO: 437, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, SEQ ID NO: 490, SEQ ID NO: 491, SEQ ID NO: 492, SEQ ID NO: 493, and SEQ ID NO: 531;

a peptide linker having an amino acid sequence selected from the group consisting of SEQ ID NOs: 286, 292 and 293;

the second binding domain having an amino acid sequence selected from the group consisting of SEQ ID NO: 350, SEQ ID NO: 359, SEQ ID NO: 368, SEQ ID NO: 377, SEQ ID NO: 386, SEQ ID NO: 395, SEQ ID NO: 404, SEQ ID NO: 413, SEQ ID NO: 422, SEQ ID NO: 431, and SEQ ID NO: 434;

a peptide linker having an amino acid sequence selected from the group consisting of SEQ ID NOs: 285, 286, 288, 289, 290, 292 and 293; and the third domain having an amino acid sequence selected from the group consisting of SEQ ID NOs: 541-548.

Hence, in a preferred embodiment, the antibody construct of the present invention comprises or consists of a polypeptide selected from the group consisting of those depicted in SEQ ID NO: 517, SEQ ID NO: 518, SEQ ID NO: 519, SEQ ID NO: 520, SEQ ID NO: 521, SEQ ID NO: 522, SEQ ID NO: 523, SEQ ID NO: 524, SEQ ID NO: 525, SEQ ID NO: 526, SEQ ID NO: 527, and SEQ ID NO: 528.

The sequence table (Table 18) also provides sequence variations of the binders denominated DLL3-4 and DLL3-14. The point mutations that were inserted into these sequence variants are identified according to the position of this mutation within the respective scFv molecule. It is understood that an alternative way of identifying these positions is also possible, depending on the polypeptide of reference, which could as well be the CDR region or the VH/VL region. For example, the variant denominated DLL3-4-001 has a G44C-G243C double mutation in its scFv molecule (SEQ ID NO: 437). This translates into a G44C mutation in the corresponding VH chain (SEQ ID NO: 435) and a G101C mutation in the corresponding VL chain (SEQ ID NO: 436).

Covalent modifications of the antibody constructs are also included within the scope of this invention, and are generally, but not always, done post-translationally. For example, several types of covalent modifications of the antibody construct are introduced into the molecule by reacting specific amino acid residues of the antibody construct with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the antibody constructs of the present invention to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates as described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antibody constructs included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody construct is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the amino acid sequence of an antibody construct is preferably altered through changes at the DNA level, particularly by mutating the DNA encoding the polypeptide at preselected bases such that codons are generated that will translate into the desired amino acids.

Another means of increasing the number of carbohydrate moieties on the antibody construct is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, 1981, CRC Crit. Rev. Biochem., pp. 259-306.

Removal of carbohydrate moieties present on the starting antibody construct may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

Other modifications of the antibody construct are also contemplated herein. For example, another type of covalent modification of the antibody construct comprises linking the antibody construct to various non-proteinaceous polymers, including, but not limited to, various polyols such as polyethylene glycol, polypropylene glycol, polyoxyalkylenes, or copolymers of polyethylene glycol and polypropylene glycol, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antibody construct, e.g. in order to facilitate the addition of polymers such as PEG.

In some embodiments, the covalent modification of the antibody constructs of the invention comprises the addition of one or more labels. The labelling group may be coupled to the antibody construct via spacer arms of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following examples include, but are not limited to:

isotopic labels, which may be radioactive or heavy isotopes, such as radioisotopes or radionuclides (e.g., 3H, 14C, 15N, 35S, 89Zr, 90Y, 99Tc, 111In, 125I, 131I)
magnetic labels (e.g., magnetic particles)
redox active moieties
optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluores or proteinaceous fluores
enzymatic groups (e.g. horseradish peroxidase, p-galactosidase, luciferase, alkaline phosphatase)
biotinylated groups
predetermined polypeptide epitopes recognized by a secondary reporter (e.g., leucine zipper pair sequences, binding sites for secondary antibodies, metal binding domains, epitope tags, etc.)

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, OR), FITC, Rhodamine, and Texas Red (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland.

Suitable proteinaceous fluorescent labels also include, but are not limited to, green fluorescent protein, including a *Renilla, Ptilosarcus*, or *Aequorea* species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), p galactosidase (Nolan et al., 1988, Proc. Natl. Acad. Sci. U.S.A. 85:2603-2607) and *Renilla* (WO92/15673, WO95/07463, WO98/14605, WO98/26277, WO99/49019, U.S. Pat. Nos. 5,292,658; 5,418,155; 5,683,888; 5,741,668; 5,777,079; 5,804,387; 5,874,304; 5,876,995; 5,925,558).

Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191. The use of a modified leucine zipper that allows for stable trimerization of a heterologous protein fused thereto is described in Fanslow et al., 1994, Semin. Immunol. 6:267-78. In one approach, recombinant fusion proteins comprising a DLL3 antibody fragment or derivative fused to a leucine zipper peptide are expressed in suitable host cells, and the soluble oligomeric DLL3 antibody fragments or derivatives that form are recovered from the culture supernatant.

The antibody construct of the invention may also comprise additional domains, which are e.g. helpful in the isolation of the molecule or relate to an adapted pharmacokinetic profile of the molecule. Domains helpful for the isolation of an antibody construct may be selected from peptide motives or secondarily introduced moieties, which can be captured in an isolation method, e.g. an isolation column. Non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. All herein disclosed antibody constructs characterized by the identified CDRs are preferred to comprise a His-tag domain, which is generally known as a repeat of consecutive His residues in the amino acid sequence of a molecule, preferably of five, and more preferably of six His residues (hexa-histidine). The His-tag may be located e.g. at the N- or C-terminus of the antibody construct, preferably it is located at the C-terminus. Most preferably, a hexa-histidine tag (HHHHHH) is linked via peptide bond to the C-terminus of the antibody construct according to the invention.

The first binding domain of the antibody construct of the present invention binds to human DLL3 on the surface of a target cell. The preferred amino acid sequence of human DLL3 is represented by SEQ ID NO: 252. It is understood that the term "on the surface", in the context of the present invention, means that the binding domain specifically binds to an epitope comprised within the DLL3 extracellular domain (DLL3 ECD). The first binding domain according to the invention hence preferably binds to DLL3 when it is expressed by naturally expressing cells or cell lines, and/or by cells or cell lines transformed or (stably/transiently) transfected with DLL3. In a preferred embodiment the first binding domain also binds to DLL3 when DLL3 is used as a "target" or "ligand" molecule in an in vitro binding assay such as BIAcore or Scatchard. The "target cell" can be any prokaryotic or eukaryotic cell expressing DLL3 on its surface; preferably the target cell is a cell that is part of the human or animal body, such as a specific DLL3 expressing cancer or tumor cell.

The term "DLL3 ECD" refers to a form of DLL3 which is essentially free of transmembrane and cytoplasmic domains of DLL3. It will be understood by the skilled artisan that the transmembrane domain identified for the DLL3 polypeptide of the present invention is identified pursuant to criteria routinely employed in the art for identifying that type of hydrophobic domain. The exact boundaries of a transmembrane domain may vary but most likely by no more than about 5 amino acids at either end of the domain specifically mentioned herein. A preferred human DLL3 ECD is shown in SEQ ID NO: 253.

The affinity of the first binding domain for human DLL3 is preferably ≤20 nM, more preferably ≤10 nM, even more preferably ≤5 nM, even more preferably ≤2 nM, even more preferably ≤1 nM, even more preferably ≤0.6 nM, even more preferably ≤0.5 nM, and most preferably ≤0.4 nM. The affinity can be measured for example in a BIAcore assay or in a Scatchard assay, e.g. as described in the Examples. Other methods of determining the affinity are also well-known to the skilled person.

T cells or T lymphocytes are a type of lymphocyte (itself a type of white blood cell) that play a central role in cell-mediated immunity. There are several subsets of T cells, each with a distinct function. T cells can be distinguished from other lymphocytes, such as B cells and NK cells, by the presence of a T cell receptor (TCR) on the cell surface. The TCR is responsible for recognizing antigens bound to major histocompatibility complex (MHC) molecules and is composed of two different protein chains. In 95% of the T cells, the TCR consists of an alpha (a) and beta (p) chain. When the TCR engages with antigenic peptide and MHC (peptide/MHC complex), the T lymphocyte is activated through a series of biochemical events mediated by associated enzymes, co-receptors, specialized adaptor molecules, and activated or released transcription factors.

The CD3 receptor complex is a protein complex and is composed of four chains. In mammals, the complex contains a CD3γ (gamma) chain, a CD35 (delta) chain, and two CD3ε (epsilon) chains. These chains associate with the T cell receptor (TCR) and the so-called ((zeta) chain to form the T cell receptor CD3 complex and to generate an activation signal in T lymphocytes. The CD3γ (gamma), CD35 (delta), and CD3ε (epsilon) chains are highly related cell-surface proteins of the immunoglobulin superfamily containing a single extracellular immunoglobulin domain. The intracellular tails of the CD3 molecules contain a single conserved motif known as an immunoreceptor tyrosine-based activation motif or ITAM for short, which is essential for the signaling capacity of the TCR. The CD3 epsilon molecule is a polypeptide which in humans is encoded by the CD3E gene which resides on chromosome 11. The most preferred epitope of CD3 epsilon is comprised within amino acid residues 1-27 of the human CD3 epsilon extracellular domain.

The redirected lysis of target cells via the recruitment of T cells by a multispecific, at least bispecific, antibody construct involves cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO 2007/042261.

Cytotoxicity mediated by DLL3×CD3 bispecific antibody constructs can be measured in various ways. See Examples 8.1 to 8.7. Effector cells can be e.g. stimulated enriched (human) CD8 positive T cells or unstimulated (human) peripheral blood mononuclear cells (PBMC). If the target cells are of macaque origin or express or are transfected with macaque DLL3, the effector cells should also be of macaque origin such as a macaque T cell line, e.g. 4119LnPx. The target cells should express (at least the extracellular domain of) DLL3, e.g. human or macaque DLL3. Target cells can be a cell line (such as CHO) which is stably or transiently transfected with DLL3, e.g. human or macaque DLL3. Alternatively, the target cells can be a DLL3 positive natural expresser cell line, such as the human lung carcinoma cell line SHP-77. Usually EC50 values are expected to be lower with target cell lines expressing higher levels of DLL3 on the cell surface. The effector to target cell (E:T) ratio is usually about 10:1, but can also vary. Cytotoxic activity of DLL3×CD3 bispecific antibody constructs can be measured in a 51-chromium release assay (incubation time of about 18 hours) or in a in a FACS-based cytotoxicity assay (incubation time of about 48 hours). Modifications of the assay incubation time (cytotoxic reaction) are also possible. Other methods of measuring cytotoxicity are well-known to the skilled person and comprise MTT or MTS assays, ATPbased assays including bioluminescent assays, the sulforhodamine B (SRB) assay, WST assay, clonogenic assay and the ECIS technology.

The cytotoxic activity mediated by DLL3×CD3 bispecific antibody constructs of the present invention is preferably measured in a cell-based cytotoxicity assay. It may also be measured in a 51-chromium release assay. It is represented by the EC50 value, which corresponds to the half maximal effective concentration (concentration of the antibody construct which induces a cytotoxic response halfway between the baseline and maximum). Preferably, the EC50 value of the DLL3×CD3 bispecific antibody constructs is ≤5000 pM or ≤4000 pM, more preferably ≤3000 pM or ≤2000 pM, even more preferably ≤1000 pM or ≤500 pM, even more preferably ≤400 pM or ≤300 pM, even more preferably ≤200 pM, even more preferably ≤100 pM, even more preferably ≤50 pM, even more preferably ≤20 pM or ≤10 pM, and most preferably ≤5 pM.

The above given EC50 values can be measured in different assays. The skilled person is aware that an EC50 value can be expected to be lower when stimulated/enriched CD8+ T cells are used as effector cells, compared with unstimulated PBMC. It can furthermore be expected that the EC50 values are lower when the target cells express a high number of the target antigen compared with a low target expression rat. For example, when stimulated/enriched human CD8+ T cells are used as effector cells (and either DLL3 transfected cells such as CHO cells or a DLL3 positive human lung carcinoma cell line SHP-77 are used as target cells), the EC50 value of the DLL3×CD3 bispecific antibody construct is preferably ≤1000 pM, more preferably ≤500 pM, even more preferably ≤250 pM, even more preferably ≤100 pM, even more preferably ≤50 pM, even more preferably ≤10 pM, and most preferably ≤5 pM. When human PBMCs are used as effector cells, the EC50 value of the DLL3×CD3 bispecific antibody construct is preferably ≤5000 pM or ≤4000 pM (in particular when the target cells are a DLL3 positive human lung carcinoma cell line SHP-77), more preferably ≤2000 pM (in particular when the target cells are DLL3 transfected cells such as CHO cells), more preferably ≤1000 pM or 5500 pM, even more preferably ≤200 pM, even more preferably ≤150 pM, even more preferably ≤100 pM, and most preferably ≤50 pM, or lower. When a macaque T cell line such as LnPx4119 is used as effector cells, and a macaque DLL3 transfected cell line such as CHO cells is used as target cell line, the EC50 value of the DLL3×CD3 bispecific antibody construct is preferably ≤2000 pM or ≤1500 pM, more preferably ≤1000 pM or ≤500 pM, even more preferably ≤300 pM or ≤250 pM, even more preferably ≤100 pM, and most preferably ≤50 pM.

Preferably, the DLL3×CD3 bispecific antibody constructs of the present invention do not induce/mediate lysis or do not essentially induce/mediate lysis of DLL3 negative cells such as CHO cells. The term "do not induce lysis", "do not essentially induce lysis", "do not mediate lysis" or "do not essentially mediate lysis" means that an antibody construct of the present invention does not induce or mediate lysis of more than 30%, preferably not more than 20%, more preferably not more than 10%, particularly preferably not more than 9%, 8%, 7%, 6% or 5% of DLL3 negative cells, whereby lysis of a DLL3 positive human lung carcinoma cell line SHP-77 (see above) is set to be 100%. This usually applies for concentrations of the antibody construct of up to 500 nM. The skilled person knows how to measure cell lysis without further ado. Moreover, the present specification teaches specific instructions how to measure cell lysis.

The difference in cytotoxic activity between the monomeric and the dimeric isoform of individual DLL3×CD3 bispecific antibody constructs is referred to as "potency gap". This potency gap can e.g. be calculated as ratio between EC50 values of the molecule's monomeric and dimeric form, see Example 15. Potency gaps of the DLL3×CD3 bispecific antibody constructs of the present invention are preferably ≤5, more preferably ≤4, even more preferably ≤3, even more preferably ≤2 and most preferably ≤1.

The first and/or the second (or any further) binding domain(s) of the antibody construct of the invention is/are preferably cross-species specific for members of the mammalian order of primates. Cross-species specific CD3 binding domains are, for example, described in WO 2008/119567. According to one embodiment, the first and/or second binding domain, in addition to binding to human DLL3 and human CD3, respectively, will also bind to DLL3/CD3 of primates including (but not limited to) new world primates (such as *Callithrix jacchus, Saguinus oedipus* or *Saimiri sciureus*), old world primates (such as baboons and macaques), gibbons, orangutans and non-human homininae. It is envisaged that the first binding domain of the antibody construct of the invention which binds to human DLL3 on the surface of a target cell also binds at least to macaque DLL3, and/or the second binding domain which binds to human CD3 on the surface of a T cell also binds at least to macaque CD3. A preferred macaque is *Macaca fascicularis. Macaca mulatta* (Rhesus) is also envisaged.

A preferred bispecific antibody construct of the invention comprises a first binding domain which binds to human DLL3 on the surface of a target cell and a second binding domain which binds to human CD3 on the surface of a T cell and at least macaque CD3. In one aspect of this embodiment, the first binding domain binds to an epitope of DLL3 which is comprised within the region as depicted in SEQ ID NO: 260.

In one aspect of the invention, the first binding domain binds to human DLL3 and further binds to macaque DLL3, such as DLL3 of *Macaca fascicularis*, and more preferably, to macaque DLL3 ECD. A preferred *Macaca fascicularis* DLL3 is depicted in SEQ ID NO: 271. A preferred macaque DLL3 ECD is depicted in SEQ ID NO: 272. The affinity of the first binding domain for macaque DLL3 is preferably ≤15 nM, more preferably ≤10 nM, even more preferably 55 nM, even more preferably ≤1 nM, even more preferably ≤0.5 nM, even more preferably 50.1 nM, and most preferably ≤0.05 nM or even 50.01 nM.

Preferably the affinity gap of the antibody constructs according to the invention for binding macaque DLL3 versus human DLL3 [ma DLL3:hu DLL3](as determined e.g. by BiaCore or by Scatchard analysis) is between 0.1 and 10, more preferably between 0.2 and 5, even more preferably between 0.3 and 4, even more preferably between 0.5 and 3 or between 0.5 and 2.5, and most preferably between 0.5 and 2 or between 0.6 and 2. See Examples 3 and 4.

In one embodiment of the antibody construct of the invention, the second binding domain binds to human CD3 epsilon and to *Callithrix jacchus, Saguinus oedipus* or *Saimiri sciureus* CD3 epsilon. Preferably, the second binding domain binds to an extracellular epitope of these CD3 epsilon chains. It is also envisaged that the second binding domain binds to an extracellular epitope of the human and the *Macaca* CD3 epsilon chain. The most preferred epitope of CD3 epsilon is comprised within amino acid residues 1-27 of the human CD3 epsilon extracellular domain. Even more specifically, the epitope comprises at least the amino acid sequence Gln-Asp-Gly-Asn-Glu (SEQ ID NO: 577).

*Callithrix jacchus* and *Saguinus oedipus* are both new world primate belonging to the family of Callitrichidae, while *Saimiri sciureus* is a new world primate belonging to the family of Cebidae.

It is particularly preferred for the antibody construct of the present invention that the second binding domain which binds to human CD3 on the surface of a T cell comprises a VL region comprising CDR-L1, CDR-L2 and CDR-L3 selected from:

(a) CDR-L1 as depicted in SEQ ID NO: 27 of WO 2008/119567 (SEQ ID NO: 342 herein), CDR-L2 as depicted in SEQ ID NO: 28 of WO 2008/119567 (SEQ ID NO: 343 herein) and CDR-L3 as depicted in SEQ ID NO: 29 of WO 2008/119567 (SEQ ID NO: 344 herein);

(b) CDR-L1 as depicted in SEQ ID NO: 117 of WO 2008/119567 (SEQ ID NO: 396 herein), CDR-L2 as depicted in SEQ ID NO: 118 of WO 2008/119567 (SEQ ID NO: 397 herein) and CDR-L3 as depicted in SEQ ID NO: 119 of WO 2008/119567 (SEQ ID NO: 398 herein); and (c) CDR-L1 as depicted in SEQ ID NO: 153 of WO 2008/119567 (SEQ ID NO: 423 herein), CDR-L2 as depicted in SEQ ID NO: 154 of WO 2008/119567 (SEQ ID NO: 424 herein) and CDR-L3 as depicted in SEQ ID NO: 155 of WO 2008/119567 (SEQ ID NO: 425 herein).

In an alternatively preferred embodiment of the antibody construct of the present invention, the second binding domain which binds to human CD3 on the surface of a T cell comprises a VH region comprising CDR-H 1, CDR-H2 and CDR-H3 selected from:

(a) CDR-H1 as depicted in SEQ ID NO: 12 of WO 2008/119567 (SEQ ID NO: 345 herein), CDR-H2 as depicted in SEQ ID NO: 13 of WO 2008/119567 (SEQ ID NO: 346 herein) and CDR-H3 as depicted in SEQ ID NO: 14 of WO 2008/119567 (SEQ ID NO: 347 herein);

(b) CDR-H1 as depicted in SEQ ID NO: 30 of WO 2008/119567 (SEQ ID NO: 354 herein), CDR-H2 as depicted in SEQ ID NO: 31 of WO 2008/119567 (SEQ ID NO: 355 herein) and CDR-H3 as depicted in SEQ ID NO: 32 (SEQ ID NO: 356 herein) of WO 2008/119567;

(c) CDR-H1 as depicted in SEQ ID NO: 48 of WO 2008/119567 (SEQ ID NO: 363 herein), CDR-H2 as depicted in SEQ ID NO: 49 of WO 2008/119567 (SEQ ID NO: 364 herein) and CDR-H3 as depicted in SEQ ID NO: 50 of WO 2008/119567 (SEQ ID NO: 365 herein);

(d) CDR-H1 as depicted in SEQ ID NO: 66 of WO 2008/119567 (SEQ ID NO 372 herein), CDR-H2 as depicted in SEQ ID NO: 67 of WO 2008/119567 (SEQ ID NO: 373 herein) and CDR-H3 as depicted in SEQ ID NO: 68 of WO 2008/119567 (SEQ ID NO: 374 herein);

(e) CDR-H1 as depicted in SEQ ID NO: 84 of WO 2008/119567 (SEQ ID NO: 381 herein), CDR-H2 as depicted in SEQ ID NO: 85 of WO 2008/119567 (SEQ ID NO: 382 herein) and CDR-H3 as depicted in SEQ ID NO: 86 of WO 2008/119567 (SEQ ID NO: 383 herein);

(f) CDR-H1 as depicted in SEQ ID NO: 102 of WO 2008/119567 (SEQ ID NO: 390 herein), CDR-H2 as depicted in SEQ ID NO: 103 of WO 2008/119567 (SEQ ID NO: 391 herein) and CDR-H3 as depicted in SEQ ID NO: 104 of WO 2008/119567 (SEQ ID NO: 392 herein);

(g) CDR-H1 as depicted in SEQ ID NO: 120 of WO 2008/119567 (SEQ ID NO: 399 herein), CDR-H2 as depicted in SEQ ID NO: 121 of WO 2008/119567 (SEQ ID NO: 400 herein) and CDR-H3 as depicted in SEQ ID NO: 122 of WO 2008/119567 (SEQ ID NO: 401 herein);

(h) CDR-H1 as depicted in SEQ ID NO: 138 of WO 2008/119567 (SEQ ID NO: 408 herein), CDR-H2 as depicted in SEQ ID NO: 139 of WO 2008/119567 (SEQ ID NO: 409 herein) and CDR-H3 as depicted in SEQ ID NO: 140 of WO 2008/119567 (SEQ ID NO: 410 herein);

(i) CDR-H1 as depicted in SEQ ID NO: 156 of WO 2008/119567 (SEQ ID NO: 417 herein), CDR-H2 as depicted in SEQ ID NO: 157 of WO 2008/119567 (SEQ ID NO: 418 herein) and CDR-H3 as depicted in SEQ ID NO: 158 of WO 2008/119567 (SEQ ID NO: 419 herein); and (j) CDR-H1 as depicted in SEQ ID NO: 174 of WO 2008/119567 (SEQ ID NO: 426 herein), CDR-H2 as depicted in SEQ ID NO: 175 of WO 2008/119567 (SEQ ID NO: 427 herein) and CDR-H3 as depicted in SEQ ID NO: 176 of WO 2008/119567 (SEQ ID NO: 428 herein).

It is further preferred for the antibody construct of the present invention that the second binding domain which binds to human CD3 on the surface of a T cell comprises a VL region selected from the group consisting of a VL region as depicted in SEQ ID NO: 35, 39, 125, 129, 161 or 165 of WO 2008/119567 (respectively, SEQ ID NO: 349, 555, 385, 556, 430, or 557 herein).

It is alternatively preferred that the second binding domain which binds to human CD3 on the surface of a T cell comprises a VH region selected from the group consisting of a VH region as depicted in SEQ ID NO: 15, 19, 33, 37, 51, 55, 69, 73, 87, 91, 105, 109, 123, 127, 141, 145, 159, 163, 177 or 181 of WO 2008/119567 (respectively, SEQ ID NO: 348, 558, 357, 559, 366, 560, 375, 561, 384, 562, 393, 563, 402, 564, 411, 565, 420, 566, 429, or 559 herein).

More preferably, the antibody construct of the present invention is characterized by the second binding domain which binds to human CD3 on the surface of a T cell comprising a VL region and a VH region selected from the group consisting of:

(a) a VL region as depicted in SEQ ID NO: 17 or 21 of WO 2008/119567 (SEQ ID NO: 349 or 555 herein) and a VH region as depicted in SEQ ID NO: 15 or 19 of WO 2008/119567 (SEQ ID NO: 348 or 558 herein);

(b) a VL region as depicted in SEQ ID NO: 35 or 39 of WO 2008/119567 (SEQ ID NO: 358 or 555 herein) and a VH region as depicted in SEQ ID NO: 33 or 37 of WO 2008/119567 (SEQ ID NO: 357 or 559 herein);

(c) a VL region as depicted in SEQ ID NO: 53 or 57 of WO 2008/119567 (SEQ ID NO: 367 or 555 herein) and a VH region as depicted in SEQ ID NO: 51 or 55 of WO 2008/119567 (SEQ ID NO: 366 or 560 herein);

(d) a VL region as depicted in SEQ ID NO: 71 or 75 of WO 2008/119567 (SEQ ID NO: 376 or 555 herein) and a VH region as depicted in SEQ ID NO: 69 or 73 of WO 2008/119567 (SEQ ID NO: 375 or 561 herein);

(e) a VL region as depicted in SEQ ID NO: 89 or 93 of WO 2008/119567 (SEQ ID NO: 385 or 556 herein) and a VH region as depicted in SEQ ID NO: 87 or 91 of WO 2008/119567 (SEQ ID NO: 384 or 562 herein);

(f) a VL region as depicted in SEQ ID NO: 107 or 111 of WO 2008/119567 (SEQ ID NO: 394 or 555 herein) and a VH region as depicted in SEQ ID NO: 105 or 109 of WO 2008/119567 (SEQ ID NO: 393 or 563 herein);

(g) a VL region as depicted in SEQ ID NO: 125 or 129 of WO 2008/119567 (SEQ ID NO: 403 or 556 herein) and a VH region as depicted in SEQ ID NO: 123 or 127 of WO 2008/119567 (SEQ ID NO:402 or 564 herein);

(h) a VL region as depicted in SEQ ID NO: 143 or 147 of WO 2008/119567 (SEQ ID NO: 412 or 555 herein) and a VH region as depicted in SEQ ID NO: 141 or 145 of WO 2008/119567 (SEQ ID NO: 411 or 565 herein);

(i) a VL region as depicted in SEQ ID NO: 161 or 165 of WO 2008/119567 (SEQ ID NO: 421 or 557 herein) and a VH region as depicted in SEQ ID NO: 159 or 163 of WO 2008/119567 (SEQ ID NO: 420 or 566 herein); and (j) a VL region as depicted in SEQ ID NO: 179 or 183 of WO 2008/119567 (SEQ ID NO: 430 or 557 herein) and a VH region as depicted in SEQ ID NO: 177 or 181 of WO 2008/119567 (SEQ ID NO: 429 or 559 herein).

According to a preferred embodiment of the antibody construct of the present invention, the binding domains and in particular the second binding domain (which binds to human CD3 on the surface of a T cell) have the following format: The pairs of VH regions and VL regions are in the format of a single chain antibody (scFv). The VH and VL regions are arranged in the order VH-VL or VL-VH. It is preferred that the VH-region is positioned N-terminally of a linker sequence, and the VL-region is positioned C-terminally of the linker sequence.

A preferred embodiment of the above described antibody construct of the present invention is characterized by the second binding domain which binds to human CD3 on the surface of a T cell comprising an amino acid sequence selected from the group consisting of SEQ ID NOs: 23, 25, 41, 43, 59, 61, 77, 79, 95, 97, 113, 115, 131, 133, 149, 151, 167, 169, 185 or 187 of WO 2008/119567 (respectively, SEQ ID NO: 350, 567, 359, 568, 368, 569, 377, 570, 386, 571, 395, 572, 404, 573, 413, 574, 422, 575, 431 or 576 herein).

Hence, in one embodiment, the antibody construct of the invention comprises a polypeptide selected from the group consisting of those depicted in SEQ ID NO: 40, SEQ ID NO: 50, SEQ ID NO: 60, SEQ ID NO: 70, SEQ ID NO: 80, SEQ ID NO: 90, SEQ ID NO: 100, SEQ ID NO: 110, SEQ ID NO: 120, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 438 and SEQ ID NO: 532. These antibody constructs have a first binding domain which binds to an epitope of DLL3 which is comprised within the region as depicted in SEQ ID NO: 258.

In an alternative embodiment, the antibody construct of the invention comprises a polypeptide selected from the group consisting of those depicted in SEQ ID NO: 130, SEQ ID NO: 140, SEQ ID NO: 150, SEQ ID NO: 160, SEQ ID NO: 170; SEQ ID NO: 218, SEQ ID NO: 219, SEQ ID NO: 220, SEQ ID NO: 494, SEQ ID NO: 495, SEQ ID NO: 496, SEQ ID NO: 497, SEQ ID NO: 498, SEQ ID NO: 499, SEQ ID NO: 500, SEQ ID NO: 501, SEQ ID NO: 502, SEQ ID NO: 503, SEQ ID NO: 504, SEQ ID NO: 505, SEQ ID NO: 506, SEQ ID NO: 507, SEQ ID NO: 508, SEQ ID NO: 509, SEQ ID NO: 510, SEQ ID NO: 511, SEQ ID NO: 512, SEQ ID NO: 513, SEQ ID NO: 514, SEQ ID NO: 515, and SEQ ID NO: 516. These antibody constructs have a first binding domain which binds to an epitope of DLL3 which is comprised within the region as depicted in SEQ ID NO: 259.

Amino acid sequence modifications of the antibody constructs described herein are also contemplated. For example, it may be desirable to improve the binding affinity and/or other biological properties of the antibody construct. Amino acid sequence variants of the antibody constructs are prepared by introducing appropriate nucleotide changes into the antibody constructs nucleic acid, or by peptide synthesis. All of the below described amino acd sequence modifications should result in an antibody construct which still retains the desired biological activity (binding to DLL3 and to CD3) of the unmodified parental molecule.

The term “amino acid” or “amino acid residue” typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

Amino acid modifications include, for example, deletions from, and/or insertions into, and/or substitutions of, residues within the amino acid sequences of the antibody constructs. Any combination of deletion, insertion, and substitution is made to arrive at the final construct, provided that the final construct possesses the desired characteristics. The amino acid changes also may alter post-translational processes of the antibody constructs, such as changing the number or position of glycosylation sites.

For example, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs. Preferably, amino acid sequence insertions include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. An insertional variant of the antibody construct of the invention includes the fusion to the N-terminus or to the C-terminus of the antibody construct of an enzyme or the fusion to a polypeptide which increases the serum half-life of the antibody construct.

The sites of greatest interest for substitutional mutagenesis include the CDRs of the heavy and/or light chain, in particular the hypervariable regions, but FR alterations in the heavy and/or light chain are also contemplated. The substitutions are preferably conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

A useful method for identification of certain residues or regions of the antibody constructs that are preferred locations for mutagenesis is called “alanine scanning mutagenesis" as described by Cunningham and Wells in Science, 244: 1081-1085 (1989). Here, a residue or group of target residues within the antibody construct is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions are then refined by introducing further or other variants at, or for, the sites of substitution. Thus, while the site or region for introducing an amino acid sequence variation is predetermined, the nature of the mutation per se needs not to be predetermined. For example, to analyze or optimize the performance of a mutation at a given site, alanine scanning or random mutagenesis may be conducted at a target codon or region, and the expressed antibody construct variants are screened for the optimal combination of desired activity. Techniques for making substitution mutations at predetermined sites in the DNA having a known sequence are well known, for example, M13 primer mutagenesis and PCR mutagenesis. Screening of the mutants is done using assays of antigen binding activities, such as DLL3 or CD3 binding.

Generally, if amino acids are substituted in one or more or all of the CDRs of the heavy and/or light chain, it is preferred that the then-obtained "substituted" sequence is at least 60% or 65%, more preferably 70% or 75%, even more preferably 80% or 85%, and particularly preferably 90% or 95% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the antibody construct may have different degrees of identity to their substituted sequences, e.g., CDRL1 may have 80%, while CDRL3 may have 90%.

Preferred substitutions (or replacements) are conservative substitutions. However, any substitution (including non-conservative substitution or one or more from the "exemplary substitutions" listed in Table 1, below) is envisaged as long as the antibody construct retains its capability to bind to DLL3 via the first binding domain and to CD3 or CD3 epsilon via the second binding domain and/or its CDRs have an identity to the then substituted sequence (at least 60% or 65%, more preferably 70% or 75%, even more preferably 80% or 85%, and particularly preferably 90% or 95% identical to the "original" CDR sequence).

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE 1

Amino acid substitutions

| Original | Exemplary Substitutions | Preferred Substitutions |
|---|---|---|
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | Ala | ala |
| His (H) | asn, gln, lys, arg | arg |
| Ile (I) | leu, val, met, ala, phe | leu |
| Leu (L) | norleucine, ile, val, met, ala | ile |
| Lys (K) | arg, gln, asn | arg |
| Met (M) | leu, phe, ile | leu |
| Phe (F) | leu, val, ile, ala, tyr | tyr |
| Pro (P) | Ala | ala |
| Ser (S) | Thr | thr |
| Thr (T) | Ser | ser |
| Trp (W) | tyr, phe | tyr |
| Tyr (Y) | trp, phe, thr, ser | phe |
| Val (V) | ile, leu, met, phe, ala | leu |

Substantial modifications in the biological properties of the antibody construct of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the antibody construct may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

For amino acid sequences, sequence identity and/or similarity is determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, Nucl. Acid Res. 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, J. Mol. Evol. 35:351-360; the method is similar to that described by Higgins and Sharp, 1989, CABIOS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, J. Mol. Biol. 215:403-410; Altschul et al., 1997, Nucleic Acids Res. 25:3389-3402; and Karin et al., 1993, Proc. Natl. Acad. Sci. U.S.A. 90:5873-5787. A particularly useful BLAST program is the WU-BLAST-2 program which was obtained from Altschul et al., 1996, Methods in Enzymology 266: 460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, Nucl. Acids Res. 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs are at least 60% to the sequences depicted herein, and more typically with preferably increasing homologies or identities of at least 65% or 70%, more preferably at least 75% or 80%, even more preferably at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%. Thus, a "variant CDR" is one with the specified homology, similarity, or identity to the parent CDR of the invention, and shares biological function, including, but not limited to, at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

In one embodiment, the percentage of identity to human germline of the antibody constructs according to the invention is 70% or 75%, more preferably 80% or 85%, even more preferably 90%, and most preferably 91%, 92%, 93%, 94%, 95% or even 96%. See Example 7. Identity to human antibody germline gene products is thought to be an important feature to reduce the risk of therapeutic proteins to elicit an immune response against the drug in the patient during treatment. Hwang & Foote ("Immunogenicity of engineered antibodies"; Methods 36 (2005) 3-10) demonstrate that the reduction of non-human portions of drug antibody constructs leads to a decrease of risk to induce anti-drug antibodies in the patients during treatment. By comparing an exhaustive number of clinically evaluated antibody drugs and the respective immunogenicity data, the trend is shown that humanization of the V-regions of antibodies makes the protein less immunogenic (average 5.1% of patients) than antibodies carrying unaltered non-human V regions (average 23.59% of patients). A higher degree of identity to human sequences is hence desirable for V-region based protein therapeutics in the form of antibody constructs. For this purpose of determining the germline identity, the V-regions of VL can be aligned with the amino acid sequences of human germline V segments and J segments (http colon forward slash forward slash vbase.mrc-cpc.cam.ac.uk forward slash) using Vector NTI software and the amino acid sequence calculated by dividing the identical amino acid residues by the total number of amino acid residues of the VL in percent. The same can be for the VH segments (http colon forward slash forward slash vbase.mrc-cpc.cam.ac.uk forward slash) with the exception that the VH CDR3 may be excluded due to its high diversity and a lack of existing human germline VH CDR3 alignment partners. Recombinant techniques can then be used to increase sequence identity to human antibody germline genes.

In a further embodiment, the bispecific antibody constructs of the present invention exhibit high monomer yields under standard research scale conditions, e.g., in a standard two-step purification process. Preferably the monomer yield of the antibody constructs according to the invention is 0.25 mg/L supernatant, more preferably 0.5 mg/L, even more preferably 1 mg/L, and most preferably 3 mg/L supernatant.

Likewise, the yield of the dimeric antibody construct isoforms and hence the monomer percentage (i.e., monomer: (monomer+dimer)) of the antibody constructs can be determined. The productivity of monomeric and dimeric antibody constructs and the calculated monomer percentage can e.g. be obtained in the SEC purification step of culture supernatant from standardized research-scale production in roller bottles. In one embodiment, the monomer percentage of the antibody constructs is 80%, more preferably 85%, even more preferably 90%, and most preferably 95%.

In one embodiment, the antibody constructs have a preferred plasma stability (ratio of EC50 with plasma to EC50 w/o plasma) of ≤5 or ≤4, more preferably ≤3.5 or ≤3, even more preferably ≤2.5 or ≤2, and most preferably ≤1.5 or ≤1. The plasma stability of an antibody construct can be tested by incubation of the construct in human plasma at 37° C. for 24 hours followed by EC50 determination in a 51-chromium release cytotoxicity assay. The effector cells in the cytotoxicity assay can be stimulated enriched human CD8 positive T cells. Target cells can e.g. be CHO cells transfected with human DLL3. The effector to target cell (E:T) ratio can be chosen as 10:1. The human plasma pool used for this purpose is derived from the blood of healthy donors collected by EDTA coated syringes. Cellular components are removed by centrifugation and the upper plasma phase is collected and subsequently pooled. As control, antibody constructs are diluted immediately prior to the cytotoxicity assay in RPMI-1640 medium. The plasma stability is calculated as ratio of EC50 (after plasma incubation) to EC50 (control). See Example 11.

It is furthermore preferred that the monomer to dimer conversion of antibody constructs of the invention is low. The conversion can be measured under different conditions and analyzed by high performance size exclusion chromatography. See Example 9. For example, incubation of the monomeric isoforms of the antibody constructs can be carried out for 7 days at 37° C. and concentrations of e.g. 100 μg/ml or 250 μg/ml in an incubator. Under these conditions, it is preferred that the antibody constructs of the invention show a dimer percentage that is ≤5%, more preferably ≤4%, even more preferably ≤3%, even more preferably ≤52.5%, even more preferably ≤2%, even more preferably ≤1.5%, and most preferably ≤1% or 50.5% or even 0%.

It is also preferred that the bispecific antibody constructs of the present invention present with very low dimer conversion after a number of freeze/thaw cycles. For example, the antibody construct monomer is adjusted to a concentration of 250 μg/ml e.g. in generic formulation buffer and subjected to three freeze/thaw cycles (freezing at −80° C. for 30 min followed by thawing for 30 min at room temperature), followed by high performance SEC to determine the percentage of initially monomeric antibody construct, which had been converted into dimeric antibody construct. Preferably the dimer percentages of the bispecific antibody constructs are ≤5%, more preferably ≤4%, even more preferably ≤3%, even more preferably 52.5%, even more preferably ≤2%, even more preferably ≤1.5%, and most preferably ≤1% or even 50.5%, for example after three freeze/thaw cycles.

The bispecific antibody constructs of the present invention preferably show a favorable thermostability with aggregation temperatures ≥45° C. or ≥50° C., more preferably 52° C. or ≥54° C., even more preferably ≥56° C. or ≥57° C., and most preferably ≥58° C. or ≥59° C. The thermostability parameter can be determined in terms of antibody aggregation temperature as follows: Antibody solution at a concentration 250 μg/ml is transferred into a single use cuvette and placed in a Dynamic Light Scattering (DLS) device. The sample is heated from 40° C. to 70° C. at a heating rate of 0.5° C./min with constant acquisition of the measured radius. Increase of radius indicating melting of the protein and aggregation is used to calculate the aggregation temperature of the antibody. See Example 10.

Alternatively, temperature melting curves can be determined by Differential Scanning Calorimetry (DSC) to determine intrinsic biophysical protein stabilities of the antibody constructs. These experiments are performed using a MicroCal LLC (Northampton, MA, U.S.A) VP-DSC device. The energy uptake of a sample containing an antibody construct is recorded from 20° C. to 90° C. compared to a sample containing only the formulation buffer. The antibody constructs are adjusted to a final concentration of 250 μg/ml e.g. in SEC running buffer. For recording of the respective melting curve, the overall sample temperature is increased stepwise. At each temperature T energy uptake of the sample and the formulation buffer reference is recorded. The difference in energy uptake Cp (kcal/mole/° C.) of the sample minus the reference is plotted against the respective temperature. The melting temperature is defined as the temperature at the first maximum of energy uptake.

It is furthermore envisaged that the DLL3×CD3 bispecific antibody constructs of the invention do not cross-react with (i.e., do not essentially bind to) the human DLL3 paralogues DLL1 and/or DLL4. Furthermore, it is envisaged that the DLL3×CD3 bispecific antibody constructs of the invention do not cross-react with (i.e., do not essentially bind to) the macaque/cyno DLL3 paralogues DLL1 and/or DLL4. See Example 6.

The DLL3×CD3 bispecific antibody constructs of the invention are also envisaged to have a turbidity (as measured by OD340 after concentration of purified monomeric antibody construct to 2.5 mg/ml and over night incubation) of ≤0.2, preferably of ≤0.15, more preferably of ≤0.12, even more preferably of ≤0.1, and most preferably of ≤0.08. See Example 12.

The DLL3×CD3 bispecific antibody constructs of the invention are also envisaged to not be internalized or to not undergo significant internalization by the target cell. The rate of internalization can be assayed e.g. as described in Example 16. Preferably, the internalization rate (e.g. measured as a decrease in cytotoxicity) is ≤20% after a 2 hour (pre-)incubation of the antibody construct with the target cell, more preferably ≤15%, even more preferably ≤10%, and most preferably ≤5%.

It is furthermore envisaged that shed or soluble DLL3 does not significantly impair the efficacy or biologic activity of the DLL3×CD3 bispecific antibody constructs of the invention. This can be measured e.g. in a cytotoxicity assay where soluble DLL3 is added at increasing concentrations to the assay, e.g. at 0 nM-0.3 nM-0.7 nM-1 nM-3 nM-7 nM-12 nM. The EC50 value of the tested antibody construct should not be significantly increased in the presence of soluble DLL3. See Example 17.

In a further embodiment the antibody construct according to the invention is stable at acidic pH. The more tolerant the antibody construct behaves at unphysiologic pH such as pH 5.5 (a pH which is required to run e.g. a cation exchange chromatography), the higher is the recovery of the antibody construct eluted from an ion exchange column relative to the total amount of loaded protein. Recovery of the antibody construct from an ion (e.g., cation) exchange column at pH 5.5 is preferably 30%, more preferably 40%, more preferably 50%, even more preferably 60%, even more preferably 70%, even more preferably 80%, even more preferably 90%, even more preferably 95%, and most preferably 99%. See Example 13.

It is furthermore envisaged that the bispecific antibody constructs of the present invention exhibit therapeutic efficacy or anti-tumor activity. This can e.g. be assessed in a study as disclosed in the following example of an advanced stage human tumor xenograft model:

On day 1 of the study, $5\times10^6$ cells of a human DLL3 positive cancer cell line (e.g. SHP-77) are subcutaneously injected in the right dorsal flank of female NOD/SCID mice. When the mean tumor volume reaches about 100 $mm^3$, in vitro expanded human CD3 positive T cells are transplanted into the mice by injection of about $2\times10^7$ cells into the peritoneal cavity of the animals. Mice of vehicle control group 1 do not receive effector cells and are used as an untransplanted control for comparison with vehicle control group 2 (receiving effector cells) to monitor the impact of T cells alone on tumor growth. The antibody treatment starts when the mean tumor volume reaches about 200 $mm^3$. The mean tumor size of each treatment group on the day of treatment start should not be statistically different from any other group (analysis of variance). Mice are treated with 0.5 mg/kg/day of a DLL3×CD3 bispecifc antibody construct by intravenous bolus injection for about 15 to 20 days. Tumors are measured by caliper during the study and progress evaluated by intergroup comparison of tumor volumes (TV). The tumor growth inhibition T/C [%] is determined by calculating TV as T/C %=100×(median TV of analyzed group)/(median TV of control group 2).

The skilled person knows how to modify or adapt certain parameters of this study, such as the number of injected tumor cells, the site of injection, the number of transplanted human T cells, the amount of bispecific antibody constructs to be administered, and the timelines, while still arriving at a meaningful and reproducible result. Preferably, the tumor growth inhibition T/C [%] is ≤70 or ≤60, more preferably ≤50 or ≤40, even more preferably ≤30 or ≤20 and most preferably ≤10 or ≤5 or even ≤2.5.

The invention further provides a polynucleotide/nucleic acid molecule encoding an antibody construct of the invention.

A polynucleotide is a biopolymer composed of 13 or more nucleotide monomers covalently bonded in a chain. DNA (such as cDNA) and RNA (such as mRNA) are examples of polynucleotides with distinct biological function. Nucleotides are organic molecules that serve as the monomers or subunits of nucleic acid molecules like DNA or RNA. The nucleic acid molecule or polynucleotide can be double stranded and single stranded, linear and circular. It is preferably comprised in a vector which is preferably comprised in a host cell. Said host cell is, e.g. after transformation or transfection with the vector or the polynucleotide of the invention, capable of expressing the antibody construct. For that purpose the polynucleotide or nucleic acid molecule is operatively linked with control sequences.

The genetic code is the set of rules by which information encoded within genetic material (nucleic acids) is translated into proteins. Biological decoding in living cells is accomplished by the ribosome which links amino acids in an order specified by mRNA, using tRNA molecules to carry amino acids and to read the mRNA three nucleotides at a time. The code defines how sequences of these nucleotide triplets, called codons, specify which amino acid will be added next during protein synthesis. With some exceptions, a three-nucleotide codon in a nucleic acid sequence specifies a single amino acid. Because the vast majority of genes are encoded with exactly the same code, this particular code is often referred to as the canonical or standard genetic code. While the genetic code determines the protein sequence for a given coding region, other genomic regions can influence when and where these proteins are produced.

Furthermore, the invention provides a vector comprising a polynucleotide/nucleic acid molecule of the invention.

A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density.

Moreover, the invention provides a host cell transformed or transfected with the polynucleotide/nucleic acid molecule or with the vector of the invention.

As used herein, the terms "host cell" or "recipient cell" are intended to include any individual cell or cell culture that can be or has/have been recipients of vectors, exogenous nucleic acid molecules, and polynucleotides encoding the antibody construct of the present invention; and/or recipients of the antibody construct itself. The introduction of the respective material into the cell is carried out by way of transformation, transfection and the like. The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell, but is still included within the scope of the term as used herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

The antibody construct of the invention can be produced in bacteria. After expression, the antibody construct of the invention is isolated from the *E. coli* cell paste in a soluble fraction and can be purified through, e.g., affinity chromatography and/or size exclusion. Final purification can be carried out similar to the process for purifying antibody expressed e.g., in CHO cells.

In addition to prokaryotes, eukaryotic microbes such as filamentous fungi or yeast are suitable cloning or expression hosts for the antibody construct of the invention. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such as *K. lactis, K. fragilis* (ATCC 12424), K. *bulgaricus* (ATCC 16045), K. wickeramii (ATCC 24178), *K. waltii* (ATCC 56500), K. *drosophilarum* (ATCC 36906), *K. thermotolerans*, and *K. marxianus; yarrowia* (EP 402 226); *Pichia pastoris* (EP 183 070); *Candida; Trichoderma* reesia (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger.*

Suitable host cells for the expression of glycosylated antibody construct of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, *petunia*, tomato, *Arabidopsis* and tobacco can also be used as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/−DHFR (CHO, Urlaub et al., Proc. Natl. Acad. Sci. USA 77: 4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL51); TRI cells (Mather et al., Annals N. Y Acad. Sci. (1982) 383: 44-68); MRC 5 cells; FS4 cells; and a human hepatoma line (Hep G2).

In a further embodiment the invention provides a process for the production of an antibody construct of the invention, said process comprising culturing a host cell of the invention under conditions allowing the expression of the antibody construct of the invention and recovering the produced antibody construct from the culture.

As used herein, the term "culturing" refers to the in vitro maintenance, differentiation, growth, proliferation and/or propagation of cells under suitable conditions in a medium. The term "expression" includes any step involved in the production of an antibody construct of the invention including, but not limited to, transcription, post-transcriptional modification, translation, post-translational modification, and secretion.

When using recombinant techniques, the antibody construct can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody construct of the invention prepared from the host cells can be recovered or purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromato-focusing, SDS-PAGE, and ammonium sulfate precipitation are also available depending on the antibody to be recovered. Where the antibody construct of the invention comprises a CH3 domain, the Bakerbond ABX resin (J. T. Baker, Phillipsburg, NJ) is useful for purification.

Affinity chromatography is a preferred purification technique. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose.

Moreover, the invention provides a pharmaceutical composition comprising an antibody construct of the invention or an antibody construct produced according to the process of the invention.

As used herein, the term "pharmaceutical composition" relates to a composition which is suitable for administration to a patient, preferably a human patient. The particularly preferred pharmaceutical composition of this invention comprises one or a plurality of the antibody construct(s) of the invention, preferably in a therapeutically effective amount. Preferably, the pharmaceutical composition further comprises suitable formulations of one or more (pharmaceutically effective) carriers, stabilizers, excipients, diluents, solubilizers, surfactants, emulsifiers, preservatives and/or adjuvants. Acceptable constituents of the composition are preferably nontoxic to recipients at the dosages and concentrations employed. Pharmaceutical compositions of the invention include, but are not limited to, liquid, frozen, and lyophilized compositions.

The inventive compositions may comprise a pharmaceutically acceptable carrier. In general, as used herein, "pharmaceutically acceptable carrier" means any and all aqueous and non-aqueous solutions, sterile solutions, solvents, buffers, e.g. phosphate buffered saline (PBS) solutions, water, suspensions, emulsions, such as oil/water emulsions, various types of wetting agents, liposomes, dispersion media and coatings, which are compatible with pharmaceutical administration, in particular with parenteral administration. The use of such media and agents in pharmaceutical compositions is well known in the art, and the compositions comprising such carriers can be formulated by well-known conventional methods.

Certain embodiments provide pharmaceutical compositions comprising the antibody construct of the invention and further one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

In certain embodiments, the pharmaceutical composition may contain formulation materials for the purpose of modifying, maintaining or preserving, e.g., the pH, osmolarity, viscosity, clarity, color, isotonicity, odor, sterility, stability, rate of dissolution or release, adsorption or penetration of the composition (see, REMINGTON'S PHARMACEUTICAL SCIENCES, $18^{th}$ Edition, (A. R. Genrmo, ed.), 1990, Mack Publishing Company). In such embodiments, suitable formulation materials may include, but are not limited to:

- amino acids such as glycine, alanine, glutamine, asparagine, threonine, proline, 2-phenylalanine, including charged amino acids, preferably lysine, lysine acetate, arginine, glutamate and/or histidine
- antimicrobials such as antibacterial and antifungal agents
- antioxidants such as ascorbic acid, methionine, sodium sulfite or sodium hydrogen-sulfite;
- buffers, buffer systems and buffering agents which are used to maintain the composition at physiological pH or at a slightly lower pH, typically within a pH range of from about 5 to about 8 or 9; examples of buffers are borate, bicarbonate, Tris-HCl, citrates, phosphates or other organic acids, succinate, phosphate, histidine and acetate; for example Tris buffer of about pH 7.0-8.5, or acetate buffer of about pH 4.0-5.5;
- non-aqueous solvents such as propylene glycol, polyethylene glycol, vegetable oils such as olive oil, and injectable organic esters such as ethyl oleate;
- aqueous carriers including water, alcoholic/aqueous solutions, emulsions or suspensions, including saline and buffered media;
- biodegradable polymers such as polyesters;
- bulking agents such as mannitol or glycine;
- chelating agents such as ethylenediamine tetraacetic acid (EDTA);
- isotonic and absorption delaying agents;
- complexing agents such as caffeine, polyvinylpyrrolidone, beta-cyclodextrin or hydroxypropyl-beta-cyclodextrin)
- fillers;
- monosaccharides; disaccharides; and other carbohydrates (such as glucose, mannose or dextrins); carbohydrates may be non-reducing sugars, preferably trehalose, sucrose, octasulfate, sorbitol or xylitol;
- (low molecular weight) proteins, polypeptides or proteinaceous carriers such as human or bovine serum albumin, gelatin or immunoglobulins, preferably of human origin;
- coloring and flavouring agents;
- sulfur containing reducing agents, such as glutathione, thioctic acid, sodium thioglycolate, thioglycerol, [alpha]-monothioglycerol, and sodium thio sulfate
- diluting agents;
- emulsifying agents;
- hydrophilic polymers such as polyvinylpyrrolidone)
- salt-forming counter-ions such as sodium;
- preservatives such as antimicrobials, anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide);
- metal complexes such as Zn-protein complexes;
- solvents and co-solvents (such as glycerin, propylene glycol or polyethylene glycol);
- sugars and sugar alcohols, such as trehalose, sucrose, octasulfate, mannitol, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; and polyhydric sugar alcohols;
- suspending agents;
- surfactants or wetting agents such as pluronics, PEG, sorbitan esters, polysorbates such as polysorbate 20, polysorbate, triton, tromethamine, lecithin, cholesterol, tyloxapal; surfactants may be detergents, preferably with a molecular weight of >1.2 KD and/or a polyether, preferably with a molecular weight of >3 KD; non-limiting examples for preferred detergents are Tween 20, Tween 40, Tween 60, Tween 80 and Tween 85; non-limiting examples for preferred polyethers are PEG 3000, PEG 3350, PEG 4000 and PEG 5000;
- stability enhancing agents such as sucrose or sorbitol;
- tonicity enhancing agents such as alkali metal halides, preferably sodium or potassium chloride, mannitol sorbitol;
- parenteral delivery vehicles including sodium chloride solution, Ringer's dextrose, dextrose and sodium chloride, lactated Ringer's, or fixed oils;
- intravenous delivery vehicles including fluid and nutrient replenishers, electrolyte replenishers (such as those based on Ringer's dextrose).

It is evident to those skilled in the art that the different constituents of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

It is envisaged that the composition of the invention might comprise, in addition to the polypeptide of the invention defined herein, further biologically active agents, depending on the intended use of the composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art. It is also envisaged that the antibody construct of the present invention is applied in a co-therapy, i.e., in combination with another anti-cancer medicament.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibody construct of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In certain embodiments, the antibody construct of the invention compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the antibody construct of the invention may be formulated as a lyophilizate using appropriate excipients such as sucrose.

When parenteral administration is contemplated, the therapeutic compositions for use in this invention may be provided in the form of a pyrogen-free, parenterally acceptable aqueous solution comprising the desired antibody construct of the invention in a pharmaceutically acceptable vehicle. A particularly suitable vehicle for parenteral injection is sterile distilled water in which the antibody construct of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody construct.

Additional pharmaceutical compositions will be evident to those skilled in the art, including formulations involving the antibody construct of the invention in sustained- or controlled-delivery/release formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949.

The antibody construct may also be entrapped in microcapsules prepared, for example, by coacervation techniques or by interfacial polymerization (for example, hydroxymethylcellulose or gelatine-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Another aspect of the invention includes self-buffering antibody construct of the invention formulations, which can be used as pharmaceutical compositions, as described in international patent application WO 06138181A2 (PCT/US2006/022599). A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution" in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions", Pharm Biotechnol. 13: 159-75 (2002), see particularly the parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as “kosmotropic”. Destabilizing solutes are referred to as “chaotropic”. Kosmotropes commonly are used at high concentrations (e.g., >1 molar ammonium sulfate) to precipitate proteins from solution (“salting-out”). Chaotropes commonly are used to denture and/or to solubilize proteins (“salting-in”). The relative effectiveness of ions to “salt-in” and “salt-out” defines their position in the Hofmeister series.

Free amino acids can be used in the antibody construct of the invention formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations. Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the antibody construct of the invention formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the antibody construct of the invention formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard. Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the antibody construct of the invention formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized--dual chamber cartridge, Pharmacia & Upjohn) contain phenol while Somatrope (Eli Lilly) is formulated with m-cresol. Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition of the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R I, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4):1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Half-life" means the time where 50% of an administered drug are eliminated through biological processes, e.g. metabolism, excretion, etc. By "hepatic first-pass metabolism" is meant the propensity of a drug to be metabolized upon first contact with the liver, i.e. during its first pass through the liver. "Volume of distribution" means the degree of retention of a drug throughout the various compartments of the body, like e.g. intracellular and extracellular spaces, tissues and organs, etc. and the distribution of the drug within these compartments. "Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma. "Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of bispecific antibody constructs exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12).

One embodiment provides the antibody construct of the invention or the antibody construct produced according to the process of the invention for use in the prevention, treatment or amelioration of a tumor or cancer disease or of a metastatic cancer disease.

The formulations described herein are useful as pharmaceutical compositions in the treatment, amelioration and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

The term "amelioration" as used herein refers to any improvement of the disease state of a patient having a tumor or cancer or a metastatic cancer as specified herein below, by the administration of an antibody construct according to the invention to a subject in need thereof. Such an improvement may also be seen as a slowing or stopping of the p progression of the tumor or cancer or metastatic cancer of the patient. The term "prevention" as used herein means the avoidance of the occurrence or re-occurrence of a patient having a tumor or cancer or a metastatic cancer as specified herein below, by the administration of an antibody construct according to the invention to a subject in need thereof.

The term "disease" refers to any condition that would benefit from treatment with the antibody construct or the pharmaceutic composition described herein. This includes chronic and acute disorders or diseases including those pathological conditions that predispose the mammal to the disease in question.

A "neoplasm" is is an abnormal growth of tissue, usually but not always forming a mass. When also forming a mass, it is commonly referred to as a "tumor". Neoplasms or tumors can be benign, potentially malignant (pre-cancerous), or malignant. Malignant neoplasms are commonly called cancer. They usually invade and destroy the surrounding tissue and may form metastases, i.e., they spread to other parts, tissues or organs of the body. Hence, the term "metatstatic cancer" encompasses metastases to other tissues or organs than the one of the original tumor. Lymphomas and leukemias are lymphoid neoplasms. For the purposes of the present invention, they are also encompassed by the terms "tumor" or "cancer".

In a preferred embodiment of the invention, the tumor or cancer disease is selected from the group including, but not limited to, (or consisting of) lung cancer, preferably SCLC, breast, cervical, colon, colorectal, endometrial, head and neck, liver, ovarian, pancreatic, prostate, skin, gastric, testis, thyroid, adrenal, renal, bladder, uterine, esophageal, urothelial and brain tumor or cancer, lymphoma, carcinoma, and sarcoma, and a metastatic cancer disease derived from any of the foregoing.

More specifically, the tumor or cancer disease can be selected from the group consisting of small cell lung cancer (SCLC), non-small ceil lung cancer (NSCLC), glioma, glioblastoma, melanoma, neuroendocrine prostate cancer, neuroendocrine pancreatic cancer, hepatoblastoma, and hepatocellular carcinoma. The metastatic cancer disease can be derived from any of the foregoing.

The invention also provides a method for the treatment or amelioration of tumor or cancer disease or a metastatic cancer disease, comprising the step of administering to a subject in need thereof the antibody construct of the invention or the antibody construct produced according to the process of the invention.

The terms "subject in need" or those "in need of treatment" includes those already with the disorder, as well as those in which the disorder is to be prevented. The subject in need or "patient" includes human and other mammalian subjects that receive either prophylactic or therapeutic treatment.

The antibody construct of the invention will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed in accordance with the invention for delivery by any suitable route of administration. In the context of the present invention, the routes of administration include, but are not limited to

- topical routes (such as epicutaneous, inhalational, nasal, opthalmic, auricular/aural, vaginal, mucosal);
- enteral routes (such as oral, gastrointestinal, sublingual, sublabial, buccal, rectal); and
- parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions and the antibody construct of this invention are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163.

In particular, the present invention provides for an uninterrupted administration of the suitable composition. As a non-limiting example, uninterrupted or substantially uninterrupted, i.e. continuous administration may be realized by a small pump system worn by the patient for metering the influx of therapeutic agent into the body of the patient. The pharmaceutical composition comprising the antibody construct of the invention can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the antibody constructs of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may also be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

The compositions of the present invention can be administered to the subject at a suitable dose which can be determined e.g. by dose escalating studies by administration of increasing doses of the antibody construct of the invention exhibiting cross-species specificity described herein to non-chimpanzee primates, for instance macaques. As set forth above, the antibody construct of the invention exhibiting cross-species specificity described herein can be advantageously used in identical form in preclinical testing in non-chimpanzee primates and as drug in humans. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts or doses effective for this use will depend on the condition to be treated (the indication), the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted according to the judgment of the attending physician such that it can be administered to the patient once or over a series of administrations, and in order to obtain the optimal therapeutic effect.

A typical dosage may range from about 0.1 μg/kg to up to about 30 mg/kg or more, depending on the factors mentioned above. In specific embodiments, the dosage may range from 1.0 μg/kg up to about 20 mg/kg, optionally from 10 μg/kg up to about 10 mg/kg or from 100 μg/kg up to about 5 mg/kg.

A therapeutic effective amount of an antibody construct of the invention preferably results in a decrease in severity of disease symptoms, an increase in frequency or duration of disease symptom-free periods or a prevention of impairment or disability due to the disease affliction. For treating DLL3-expressing tumors, a therapeutically effective amount of the antibody construct of the invention, e.g. an anti-DLL3/anti-CD3 antibody construct, preferably inhibits cell growth or tumor growth by at least about 20%, at least about 40%, at least about 50%, at least about 60%, at least about 70%, at least about 80%, or at least about 90% relative to untreated patients. The ability of a compound to inhibit tumor growth may be evaluated in an animal model predictive of efficacy in human tumors.

The pharmaceutical composition can be administered as a sole therapeutic or in combination with additional therapies such as anti-cancer therapies as needed, e.g. other proteinaceous and non-proteinaceous drugs. These drugs may be administered simultaneously with the composition comprising the antibody construct of the invention as defined herein or separately before or after administration of said antibody construct in timely defined intervals and doses.

The term "effective and non-toxic dose" as used herein refers to a tolerable dose of an inventive antibody construct which is high enough to cause depletion of pathologic cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

In a further embodiment, the invention provides a kit comprising an antibody construct of the invention, an antibody construct produced according to the process of the invention, a polypeptide of the invention, a vector of the invention, and/or a host cell of the invention.

In the context of the present invention, the term "kit" means two or more components—one of which corresponding to the antibody construct, the pharmaceutical composition, the vector or the host cell of the invention—packaged together in a container, recipient or otherwise. A kit can hence be described as a set of products and/or utensils that are sufficient to achieve a certain goal, which can be marketed as a single unit.

The kit may comprise one or more recipients (such as vials, ampoules, containers, syringes, bottles, bags) of any appropriate shape, size and material (preferably waterproof, e.g. plastic or glass) containing the antibody construct or the pharmaceutical composition of the present invention in an appropriate dosage for administration (see above). The kit may additionally contain directions for use (e.g. in the form of a leaflet or instruction manual), means for administering the antibody construct of the present invention such as a syringe, pump, infuser or the like, means for reconstituting the antibody construct of the invention and/or means for diluting the antibody construct of the invention.

The invention also provides kits for a single-dose administration unit. The kit of the invention may also contain a first recipient comprising a dried/lyophilized antibody construct and a second recipient comprising an aqueous formulation. In certain embodiments of this invention, kits containing single-chambered and multi-chambered pre-filled syringes (e.g., liquid syringes and lyosyringes) are provided.

Schematic representation of the DLL3 ECD/truncated DLL3 constructs expressed on CHO cells for epitope mapping. The transmembrane and the intracellular domain are derived from EpCAM. See Example 1.

FIGS. 2A-2B

Epitope mapping of the anti-DLL3 antibody constructs. Examples of bispecific antibody constructs recognizing the EGF-3 domain and the EGF-4 domain, respectively, as detected by epitope mapping. The x-axis depicts PE-A (PE=phycoerythrin, A=signal area), and the y-axis depicts counts. See Example 2.

FIGS. 3A-3C

Cross-Reactivity of anti-DLL3 antibody constructs as detected by flow cytometry: binding to human and macaque DLL3 and CD3. The x-axis depicts FL2-H, and the y-axis depicts counts. See Example 5.

FIG. 4

Analysis of anti-DLL3 antibody constructs by flow cytometry: non-binding to human paralogues DLL1 and DLL4. The x-axis depicts FL1-H, and the y-axis depicts counts. See Example 6.

FIG. 5

Stability of anti-DLL3 antibody constructs after incubation for 96 hours in human plasma. See Example 11.

FIG. 6

Potency gap between the monomeric and the dimeric isoform of the anti-DLL3 antibody constructs. See Example 15.

FIG. 7

In vitro internalization assay, carried out as described in Example 16. Antibody construct was pre-incubated on target cells (SHP-77) in the absence of T cells in order to measure loss of antibody construct due to internalization. Results suggest that no significant internalization occurs. The results achieved with a control target which is well known for its internalization are shown for comparison at the right.

FIGS. 8A-8B

Figure 8A:
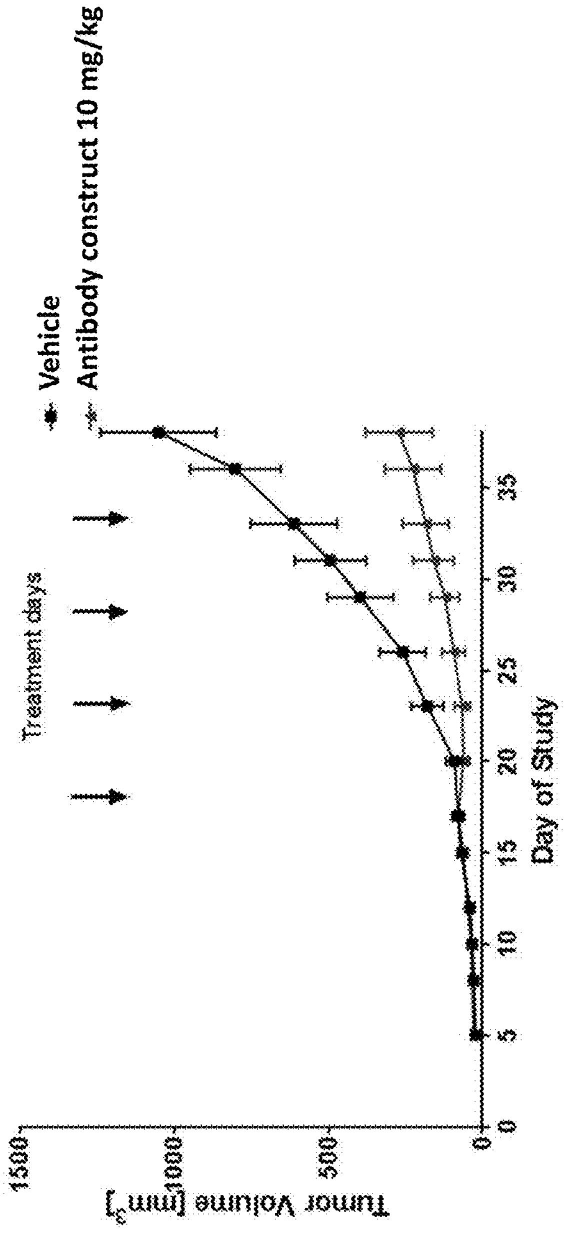
Figure 8B:
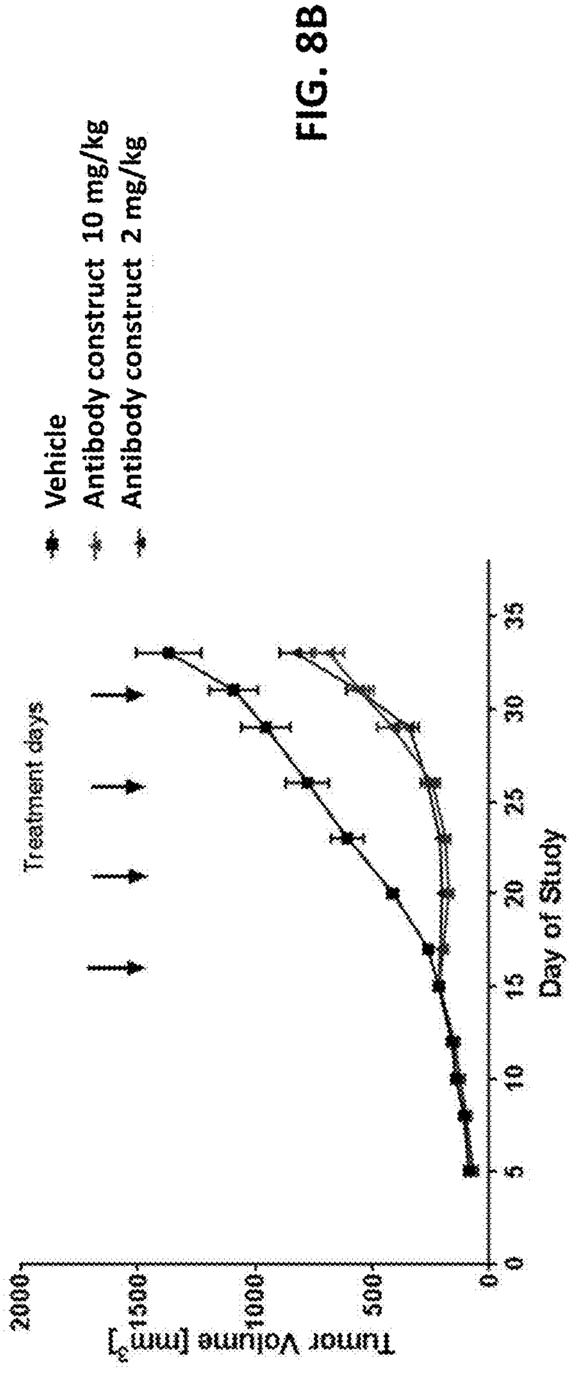

Results of the mouse xenograft efficacy study of the SHP-77 model (FIG. 8A) and the WM266-4 model (FIG. 8B). The tumor volume is plotted against the time. See Example 18.

FIGS. 9A-9B

Pharmacokinetics of different HLE antibody constructs (albumin fusion in FIG. 9A and Fc fusions in FIG. 9B) as determined in Example 20.

EXAMPLES

The following examples illustrate the invention. These examples should not be construed as to limit the scope of this invention. The present invention is limited only by the claims.

Example 1

Generation of CHO Cells Expressing Wild Type and Truncated DLL3

The extracellular domain of the DLL3 antigen can be subdivided into different sub-domains or regions that are defined, for the purposes of Examples 1 and 2, by the following amino acid positions:

Signal peptide: 1-26
N-terminus: 27-175
DSL: 176-215
EGF-1: 216-249
EGF-2: 274-310
EGF-3: 312-351
EGF-4: 353-389
EGF-5: 391-427
EGF-6: 429-465

Figure 1:
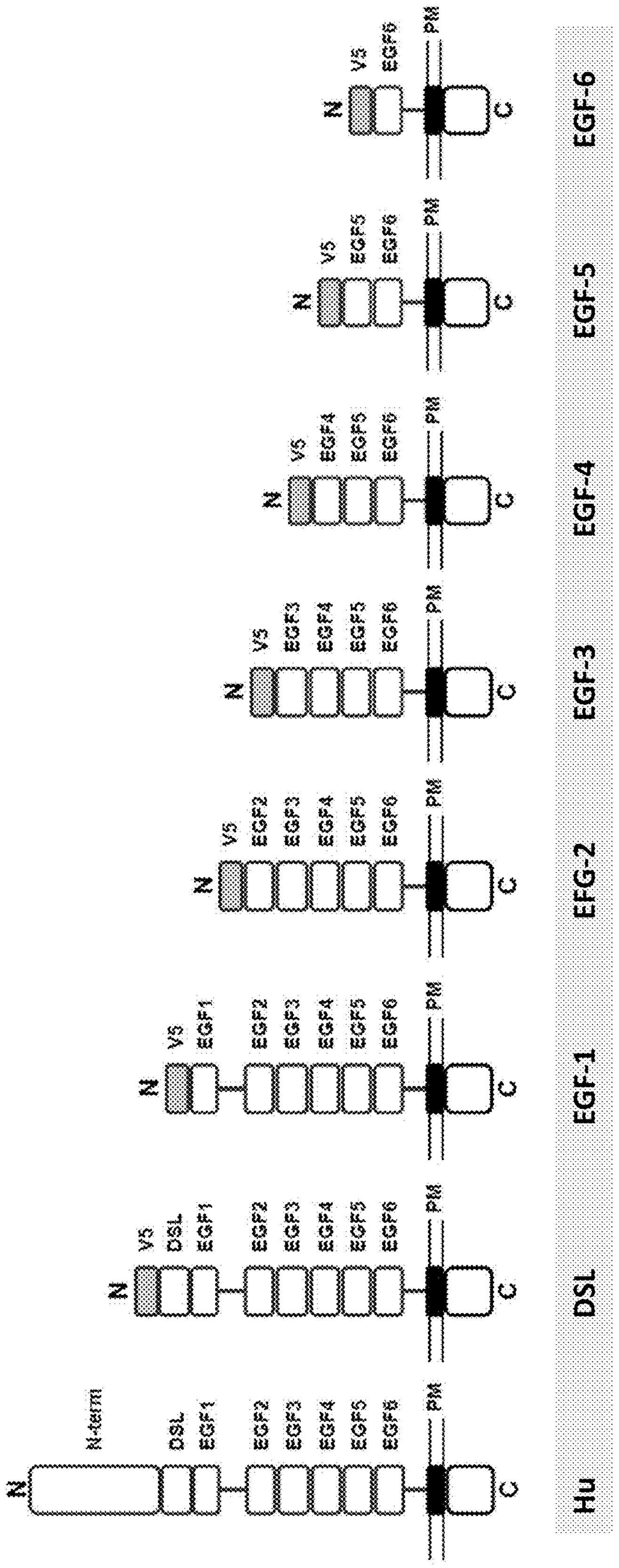
FIG. 1

For the construction of the truncated DLL3 molecules used for epitope mapping, the sequences of the respective eight extracellular domains (Signal peptide plus N-terminus, DSL, EGF1, EGF2, EGF3, EGF4, EGF5 and EGF6) of human DLL3 were stepwise deleted from the antigen, starting from the N-terminus. The following molecules were generated; see also FIG. 1:

| | |
|---|---|
| Hu DLL3 ECD/complete ECD | SEQ ID NO: 263 |
| Hu DLL3 ECD/up to DSL | SEQ ID NO: 264 |
| Hu DLL3 ECD/up to EGF-1 | SEQ ID NO: 265 |
| Hu DLL3 ECD/up to EGF-2 | SEQ ID NO: 266 |
| Hu DLL3 ECD/up to EGF-3 | SEQ ID NO: 267 |
| Hu DLL3 ECD/up to EGF-4 | SEQ ID NO: 268 |
| Hu DLL3 ECD/up to EGF-5 | SEQ ID NO: 269 |
| Hu DLL3 ECD/only EGF-6 | SEQ ID NO: 270 |

For the generation of CHO cells expressing human, cynomolgus macaque ("cyno") and truncated human N-terminal V5 tagged DLL3, the respective coding sequences for human DLL3-ECD (SEQ ID NO: 253; see also GeneBank accession number NM_016941), cyno DLL3-ECD (SEQ ID NO: 272) and the seven truncated human N-terminal V5 tagged DLL3-ECD versions (see above) were cloned into a plasmid designated pEF-DHFR (pEF-DHFR is described in Raum et al. Cancer Immunol Immunother 50 (2001) 141-150). For cell surface expression of human and cyno DLL3 the original signal peptide was used, and for cell surface expression of the truncated human N-terminal DLL3 a mouse IgG heavy chain signal peptide was used, followed by a V5 tag. All mentioned DLL3-ECD sequences were followed in frame by the coding sequence of an artificial Ser/Gly-linker followed by a domain derived from the transmembrane/intracellular domain of human EpCAM (amino acids 266-314 of the sequence as published in GenBank accession number NM_002354). All cloning procedures were carried out according to standard protocols (Sambrook, Molecular Cloning; A Laboratory Manual, 3rd edition, Cold Spring Harbour Laboratory Press, Cold Spring Harbour, New York (2001)). For each construct, a corresponding plasmid was transfected into DHFR deficient CHO cells for eukaryotic expression, as described by Kaufman R. J. (1990) Methods Enzymol. 185, 537-566.

The expression of human and cyno DLL3 on CHO cells was verified in a FACS assay using a monoclonal mouse IgG2b anti-human DLL3 antibody. The expression of the seven truncated versions of human DLL3-ECD was verified using a monoclonal mouse IgG2a anti-v5 tag antibody. Bound monoclonal antibody was detected with an anti-mouse IgG Fc-gamma-PE. As negative control, cells were incubated with isotype control antibody instead of the first antibody. The samples were measured by flow cytometry.

Example 2

Epitope Mapping of Anti-DLL3 Antibody Constructs

Cells transfected with human DLL3 and with the truncated human DLL3 molecules (see Example 1) were stained with crude, undiluted periplasmic extract containing bispecific DLL3×CD3 antibody constructs (with the CD3 binding domain being denominated 12C) fused to a human albumin (variant 1), in PBS/1.5% FCS. Bound molecules were detected with an in-house mouse monoclonal anti-CD3 binding domain antibody (50 µl) followed by an anti-mouse IgG Fc-gamma-PE (1:100, 50 µl; Jackson Immunoresearch #115-116-071) All antibodies were diluted in PBS/1.5% FCS. As negative control, cells were incubated with PBS/2% FCS instead of the periplasmic extract. The samples were measured by flow cytometry.

The regions that were recognized by the respective DLL3 binding domains are indicated in the sequence table (Table 18). Binders were mapped that were specific for an epitope located within the N-terminus of DLL3, within the DSL domain, and within the different EGF domains.

Figure 2A:
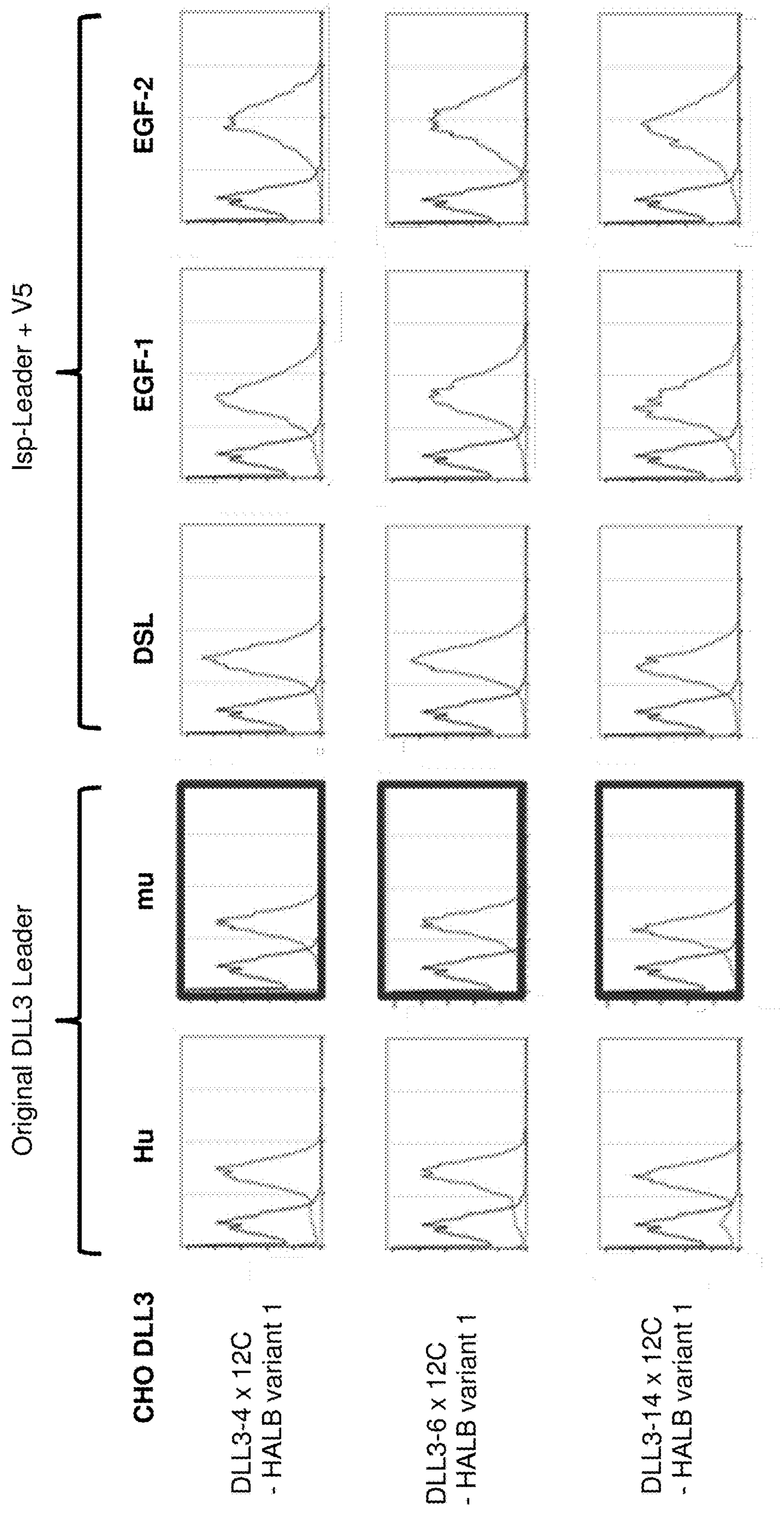
Figure 2B:
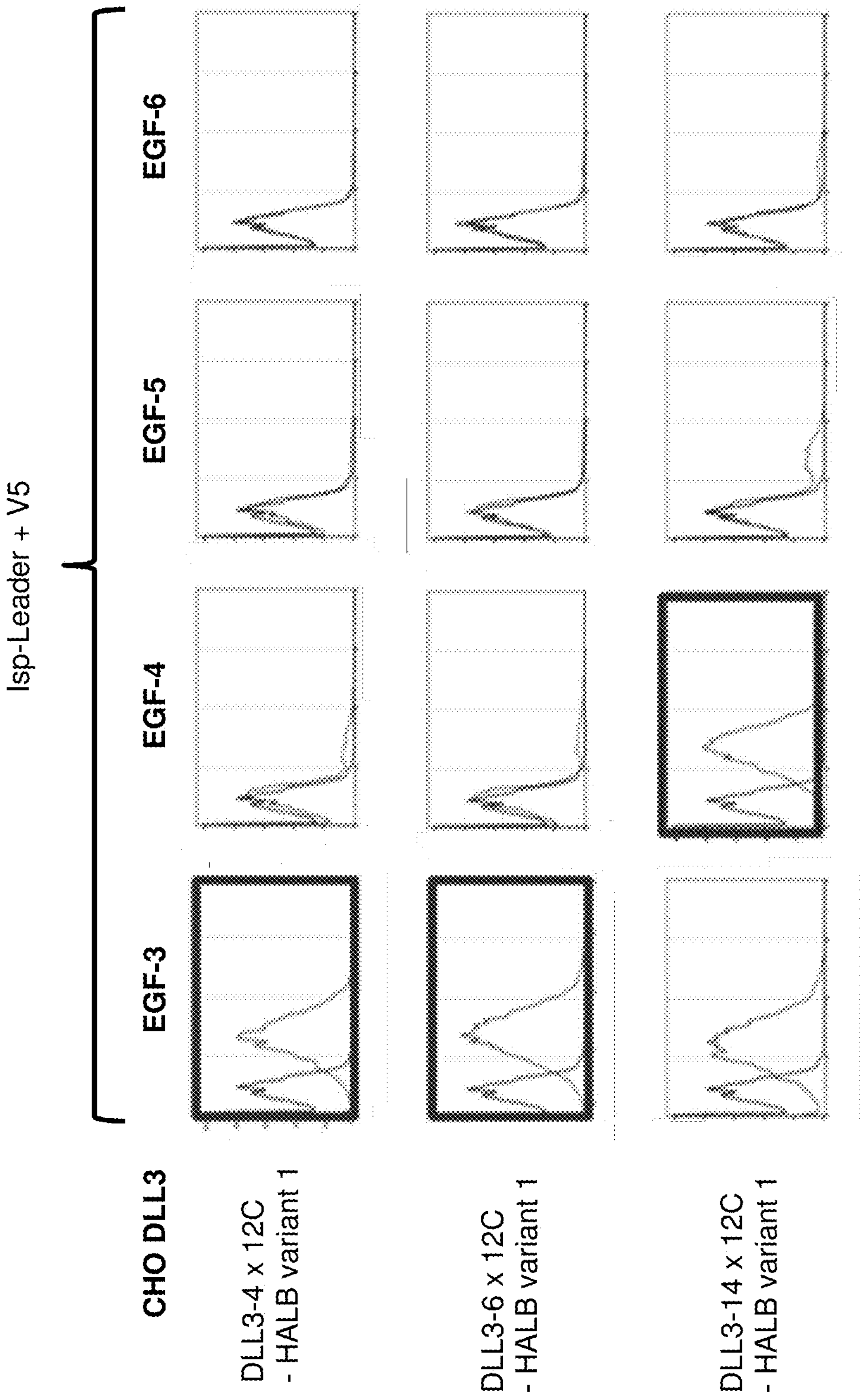

FIGS. 2A-2B shows two exemplary binders which bind to a DLL3 epitope comprised within the EGF-3 region (loss of the FACS signal in the respective truncated DLL3 constructs not comprising EGF-3). FIGS. 2A-2B also shows an exemplary binder which binds to a DLL3 epitope comprised within the EGF-3 region (loss of the FACS signal in the respective truncated DLL3 constructs not comprising EGF-4).

Some of the binders are described to be specific for an epitope located with the region denominated EGF-5/[6]. The squared brackets are meant to indicate that the FACS signal of the binder is decreased (i.e., neither fully present nor fully lost) for the truncated DLL3 construct having only the EGF-6 domain left (last construct in FIG. 1).

The bispecific DLL3×CD3 constructs used in the following examples are chosen from those constructs having "12C" as the CD3 binding domain and having a C-terminal fusion to a wild-type human serum albumin, see e.g. SEQ ID NOs: 224-230, 233-235, 238-241.

Example 3

Biacore-Based Determination of Antibody Affinity to Human and Cynomolgus DLL3

Biacore analysis experiments were performed using recombinant human/cyno DLL3-ECD fusion proteins with chicken albumin to determine target binding of the antibody constructs of the invention.

In detail, CM5 Sensor Chips (GE Healthcare) were immobilized with approximately 600-800 RU of the respective recombinant antigen using acetate buffer pH 4.5 according to the manufacturer's manual. The DLL3×CD3 bispecific antibody construct samples were loaded in a dilution series of the following concentrations: 50 nM, 25 nM, 12.5 nM, 6.25 nM and 3.13 nM diluted in HBS-EP running buffer (GE Healthcare). Flow rate was 30 µl/min for 3 min, then HBS-EP running buffer was applied for 8 min to 20 min again at a flow rate of 30 µl/ml. Regeneration of the chip was performed using 10 mM glycine 10 mM NaCl pH 1.5 solution. Data sets were analyzed using BiaEval Software. In general two independent experiments were performed.

The DLL3×CD3 bispecific antibody constructs according to the invention showed very high affinities to human DLL3 in the subnanomolar range (with the exception of DLL3-13 having a KD value in the very low one-digit nanomolar range). Binding to macaque DLL3 was balanced, also showing affinities in similar ranges. The affinity values as well as the calculated affinity gap are shown in Table 2.

TABLE 2

Affinities of DLL3 × CD3 bispecific antibody constructs to human and macaque DLL3 as determined by Biacore analysis, as well as the calculated interspecies affinity gaps.

| DLL3 × CD3 bispecific antibody construct | KD hu DLL3 [nM] | KD cyno DLL3 [nM] | Affinity gap KD mac/KD hu |
|---|---|---|---|
| DLL3-4 | 0.41 | 0.55 | 1.34 |
| DLL3-5 | 0.82 | 1.03 | 1.26 |
| DLL3-6 | 0.55 | 0.75 | 1.36 |
| DLL3-7 | 0.19 | 0.29 | 1.52 |
| DLL3-8 | 0.69 | 0.96 | 1.39 |
| DLL3-9 | 0.35 | 0.54 | 1.54 |
| DLL3-10 | 0.24 | 0.33 | 1.38 |
| DLL3-13 | 1.74 | 5.55 | 3.19 |
| DLL3-14 | 0.47 | 0.86 | 1.83 |
| DLL3-15 | 0.45 | 0.69 | 1.53 |

Furthermore, the binding of the bispecific antibody constructs to both human CD3 and macaque CD3 was confirmed in a Biacore assay to be in a low 2-digit nanomolar range (data not shown).

Example 4

Scatchard-Based Analysis of DLL3×CD3 Bispecific Antibody Construct Affinity to Human and Macaque DLL3 on Target Antigen Positive Cells and Determination of the Interspecies Affinity Gap The affinities of DLL3×CD3 bispecific antibody constructs to CHO cells transfected with human or macaque DLL3 were also determined by Scatchard analysis as the most reliable method for measuring potential affinity gaps between human and macaque DLL3. For the Scatchard analysis, saturation binding experiments are performed using a monovalent detection system to precisely determine monovalent binding of the DLL3×CD3 bispecific antibody constructs to the respective cell line.

$2\times10^4$ cells of the respective cell line (recombinantly human DLL3-expressing CHO cell line, recombinantly macaque DLL3-expressing CHO cell line) were incubated each with 50 μl of a triplet dilution series (twelve dilutions at 1:2) of the respective DLL3×CD3 bispecific antibody construct (until saturation is reached) starting at 10-20 nM followed by 16 h incubation at 4° C. under agitation and one residual washing step. Then, the cells were incubated for another hour with 30 μl of a CD3×ALEXA488 conjugate solution. After one washing step, the cells were resuspended in 150 μl FACS buffer containing 3.5% formaldehyde, incubated for further 15 min, centrifuged, resuspended in FACS buffer and analyzed using a FACS CantoII machine and FACS Diva software. Data were generated from two independent sets of experiments, each using triplicates. Respective Scatchard analysis was calculated to extrapolate maximal binding (Bmax). The concentrations of DLL3×CD3 bispecific antibody constructs at half-maximal binding were determined reflecting the respective KDs. Values of triplicate measurements were plotted as hyperbolic curves and as S-shaped curves to demonstrate proper concentration ranges from minimal to optimal binding.

Values depicted in Table 3 were derived from two independent experiments per DLL3×CD3 bispecific antibody construct. Cell based Scatchard analysis confirmed that the DLL3×CD3 bispecific antibody constructs of the invention are subnanomolar in affinity to human DLL3 and to mac DLL3 and present with a small cyno/human interspecies affinity gap of around 1.

TABLE 3

Affinities (KD) of DLL3 × CD3 bispecific antibody constructs as determined in cell based Scatchard analysis with the calculated affinity gap KD macaque DLL3/KD human DLL3. Antibody constructs were measured in two independent experiments, each using triplicates.

| DLL3 × CD3 bispecific antibody construct | Cell based affinity hu DLL3 [nM] | Cell based affinity mac DLL3 [nM] | Affinity gap KD mac/KD hu |
|---|---|---|---|
| DLL3-4 | 0.39 | 0.24 | 0.6 |
| DLL3-5 | 0.33 | 0.22 | 0.7 |
| DLL3-6 | 0.33 | 0.23 | 0.7 |
| DLL3-7 | 0.21 | 0.33 | 1.6 |
| DLL3-8 | 0.18 | 0.34 | 1.9 |
| DLL3-9 | 0.30 | 0.49 | 1.6 |
| DLL3-10 | 0.37 | 0.32 | 0.8 |
| DLL3-13 | 0.24 | 0.29 | 1.2 |
| DLL3-14 | 0.53 | 0.51 | 1.0 |
| DLL3-15 | 0.25 | 0.50 | 2.0 |

Example 5

Bispecific Binding and Interspecies Cross-Reactivity

For confirmation of binding to human DLL3 and CD3 and to cyno DLL3 and CD3, bispecific antibody constructs of the invention were tested by flow cytometry using

- CHO cells transfected with human DLL3, with an artificial human DLL3 isoform (characterized by the point mutations F172C and L218P), and with macaque DLL3, respectively,
- the human DLL3 positive human lung carcinoma cell line SHP-77,
- CD3-expressing human T cell leukemia cell line HPB-all (DSMZ, Braunschweig, ACC483), and
- the cynomolgus CD3-expressing T cell line LnPx 4119

For flow cytometry 200,000 cells of the respective cell lines were incubated for 60 min at 4° C. with 50 μl of purified bispecific antibody construct at a concentration of 5 μg/ml. The cells were washed twice in PBS/2% FCS and then incubated with an in-house mouse antibody (2 pg/ml) specific for the CD3 binding part of the bispecific antibody constructs for 30 min at 4° C. After washing, bound mouse antibodies were detected with a goat anti-mouse Fcγ-PE (1:100) for 30 min at 4° C. Samples were measured by flow cytometry. Non-transfected CHO cells were used as negative control.

Figure 3A:
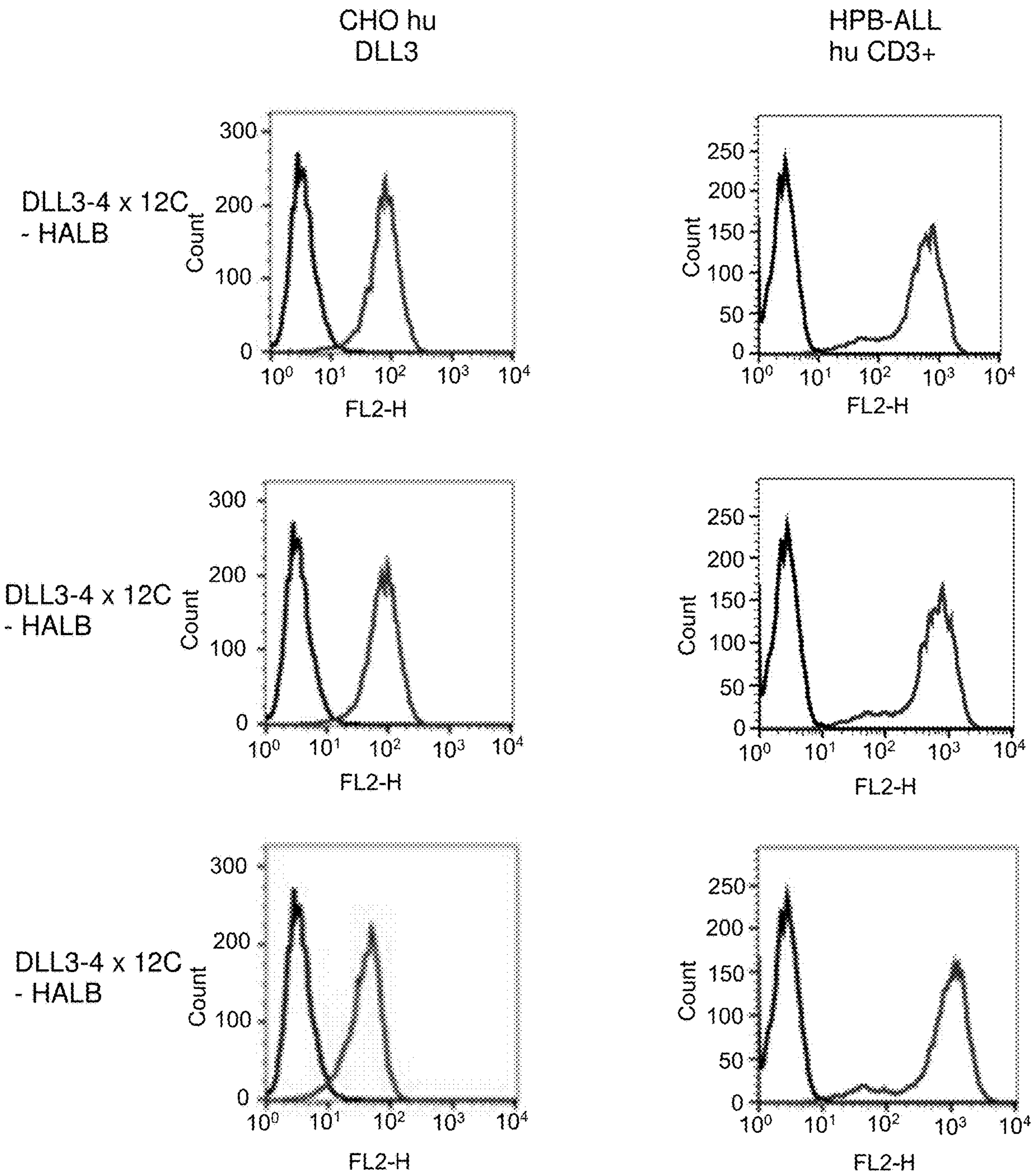
Figure 3B:
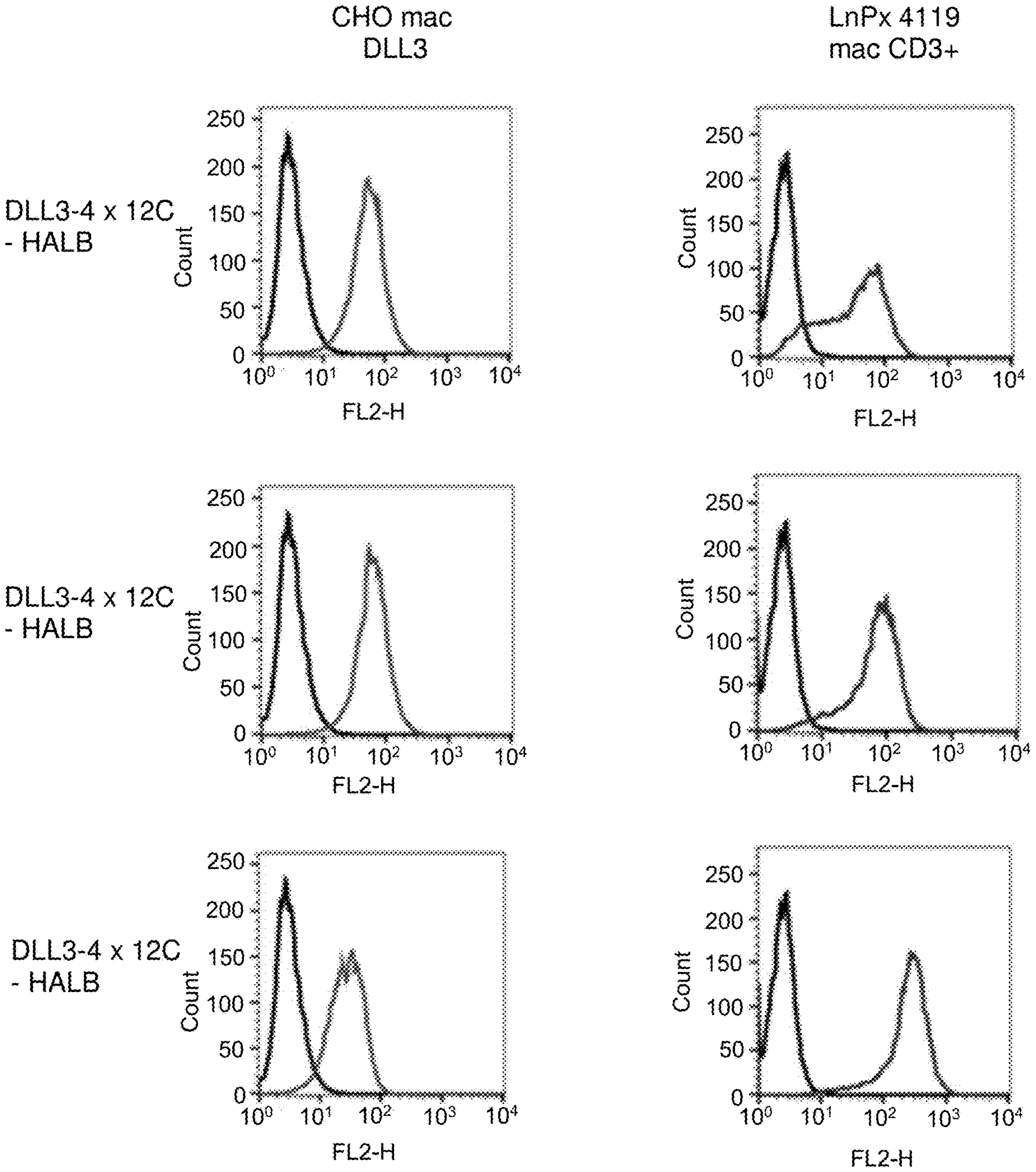
Figure 3C:
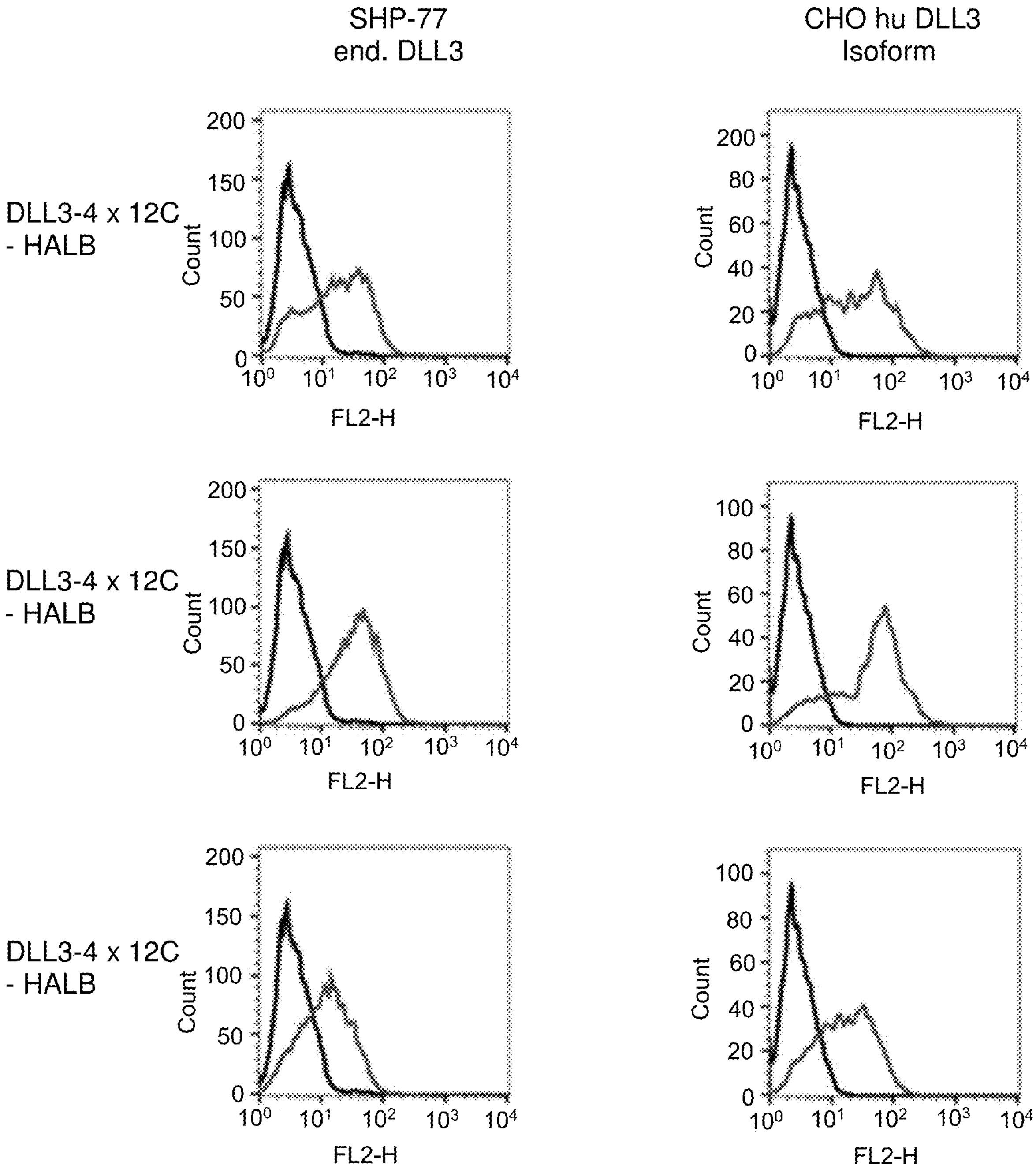

The results are shown in FIGS. 3A-3C. The DLL3×CD3 bispecific antibody constructs of the invention stained CHO cells transfected with human DLL3, the artificial DLL3 isoform and with cyno DLL3, and they also stained the human DLL3 positive human lung carcinoma cell line SHP-77 (natural expresser). Human and cyno T cell lines expressing CD3 were also recognized by the bispecific antibody constructs. Moreover, there was no staining of the negative control cells (non-transfected CHO, data shown in Example 6).

Example 6

Confirmation of the Absence of Binding to Human Paralogues

Human DLL3 paralogues DLL1 and DLL4 were stably transfected into CHO cells. The sequences of the paralogues as used in the present Example are identified in the sequence listing (SEQ ID NOs: 283 and 284). Protein expression was confirmed in FACS analyses with antibodies specific for the respective paralogues: Antibodies were anti-human DLL1 MAB1818 (R&D; 5 μg/ml), and anti-human DLL4 MAB1506 (R&D; 5 μg/ml) for DLL4.

Figure 4:
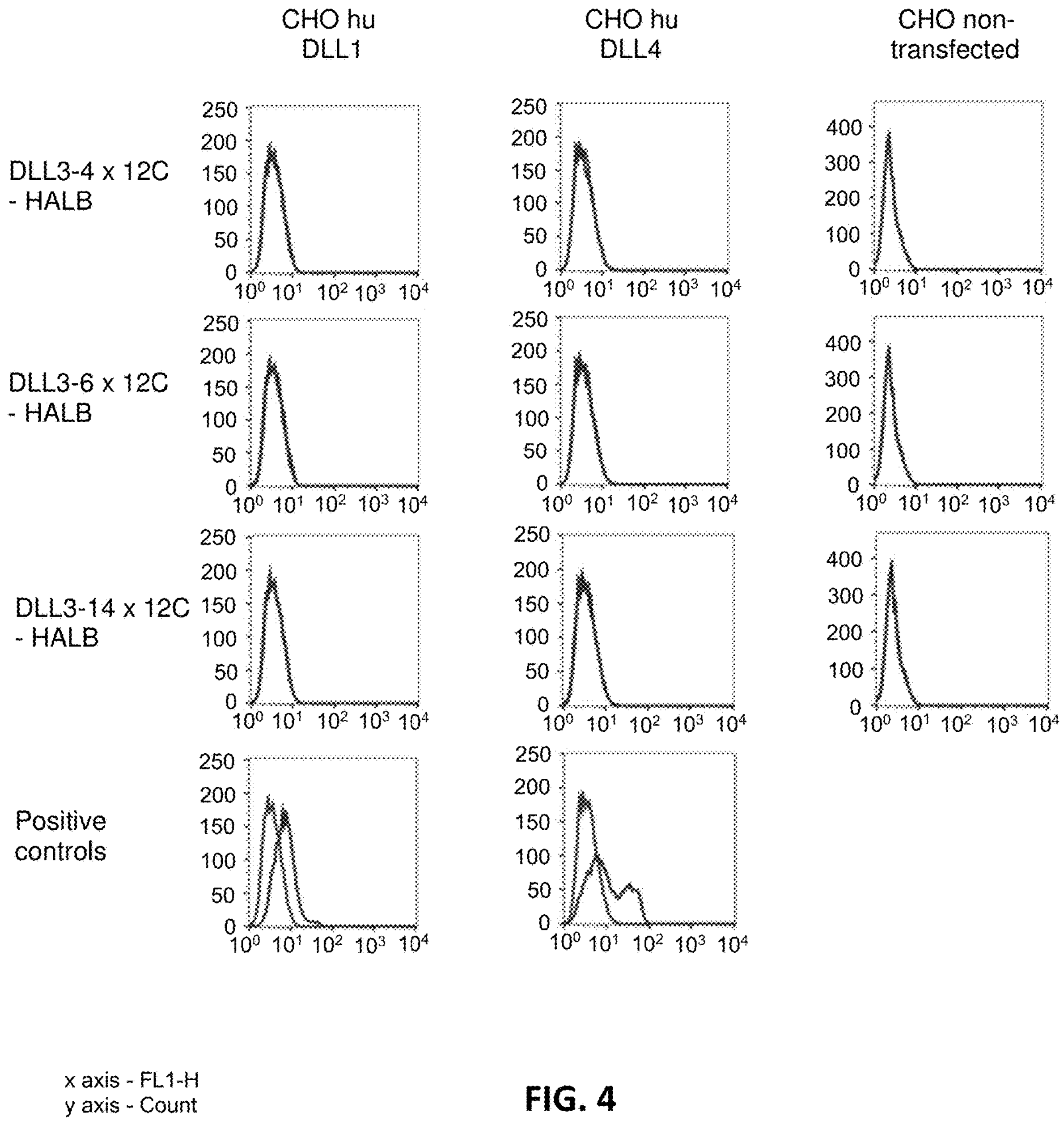

The flow cytometry assay was carried out as described in Example 5, with the exception that bound mouse antibodies were detected with a goat anti-mouse FITC (1:100). The results are shown in FIG. 4. The analysis confirmed that none of the DLL3×CD3 bispecific antibody constructs of the invention cross-reacts with the human DLL3 paralogues DLL1 and DLL4.

Example 7

Identity to Human Germline

In order to analyze the identity/similarity of the sequence of the antibody constructs to the human antibody germline genes, the DLL3 binding domains of the invention were aligned as follows: Full VL including all CDRs was aligned; full VH including CDRs 1 and 2 but except CDR3 was aligned against human antibody germline genes (Vbase). More details can be found in the specification of this application. The results are shown in Table 4 below:

TABLE 4

Identity of VH and VL to human germline

| DLL3 × CD3 bispecific antibody construct | % identity to human germline [VH/VL] |
|---|---|
| DLL3-4 | 96.9/93.3 |
| DLL3-5 | 96.9/96.6 |

TABLE 4-continued

| Identity of VH and VL to human germline | |
|---|---|
| DLL3 × CD3 bispecific antibody construct | % identity to human germline [VH/VL] |
| DLL3-6 | 96.9/96.6 |
| DLL3-7 | 93.9/96.6 |
| DLL3-8 | 94.8/96.6 |
| DLL3-9 | 96.9/95.5 |
| DLL3-10 | 91.9/95.5 |
| DLL3-13 | 95.9/95.7 |
| DLL3-14 | 94.9/94.6 |
| DLL3-15 | 93.9/94.6 |

Example 8

Cytotoxic Activity

The potency of DLL3×CD3 bispecific antibody constructs of the invention in redirecting effector T cells against DLL3-expressing target cells was analyzed in five in vitro cytotoxicity assays:

- The potency of DLL3×CD3 bispecific antibody constructs in redirecting stimulated human CD8+ effector T cells against human DLL3-transfected CHO cells was measured in an 18 hour 51-chromium release assay.
- The potency of DLL3×CD3 bispecific antibody constructs in redirecting stimulated human CD8+ effector T cells against the DLL3 positive human lung carcinoma cell line SHP-77 was measured in an 18 hour 51-chromium release assay.
- The potency of DLL3×CD3 bispecific antibody constructs in redirecting the T cells in unstimulated human PBMC against human DLL3-transfected CHO cells was measured in a 48 hour FACS-based cytotoxicity assay.
- The potency of DLL3×CD3 bispecific antibody constructs in redirecting the T cells in unstimulated human PBMC against the DLL3-positive human cell line SHP-77 was measured in a 48 hour FACS-based cytotoxicity assay.
- For confirmation that the cross-reactive DLL3×CD3 bispecific antibody constructs are capable of redirecting macaque T cells against macaque DLL3-transfected CHO cells, a 48 hour FACS-based cytotoxicity assay was performed with a macaque T cell line as effector T cells.

Example 8.1

Chromium Release Assay with Stimulated Human T Cells

Stimulated T cells enriched for CD8+ T cells were obtained as described in the following. A petri dish (145 mm diameter, Greiner bio-one GmbH, Kremsmünster) was coated with a commercially available anti-CD3 specific antibody (OKT3, Orthoclone) in a final concentration of 1 μg/ml for 1 hour at 37° C. Unbound protein was removed by one washing step with PBS. 3-5×$10^7$ human PBMC were added to the precoated petri dish in 120 ml of RPMI 1640 with stabilized glutamine/10% FCS/IL-2 20 U/ml (Proleukin®, Chiron) and stimulated for 2 days. On the third day, the cells were collected and washed once with RPMI 1640. IL-2 was added to a final concentration of 20 U/ml and the cells were cultured again for one day in the same cell culture medium as above. CD8+ cytotoxic T lymphocytes (CTLs) were enriched by depletion of CD4+ T cells and CD56+NK cells using Dynal-Beads according to the manufacturer's protocol.

Cyno DLL3- or human DLL3-transfected CHO target cells were washed twice with PBS and labeled with 11.1 MBq $^{51}Cr$ in a final volume of 100 μl RPMI with 50% FCS for 60 minutes at 37° C. Subsequently, the labeled target cells were washed 3 times with 5 ml RPMI and then used in the cytotoxicity assay. The assay was performed in a 96-well plate in a total volume of 200 μl supplemented RPMI with an E:T ratio of 10:1. A starting concentration of 0.01-1 μg/ml of purified bispecific antibody construct and threefold dilutions thereof were used. Incubation time for the assay was 18 hours. Cytotoxicity was determined as relative values of released chromium in the supernatant relative to the difference of maximum lysis (addition of Triton-X) and spontaneous lysis (without effector cells). All measurements were carried out in quadruplicates. Measurement of chromium activity in the supernatants was performed in a Wizard 3" gamma counter (Perkin Elmer Life Sciences GmbH, Koln, Germany). Analysis of the results was carried out with Prism 5 for Windows (version 5.0, GraphPad Software Inc., San Diego, California, USA). EC50 values calculated by the analysis program from the sigmoidal dose response curves were used for comparison of cytotoxic activity.

Example 8.2

Potency of Redirecting Stimulated Human Effector T Cells Against Human DLL3-Transfected CHO Cells The cytotoxic activity of DLL3×CD3 bispecific antibody constructs according to the invention was analyzed in a 51-chromium ($^{51}Cr$) release cytotoxicity assay using CHO cells transfected with human DLL3 as target cells, and stimulated human CD8+ T cells as effector cells. The experiment was carried out as described in Example 8.1.

The results are shown in Table 5. The DLL3×CD3 bispecific antibody constructs showed very potent cytotoxic activity against human DLL3 transfected CHO cells in the 1-digit picomolar range.

TABLE 5

| EC50 values [pM] of DLL3 × CD3 bispecific antibody constructs analyzed in a 51-chromium ($^{51}Cr$) release cytotoxicity assay using CHO cells transfected with human DLL3 as target cells, and stimulated human CD8 T cells as effector cells. | |
|---|---|
| DLL3 × CD3 bispecific antibody construct | EC50 [pM] |
| DLL3-4 | 3.8 |
| DLL3-5 | 4.2 |
| DLL3-6 | 2.1 |
| DLL3-7 | 2.2 |
| DLL3-8 | 1.2 |
| DLL3-9 | 1.2 |
| DLL3-10 | 1.4 |
| DLL3-13 | 1.8 |
| DLL3-14 | 5.4 |
| DLL3-15 | 9.8 |

Example 8.3

Potency of Redirecting Stimulated Human Effector T Cells Against the DLL3 Positive Human Lung Carcinoma Cell Line SHP-77

The cytotoxic activity of DLL3×CD3 bispecific antibody constructs was analyzed in a 51-chromium ($^{51}Cr$) release cytotoxicity assay using the DLL3-positive human lung carcinoma cell line SHP-77 as source of target cells, and stimulated human CD8+ T cells as effector cells. The assay was carried out as described in Example 8.1.

In accordance with the results of the 51-chromium release assays with stimulated enriched human CD8+T lymphocytes as effector cells and human DLL3-transfected CHO cells as target cells, DLL3×CD3 bispecific antibody constructs of the present invention are also potent in cytotoxic activity against natural expresser target cells (see Table 6).

TABLE 6

EC50 values [pM] of DLL3 × CD3 bispecific antibody constructs analyzed in an 18-hour 51-chromium ($^{51}$Cr) release cytotoxicity assay with the DLL3-positive human lung carcinoma cell line SHP-77 as source of target cells, and stimulated enriched human CD8 T cells as effector cells.

| Row | DLL3 × CD3 bispecific antibody construct | EC50 [pM] |
|---|---|---|
| 1 | DLL3-4 | 27 |
| 2 | DLL3-5 | 26 |
| 3 | DLL3-6 | 18 |
| 4 | DLL3-7 | 23 |
| 5 | DLL3-8 | 39 |
| 6 | DLL3-9 | 18 |
| 7 | DLL3-10 | 31 |
| 8 | DLL3-13 | 22 |
| 9 | DLL3-14 | 31 |
| 10 | DLL3-15 | 36 |
| 11 | DLL3-18 | 38 |
| 12 | DLL3-19 | 142 |
| 13 | DLL3-20 | 171 |
| 14 | DLL3-21 | 324 |

Rows 1-10: Antibody constructs according to the invention, which bind to a DLL3 epitope comprised within the region as depicted in SEQ ID NO: 260. (Rows 1-7: Antibody constructs binding to a DLL3 epitope comprised within the EGF-3 region. Rows 8-10: Antibody constructs binding to a DLL3 epitope comprised within the EGF-4 region.) Rows 11-14: Antibody constructs binding to a DLL3 epitope which is comprised within the EGF-5/[EGF-6] region.

Example 8.4

FACS-Based Cytotoxicity Assay with Unstimulated Human PBMC

Isolation of Effector Cells

Human peripheral blood mononuclear cells (PBMC) were prepared by Ficoll density gradient centrifugation from enriched lymphocyte preparations (buffy coats), a side product of blood banks collecting blood for transfusions. Buffy coats were supplied by a local blood bank and PBMC were prepared on the same day of blood collection. After Ficoll density centrifugation and extensive washes with Dulbecco's PBS (Gibco), remaining erythrocytes were removed from PBMC via incubation with erythrocyte lysis buffer (155 mM $NH_4Cl$, 10 mM $KHCO_3$, 100 pM EDTA). Platelets were removed via the supernatant upon centrifugation of PBMC at 100×g. Remaining lymphocytes mainly encompass B and T lymphocytes, NK cells and monocytes. PBMC were kept in culture at 37° C./5% $CO_2$ in RPMI medium (Gibco) with 10% FCS (Gibco).

Depletion of CD14+ and CD56+ Cells

For depletion of CD14+ cells, human CD14 MicroBeads (Milteny Biotec, MACS, #130-050-201) were used, for depletion of NK cells human CD56 MicroBeads (MACS, #130-050-401). PBMC were counted and centrifuged for 10 min at room temperature with 300×g. The supernatant was discarded and the cell pellet resuspended in MACS isolation buffer [80 μL/$10^7$ cells; PBS (Invitrogen, #20012-043), 0.5% (v/v) FBS (Gibco, #10270-106), 2 mM EDTA (Sigma-Aldrich, #E-6511)]. CD14 MicroBeads and CD56 MicroBeads (20 μL/$10^7$ cells) were added and incubated for 15 min at 4-8° C. The cells were washed with MACS isolation buffer (1-2 mL/$10^7$ cells). After centrifugation (see above), supernatant was discarded and cells resuspended in MACS isolation buffer (500 μL/$10^8$ cells). CD14/CD56 negative cells were then isolated using LS Columns (Miltenyi Biotec, #130-042-401). PBMC w/o CD14+/CD56+ cells were cultured in RPMI complete medium i.e. RPMI1640 (Biochrom AG, #FG1215) supplemented with 10% FBS (Biochrom AG, #S0115), 1× non-essential amino acids (Biochrom AG, #K0293), 10 mM Hepes buffer (Biochrom AG, #L1613), 1 mM sodium pyruvate (Biochrom AG, #L0473) and 100 U/mL penicillin/streptomycin (Biochrom AG, #A2213) at 37° C. in an incubator until needed.

Target Cell Labeling

For the analysis of cell lysis in flow cytometry assays, the fluorescent membrane dye $DiOC_{18}$ (DiO) (Molecular Probes, #V22886) was used to label human DLL3- or macaque DLL3-transfected CHO cells as target cells and distinguish them from effector cells. Briefly, cells were harvested, washed once with PBS and adjusted to $10^6$ cell/mL in PBS containing 2% (v/v) FBS and the membrane dye DiO (5 μL/$10^6$ cells). After incubation for 3 min at 37° C., cells were washed twice in complete RPMI medium and the cell number adjusted to 1.25×$10^5$ cells/mL. The vitality of cells was determined using 0.5% (v/v) isotonic EosinG solution (Roth, #45380).

Flow Cytometry Based Analysis

This assay was designed to quantify the lysis of cyno or human DLL3-transfected CHO cells in the presence of serial dilutions of DLL3 bispecific antibody constructs. Equal volumes of DiO-labeled target cells and effector cells (i.e., PBMC w/o CD14+ cells) were mixed, resulting in an E:T cell ratio of 10:1. 160 μl of this suspension were transferred to each well of a 96-well plate. 40 μL of serial dilutions of the DLL3×CD3 bispecific antibody constructs and a negative control bispecific (a CD3-based bispecific antibody construct recognizing an irrelevant target antigen) or RPMI complete medium as an additional negative control were added. The bispecific antibody-mediated cytotoxic reaction proceeded for 48 hours in a 7% $CO_2$ humidified incubator. Then cells were transferred to a new 96-well plate and loss of target cell membrane integrity was monitored by adding propidium iodide (PI) at a final concentration of 1 μg/mL. PI is a membrane impermeable dye that normally is excluded from viable cells, whereas dead cells take it up and become identifiable by fluorescent emission.

Samples were measured by flow cytometry on a FACSCanto II instrument and analyzed by FACSDiva software (both from Becton Dickinson). Target cells were identified as DiO-positive cells. PI-negative target cells were classified as living target cells. Percentage of cytotoxicity was calculated according to the following formula:

$$Cytotoxictiy\ [\%] = \frac{n_{deadtargetcells}}{n_{targetcells}} \times 100$$

$n$ = number of events

Using GraphPad Prism 5 software (Graph Pad Software, San Diego), the percentage of cytotoxicity was plotted against the corresponding bispecific antibody construct concentrations. Dose response curves were analyzed with the four parametric logistic regression models for evaluation of sigmoid dose response curves with fixed hill slope and EC50 values were calculated.

Example 8.5

Potency of Redirecting Unstimulated Human PBMC Against Human DLL3-Transfected CHO Cells The cytotoxic activity of DLL3×CD3 bispecific antibody constructs was analyzed in a FACS-based cytotoxicity assay using CHO cells transfected with human DLL3 as target cells, and unstimulated human PBMC as effector cells. The assay was carried out as described in Example 8.4 above.

The results of the FACS-based cytotoxicity assays with unstimulated human PBMC as effector cells and human DLL3-transfected CHO cells as targets are shown in Table 7.

TABLE 7

EC50 values [pM] of DLL3 × CD3 bispecific antibody constructs as measured in a 48-hour FACS-based cytotoxicity assay with unstimulated human PBMC as effector cells and CHO cells transfected with human DLL3 as target cells.

| Row | DLL3 × CD3 bispecific antibody construct | EC50 [pM] |
|---|---|---|
| Fiogl | DLL3-4 | 53 |
| 2 | DLL3-5 | 36 |
| 3 | DLL3-6 | 44 |
| 4 | DLL3-7 | 40 |
| 5 | DLL3-8 | 43 |
| 6 | DLL3-9 | 43 |
| 7 | DLL3-10 | 40 |
| 8 | DLL3-13 | 116 |
| 9 | DLL3-14 | 66 |
| 10 | DLL3-15 | 57 |
| 11 | DLL3-18 | 169 |
| 12 | DLL3-19 | 107 |
| 13 | DLL3-20 | 171 |
| 14 | DLL3-21 | 85 |

Rows 1-10: Antibody constructs according to the invention, which bind to a DLL3 epitope comprised within the region as depicted in SEQ ID NO: 260. (Rows 1-7: Antibody constructs binding to a DLL3 epitope comprised within the EGF-3 region. Rows 8-10: Antibody constructs binding to a DLL3 epitope comprised within the EGF-4 region.) Rows 11-14: Antibody constructs binding to a DLL3 epitope which is comprised within the EGF-5/[EGF-6] region.

Expectedly, EC50 values were generally higher in cytotoxicity assays with unstimulated PBMC as effector cells compared with cytotoxicity assays using stimulated human CD8+ T cells (see Example 8.2).

Example 8.6

Potency of Redirecting Unstimulated Human PBMC Against the DLL3-Positive Lung Carcinoma Cell Line SHP-77

The cytotoxic activity of DLL3×CD3 bispecific antibody constructs was furthermore analyzed in a FACS-based cytotoxicity assay using the DLL3-positive human lung carcinoma cell line SHP-77 as a source of target cells and unstimulated human PBMC as effector cells. The assay was carried out as described in Example 8.4 above. The results are shown in Table 8.

TABLE 8

EC50 values [pM] of DLL3 × CD3 bispecific antibody constructs as measured in a 48-hour FACS-based cytotoxicity assay with unstimulated human PBMC as effector cells and the human cell line SHP-77 as source of target cells.

| Row | DLL3 × CD3 bispecific antibody construct | EC50 [pM] |
|---|---|---|
| 1 | DLL3-4 | 44 |
| 2 | DLL3-5 | 65 |
| 3 | DLL3-6 | 31 |
| 4 | DLL3-7 | 30 |
| 5 | DLL3-8 | 24 |
| 6 | DLL3-9 | 33 |
| 7 | DLL3-10 | 32 |
| 8 | DLL3-13 | 49 |
| 9 | DLL3-14 | 65 |
| 10 | DLL3-15 | 66 |
| 11 | DLL3-18 | 76 |
| 12 | DLL3-19 | 180 |
| 13 | DLL3-20 | 1540 |
| 14 | DLL3-21 | 770 |

Rows 1-10: Antibody constructs according to the invention, which bind to a DLL3 epitope comprised within the region as depicted in SEQ ID NO: 260. (Rows 1-7: Antibody constructs binding to a DLL3 epitope comprised within the EGF-3 region. Rows 8-10: Antibody constructs binding to a DLL3 epitope comprised within the EGF-4 region.) Rows 11-14: Antibody constructs binding to a DLL3 epitope which is comprised within the EGF-5/[EGF-6] region.

Example 8.7

Potency of Redirecting Macaque T Cells Against Macaque DLL3-Expressing CHO Cells Finally, the cytotoxic activity of DLL3×CD3 bispecific antibody constructs was analyzed in a FACS-based cytotoxicity assay using CHO cells transfected with macaque (cyno) DLL3 as target cells, and the macaque T cell line 4119LnPx (Knappe et al. Blood 95:3256-61 (2000)) as source of effector cells. Target cell labeling of macaque DLL3-transfected CHO cells and flow cytometry based analysis of cytotoxic activity was performed as described above.

Results are shown in Table 9. Macaque T cells from cell line 4119LnPx were induced to efficiently kill macaque DLL3-transfected CHO cells by DLL3×CD3 bispecific antibody constructs according to the invention. The antibody constructs presented potently with 2-digit picomolar EC50-values in this assay, confirming that they are very active in the macaque system.

TABLE 9

EC50 values [pM] of DLL3 × CD3 bispecific antibody constructs as measured in a 48-hour FACS-based cytotoxicity assay with macaque T cell line 4119LnPx as effector cells and CHO cells transfected with macaque DLL3 as target cells.

| Row | DLL3 × CD3 bispecific antibody construct | EC50 [pM] |
|---|---|---|
| 1 | DLL3-4 | 36 |
| 2 | DLL3-5 | 42 |
| 3 | DLL3-6 | 40 |
| 4 | DLL3-7 | 101 |
| 5 | DLL3-8 | 44 |
| 6 | DLL3-9 | 58 |
| 7 | DLL3-10 | 42 |
| 8 | DLL3-13 | 65 |
| 9 | DLL3-14 | 28 |
| 10 | DLL3-15 | 32 |
| 11 | DLL3-18 | 134 |
| 12 | DLL3-19 | 66 |

TABLE 9-continued

EC50 values [pM] of DLL3 × CD3 bispecific antibody constructs as measured in a 48-hour FACS-based cytotoxicity assay with macaque T cell line 4119LnPx as effector cells and CHO cells transfected with macaque DLL3 as target cells.

| Row | DLL3 × CD3 bispecific antibody construct | EC50 [pM] |
|---|---|---|
| 13 | DLL3-20 | 231 |
| 14 | DLL3-21 | 86 |

Rows 1-10: Antibody constructs according to the invention, which bind to a DLL3 epitope comprised within the region as depicted in SEQ ID NO: 260. (Rows 1-7: Antibody constructs binding to a DLL3 epitope comprised within the EGF-3 region. Rows 8-10: Antibody constructs binding to a DLL3 epitope comprised within the EGF-4 region.) Rows 11-14: Antibody constructs binding to a DLL3 epitope which is comprised within the EGF-5/[EGF-6] region.

Example 9

Monomer to Dimer Conversion after (i) Three Freeze/Thaw Cycles and (ii) 7 Days of Incubation at 250 μg/Ml Bispecific DLL3×CD3 antibody monomeric construct were subjected to different stress conditions followed by high performance SEC to determine the percentage of initially monomeric antibody construct, which had been converted into dimeric antibody construct.

(i) 25 μg of monomeric antibody construct were adjusted to a concentration of 250 μg/ml with generic formulation buffer and then frozen at −80° C. for 30 min followed by thawing for 30 min at room temperature. After three freeze/thaw cycles the dimer content was determined by HP-SEC.

(ii) 25 μg of monomeric antibody construct were adjusted to a concentration of 250 μg/ml with generic formulation buffer followed by incubation at 37° C. for 7 days. The dimer content was determined by HP-SEC.

A high resolution SEC Column TSK Gel G3000 SWXL (Tosoh, Tokyo-Japan) was connected to an Akta Purifier 10 FPLC (GE Lifesciences) equipped with an A905 Autosampler. Column equilibration and running buffer consisted of 100 mM KH2PO4-200 mM Na2SO4 adjusted to pH 6.6. The antibody solution (25 pg protein) was applied to the equilibrated column and elution was carried out at a flow rate of 0.75 ml/min at a maximum pressure of 7 MPa. The whole run was monitored at 280, 254 and 210 nm optical absorbance. Analysis was done by peak integration of the 210 nm signal recorded in the Akta Unicorn software run evaluation sheet. Dimer content was calculated by dividing the area of the dimer peak by the total area of monomer plus dimer peak.

The results are shown in Table 10 below. The DLL3×CD3 bispecific antibody constructs of the invention presented with dimer percentages of 0.0% after three freeze/thaw cycles, and with dimer percentages of ≤2% after 7 days of incubation at 37° C.

TABLE 10

Percentage of monomeric versus dimeric DLL3 × CD3 bispecific antibody constructs as determined by High Performance Size Exclusion Chromatography (HP-SEC).

| DLL3 × CD3 bispecific antibody construct | Percentage of dimer after three freeze/thaw cycles | Percentage of dimer after 7 days of incubation at 37° C. |
|---|---|---|
| DLL3-4 | 0.7 | 0.0 |
| DLL3-5 | 1.5 | 0.0 |
| DLL3-6 | 1.3 | 0.0 |
| DLL3-7 | 1.2 | 0.0 |
| DLL3-8 | 1.5 | 0.0 |
| DLL3-9 | 1.8 | 0.0 |
| DLL3-10 | 0.6 | 0.0 |
| DLL3-13 | 1.6 | 0.0 |
| DLL3-14 | 0.4 | 0.0 |
| DLL3-15 | 1.2 | 0.0 |

Example 10

Thermostability

Antibody aggregation temperature was determined as follows: 40 μl of antibody construct solution at 250 μg/ml were transferred into a single use cuvette and placed in a Wyatt Dynamic Light Scattering device DynaPro Nanostar (Wyatt). The sample was heated from 40° C. to 70° C. at a heating rate of 0.5° C./min with constant acquisition of the measured radius. Increase of radius indicating melting of the protein and aggregation was used by the software package delivered with the DLS device to calculate the aggregation temperature of the antibody construct.

All tested DLL3×CD3 bispecific antibody constructs of the invention showed thermal stability with aggregation temperatures >45° C., as shown in Table 11 below. The group of antibody constructs binding to an epitope of DLL3 which is comprised within the EGF-4 region (as depicted in SEQ ID NO: 259) even had a thermal stability of ≥50° C., more precisely, of ≥54° C.

TABLE 11

Thermostability of the bispecific antibody constructs as determined by DLS (dynamic light scattering)

| DLL3 × CD3 bispecific antibody construct | Thermostability (DLS ° C. aggregation) |
|---|---|
| DLL3-4 | 59.3 |
| DLL3-5 | 45.4 |
| DLL3-6 | 58.8 |
| DLL3-7 | 58.2 |
| DLL3-8 | 49.8 |
| DLL3-9 | 49.6 |
| DLL3-10 | 52.9 |
| DLL3-13 | 54.0 |
| DLL3-14 | 57.0 |
| DLL3-15 | 56.3 |

Example 11

Stability after Incubation for 24 Hours in Human Plasma

Purified bispecific antibody constructs were incubated at a ratio of 1:5 in a human plasma pool at 37° C. for 96 hours at a final concentration of 2-20 pg/ml. After plasma incubation the antibody constructs were compared in a 51-chromium release assay with stimulated enriched human CD8+ T cells and human DLL3-transfected CHO cells at a starting concentration of 0.01-0.1 pg/ml and with an effector to target cell (E:T) ratio of 10:1 (assay as described in Example 8.1). Non-incubated, freshly thawed bispecific antibody constructs were included as controls.

Figure 5:
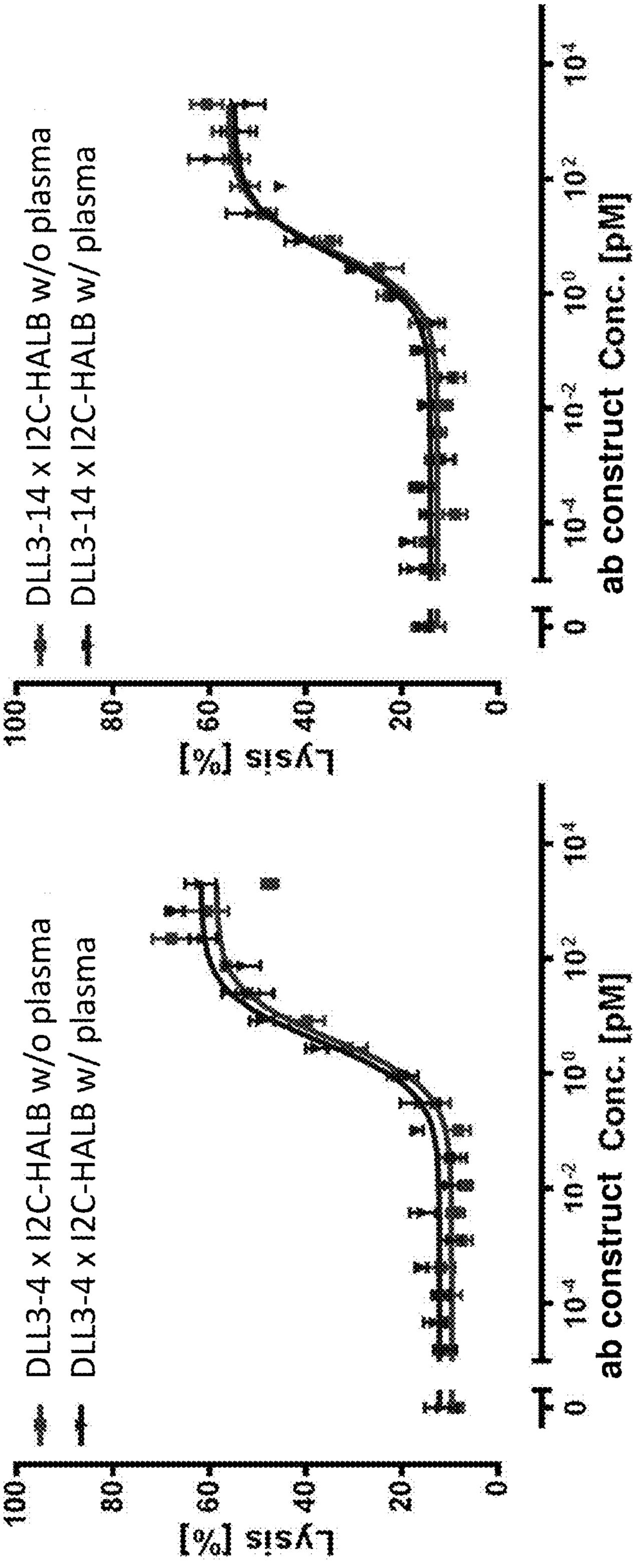

The results are shown in Table 12 below; exemplary results for the two antibody constructs DLL-4 and DLL-14 are also shown in FIG. 5. All tested antibody constructs had a very favourable plasma stability (EC50 plasma/EC50 control) of ≤2.5. The group of antibody constructs binding to an epitope of DLL3 which is comprised within the EGF-4 region (as depicted in SEQ ID NO: 259) even had a plasma stability of ≤1.5, more precisely, of ≤1.1.

TABLE 12

EC50 values of the antibody constructs with and without plasma incubation and calculated plasma/control value

| DLL3 × CD3 bispecific antibody construct | $EC_{50}$ [pM] w/plasma | $EC_{50}$ [pM] w/o plasma | Plasma to Control ratio ($EC_{50}$ plasma/ $EC_{50}$ control) |
|---|---|---|---|
| DLL3-4 | 3.6 | 3.8 | 0.9 |
| DLL3-5 | 5.4 | 4.2 | 1.3 |
| DLL3-6 | 4.8 | 2.1 | 2.3 |
| DLL3-7 | 2.7 | 2.2 | 1.2 |
| DLL3-8 | 1.0 | 1.2 | 0.8 |
| DLL3-9 | 1.2 | 1.2 | 1.0 |
| DLL3-10 | 2.5 | 1.4 | 1.8 |
| DLL3-13 | 2.0 | 1.8 | 1.1 |
| DLL3-14 | 4.8 | 5.4 | 0.9 |
| DLL3-15 | 7.8 | 9.8 | 0.8 |

Example 12

Turbidity at 2500 μg/Ml Antibody Concentration 1 ml of purified antibody construct solution of a concentration of 250 μg/ml was concentrated by spin concentration units to 2500 μg/ml. After 16 h storage at 5° C. the turbidity of the antibody solution was determined by OD340 nm optical absorption measurement against the generic formulation buffer.

The results are shown in Table 13 below. All tested antibody constructs have a very favourable turbidity of ≤0.1, with the exception of one construct with a turbidity slightly above 0.1. The group of antibody constructs binding to an epitope of DLL3 which is comprised within the EGF-4 region (as depicted in SEQ ID NO: 259) even have a turbidity of ≤0.08.

TABLE 13

Turbidity of the antibody constructs after concentration to 2.5 mg/ml over night

| DLL3 × CD3 bispecific antibody construct | Turbidity at 2500 μg/ml [OD340] |
|---|---|
| DLL3-4 | 0.073 |
| DLL3-5 | 0.106 |
| DLL3-6 | 0.080 |
| DLL3-7 | 0.089 |
| DLL3-8 | 0.069 |
| DLL3-9 | 0.085 |
| DLL3-10 | 0.091 |
| DLL3-13 | 0.075 |
| DLL3-14 | 0.073 |
| DLL3-15 | 0.078 |

Example 13

Protein Homogeneity by High Resolution Cation Exchange Chromatography

The protein homogeneity the antibody constructs of the invention was analyzed by high resolution cation exchange chromatography CIEX.

50 μg of antibody construct monomer were diluted with 50 ml binding buffer A (20 mM sodium dihydrogen phosphate, 30 mM NaCl, 0.01% sodium octanate, pH 5.5), and 40 ml of this solution were applied to a 1 ml BioPro SP-F column (YMC, Germany) connected to an Akta Micro FPLC device (GE Healthcare, Germany). After sample binding, a wash step with further binding buffer was carried out. For protein elution, a linear increasing salt gradient using buffer B (20 mM sodium dihydrogen phosphate, 1000 mM NaCl, 0.01% sodium octanate, pH 5.5) up to 50% percent buffer B was applied over 10 column volumes. The whole run was monitored at 280, 254 and 210 nm optical absorbance. Analysis was done by peak integration of the 280 nm signal recorded in the Akta Unicorn software run evaluation sheet.

The results are shown in Table 14 below. All tested antibody constructs have a very favourable homogeneity of 80% (area under the curve (=AUC) of the main peak), The group of antibody constructs binding to an epitope of DLL3 which is comprised within the EGF-3 region (as depicted in SEQ ID NO: 258) even have a homogeneity of 90%.

TABLE 14

Protein homogeneity of the antibody constructs (% AUC of main peak)

| DLL3 × CD3 bispecific antibody construct | Protein homogeneity % AUC of main peak |
|---|---|
| DLL3-4 | 96 |
| DLL3-5 | 100 |
| DLL3-6 | 95 |
| DLL3-7 | 93 |
| DLL3-8 | 100 |
| DLL3-9 | 93 |
| DLL3-10 | 90 |
| DLL3-13 | 100 |
| DLL3-14 | 100 |
| DLL3-15 | 83 |

Example 14

Surface Hydrophobicity as Measured by HIC Butyl

The surface hydrophobicity of bispecific antibody constructs of the invention was tested in Hydrophobic Interaction Chromatography HIC in flow-through mode.

50 μg of antibody construct monomer were diluted with generic formulation buffer to a final volume of 500 μl (10 mM citric acid, 75 mM lysine HCl, 4% trehalose, pH 7.0) and applied to a 1 ml Butyl Sepharose FF column (GE Healthcare, Germany) connected to a Akta Purifier FPLC system (GE Healthcare, Germany). The whole run was monitored at 280, 254 and 210 nm optical absorbance. Analysis was done by peak integration of the 280 nm signal recorded in the Akta Unicorn software run evaluation sheet. Elution behavior was evaluated by comparing area and velocity of rise and decline of protein signal thereby indicating the strength of interaction of the BiTE albumin fusion with the matrix.

The antibody constructs had a good elution behaviour, which was mostly rapid and complete.

Example 15

Potency Gap Between the Monomeric and the Dimeric Isoform of Bispecific Antibody Constructs In order to determine the difference in cytotoxic activity between the monomeric and the dimeric isoform of individual DLL3×CD3 bispecific antibody constructs (referred to as potency gap), an 18 hour 51-chromium release cytotoxicity assay was carried out as described hereinabove (Example 8.1) with purified bispecific antibody construct monomer and dimer. Effector cells were stimulated enriched human CD8+ T cells. Target cells were hu DLL3 transfected CHO cells. Effector to target cell (E:T) ratio was 10:1. The potency gap was calculated as ratio between EC50 values.

Figure 6:
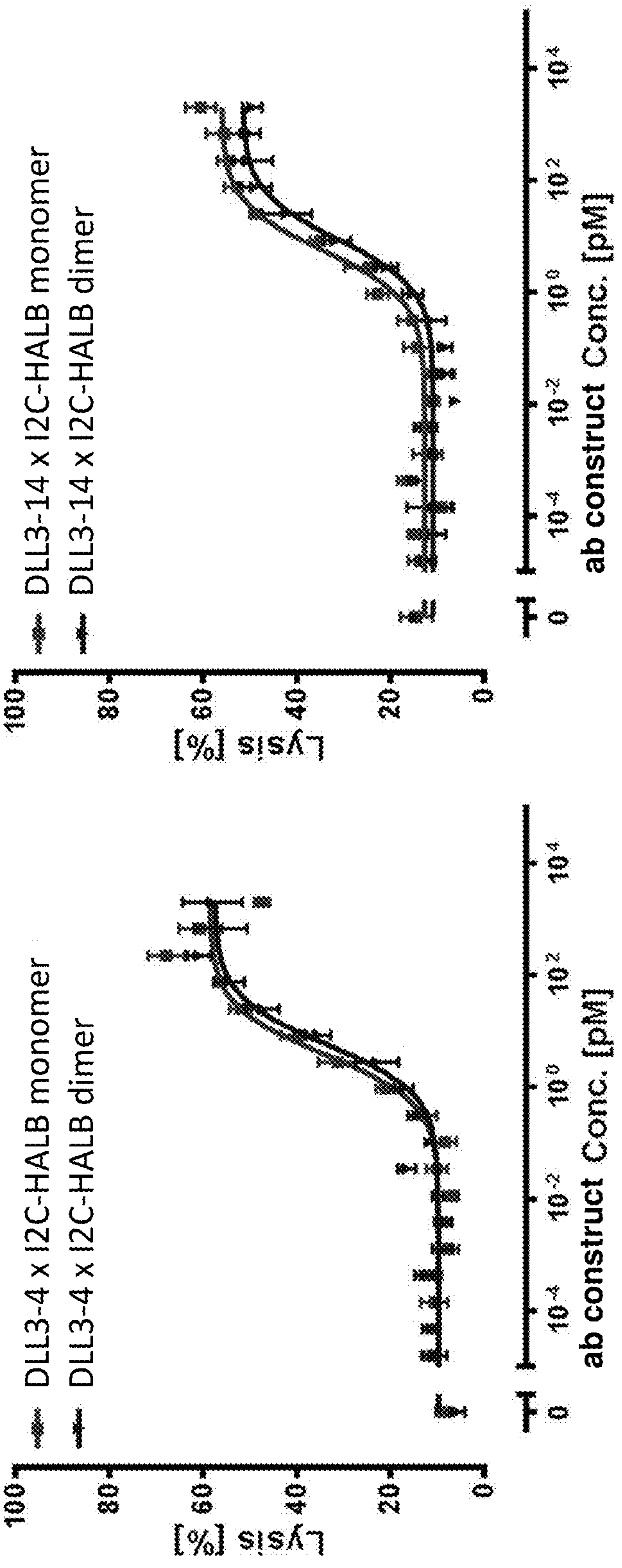

The results are shown in Table 15 below; exemplary results for the two antibody constructs DLL-4 and DLL-14 are also shown in FIG. 6. Potency gaps of the tested DLL3×CD3 bispecific antibody constructs were between 0.2 and 1.0. There is hence no substantially more active dimer compared to its respective monomer.

TABLE 15

Potency gap between the monomeric and the dimeric isoform

| DLL3 × CD3 bispecific antibody construct | $EC_{50}$ [pM] monomer | $EC_{50}$ [pM] dimer | Ratio $EC_{50}$ monomer/ $EC_{50}$ dimer |
|---|---|---|---|
| DLL3-4 | 3.8 | 5.7 | 0.7 |
| DLL3-5 | 4.2 | 11 | 0.4 |
| DLL3-6 | 2.1 | 13 | 0.2 |
| DLL3-7 | 2.2 | 4.2 | 0.5 |
| DLL3-8 | 1.2 | 3.4 | 0.4 |
| DLL3-9 | 1.2 | 3.8 | 0.3 |
| DLL3-10 | 1.4 | 1.4 | 1.0 |
| DLL3-13 | 1.8 | 3.0 | 0.6 |
| DLL3-14 | 5.4 | 8.7 | 0.6 |
| DLL3-15 | 9.8 | 25 | 0.4 |

Example 16

In Vitro Internalization Assay

Figure 7:
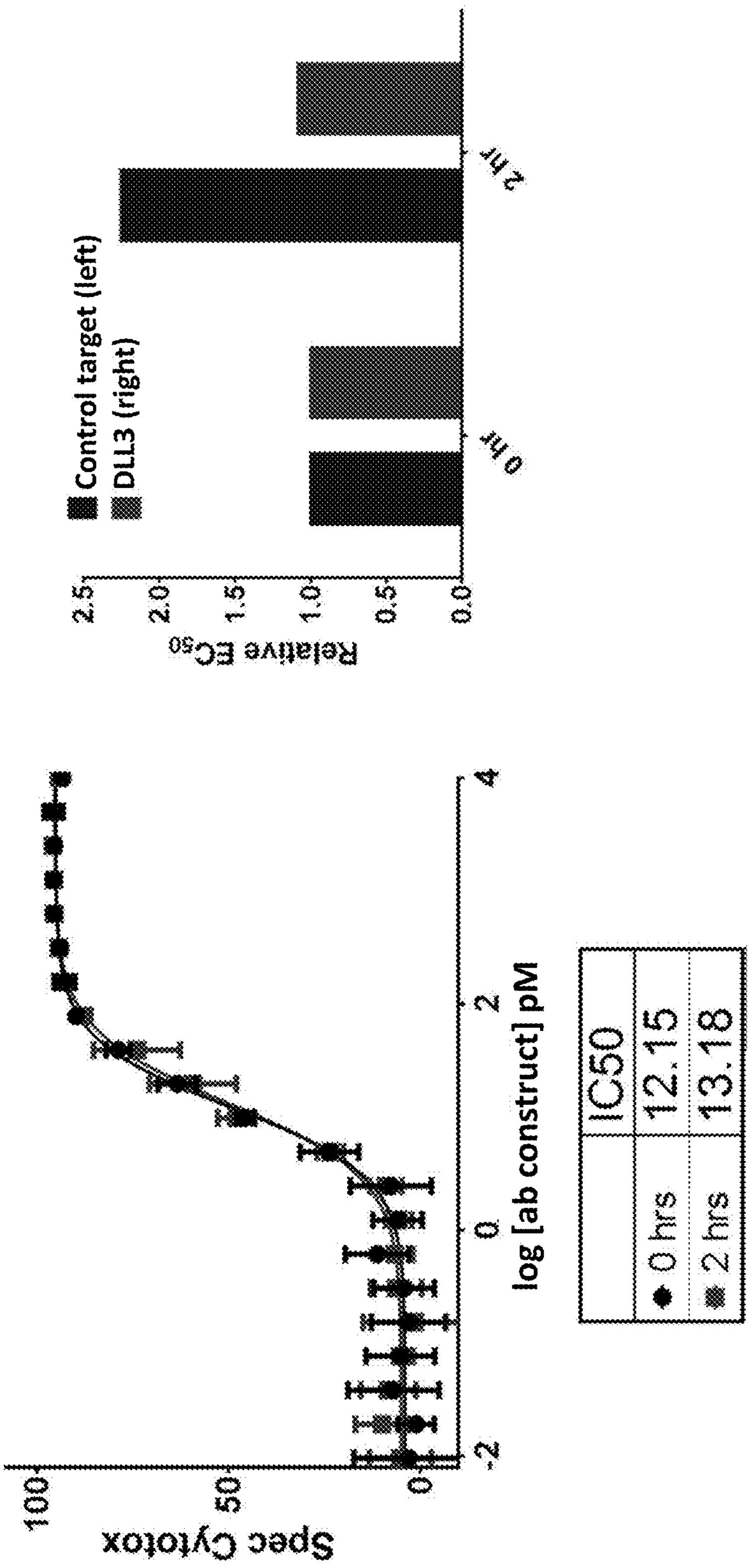

Changes in the potency of the DLL3×CD3 bispecific antibody construct as a function of preincubation of the construct on the target cells in the absence of T cells were measured. If the antibody construct is internalized, it should undergo lysosomal degradation. The effective concentration should decrease with time, and thus the apparent potency should decrease as well. The effect is observed with other targets, for which this is a known phenomenon, but no impact was observed with the DLL3×CD3 bispecific antibody construct. The assay was carried out as follows:

T cells were counted and diluted to a concentration of $1\times10^5$/ml in assay media. SHP-77 cells were counted and plated at 2500 cells per well (cpw). The antibody construct was diluted serially 1:2 (with Bravo), at a starting concentration of 100 nM. The antibody construct was added to the culture assay plates to allow for 0 hours, 1 hour or 2 hours of incubation prior to addition of the T cells. Then the T cells were plated at 25000 cpw, and the assay was incubated for 48 hours at 37° C. SHP-77 cell survival was analyzed with the Steady-Glo® system (25 µl/well). The results are shown in FIG. 7 and suggest no significant internalization of the antibody construct DLL3-4×CD3 (12C).

Example 17

Shedding Study

In order to analyze whether the cytotoxic activity of the DLL3×CD3 bispecific antibody constructs of the invention is significantly impaired by the presence of shed DLL, the following assay was carried out: T cells were counted and diluted to a concentration of $1\times10^5$/ml in assay media. SHP-77 cells were counted and diluted to a concentration of $1.25\times10^5$/ml in assay media with increasing concentrations of soluble DLL3 between 0.3 nM and 12 nM. SHP-77 cells were plated at 2500 cells per well (cpw), and T cells were added at 25000 cpw. The antibody construct was diluted serially 1:2 (with Bravo), and added to the culture assay (with Bravo). Incubation occurred for 48 hours at 37° C. SHP-77 cell survival was analyzed with the Steady-Glo® system (25 µl/well).

Example 18

Mouse Xenograft Efficacy Study

The anti-tumor activity of an HLE DLL3×CD3 bispecific antibody construct (SEQ ID NO: 517) was tested in a model of female NOD/SCID mice which were subcutaneously injected on day 1 of the study with $5\times10^6$ human DLL3 positive SCLC (SHP-77 luc) or $5\times10^6$ human DLL3 positive melanoma (WM 266-4) cells. Effector cells (2×107 in vitro expanded and activated living human CD3+ T cells) were injected intraperitoneally on day 12. Treatment start was on day 16 (WM 266-4) or on day 18 (SHP-77 luc). The antibody construct was administered four times every five days (q5dx4) by i.v. bolus injections. The treatment groups were as follows:

- SCLC model (SHP-77 luc)/7 mice per group
  - Vehicle-treated group with T cells
  - DLL3×CD3 bispecific antibody construct: 10 mg/kg per administration
- Melanoma model (WM266-4)/9 mice per group
  - Vehicle-treated group with T cells
  - DLL3×CD3 bispecific antibody construct: 10 mg/kg per administration
  - DLL3×CD3 bispecific antibody construct: 2 mg/kg per administration Tumors were measured by caliper during the study and progress evaluated by intergroup comparison of tumor volumes (TV). The tumor growth inhibition T/C [%] on day x is determined by calculating the tumor volume as T/C (%)=100×(median TV of analyzed group)/(median TV of control group), and the calculated values are depicted in the following table 16:

TABLE 16

T/C values of the mouse xenograft studies with SHP-77 luc cells and WM266-4 cells

| Day of Study | T/C (%) SHP-77 model 10 mg/kg | T/C (%) WM266-4 model 10 mg/kg | T/C (%) WM266-4 model 2 mg/kg |
|---|---|---|---|
| 15 | 103 | 101 | 101 |
| 17 | 92 | 76 | 77 |
| 20 | 64 | 42 | 47 |
| 23 | 50 | 36 | 38 |
| 26 | 52 | 31 | 35 |
| 29 | 34 | 46 | 40 |
| 31 | 33 | 56 | 55 |
| 33 | 30 | 64 | 75 |
| 36 | 24 | n.a | n.a |
| 38 | 19 | n.a | n.a |

The results are furthermore shown in FIGS. 8A and 8B. Significant tumor growth inhibition was shown in both tumor models and at both tested dose levels of 2 and 10 mg/kg.

Example 19

Cyno Exploratory Toxicology Study

An exploratory toxicology study was carried out with a non half-life extended DLL3×CD3 bispecific antibody construct (SEQ ID NO: 554). Three female cynomolgus monkeys were dosed via continuous i.v. infusion for 16 days (5, 15, and 45 µg/kg/day for 3 days each, followed by 100 µg/kg/day for 7 days). No test article-related clinical observations, changes in body temperature, food consumption or body weight were observed.

Consistent with expectations for the pharmacology of a DLL3×CD3 bispecific antibody construct, circulating T lymphocyte populations (total T-lymphocytes, T-helper and T-cytotoxic lymphocytes, NK cells, B-lymphocytes, and CD25+ activated T-lymphocytes) were decreased on the first day of dosing and remained lower throughout the duration of the study in all animals. Activation markers (CD69 and CD25 on activated T cells) were increased on day 1, but not at later time points in the study.

To summarize, the DLL3×CD3 bispecific antibody construct was very well tolerated even at the highest dose tested (100 µg/kg/d, >300×$EC_{50}$).

Example 20

Cyno PK Studys

A cyno PK study was performed with naïve male cynomolgus monkeys. Three different albumin-fused DLL3×CD3 (12C) bispecific antibody constructs (DLL3-4, DLL3-6 and DLL3-14) were administered as i.v. single bolus at a concentration of 12 µg/kg. For each of the molecules a group of two animals was used.

A separate cyno PK study was performed under the same conditions, but with DLL3-4 in different Fc fusion versions.

Blood samples were collected pre-dose and at 0.05, 0.5, 1, 4, 8, 24, 48, 72, 120, 168, 240, and 336 hours post-dose. Serum was prepared for determination of serum concentrations of the molecules in an immunoassay. The assay was performed by capturing the antibody constructs via their target moiety, while an antibody directed against the CD3-binding part of the construct was used for detection. The serum concentration-time profiles were used to determine PK parameters. The pharmacokinetic parameters were determined using standard non-compartmental analysis (NCA) methods. The following PK parameters were assessed: $AUC_{inf}$ (Area under the serum concentration-time curve), $V_{ss}$ (volume of distribution at steady state), CL (systemic clearance) and terminal $t_{1/2}$ (terminal half-life). For all antibody constructs, serum levels were quantifiable for all time points in all animals after their administration. No clinical observations were made in any of the treated animals.

Figure 9B:
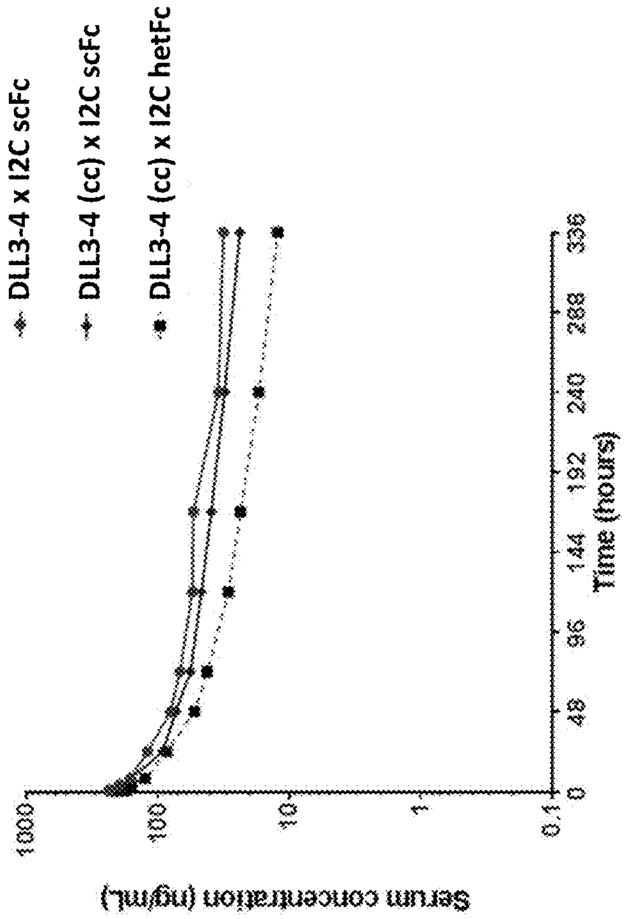
Figure 9A:
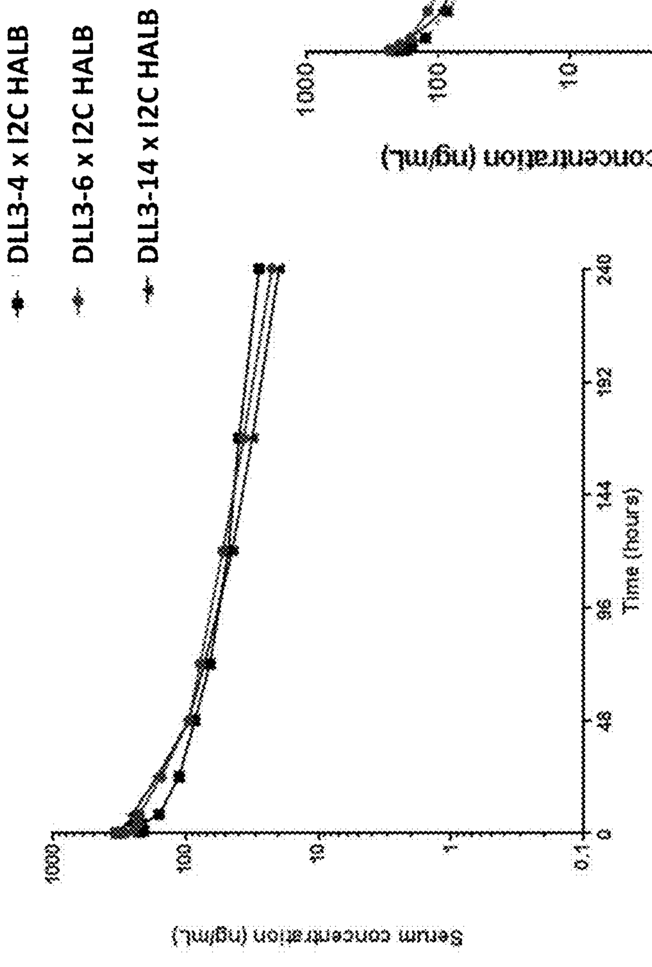

The pharmacokinetics of the tested antibody constructs are shown in FIGS. 9A-9B, and the PK parameters are summarized as mean of n=2 in table 17 below.

The albumin-fused constructs showed a favorable PK profile consistent with a once or twice weekly dosing schedule in a human patient. An even more favorable PK profile supporting once weekly dosing or even every other week dosing was observed with an Fc fusion construct (scFc).

TABLE 17

Pharmacokinetic parameters of HLE variants of DLL3 × CD3 bispecific antibody constructs in cynomolgus monkeys

| Antibody construct | $AUC_{inf}$ [ng * h/mL] | $V_{SS}$ [mL/kg] | CL [mL/h/kg] | $t_{1/2}$ [h] |
|---|---|---|---|---|
| DLL3-4 × I2C HALB | 20,669 | 70 | 0.58 | 98 |
| DLL3-6 × I2C HALB | 20,228 | 67 | 0.59 | 103 |
| DLL3-14 × I2C HALB | 21,597 | 107 | 0.55 | 154 |
| DLL3-4 × I2C scFc | 29,746 | 118 | 0.40 | 213 |
| DLL3-4 (cc) × I2C scFc | 24,769 | 144 | 0.48 | 234 |
| DLL3-4 × I2C hetero Fc | 14,639 | 166 | 0.82 | 173 |

TABLE 18

| SEQ ID NO | DLL3-epitope | Designation | Format / Source | Amino acid sequence |
|---|---|---|---|---|
| 1 | | DLL3-1 | VH CDR1 | DYGIH |
| 2 | | DLL3-1 | VH CDR2 | VISYHGSNKYYARSVKG |
| 3 | | DLL3-1 | VH CDR3 | EIPFGMDV |
| 4 | | DLL3-1 | VL CDR1 | RSSQSLLHSDGYNYLD |
| 5 | | DLL3-1 | VL CDR2 | LGSNRAS |
| 6 | | DLL3-1 | VL CDR3 | MQALQTPLT |
| 7 | | DLL3-1 | VH | QVQLVESGGGVVQSGRSLRLSCAASGFTFSDYGIHWVRQAPGKGLEWVAVISYHGSNKYYAR SVKGRFTVSRDNSKNTLYLQMNSLRAEDTAVYYCAREIPFGMDVWGQGTTVTVSS |
| 8 | | DLL3-1 | VL | DIVMTQTPLSLPVTPGEPASISCRSSQSLLHSDGYNYLDWYLQKPGQSPQLLIYLGSNRASG VPDRFSGSGSGTDFTLTISRVEAEDVGVYYCMQALQTPLTFGGGTKVDIK |
| 9 | N-term | DLL3-1 | scFv | QVQLVESGGGVVQSGRSLRLSCAASGFTFSDYGIHWVRQAPGKGLEWVAVISYHGSNKYYAR SVKGRFTVSRDNSKNTLYLQMNSLRAEDTAVYYCAREIPFGMDVWGQGTTVTVSSGGGGSGG GGSGGGGSDIVMTQTPLSLPVTPGEPASISCRSSQSLLHSDGYNYLDWYLQKPGQSPQLLIY LGSNRASGVPDRFSGSGSGTDFTLTISRVEAEDVGVYYCMQALQTPLTFGGGTKVDIK |
| 10 | | DLL3-1 xI2C | bispecific molecule | QVQLVESGGGVVQSGRSLRLSCAASGFTFSDYGIHWVRQAPGKGLEWVAVISYHGSNKYYAR SVKGRFTVSRDNSKNTLYLQMNSLRAEDTAVYYCAREIPFGMDVWGQGTTVTVSSGGGGSGG GGSGGGGSDIVMTQTPLSLPVTPGEPASISCRSSQSLLHSDGYNYLDWYLQKPGQSPQLLIY LGSNRASGVPDRFSGSGSGTDFTLTISRVEAEDVGVYYCMQALQTPLTFGGGTKVDIKSGGG GSEVQLVESGGGLVQPGGSLKLSCAASGFTFNKYAMNWVRQAPGKGLEWVARIRSKYNNYAT |

TABLE 18-continued

| SEQ ID NO | DLL3-epi-tope | Desig-nation | Format / Source | Amino acid sequence |
|---|---|---|---|---|
| | | | | YYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 11 | | DLL3-2 | VH CDR1 | GYYMH |
| 12 | | DLL3-2 | VH CDR2 | WINPNSGDTNYAQKFQG |
| 13 | | DLL3-2 | VH CDR3 | DANIAALDAFEI |
| 14 | | DLL3-2 | VL CDR1 | RASQSISSYLN |
| 15 | | DLL3-2 | VL CDR2 | AASSLQS |
| 16 | | DLL3-2 | VL CDR3 | QQSYSTPLT |
| 17 | | DLL3-2 | VH | QVQLVQSGAEVKKPGASVKVSCKASGYTFTGYYMHWVRQAPGQGLEWMGWINPNSGDTNYAQKFQGRVTMTRDTSISTAYMELSRLTSDDTAVYYCARDANIAALDAFEIWGQGTMVTVSS |
| 18 | | DLL3-2 | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK |
| 19 | N-term. | DLL3-2 | scFv | QVQLVQSGAEVKKPGASVKVSCKASGYTFTGYYMHWVRQAPGQGLEWMGWINPNSGDTNYAQKFQGRVTMTRDTSISTAYMELSRLTSDDTAVYYCARDANIAALDAFEIWGQGTMVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK |
| 20 | | DLL3-2 xI2C | bispecific molecule | QVQLVQSGAEVKKPGASVKVSCKASGYTFTGYYMHWVRQAPGQGLEWMGWINPNSGDTNYAQKFQGRVTMTRDTSISTAYMELSRLTSDDTAVYYCARDANIAALDAFEIWGQGTMVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 21 | | DLL3-3 | VH CDR1 | SYGMH |
| 22 | | DLL3-3 | VH CDR2 | VISYHGRDTYYARSVKG |
| 23 | | DLL3-3 | VH CDR3 | DGATVTSYYYSGMDV |
| 24 | | DLL3-3 | VL CDR1 | RASQGISNYLA |
| 25 | | DLL3-3 | VL CDR2 | LASSLQS |
| 26 | | DLL3-3 | VL CDR3 | QQYNFYPFT |
| 27 | | DLL3-3 | VH | QVQLVESGGGVVQPGRSLRLSCAASGFTFSSYGMHWVRQAPGKGLEWVAVISYHGRDTYYARSVKGRFTISRDNSKNTLYLHMNSLRAEDTAVYYCARDGATVTSYYYSGMDVWGQGTTVTVSSK |
| 28 | | DLL3-3 | VL | DIQMTQSPSSLSASVGDRVTITCRASQGISNYLAWFQQKPGKAPKSLIYLASSLQSGVPSKFSGSGSGTDFTLTISSLQPEDFATYYCQQYNFYPFTFGPGTKVDIK |
| 29 | EGF-1 | DLL3-3 | scFv | QVQLVESGGGVVQPGRSLRLSCAASGFTFSSYGMHWVRQAPGKGLEWVAVISYHGRDTYYARSVKGRFTISRDNSKNTLYLHMNSLRAEDTAVYYCARDGATVTSYYYSGMDVWGQGTTVTVSSGGGGSGGGGSGGGGSDIQMTQSPSSLSASVGDRVTITCRASQGISNYLAWFQQKPGKAPKSLIYLASSLQSGVPSKFSGSGSGTDFTLTISSLQPEDFATYYCQQYNFYPFTFGPGTKVDIK |
| 30 | | DLL3-3 xI2C | bispecific molecule | QVQLVESGGGVVQPGRSLRLSCAASGFTFSSYGMHWVRQAPGKGLEWVAVISYHGRDTYYARSVKGRFTISRDNSKNTLYLHMNSLRAEDTAVYYCARDGATVTSYYYSGMDVWGQGTTVTVSSGGGGSGGGGSGGGGSDIQMTQSPSSLSASVGDRVTITCRASQGISNYLAWFQQKPGKAPKSLIYLASSLQSGVPSKFSGSGSGTDFTLTISSLQPEDFATYYCQQYNFYPFTFGPGTKVDIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 31 | | DLL3-4 | VH CDR1 | SYYWS |
| 32 | | DLL3-4 | VH CDR2 | YVYYSGTTNYNPSLKS |

TABLE 18-continued

| SEQ ID NO | DLL3-epi-tope | Desig-nation | Format / Source | Amino acid sequence |
|---|---|---|---|---|
| 33 | | DLL3-4 | VH CDR3 | IAVTGFYFDY |
| 34 | | DLL3-4 | VL CDR1 | RASQRVNNNYLA |
| 35 | | DLL3-4 | VL CDR2 | GASSRAT |
| 36 | | DLL3-4 | VL CDR3 | QQYDRSPLT |
| 37 | | DLL3-4 | VH | QVQLQESGPGLVKPSETLSLTCTVSGGSISSYYWSWIRQPPGKGLEWIGYVYYSGTTNYNPS LKSRVTISVDTSKNQFSLKLSSVTAADTAVYYCASIAVTGFYFDYWGQGTLVTVSS |
| 38 | | DLL3-4 | VL | EIVLTQSPGTLSLSPGERVTLSCRASQRVNNNYLAWYQQRPGQAPRLLIYGASSRATGIPDR FSGSGSGTDFTLTISRLEPEDFAVYYCQQYDRSPLTFGGGTKLEIK |
| 39 | EGF-3 | DLL3-4 | scFv | QVQLQESGPGLVKPSETLSLTCTVSGGSISSYYWSWIRQPPGKGLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGGGTKLEIK |
| 40 | | DLL3-4 xI2C | bispecific molecule | QVQLQESGPGLVKPSETLSLTCTVSGGSISSYYWSWIRQPPGKGLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGGGTKLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 41 | | DLL3-5 | VH CDR1 | SYYWS |
| 42 | | DLL3-5 | VH CDR2 | YIYYSGRTNYYPSLKS |
| 43 | | DLL3-5 | VH CDR3 | IAVAGFFFDY |
| 44 | | DLL3-5 | VL CDR1 | RASQSVNKNYLA |
| 45 | | DLL3-5 | VL CDR2 | GASSRAT |
| 46 | | DLL3-5 | VL CDR3 | QQYDRSPLT |
| 47 | | DLL3-5 | VH | QVQLQESGPGLVKPSETLSLTCTVSGGSISSYYWSWIRQPPGKGLEWIGYIYYSGRTNYYPS LKSRVTISIDTSKNQFSLKLSSVTAADTAVYYCARIAVAGFFFDYWGQGTLVTVSS |
| 48 | | DLL3-5 | VL | EIVLTQSPGTLSLSPGERATLSCRASQSVNKNYLAWYQQKPGQAPRLLIYGASSRATGIPDR FSGSGSGTDFTLTISRLEPEDFAVYYCQQYDRSPLTFGGGTKLEIK |
| 49 | EGF-3 | DLL3-5 | scFv | QVQLQESGPGLVKPSETLSLTCTVSGGSISSYYWSWIRQPPGKGLEWIGYIYYSGRTNYYPS LKSRVTISIDTSKNQFSLKLSSVTAADTAVYYCARIAVAGFFFDYWGQGTLVTVSSGGGGSG GGGSGGGGSEIVLTQSPGTLSLSPGERATLSCRASQSVNKNYLAWYQQKPGQAPRLLIYGAS SRATGIPDRFSGSGSGTDFTLTISRLEPEDFAVYYCQQYDRSPLTFGGGTKLEIK |
| 50 | | DLL3-5 xI2C | bispecific molecule | QVQLQESGPGLVKPSETLSLTCTVSGGSISSYYWSWIRQPPGKGLEWIGYIYYSGRTNYYPS LKSRVTISIDTSKNQFSLKLSSVTAADTAVYYCARIAVAGFFFDYWGQGTLVTVSSGGGGSG GGGSGGGGSEIVLTQSPGTLSLSPGERATLSCRASQSVNKNYLAWYQQKPGQAPRLLIYGAS SRATGIPDRFSGSGSGTDFTLTISRLEPEDFAVYYCQQYDRSPLTFGGGTKLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 51 | | DLL3-6 | VH CDR1 | SFYWS |
| 52 | | DLL3-6 | VH CDR2 | YIYYSGTTNYNPSLKS |
| 53 | | DLL3-6 | VH CDR3 | IAVAGFFFDY |
| 54 | | DLL3-6 | VL CDR1 | RASQSVNKNYLA |
| 55 | | DLL3-6 | VL CDR2 | GASSRAT |
| 56 | | DLL3-6 | VL CDR3 | QQYDRSPLT |
| 57 | | DLL3-6 | VH | QVQLQESGPGLVKPSETLSLTCTVSGASISSFYWSWIRQPPGKGLEWIGYIYYSGTTNYNPS LKSRVTISVDTSKNQFSLKLSSVTAADTAVYYCARIAVAGFFFDYWGQGTLVTVSS |

TABLE 18-continued

| SEQ ID NO | DLL3-epi-tope | Desig-nation | Format / Source | Amino acid sequence |
|---|---|---|---|---|
| 58 | | DLL3-6 | VL | EIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVEIK |
| 59 | EGF-3 | DLL3-6 | scFv | QVQLQESGPGLVKPSETLSLTCTVSGASISSFYWSWIRQPPGKGLEWIGYIYYSGTTNYNPSLKSRVTISVDTSKNQFSLKLSSVTAADTAVYYCARIAVAGFFFDYWGQGTLVTVSSGGGGSGGGGSGGGGSEIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVEIK |
| 60 | | DLL3-6 xI2C | bispecific molecule | QVQLQESGPGLVKPSETLSLTCTVSGASISSFYWSWIRQPPGKGLEWIGYIYYSGTTNYNPSLKSRVTISVDTSKNQFSLKLSSVTAADTAVYYCARIAVAGFFFDYWGQGTLVTVSSGGGGSGGGGSGGGGSEIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 61 | | DLL3-7 | VH CDR1 | SFYWS |
| 62 | | DLL3-7 | VH CDR2 | YIYYSGTTNYNPSLKS |
| 63 | | DLL3-7 | VH CDR3 | IAVAGFFFDY |
| 64 | | DLL3-7 | VL CDR1 | RASQSVNKNYLA |
| 65 | | DLL3-7 | VL CDR2 | GASSRAT |
| 66 | | DLL3-7 | VL CDR3 | QQYDRSPLT |
| 67 | | DLL3-7 | VH | QVQLQESGPGLVKPSQTLSLTCTVSGASISSFYWSWIRQPPGKGLEWIGYIYYSGTTNYNPSLKSRVTISVDTSKNQFSLKLSSVTAADTAVYYCARIAVAGFFFDYWGQGTLVTVSS |
| 68 | | DLL3-7 | VL | EIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVEIK |
| 69 | EGF-3 | DLL3-7 | scFv | QVQLQESGPGLVKPSQTLSLTCTVSGASISSFYWSWIRQPPGKGLEWIGYIYYSGTTNYNPSLKSRVTISVDTSKNQFSLKLSSVTAADTAVYYCARIAVAGFFFDYWGQGTLVTVSSGGGGSGGGGSGGGGSEIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVEIK |
| 70 | | DLL3-7 xI2C | bispecific molecule | QVQLQESGPGLVKPSQTLSLTCTVSGASISSFYWSWIRQPPGKGLEWIGYIYYSGTTNYNPSLKSRVTISVDTSKNQFSLKLSSVTAADTAVYYCARIAVAGFFFDYWGQGTLVTVSSGGGGSGGGGSGGGGSEIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 71 | | DLL3-8 | VH CDR1 | SFYWS |
| 72 | | DLL3-8 | VH CDR2 | YIYYSGTTNYNPSLKS |
| 73 | | DLL3-8 | VH CDR3 | IAVAGFFFDY |
| 74 | | DLL3-8 | VL CDR1 | RASQSVNKNYLA |
| 75 | | DLL3-8 | VL CDR2 | GASSRAT |
| 76 | | DLL3-8 | VL CDR3 | QQYDRSPLT |
| 77 | | DLL3-8 | VH | QVQLQEWGPGLVKPSETLSLTCTVSGASISSFYWSWIRQPPGKGLEWIGYIYYSGTTNYNPSLKSRVTISVDTSKNQLSLKLSSVTAADTAVYYCARIAVAGFFFDYWGQGTLVTVSSK |
| 78 | | DLL3-8 | VL | EIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVDIK |
| 79 | EGF-3 | DLL3-8 | scFv | QVQLQEWGPGLVKPSETLSLTCTVSGASISSFYWSWIRQPPGKGLEWIGYIYYSGTTNYNPSLKSRVTISVDTSKNQLSLKLSSVTAADTAVYYCARIAVAGFFFDYWGQGTLVTVSSGGGGSGGGGSGGGGSEIVLTQSPGTLSLSPGERATLSCRASQSVNKNYLAWYQQKPGQAPRLLIYGASSRATGIPDRFSGSGSGTDFTLTISRLEPEDFAVYYCQQYDRSPLTFGGGTKVDIK |

TABLE 18-continued

| SEQ ID NO | DLL3-epi-tope | Desig-nation | Format / Source | Amino acid sequence |
|---|---|---|---|---|
| 80 | | DLL3-8 xI2C | bispecific molecule | QVQLQEWGPGLVKPSETLSLTCTVSGASISSFYWSWIRQPPGKGLEWIGYIYYSGTTNYNPS LKSRVTISVDTSKNQLSLKLSSVTAADTAVYYCARIAVAGFFFDYWGQGTLVTVSSGGGGSG GGGSGGGGSEIVLTQSPGTLSLSPGERATLSCRASQSVNKNYLAWYQQKPGQAPRLLIYGAS SRATGIPDRFSGSGSGTDFTLTISRLEPEDFAVYYCQQYDRSPLTFGGGTKVDIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 81 | | DLL3-9 | VH CDR1 | SFYWS |
| 82 | | DLL3-9 | VH CDR2 | YIYYSGTTNYNPSLKS |
| 83 | | DLL3-9 | VH CDR3 | IAVAGFFFDY |
| 84 | | DLL3-9 | VL CDR1 | RASQSVNKNYLA |
| 85 | | DLL3-9 | VL CDR2 | GASSRAT |
| 86 | | DLL3-9 | VL CDR3 | QQYDRSPLT |
| 87 | | DLL3-9 | VH | QVQLQESGPGLVKPSETLSLTCTVSGASISSFYWSWIRQPPGKGLEWIGYIYYSGTTNYNPS LKSRVTISVDTSKNQFSLKLSSVTAADTAVYYCARIAVAGFFFDYWGQGTLVTVSS |
| 88 | | DLL3-9 | VL | EIVLTQSPGTLSLSPGESATLSCRASQSVNKNYLAWYQQKPGQAPRLLIYGASSRATGIPDR FSGSGSGTDFTLTISRLEPEDFAVYYCQQYDRSPLTFGGGTRLEIK |
| 89 | EGF-3 | DLL3-9 | scFv | QVQLQESGPGLVKPSETLSLTCTVSGASISSFYWSWIRQPPGKGLEWIGYIYYSGTTNYNPS LKSRVTISVDTSKNQFSLKLSSVTAADTAVYYCARIAVAGFFFDYWGQGTLVTVSSGGGGSG GGGSGGGGSEIVLTQSPGTLSLSPGESATLSCRASQSVNKNYLAWYQQKPGQAPRLLIYGAS SRATGIPDRFSGSGSGTDFTLTISRLEPEDFAVYYCQQYDRSPLTFGGGTRLEIK |
| 90 | | DLL3-9 xI2C | bispecific molecule | QVQLQESGPGLVKPSETLSLTCTVSGASISSFYWSWIRQPPGKGLEWIGYIYYSGTTNYNPS LKSRVTISVDTSKNQFSLKLSSVTAADTAVYYCARIAVAGFFFDYWGQGTLVTVSSGGGGSG GGGSGGGGSEIVLTQSPGTLSLSPGESATLSCRASQSVNKNYLAWYQQKPGQAPRLLIYGAS SRATGIPDRFSGSGSGTDFTLTISRLEPEDFAVYYCQQYDRSPLTFGGGTRLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 91 | | DLL3-10 | VH CDR1 | SYYWS |
| 92 | | DLL3-10 | VH CDR2 | YIFYNGITNYNPSLKS |
| 93 | | DLL3-10 | VH CDR3 | IHSGSFSFDY |
| 94 | | DLL3-10 | VL CDR1 | RASQSVSRGYLA |
| 95 | | DLL3-10 | VL CDR2 | GASSRAT |
| 96 | | DLL3-10 | VL CDR3 | QQYDTSPIT |
| 97 | | DLL3-10 | VH | QVQLQESGPGLVKPSQTLSLTCTVSGGSISSYYWSWIRQPPGKGLEWIGYIFYNGITNYNPS LKSRVTISLDTSKNQFSLKLSSVTAADTAKYYCARIHSGSFSFDYWDQGTLVTVSS |
| 98 | | DLL3-10 | VL | EIVMTQSPGTLSLSPGERATLSCRASQSVSRGYLAWYQQKPGQAPRLLIYGASSRATDIPDR FSGSGSGTDFTLTISRLEPEDFAVYYCQQYDTSPITFGQGTKVEIK |
| 99 | EGF-3 | DLL3-10 | scFv | QVQLQESGPGLVKPSQTLSLTCTVSGGSISSYYWSWIRQPPGKGLEWIGYIFYNGITNYNPS LKSRVTISLDTSKNQFSLKLSSVTAADTAKYYCARIHSGSFSFDYWDQGTLVTVSSGGGGSG GGGSGGGGSEIVMTQSPGTLSLSPGERATLSCRASQSVSRGYLAWYQQKPGQAPRLLIYGAS SRATDIPDRFSGSGSGTDFTLTISRLEPEDFAVYYCQQYDTSPITFGQGTKVEIK |
| 100 | | DLL3-10 xI2C | bispecific molecule | QVQLQESGPGLVKPSQTLSLTCTVSGGSISSYYWSWIRQPPGKGLEWIGYIFYNGITNYNPS LKSRVTISLDTSKNQFSLKLSSVTAADTAKYYCARIHSGSFSFDYWDQGTLVTVSSGGGGSG GGGSGGGGSEIVMTQSPGTLSLSPGERATLSCRASQSVSRGYLAWYQQKPGQAPRLLIYGAS SRATDIPDRFSGSGSGTDFTLTISRLEPEDFAVYYCQQYDTSPITFGQGTKVEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 101 | | DLL3-11 | VH CDR1 | NAGMS |

TABLE 18-continued

| SEQ ID NO | DLL3-epi-tope | Desig-nation | Format / Source | Amino acid sequence |
|---|---|---|---|---|
| 102 | | DLL3-11 | VH CDR2 | RIKNKIDGGTTDFAAPVKG |
| 103 | | DLL3-11 | VH CDR3 | RGWYGDYFDY |
| 104 | | DLL3-11 | VL CDR1 | RSSQSLLHSNGYNYLD |
| 105 | | DLL3-11 | VL CDR2 | LGSNRAS |
| 106 | | DLL3-11 | VL CDR3 | MQALQTPFT |
| 107 | | DLL3-11 | VH | EVQLVESGGGLVKPGGSLRLSCAASGFIFNNAGMSWVRQAPGKGLEWVGRIKNKIDGGTTDF AAPVKGRFTISRDDSKNTLYLQMNSLKAEDTAVYYCTARGWYGDYFDYWGQGTLVTVSS |
| 108 | | DLL3-11 | VL | DIVMTQTPLSLPVTPGEPASISCRSSQSLLHSNGYNYLDWYLQKPGQSPQLLIYLGSNRASG VPDRFSGSGSGTDFTLKISRVEAEDVGIYYCMQALQTPFTFGPGTKVEIK |
| 109 | EGF-3 | DLL3-11 | scFv | EVQLVESGGGLVKPGGSLRLSCAASGFIFNNAGMSWVRQAPGKGLEWVGRIKNKIDGGTTDF AAPVKGRFTISRDDSKNTLYLQMNSLKAEDTAVYYCTARGWYGDYFDYWGQGTLVTVSSGGG GSGGGGSGGGGSDIVMTQTPLSLPVTPGEPASISCRSSQSLLHSNGYNYLDWYLQKPGQSPQ LLIYLGSNRASGVPDRFSGSGSGTDFTLKISRVEAEDVGIYYCMQALQTPFTFGPGTKVEIK |
| 110 | | DLL3-11 xI2C | bispecific molecule | EVQLVESGGGLVKPGGSLRLSCAASGFIFNNAGMSWVRQAPGKGLEWVGRIKNKIDGGTTDF AAPVKGRFTISRDDSKNTLYLQMNSLKAEDTAVYYCTARGWYGDYFDYWGQGTLVTVSSGGG GSGGGGSGGGGSDIVMTQTPLSLPVTPGEPASISCRSSQSLLHSNGYNYLDWYLQKPGQSPQ LLIYLGSNRASGVPDRFSGSGSGTDFTLKISRVEAEDVGIYYCMQALQTPFTFGPGTKVEIK SGGGGSEVQLVESGGGLVQPGGSLKLSCAASGFTFNKYAMNWVRQAPGKGLEWVARIRSKYN NYATYYADSVKDRFTISRDDSKNTAYLQMNNLKTEDTAVYYCVRHGNFGNSYISYWAYWGQG TLVTVSSGGGGSGGGGSGGGGSQTVVTQEPSLTVSPGGTVTLTCGSSTGAVTSGNYPNWVQQ KPGQAPRGLIGGTKFLAPGTPARFSGSLLGGKAALTLSGVQPEDEAEYYCVLWYSNRWVFGG GTKLTVL |
| 111 | | DLL3-12 | VH CDR1 | SYDIH |
| 112 | | DLL3-12 | VH CDR2 | VISSHGSNKNYARSVKG |
| 113 | | DLL3-12 | VH CDR3 | DGYSGNDPFYYYYHGMDV |
| 114 | | DLL3-12 | VL CDR1 | RASQSISSYLN |
| 115 | | DLL3-12 | VL CDR2 | AASSLQS |
| 116 | | DLL3-12 | VL CDR3 | QQSFTTPLT |
| 117 | | DLL3-12 | VH | QVQLVESGGGVVQPGRSLRLSCAASGFSFSSYDIHWVRQAPGKGLEWVAVISSHGSNKNYAR SVKGRFTISRDNSKNTLYLQMNSLKAEDTAVYYCARDGYSGNDPFYYYYHGMDVWGQGTTVT VSS |
| 118 | | DLL3-12 | VL | DIQMTQSPSSLSASVGDRVTITCRASQSISSYLNWYQQKPGKAPKLLIYAASSLQSGVPSRF SGSGSGTDFSLTISSLQPEDFATYYCQQSFTTPLTFGGGTKVEIK |
| 119 | EGF-3/[4] | DLL3-12 | scFv | QVQLVESGGGVVQPGRSLRLSCAASGFSFSSYDIHWVRQAPGKGLEWVAVISSHGSNKNYAR SVKGRFTISRDNSKNTLYLQMNSLKAEDTAVYYCARDGYSGNDPFYYYYHGMDVWGQGTTVT VSSGGGGSGGGGSGGGGSDIQMTQSPSSLSASVGDRVTITCRASQSISSYLNWYQQKPGKAP KLLIYAASSLQSGVPSRFSGSGSGTDFSLTISSLQPEDFATYYCQQSFTTPLTFGGGTKVEI K |
| 120 | | DLL3-12 xI2C | bispecific molecule | QVQLVESGGGVVQPGRSLRLSCAASGFSFSSYDIHWVRQAPGKGLEWVAVISSHGSNKNYAR SVKGRFTISRDNSKNTLYLQMNSLKAEDTAVYYCARDGYSGNDPFYYYYHGMDVWGQGTTVT VSSGGGGSGGGGSGGGGSDIQMTQSPSSLSASVGDRVTITCRASQSISSYLNWYQQKPGKAP KLLIYAASSLQSGVPSRFSGSGSGTDFSLTISSLQPEDFATYYCQQSFTTPLTFGGGTKVEI KSGGGGSEVQLVESGGGLVQPGGSLKLSCAASGFTFNKYAMNWVRQAPGKGLEWVARIRSKY NNYATYYADSVKDRFTISRDDSKNTAYLQMNNLKTEDTAVYYCVRHGNFGNSYISYWAYWGQ GTLVTVSSGGGGSGGGGSGGGGSQTVVTQEPSLTVSPGGTVTLTCGSSTGAVTSGNYPNWVQ QKPGQAPRGLIGGTKFLAPGTPARFSGSLLGGKAALTLSGVQPEDEAEYYCVLWYSNRWVFG GGTKLTVL |
| 121 | | DLL3-13 | VH CDR1 | SYYMH |
| 122 | | DLL3-13 | VH CDR2 | IINPSDGSTNYAQNFQG |
| 123 | | DLL3-13 | VH CDR3 | GGNSAFYSYYDMDV |
| 124 | | DLL3-13 | VL CDR1 | RSSQSLVYRDGNTYLS |
| 125 | | DLL3-13 | VL CDR2 | KVSNWQS |

TABLE 18-continued

| SEQ ID NO | DLL3-epi-tope | Desig-nation | Format / Source | Amino acid sequence |
|---|---|---|---|---|
| 126 | | DLL3-13 | VL CDR3 | MQGTHWPPT |
| 127 | | DLL3-13 | VH | QVQLVQSGAEVKKPGASVKVSCKASGYTFTSYYMHWVRQAPGQGLEWMGIINPSDGSTNYAQ NFQGRVTMTRDTSTNTVYMELSSLRSEDTAVYYCARGGNSAFYSYYDMDVWGQGTTVTVSS |
| 128 | | DLL3-13 | VL | DVVMTQSPLSLPVTLGQPASISCRSSQSLVYRDGNTYLSWFQQRPGQSPRRLIYKVSNWQSG VPDRFSGSGSGTDFTLKISRVEAEDVGVYFCMQGTHWPPTFGQGTKVEIK |
| 129 | EGF-4 | DLL3-13 | scFv | QVQLVQSGAEVKKPGASVKVSCKASGYTFTSYYMHWVRQAPGQGLEWMGIINPSDGSTNYAQ NFQGRVTMTRDTSTNTVYMELSSLRSEDTAVYYCARGGNSAFYSYYDMDVWGQGTTVTVSSG GGGSGGGGSGGGGSDVVMTQSPLSLPVTLGQPASISCRSSQSLVYRDGNTYLSWFQQRPGQS PRRLIYKVSNWQSGVPDRFSGSGSGTDFTLKISRVEAEDVGVYFCMQGTHWPPTFGQGTKVE IK |
| 130 | | DLL3-13 xI2C | bispecific molecule | QVQLVQSGAEVKKPGASVKVSCKASGYTFTSYYMHWVRQAPGQGLEWMGIINPSDGSTNYAQ NFQGRVTMTRDTSTNTVYMELSSLRSEDTAVYYCARGGNSAFYSYYDMDVWGQGTTVTVSSG GGGSGGGGSGGGGSDVVMTQSPLSLPVTLGQPASISCRSSQSLVYRDGNTYLSWFQQRPGQS PRRLIYKVSNWQSGVPDRFSGSGSGTDFTLKISRVEAEDVGVYFCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 131 | | DLL3-14 | VH CDR1 | NYYMH |
| 132 | | DLL3-14 | VH CDR2 | IINPSDGSTSYAQKFQG |
| 133 | | DLL3-14 | VH CDR3 | GGNSAFYSYYDMDV |
| 134 | | DLL3-14 | VL CDR1 | RSSQSLVYRDGNTYLS |
| 135 | | DLL3-14 | VL CDR2 | KVSNWQS |
| 136 | | DLL3-14 | VL CDR3 | MQGTHWPPT |
| 137 | | DLL3-14 | VH | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSS |
| 138 | | DLL3-14 | VL | DVVMTQTPLSLPVTLGQPASISCRSSQSLVYRDGNTYLSWFQQRPGQSPRRLIYKVSNWQSG VPDRFSGGGSGTDFTLKISRVEAEDVGVYYCMQGTHWPPTFGQGTKVEIK |
| 139 | EGF-4 | DLL3-14 | scFv | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGGGSGTDFTLKISRVEAEDVGVYYCMQGTHWPPTFGQGTKVE IK |
| 140 | | DLL3-14 xI2C | bispecific molecule | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGGGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 141 | | DLL3-15 | VH CDR1 | GYYIH |
| 142 | | DLL3-15 | VH CDR2 | IINPSDGSTSYGQNFQG |
| 143 | | DLL3-15 | VH CDR3 | GGNSAFYSYYDMDV |
| 144 | | DLL3-15 | VL CDR1 | RSSQSLAYRDGNTYLS |
| 145 | | DLL3-15 | VL CDR2 | KVSNWQS |
| 146 | | DLL3-15 | VL CDR3 | MQGTHWPPT |
| 147 | | DLL3-15 | VH | QVQLVQSGAEVKKPGASVKVSCKASGYTFTGYYIHWVRQAPGQGLEWMGIINPSDGSTSYGQ NFQGRVTMTRDTSTNTVYMELSSLRSEDTAVYYCARGGNSAFYSYYDMDVWGQGTTVTVSS |
| 148 | | DLL3-15 | VL | DVVMTQSPLSLPVTLGQPASISCRSSQSLAYRDGNTYLSWFQQRPGQSPRRLIYKVSNWQSG VPDRFSGSGSGTDFTLKISRVEAEDVGVYFCMQGTHWPPTFGQGTKVEIK |

TABLE 18-continued

| SEQ ID NO | DLL3-epitope | Designation | Format / Source | Amino acid sequence |
|---|---|---|---|---|
| 149 | EGF-4 | DLL3-15 | scFv | QVQLVQSGAEVKKPGASVKVSCKASGYTFTGYYIHWVRQAPGQGLEWMGIINPSDGSTSYGQNFQGRVTMTRDTSTNTVYMELSSLRSEDTAVYYCARGGNSAFYSYYDMDVWGQGTTVTVSSGGGGSGGGGSGGGGSDVVMTQSPLSLPVTLGQPASISCRSSQSLAYRDGNTYLSWFQQRPGQSPRRLIYKVSNWQSGVPDRFSGSGSGTDFTLKISRVEAEDVGVYFCMQGTHWPPTFGQGTKVEIK |
| 150 | | DLL3-15 xI2C | bispecific molecule | QVQLVQSGAEVKKPGASVKVSCKASGYTFTGYYIHWVRQAPGQGLEWMGIINPSDGSTSYGQNFQGRVTMTRDTSTNTVYMELSSLRSEDTAVYYCARGGNSAFYSYYDMDVWGQGTTVTVSSGGGGSGGGGSGGGGSDVVMTQSPLSLPVTLGQPASISCRSSQSLAYRDGNTYLSWFQQRPGQSPRRLIYKVSNWQSGVPDRFSGSGSGTDFTLKISRVEAEDVGVYFCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 151 | | DLL3-16 | VH CDR1 | GHYMH |
| 152 | | DLL3-16 | VH CDR2 | IINPSDGSTNYAQKFQG |
| 153 | | DLL3-16 | VH CDR3 | GTTVVHYSYYDMDV |
| 154 | | DLL3-16 | VL CDR1 | RSSQSLVYRDGNTYLT |
| 155 | | DLL3-16 | VL CDR2 | KVSNWQS |
| 156 | | DLL3-16 | VL CDR3 | MQGTHWPPT |
| 157 | | DLL3-16 | VH | QVQLVQSGAEVKKPGASVKVSCKASGYTFTGHYMHWVRQAPGQGLEWMGIINPSDGSTNYAQKFQGRVTMTRDTSTSTVYMELRSLRSEDTAVYYCTRGTTVVHYSYYDMDVWGQGTTVTVSS |
| 158 | | DLL3-16 | VL | DVVMTQTPLSLPVTLGQPASISCRSSQSLVYRDGNTYLTWFQQRPGQSPRRLIYKVSNWQSGVPDRFSGSGSGTDFTLKISRVEAEDVGVYYCMQGTHWPPTFGGGTKVEIK |
| 159 | EGF-4 | DLL3-16 | scFv | QVQLVQSGAEVKKPGASVKVSCKASGYTFTGHYMHWVRQAPGQGLEWMGIINPSDGSTNYAQKFQGRVTMTRDTSTSTVYMELRSLRSEDTAVYYCTRGTTVVHYSYYDMDVWGQGTTVTVSSGGGGSGGGGSGGGGSDVVMTQTPLSLPVTLGQPASISCRSSQSLVYRDGNTYLTWFQQRPGQSPRRLIYKVSNWQSGVPDRFSGSGSGTDFTLKISRVEAEDVGVYYCMQGTHWPPTFGGGTKVEIK |
| 160 | | DLL3-16 xI2C | bispecific molecule | QVQLVQSGAEVKKPGASVKVSCKASGYTFTGHYMHWVRQAPGQGLEWMGIINPSDGSTNYAQKFQGRVTMTRDTSTSTVYMELRSLRSEDTAVYYCTRGTTVVHYSYYDMDVWGQGTTVTVSSGGGGSGGGGSGGGGSDVVMTQTPLSLPVTLGQPASISCRSSQSLVYRDGNTYLTWFQQRPGQSPRRLIYKVSNWQSGVPDRFSGSGSGTDFTLKISRVEAEDVGVYYCMQGTHWPPTFGGGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 161 | | DLL3-17 | VH CDR1 | NYFMH |
| 162 | | DLL3-17 | VH CDR2 | IINPSDGSTSYAQNFQG |
| 163 | | DLL3-17 | VH CDR3 | GGNSAFYSYYDMDV |
| 164 | | DLL3-17 | VL CDR1 | RSSQSLVYRDGNTYLS |
| 165 | | DLL3-17 | VL CDR2 | RVSNWQS |
| 166 | | DLL3-17 | VL CDR3 | MQGTYWPPT |
| 167 | | DLL3-17 | VH | QVQLVQSGAEVKKPGASVKVSCKASGYTFTNYFMHWVRQAPGLGLEWMGIINPSDGSTSYAQNFQGRVTMTRDTSTNTVYMELSSLRSEDTAVYYCARGGNSAFYSYYDMDVWGQGTTVTVSS |
| 168 | | DLL3-17 | VL | DVVMTQSPLSLPVTLGQPASISCRSSQSLVYRDGNTYLSWFQQRPGQSPRRLIYRVSNWQSGVPDRFSGSGSGTDFTLKISRVEAEDVGVYFCMQGTYWPPTFGQGTKVDIK |
| 169 | EGF-4 | DLL3-17 | scFv | QVQLVQSGAEVKKPGASVKVSCKASGYTFTNYFMHWVRQAPGLGLEWMGIINPSDGSTSYAQNFQGRVTMTRDTSTNTVYMELSSLRSEDTAVYYCARGGNSAFYSYYDMDVWGQGTTVTVSSGGGGSGGGGSGGGGSDVVMTQSPLSLPVTLGQPASISCRSSQSLVYRDGNTYLSWFQQRPGQSPRRLIYRVSNWQSGVPDRFSGSGSGTDFTLKISRVEAEDVGVYFCMQGTYWPPTFGQGTKVDIK |

TABLE 18-continued

| SEQ ID NO | DLL3-epi-tope | Desig-nation | Format / Source | Amino acid sequence |
|---|---|---|---|---|
| 170 | | DLL3-17 xI2C | bispecific molecule | QVQLVQSGAEVKKPGASVKVSCKASGYTFTNYFMHWVRQAPGLGLEWMGIINPSDGSTSYAQNFQGRVTMTRDTSTNTVYMELSSLRSEDTAVYYCARGGNSAFYSYYDMDVWGQGTTVTVSSGGGGSGGGGSGGGGSDVVMTQSPLSLPVTLGQPASISCRSSQSLVYRDGNTYLSWFQQRPGQSPRRLIYRVSNWQSGVPDRFSGSGSGTDFTLKISRVEAEDVGVYFCMQGTYWPPTFGQGTKVDIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 171 | | DLL3-18 | VH CDR1 | NYGMH |
| 172 | | DLL3-18 | VH CDR2 | VISHHGSSKYYARSVKG |
| 173 | | DLL3-18 | VH CDR3 | DWWELVFDY |
| 174 | | DLL3-18 | VL CDR1 | KSSQSLLHSDGKTFLY |
| 175 | | DLL3-18 | VL CDR2 | EVSNRFS |
| 176 | | DLL3-18 | VL CDR3 | LQGIHLPFT |
| 177 | | DLL3-18 | VH | QVQLVESGGGAVQPGRSLRLSCAASGFTFSNYGMHWVRQAPGKGLEWVAVISHHGSSKYYARSVKGRFTISRDNSKNTLYLEMNSLRAEDTAVYYCARDWWELVFDYWGQGTLVTVSS |
| 178 | | DLL3-18 | VL | DIVMTQTPLSLSVTPGQPASISCKSSQSLLHSDGKTFLYWYLQKPGQPPQLLIYEVSNRFSGVPDRFSGSGSGTDFTLKISRVEAEDVGVYYCLQGIHLPFTFGPGTKVEIK |
| 179 | EGF-5/[6] | DLL3-18 | scFv | QVQLVESGGGAVQPGRSLRLSCAASGFTFSNYGMHWVRQAPGKGLEWVAVISHHGSSKYYARSVKGRFTISRDNSKNTLYLEMNSLRAEDTAVYYCARDWWELVFDYWGQGTLVTVSSGGGGSGGGGSGGGGSDIVMTQTPLSLSVTPGQPASISCKSSQSLLHSDGKTFLYWYLQKPGQPPQLLIYEVSNRFSGVPDRFSGSGSGTDFTLKISRVEAEDVGVYYCLQGIHLPFTFGPGTKVEIK |
| 180 | | DLL3-18 xI2C | bispecific molecule | QVQLVESGGGAVQPGRSLRLSCAASGFTFSNYGMHWVRQAPGKGLEWVAVISHHGSSKYYARSVKGRFTISRDNSKNTLYLEMNSLRAEDTAVYYCARDWWELVFDYWGQGTLVTVSSGGGGSGGGGSGGGGSDIVMTQTPLSLSVTPGQPASISCKSSQSLLHSDGKTFLYWYLQKPGQPPQLLIYEVSNRFSGVPDRFSGSGSGTDFTLKISRVEAEDVGVYYCLQGIHLPFTFGPGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 181 | | DLL3-19 | VH CDR1 | NSRMGVS |
| 182 | | DLL3-19 | VH CDR2 | HIFSNDGKSYSTSLKS |
| 183 | | DLL3-19 | VH CDR3 | YNYDSSGYYYSFFDY |
| 184 | | DLL3-19 | VL CDR1 | RASQSISSYLN |
| 185 | | DLL3-19 | VL CDR2 | AASSLQS |
| 186 | | DLL3-19 | VL CDR3 | QQGYSSPFT |
| 187 | | DLL3-19 | VH | QVTLKESGPMLVKPTETLTLTCTVSGFSLSNSRMGVSWIRQPPGRALEWLAHIFSNDGKSYSTSLKSRLTISKDTSKSQVVLTMTNMDPVDTATYYCARYNYDSSGYYYSFFDYWGQGTLVTVSS |
| 188 | | DLL3-19 | VL | DIQMTQSPSSLSASVGDRVTITCRASQSISSYLNWYQQKPGKAPKLLIYAASSLQSGVPSRFSGSGSGTDFTLTISSLQPEDFATYYCQQGYSSPFTFGGGTKVEIK |
| 189 | EGF-5/[6] | DLL3-19 | scFv | QVTLKESGPMLVKPTETLTLTCTVSGFSLSNSRMGVSWIRQPPGRALEWLAHIFSNDGKSYSTSLKSRLTISKDTSKSQVVLTMTNMDPVDTATYYCARYNYDSSGYYYSFFDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQGYSSPFTFGGGTKVEIK |
| 190 | | DLL3-19 xI2C | bispecific molecule | QVTLKESGPMLVKPTETLTLTCTVSGFSLSNSRMGVSWIRQPPGRALEWLAHIFSNDGKSYSTSLKSRLTISKDTSKSQVVLTMTNMDPVDTATYYCARYNYDSSGYYYSFFDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQGYSSPFTFGGGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGT |

TABLE 18-continued

| SEQ ID NO | DLL3-epi-tope | Desig-nation | Format / Source | Amino acid sequence |
|---|---|---|---|---|
| | | | | LVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 191 | | DLL3-20 | VH CDR1 | NARMGVS |
| 192 | | DLL3-20 | VH CDR2 | HIFSTDEKSYSTSLKS |
| 193 | | DLL3-20 | VH CDR3 | YYYDSSGYYYSFFDY |
| 194 | | DLL3-20 | VL CDR1 | RASQSIRSYLN |
| 195 | | DLL3-20 | VL CDR2 | GASNLQS |
| 196 | | DLL3-20 | VL CDR3 | QQSYSSPFT |
| 197 | | DLL3-20 | VH | QVTLKESGPVLVKPTETLTLTCTVSGFSLSNARMGVSWLRQPPGKALEWLAHIFSTDEKSYSTSLKSRLTISKDTSKSQVVLTMTNMDPVDTATYYCARYYYDSSGYYYSFFDYWGQGTLVTVSS |
| 198 | | DLL3-20 | VL | DIQMTQSPSSLSASVGDRVTITCRASQSIRSYLNWYQQKPGKAPKLLIYGASNLQSGVPSRFSGSGSGTDFTLTISSLQPEDFATYYCQQSYSSPFTFGGGTKVEIK |
| 199 | EGF-5/[6] | DLL3-20 | scFv | QVTLKESGPVLVKPTETLTLTCTVSGFSLSNARMGVSWLRQPPGKALEWLAHIFSTDEKSYSTSLKSRLTISKDTSKSQVVLTMTNMDPVDTATYYCARYYYDSSGYYYSFFDYWGQGTLVTVSSGGGGSGGGGSGGGGSDIQMTQSPSSLSASVGDRVTITCRASQSIRSYLNWYQQKPGKAPKLLIYGASNLQSGVPSRFSGSGSGTDFTLTISSLQPEDFATYYCQQSYSSPFTFGGGTKVEIK |
| 200 | | DLL3-20 xI2C | bispecific molecule | QVTLKESGPVLVKPTETLTLTCTVSGFSLSNARMGVSWLRQPPGKALEWLAHIFSTDEKSYSTSLKSRLTISKDTSKSQVVLTMTNMDPVDTATYYCARYYYDSSGYYYSFFDYWGQGTLVTVSSGGGGSGGGGSGGGGSDIQMTQSPSSLSASVGDRVTITCRASQSIRSYLNWYQQKPGKAPKLLIYGASNLQSGVPSRFSGSGSGTDFTLTISSLQPEDFATYYCQQSYSSPFTFGGGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 201 | | DLL3-21 | VH CDR1 | SYYIH |
| 202 | | DLL3-21 | VH CDR2 | IINPSGGSKSYAQKFRG |
| 203 | | DLL3-21 | VH CDR3 | SMSTVTSDAFDI |
| 204 | | DLL3-21 | VL CDR1 | RASQSISNYLN |
| 205 | | DLL3-21 | VL CDR2 | AASSLQS |
| 206 | | DLL3-21 | VL CDR3 | QQSYSAPLT |
| 207 | | DLL3-21 | VH | QVQLVQSGAEVKKPGASVKVSCKASGYAFTSYYIHWVRQAPGQGLEWMGIINPSGGSKSYAQKFRGRVTMTRDTSTSTVYMELSSLTSEDTAVYYCARSMSTVTSDAFDIWGQGTMVTVSS |
| 208 | | DLL3-21 | VL | DIQMTQSPSSLSASVGDRVTITCRASQSISNYLNWYQQKPGKAPKLLIYAASSLQSGVPSRFSGSGSGTEFTLTISSLQPEDFATYYCQQSYSAPLTFGGGTKVDIK |
| 209 | EGF-5/[6] | DLL3-21 | scFv | QVQLVQSGAEVKKPGASVKVSCKASGYAFTSYYIHWVRQAPGQGLEWMGIINPSGGSKSYAQKFRGRVTMTRDTSTSTVYMELSSLTSEDTAVYYCARSMSTVTSDAFDIWGQGTMVTVSSGGGGSGGGGSGGGGSDIQMTQSPSSLSASVGDRVTITCRASQSISNYLNWYQQKPGKAPKLLIYAASSLQSGVPSRFSGSGSGTEFTLTISSLQPEDFATYYCQQSYSAPLTFGGGTKVDIK |
| 210 | | DLL3-21 xI2C | bispecific molecule | QVQLVQSGAEVKKPGASVKVSCKASGYAFTSYYIHWVRQAPGQGLEWMGIINPSGGSKSYAQKFRGRVTMTRDTSTSTVYMELSSLTSEDTAVYYCARSMSTVTSDAFDIWGQGTMVTVSSGGGGSGGGGSGGGGSDIQMTQSPSSLSASVGDRVTITCRASQSISNYLNWYQQKPGKAPKLLIYAASSLQSGVPSRFSGSGSGTEFTLTISSLQPEDFATYYCQQSYSAPLTFGGGTKVDIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 211 | EGF-3 | DLL3-4 xF12Q | bispecific molecule | QVQLQESGPGLVKPSETLSLTCTVSGGSISSYYWSWIRQPPGKGLEWIGYVYYSGTTNYNPSLKSRVTISVDTSKNQFSLKLSSVTAADTAVYYCASIAVTGFYFDYWGQGTLVTVSSGGGGSGGGGSGGGGSEIVLTQSPGTLSLSPGERVTLSCRASQRVNNNYLAWYQQRPGQAPRLLIYGASSRATGIPDRFSGSGSGTDFTLTISRLEPEDFAVYYCQQYDRSPLTFGGGTKLEIKSGGGGSEVQLVESGGGLVQPGGSLRLSCAASGFTFNSYAMNWVRQAPGKGLEWVARIRSKYNNYATYYA |

TABLE 18-continued

| SEQ ID NO | DLL3-epitope | Designation | Format / Source | Amino acid sequence |
|---|---|---|---|---|
| | | | | DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 212 | EGF-3 | DLL3-5 xF12Q | bispecific molecule | QVQLQESGPGLVKPSETLSLTCTVSGGSISSYYWSWIRQPPGKGLEWIGYIYYSGRTNYYPS<br>LKSRVTISIDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKLEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 213 | EGF-3 | DLL3-6 xF12Q | bispecific molecule | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 214 | EGF-3 | DLL3-7 xF12Q | bispecific molecule | QVQLQESGPGLVKPSQTLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 215 | EGF-3 | DLL3-8 xF12Q | bispecific molecule | QVQLQEWGPGLVKPSETLSLTCTVSGASISSFYWSWIRQPPGKGLEWIGYIYYSGTTNYNPS<br>LKSRVTISVDTSKNQLSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVDIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 216 | EGF-3 | DLL3-9 xF12Q | bispecific molecule | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGESATLSCRASQSVNKNYLAWYQQKPGQAPRLLIYGAS<br>SRATGIPDRFSGSGSGTDFTLTISRLEPEDFAVYYCQQYDRSPLTFGGGTRLEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 217 | EGF-3 | DLL3-10 xF12Q | bispecific molecule | QVQLQESGPGLVKPSQTLSLTCTVSGGSISSYYWSWIRQPPGKGLEWIGYIFYNGITNYNPS<br>LKSRVTISLDTSKNQFSLKLSSVTAADTAKYYCARIHSGSFSFDYWDQGTLVTVSSGGGGSG<br>GGGSGGGGSEIVMTQSPGTLSLSPGERATLSCRASQSVSRGYLAWYQQKPGQAPRLLIYGAS<br>SRATDIPDRFSGSGSGTDFTLTISRLEPEDFAVYYCQQYDTSPITFGQGTKVEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL |
| 218 | EGF-4 | DLL3-13 xF12Q | bispecific molecule | QVQLVQSGAEVKKPGASVKVSCKASGYTFTSYYMHWVRQAPGQGLEWMGIINPSDGSTNYAQ<br>NFQGRVTMTRDTSTNTVYMELSSLRSEDTAVYYCARGGNSAFYSYYDMDVWGQGTTVTVSSG<br>GGGSGGGGSGGGGSDVVMTQSPLSLPVTLGQPASISCRSSQSLVYRDGNTYLSWFQQRPGQS<br>PRRLIYKVSNWQSGVPDRFSGSGSGTDFTLKISRVEAEDVGVYFCMQGTHWPPTFGQGTKVE<br>IKSGGGGSEVQLVESGGGLVQPGGSLRLSCAASGFTFNSYAMNWVRQAPGKGLEWVARIRSK<br>YNNYATYYADSVKGRFTISRDDSKNTAYLQMNSLKTEDTAVYYCVRHGNFGNSYVSWWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 219 | EGF-4 | DLL3-14 xF12Q | bispecific molecule | QVQLVQSGAEVKKPGASVKVSCKASGYTFTNYYMHWVRQAPGLGLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGQGTKVE<br>IKSGGGGSEVQLVESGGGLVQPGGSLRLSCAASGFTFNSYAMNWVRQAPGKGLEWVARIRSK<br>YNNYATYYADSVKGRFTISRDDSKNTAYLQMNSLKTEDTAVYYCVRHGNFGNSYVSWWAYWG |

TABLE 18-continued

| SEQ ID NO | DLL3-epi-tope | Desig-nation | Format / Source | Amino acid sequence |
|---|---|---|---|---|
| | | | | QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 220 | EGF-4 | DLL3-15 xF12Q | bispecific molecule | QVQLVQSGAEVKKPGASVKVSCKASGYTFTGYYIHWVRQAPGQGLEWMGIINPSDGSTSYGQ<br>NFQGRVTMTRDTSTNTVYMELSSLRSEDTAVYYCARGGNSAFYSYYDMDVWGQGTTVTVSSG<br>GGGSGGGGSGGGGSDVVMTQSPLSLPVTLGQPASISCRSSQSLAYRDGNTYLSWFQQRPGQS<br>PRRLIYKVSNWQSGVPDRFSGSGSGTDFTLKISRVEAEDVGVYFCMQGTHWPPTFGQGTKVE<br>IKSGGGGSEVQLVESGGGLVQPGGSLRLSCAASGFTFNSYAMNWVRQAPGKGLEWVARIRSK<br>YNNYATYYADSVKGRFTISRDDSKNTAYLQMNSLKTEDTAVYYCVRHGNFGNSYVSWWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 221 | N-term. | DLL3-15 xI2C - HALB variant 1 | bispecific molecule — HALB variant 1 | QVQLVESGGGVVQSGRSLRLSCAASGFTFSDYGIHWVRQAPGKGLEWVAVISYHGSNKYYAR<br>SVKGRFTVSRDNSKNTLYLQMNSLRAEDTAVYYCAREIPFGMDVWGQGTTVTVSSGGGGSGG<br>GGSGGGGSDIVMTQTPLSLPVTPGEPASISCRSSQSLLHSDGYNYLDWYLQKPGQSPQLLIY<br>LGSNRASGVPDRFSGSGSGTDFTLTISRVEAEDVGVYYCMQALQTPLTFGGGTKVDIKSGGG<br>GSEVQLVESGGGLVQPGGSLKLSCAASGFTFNKYAMNWVRQAPGKGLEWVARIRSKYNNYAT<br>YYADSVKDRFTISRDDSKNTAYLQMNNLKTEDTAVYYCVRHGNFGNSYISYWAYWGQGTLVT<br>VSSGGGGSGGGGSGGGGSQTVVTQEPSLTVSPGGTVTLTCGSSTGAVTSGNYPNWVQQKPGQ<br>APRGLIGGTKFLAPGTPARFSGSLLGGKAALTLSGVQPEDEAEYYCVLWYSNRWVFGGGTKL<br>TVLPGGGGSDAHKSEVAHRFKDLGEENFKALVLIAFAQYLQQCPFEDHVKLVNEVTEFAKTC<br>VADESAENCDKSLHTLFGDKLCTVATLRETYGEMADCCAKQEPERNECFLQHKDDNPNLPRL<br>VRPEVDVMCTAFHDNEETFLKKYLYEIARRHPYFYAPELLFFAKRYKAAFTECCQAADKAAC<br>LLPKLDELRDEGKASSAKQRLKCASLQKFGERAFKAWAVARLSQRFPKAEFAEVSKLVTDLT<br>KVHTECCHGDLLECADDRADLAKYICENQDSISSKLKECCEKPLLEKSHCIAEVENDEMPAD<br>LPSLAADFVESKDVCKNYAEAKDVFLGMFLYEYARRHPDYSVVLLLRLAKTYETTLEKCCAA<br>ADPHECYAKVFDEFKPLVEEPQNLIKQNCELFEQLGEYKFQNALLVRYTKKVPQVSTPTLVE<br>VSRNLGKVGSKCCKHPEAKRMPCAEDYLSVVLNQLCVLHEKTPVSDRVTKCCTESLVNRRPC<br>FSALEVDETYVPKEFNAGTFTFHADICTLSEKERQIKKQTALVELVKHKPKATKEQLKAAMD<br>DFAAFVEKCCKADDKETCFAEEGKKLVAASQAALGLHHHHHH |
| 222 | N-term. | DLL3-2 xI2C - HALB variant 1 | bispecific molecule — HALB variant 1 | QVQLVQSGAEVKKPGASVKVSCKASGYTFTGYYMHWVRQAPGQGLEWMGWINPNSGDTNYAQ<br>KFQGRVTMTRDTSISTAYMELSRLTSDDTAVYYCARDANIAALDAFEIWGQGTMVTVSSGGG<br>GSGGGGSGGGGSDIQMTQSPSSLSASVGDRVTITCRASQSISSYLNWYQQKPGKAPKLLIYA<br>ASSLQSGVPSRFSGSGSGTDFTLTISSLQPEDFATYYCQQSYSTPLTFGGGTKVEIKSGGGG<br>SEVQLVESGGGLVQPGGSLKLSCAASGFTFNKYAMNWVRQAPGKGLEWVARIRSKYNNYATY<br>YADSVKDRFTISRDDSKNTAYLQMNNLKTEDTAVYYCVRHGNFGNSYISYWAYWGQGTLVTV<br>SSGGGGSGGGGSGGGGSQTVVTQEPSLTVSPGGTVTLTCGSSTGAVTSGNYPNWVQQKPGQA<br>PRGLIGGTKFLAPGTPARFSGSLLGGKAALTLSGVQPEDEAEYYCVLWYSNRWVFGGGTKLT<br>VLPGGGGSDAHKSEVAHRFKDLGEENFKALVLIAFAQYLQQCPFEDHVKLVNEVTEFAKTCV<br>ADESAENCDKSLHTLFGDKLCTVATLRETYGEMADCCAKQEPERNECFLQHKDDNPNLPRLV<br>RPEVDVMCTAFHDNEETFLKKYLYEIARRHPYFYAPELLFFAKRYKAAFTECCQAADKAACL<br>LPKLDELRDEGKASSAKQRLKCASLQKFGERAFKAWAVARLSQRFPKAEFAEVSKLVTDLTK<br>VHTECCHGDLLECADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKTYETTLEKCCAAA<br>DPHECYAKVFDEFKPLVEEPQNLIKQNCELFEQLGEYKFQNALLVRYTKKVPQVSTPTLVEV<br>SRNLGKVGSKCCKHPEAKRMPCAEDYLSVVLNQLCVLHEKTPVSDRVTKCCTESLVNRRPCF<br>SALEVDETYVPKEFNAGTFTFHADICTLSEKERQIKKQTALVELVKHKPKATKEQLKAAMDD<br>FAAFVEKCCKADDKETCFAEEGKKLVAASQAALGLHHHHHH |
| 223 | EGF-1 | DLL3-3 xI2C - HALB | bispecific molecule-HALB | QVQLVESGGGVVQPGRSLRLSCAASGFTFSSYGMHWVRQAPGKGLEWVAVISYHGRDTYYAR<br>SVKGRFTISRDNSKNTLYLHMNSLRAEDTAVYYCARDGATVTSYYYSGMDVWGQGTTVTVSS<br>GGGGSGGGGSGGGGSDIQMTQSPSSLSASVGDRVTITCRASQGISNYLAWFQQKPGKAPKSL<br>IYLASSLQSGVPSKFSGSGSGTDFTLTISSLQPEDFATYYCQQYNFYPFTFGPGTKVDIKSG<br>GGGSEVQLVESGGGLVQPGGSLKLSCAASGFTFNKYAMNWVRQAPGKGLEWVARIRSKYNNY<br>ATYYADSVKDRFTISRDDSKNTAYLQMNNLKTEDTAVYYCVRHGNFGNSYISYWAYWGQGTL<br>VTVSSGGGGSGGGGSGGGGSQTVVTQEPSLTVSPGGTVTLTCGSSTGAVTSGNYPNWVQQKP<br>GQAPRGLIGGTKFLAPGTPARFSGSLLGGKAALTLSGVQPEDEAEYYCVLWYSNRWVFGGGT<br>KLTVLPGGGGSDAHKSEVAHRFKDLGEENFKALVLIAFAQYLQQCPFEDHVKLVNEVTEFAK<br>TCVADESAENCDKSLHTLFGDKLCTVATLRETYGEMADCCAKQEPERNECFLQHKDDNPNLP<br>RLVRPEVDVMCTAFHDNEETFLKKYLYEIARRHPYFYAPELLFFAKRYKAAFTECCQAADKA<br>ACLLPKLDELRDEGKASSAKQRLKCASLQKFGERAFKAWAVARLSQRFPKAEFAEVSKLVTD<br>LTKVHTECCHGDLLECADDRADLAKYICENQDSISSKLKECCEKPLLEKSHCIAEVENDEMP<br>ADLPSLAADFVESKDVCKNYAEAKDVFLGMFLYEYARRHPDYSVVLLLRLAKTYETTLEKCC<br>AAADPHECYAKVFDEFKPLVEEPQNLIKQNCELFEQLGEYKFQNALLVRYTKKVPQVSTPTL<br>VEVSRNLGKVGSKCCKHPEAKRMPCAEDYLSVVLNQLCVLHEKTPVSDRVTKCCTESLVNRR<br>PCFSALEVDETYVPKEFNAETFTFHADICTLSEKERQIKKQTALVELVKHKPKATKEQLKAV<br>MDDFAAFVEKCCKADDKETCFAEEGKKLVAASQAALGLHHHHHH |
| 224 | EGF-3 | DLL3-4 xI2C - HALB | bispecific molecule - HALB | QVQLQESGPGLVKPSETLSLTCTVSGGSISSYYWSWIRQPPGKGLEWIGYVYYSGTTNYNPS<br>LKSRVTISVDTSKNQFSLKLSSVTAADTAVYYCASIAVTGFYFDYWGQGTLVTVSSGGGGSG<br>GGGSGGGGSEIVLTQSPGTLSLSPGERVTLSCRASQRVNNNYLAWYQQRPGQAPRLLIYGAS<br>SRATGIPDRFSGSGSGTDFTLTISRLEPEDFAVYYCQQYDRSPLTFGGGTKLEIKSGGGGSE<br>VQLVESGGGLVQPGGSLKLSCAASGFTFNKYAMNWVRQAPGKGLEWVARIRSKYNNYATYYA |

TABLE 18-continued

| SEQ ID NO | DLL3-epi-tope | Desig-nation | Format / Source | Amino acid sequence |
|---|---|---|---|---|
| | | | | DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 225 | EGF-3 | DLL3-5 xI2C - HALB | bispecific molecule — HALB | QVQLQESGPGLVKPSETLSLTCTVSGGSISSYYWSWIRQPPGKGLEWIGYIYYSGRTNYYPS<br>LKSRVTISIDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKLEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 226 | EGF-3 | DLL3-6 xI2C - HALB | bispecific molecule — HALB | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 227 | EGF-3 | DLL3-7 xI2C - HALB | bispecific molecule — HALB | QVQLQESGPGLVKPSQTLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 228 | EGF-3 | DLL3-8 xI2C - HALB | bispecific molecule — HALB | QVQLQEWGPGLVKPSETLSLTCTVSGASISSFYWSWIRQPPGKGLEWIGYIYYSGTTNYNPS<br>LKSRVTISVDTSKNQLSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVDIKSGGGGSE<br>VQLVESGGGLVQPGGSLKLSCAASGFTFNKYAMNWVRQAPGKGLEWVARIRSKYNNYATYYA |

TABLE 18-continued

| SEQ ID NO | DLL3-epitope | Designation | Format / Source | Amino acid sequence |
|---|---|---|---|---|
| | | | | DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 229 | EGF-3 | DLL3-9 xI2C - HALB | bispecific molecule - HALB | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGESATLSCRASQSVNKNYLAWYQQKPGQAPRLLIYGAS<br>SRATGIPDRFSGSGSGTDFTLTISRLEPEDFAVYYCQQYDRSPLTFGGGTRLEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 230 | EGF-3 | DLL3-10 xI2C - HALB | bispecific molecule- HALB | QVQLQESGPGLVKPSQTLSLTCTVSGGSISSYYWSWIRQPPGKGLEWIGYIFYNGITNYNPS<br>LKSRVTISLDTSKNQFSLKLSSVTAADTAKYYCARIHSGSFSFDYWDQGTLVTVSSGGGGSG<br>GGGSGGGGSEIVMTQSPGTLSLSPGERATLSCRASQSVSRGYLAWYQQKPGQAPRLLIYGAS<br>SRATDIPDRFSGSGSGTDFTLTISRLEPEDFAVYYCQQYDTSPITFGQGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 231 | EGF-3 | DLL3-11 xI2C - HALB | bispecific molecule - HALB | EVQLVESGGGLVKPGGSLRLSCAASGFIFNNAGMSWVRQAPGKGLEWVGRIKNKIDGGTTDF<br>AAPVKGRFTISRDDSKNTLYLQMNSLKAEDTAVYYCTARGWYGDYFDYWGQGTLVTVSSGGG<br>GSGGGGSGGGGSDIVMTQTPLSLPVTPGEPASISCRSSQSLLHSNGYNYLDWYLQKPGQSPQ<br>LLIYLGSNRASGVPDRFSGSGSGTDFTLKISRVEAEDVGIYYCMQALQTPFTFGPGTKVEIK<br>SGGGGSEVQLVESGGGLVQPGGSLKLSCAASGFTFNKYAMNWVRQAPGKGLEWVARIRSKYN<br>NYATYYADSVKDRFTISRDDSKNTAYLQMNNLKTEDTAVYYCVRHGNFGNSYISYWAYWGQG<br>TLVTVSSGGGGSGGGGSGGGGSQTVVTQEPSLTVSPGGTVTLTCGSSTGAVTSGNYPNWVQQ<br>KPGQAPRGLIGGTKFLAPGTPARFSGSLLGGKAALTLSGVQPEDEAEYYCVLWYSNRWVFGG<br>GTKLTVLPGGGGSDAHKSEVAHRFKDLGEENFKALVLIAFAQYLQQCPFEDHVKLVNEVTEF<br>AKTCVADESAENCDKSLHTLFGDKLCTVATLRETYGEMADCCAKQEPERNECFLQHKDDNPN<br>LPRLVRPEVDVMCTAFHDNEETFLKKYLYEIARRHPYFYAPELLFFAKRYKAAFTECCQAAD<br>KAACLLPKLDELRDEGKASSAKQRLKCASLQKFGERAFKAWAVARLSQRFPKAEFAEVSKLV<br>TDLTKVHTECCHGDLLECADDRADLAKYICENQDSISSKLKECCEKPLLEKSHCIAEVENDE<br>MPADLPSLAADFVESKDVCKNYAEAKDVFLGMFLYEYARRHPDYSVVLLLRLAKTYETTLEK<br>CCAAADPHECYAKVFDEFKPLVEEPQNLIKQNCELFEQLGEYKFQNALLVRYTKKVPQVSTP<br>TLVEVSRNLGKVGSKCCKHPEAKRMPCAEDYLSVVLNQLCVLHEKTPVSDRVTKCCTESLVN<br>RRPCFSALEVDETYVPKEFNAETFTFHADICTLSEKERQIKKQTALVELVKHKPKATKEQLK<br>AVMDDFAAFVEKCCKADDKETCFAEEGKKLVAASQAALGLHHHHHH |
| 232 | EGF-3/[4] | DLL3-12 xI2C - HALB | bispecific molecule - HALB | QVQLVESGGGVVQPGRSLRLSCAASGFSFSSYDIHWVRQAPGKGLEWVAVISSHGSNKNYAR<br>SVKGRFTISRDNSKNTLYLQMNSLKAEDTAVYYCARDGYSGNDPFYYYYHGMDVWGQGTTVT<br>VSSGGGGSGGGGSGGGGSDIQMTQSPSSLSASVGDRVTITCRASQSISSYLNWYQQKPGKAP<br>KLLIYAASSLQSGVPSRFSGSGSGTDFSLTISSLQPEDFATYYCQQSFTTPLTFGGGTKVEI<br>KSGGGGSEVQLVESGGGLVQPGGSLKLSCAASGFTFNKYAMNWVRQAPGKGLEWVARIRSKY |

TABLE 18-continued

| SEQ ID NO | DLL3-epi-tope | Desig-nation | Format / Source | Amino acid sequence |
|---|---|---|---|---|
| | | | | NNYATYYADSVKDRFTISRDDSKNTAYLQMNNLKTEDTAVYYCVRHGNFGNSYISYWAYWGQ GTLVTVSSGGGGSGGGGSGGGGSQTVVTQEPSLTVSPGGTVTLTCGSSTGAVTSGNYPNWVQ QKPGQAPRGLIGGTKFLAPGTPARFSGSLLGGKAALTLSGVQPEDEAEYYCVLWYSNRWVFG GGTKLTVLPGGGGSDAHKSEVAHRFKDLGEENFKALVLIAFAQYLQQCPFEDHVKLVNEVTE FAKTCVADESAENCDKSLHTLFGDKLCTVATLRETYGEMADCCAKQEPERNECFLQHKDDNP NLPRLVRPEVDVMCTAFHDNEETFLKKYLYEIARRHPYFYAPELLFFAKRYKAAFTECCQAA DKAACLLPKLDELRDEGKASSAKQRLKCASLQKFGERAFKAWAVARLSQRFPKAEFAEVSKL VTDLTKVHTECCHGDLLECADDRADLAKYICENQDSISSKLKECCEKPLLEKSHCIAEVEND EMPADLPSLAADFVESKDVCKNYAEAKDVFLGMFLYEYARRHPDYSVVLLLRLAKTYETTLE KCCAAADPHECYAKVFDEFKPLVEEPQNLIKQNCELFEQLGEYKFQNALLVRYTKKVPQVST PTLVEVSRNLGKVGSKCCKHPEAKRMPCAEDYLSVVLNQLCVLHEKTPVSDRVTKCCTESLV NRRPCFSALEVDETYVPKEFNAETFTFHADICTLSEKERQIKKQTALVELVKHKPKATKEQL KAVMDDFAAFVEKCCKADDKETCFAEEGKKLVAASQAALGLHHHHHH |
| 233 | EGF-4 | DLL3-13 xI2C - HALB | bispecific molecule - HALB | QVQLVQSGAEVKKPGASVKVSCKASGYTFTSYYMHWVRQAPGQGLEWMGIINPSDGSTNYAQ NFQGRVTMTRDTSTNTVYMELSSLRSEDTAVYYCARGGNSAFYSYYDMDVWGQGTTVTVSSG GGGSGGGGSGGGGSDVVMTQSPLSLPVTLGQPASISCRSSQSLVYRDGNTYLSWFQQRPGQS PRRLIYKVSNWQSGVPDRFSGSGSGTDFTLKISRVEAEDVGVYFCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVLPGGGGSDAHKSEVAHRFKDLGEENFKALVLIAFAQYLQQCPFEDHVKLVNEVT EFAKTCVADESAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAEFAEVSK LVTDLTKVHTECCHGDLLECADDRADLAKYICENQDSISSKLKECCEKPLLEKSHCIAEVEN DEMPADLPSLAADFVESKDVCKNYAEAKDVFLGMFLYEYARRHPDYSVVLLLRLAKTYETTL EKCCAAADPHECYAKVFDEFKPLVEEPQNLIKQNCELFEQLGEYKFQNALLVRYTKKVPQVS TPTLVEVSRNLGKVGSKCCKHPEAKRMPCAEDYLSVVLNQLCVLHEKTPVSDRVTKCCTESL VNRRPCFSALEVDETYVPKEFNAETFTFHADICTLSEKERQIKKQTALVELVKHKPKATKEQ LKAVMDDFAAFVEKCCKADDKETCFAEEGKKLVAASQAALGLHHHHHH |
| 234 | EGF-4 | DLL3-14 xI2C - HALB | bispecific molecule - HALB | QVQLVQSGAEVKKPGASVKVSCKASGYTFTNYYMHWVRQAPGLGLEWMGIINPSDGSTSYAQ KFQGRVTMTRDTSTNTVYMELSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGGGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVLPGGGGSDAHKSEVAHRFKDLGEENFKALVLIAFAQYLQQCPFEDHVKLVNEVT EFAKTCVADESAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAEFAEVSK LVTDLTKVHTECCHGDLLECADDRADLAKYICENQDSISSKLKECCEKPLLEKSHCIAEVEN DEMPADLPSLAADFVESKDVCKNYAEAKDVFLGMFLYEYARRHPDYSVVLLLRLAKTYETTL EKCCAAADPHECYAKVFDEFKPLVEEPQNLIKQNCELFEQLGEYKFQNALLVRYTKKVPQVS TPTLVEVSRNLGKVGSKCCKHPEAKRMPCAEDYLSVVLNQLCVLHEKTPVSDRVTKCCTESL VNRRPCFSALEVDETYVPKEFNAETFTFHADICTLSEKERQIKKQTALVELVKHKPKATKEQ LKAVMDDFAAFVEKCCKADDKETCFAEEGKKLVAASQAALGLHHHHHH |
| 235 | EGF-4 | DLL3-15 xI2C - HALB | bispecific molecule - HALB | QVQLVQSGAEVKKPGASVKVSCKASGYTFTGYYIHWVRQAPGQGLEWMGIINPSDGSTSYGQ NFQGRVTMTRDTSTNTVYMDLSSLRSEDTAVYYCARGGNSAFYSYYDMDVWGQGTTVTVSSG GGGSGGGGSGGGGSDVVMTQSPLSLPVTLGQPASISCRSSQSLAYRDGNTYLSWFQQRPGQS PRRLIYKVSNWQSGVPDRFSGSGSGTDFTLKISRVEAEDVGVYFCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVLPGGGGSDAHKSEVAHRFKDLGEENFKALVLIAFAQYLQQCPFEDHVKLVNEVT EFAKTCVADESAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAEFAEVSK LVTDLTKVHTECCHGDLLECADDRADLAKYICENQDSISSKLKECCEKPLLEKSHCIAEVEN DEMPADLPSLAADFVESKDVCKNYAEAKDVFLGMFLYEYARRHPDYSVVLLLRLAKTYETTL EKCCAAADPHECYAKVFDEFKPLVEEPQNLIKQNCELFEQLGEYKFQNALLVRYTKKVPQVS TPTLVEVSRNLGKVGSKCCKHPEAKRMPCAEDYLSVVLNQLCVLHEKTPVSDRVTKCCTESL VNRRPCFSALEVDETYVPKEFNAETFTFHADICTLSEKERQIKKQTALVELVKHKPKATKEQ LKAVMDDFAAFVEKCCKADDKETCFAEEGKKLVAASQAALGLHHHHHH |
| 236 | EGF-4 | DLL3-16 xI2C - HALB | bispecific molecule-HALB | QVQLVQSGAEVKKPGASVKVSCKASGYTFTGHYMHWVRQAPGQGLEWMGIINPSDGSTNYAQ KFQGRVTMTRDTSTSTVYMELRSLRSEDTAVYYCTRGTTVVHYSYYDMDVWGQGTTVTVSSG GGGSGGGGSGGGGSDVVMTQTPLSLPVTLGQPASISCRSSQSLVYRDGNTYLTWFQQRPGQS PRRLIYKVSNWQSGVPDRFSGSGSGTDFTLKISRVEAEDVGVYYCMQGTHWPPTFGGGTKVE IKSGGGGSEVQLVESGGGLVQPGGSLKLSCAASGFTFNKYAMNWVRQAPGKGLEWVARIRSK |

TABLE 18-continued

| SEQ ID NO | DLL3-epi-tope | Desig-nation | Format / Source | Amino acid sequence |
|---|---|---|---|---|
| | | | | YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLPGGGGSDAHKSEVAHRFKDLGEENFKALVLIAFAQYLQQCPFEDHVKLVNEVT<br>EFAKTCVADESAENCDKSLHTLFGDKLCTVATLRETYGEMADCCAKQEPERNECFLQHKDDN<br>PNLPRLVRPEVDVMCTAFHDNEETFLKKYLYEIARRHPYFYAPELLFFAKRYKAAFTECCQA<br>ADKAACLLPKLDELRDEGKASSAKQRLKCASLQKFGERAFKAWAVARLSQRFPKAEFAEVSK<br>LVTDLTKVHTECCHGDLLECADDRADLAKYICENQDSISSKLKECCEKPLLEKSHCIAEVEN<br>DEMPADLPSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRYTKKVPQVS<br>TPTLVEVSRNLGKVGSKCCKHPEAKRMPCAEDYLSVVLNQLCVLHEKTPVSDRVTKCCTESL<br>VNRRPCFSALEVDETYVPKEFNAETFTFHADICTLSEKERQIKKQTALVELVKHKPKATKEQ<br>LKAVMDDFAAFVEKCCKADDKETCFAEEGKKLVAASQAALGLHHHHHH |
| 237 | EGF-4 | DLL3-17 xI2C - HALB | bispecific molecule - HALB | QVQLVQSGAEVKKPGASVKVSCKASGYTFTNYFMHWVRQAPGLGLEWMGIINPSDGSTSYAQ<br>NFQGRVTMTRDTSTNTVYMELSSLRSEDTAVYYCARGGNSAFYSYYDMDVWGQGTTVTVSSG<br>GGGSGGGGSGGGGSDVVMTQSPLSLPVTLGQPASISCRSSQSLVYRDGNTYLSWFQQRPGQS<br>PRRLIYRVSNWQSGVPDRFSGSGSGTDFTLKISRVEAEDVGVYFCMQGTYWPPTFGQGTKVD<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLPGGGGSDAHKSEVAHRFKDLGEENFKALVLIAFAQYLQQCPFEDHVKLVNEVT<br>EFAKTCVADESAENCDKSLHTLFGDKLCTVATLRETYGEMADCCAKQEPERNECFLQHKDDN<br>PNLPRLVRPEVDVMCTAFHDNEETFLKKYLYEIARRHPYFYAPELLFFAKRYKAAFTECCQA<br>ADKAACLLPKLDELRDEGKASSAKQRLKCASLQKFGERAFKAWAVARLSQRFPKAEFAEVSK<br>LVTDLTKVHTECCHGDLLECADDRADLAKYICENQDSISSKLKECCEKPLLEKSHCIAEVEN<br>DEMPADLPSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRYTKKVPQVS<br>TPTLVEVSRNLGKVGSKCCKHPEAKRMPCAEDYLSVVLNQLCVLHEKTPVSDRVTKCCTESL<br>VNRRPCFSALEVDETYVPKEFNAETFTFHADICTLSEKERQIKKQTALVELVKHKPKATKEQ<br>LKAVMDDFAAFVEKCCKADDKETCFAEEGKKLVAASQAALGLHHHHHH |
| 238 | EGF-5/[6] | DLL3-18 xI2C - HALB | bispecific molecule-HALB | QVQLVESGGGAVQPGRSLRLSCAASGFTFSNYGMHWVRQAPGKGLEWVAVISHHGSSKYYAR<br>SVKGRFTISRDNSKNTLYLEMNSLRAEDTAVYYCARDWWELVFDYWGQGTLVTVSSGGGGSG<br>GGGSGGGGSDIVMTQTPLSLSVTPGQPASISCKSSQSLLHSDGKTFLYWYLQKPGQPPQLLI<br>YEVSNRFSGVPDRFSGSGSGTDFTLKISRVEAEDVGVYYCLQGIHLPFTFGPGTKVEIKSGG<br>GGSEVQLVESGGGLVQPGGSLKLSCAASGFTFNKYAMNWVRQAPGKGLEWVARIRSKYNNYA<br>TYYADSVKDRFTISRDDSKNTAYLQMNNLKTEDTAVYYCVRHGNFGNSYISYWAYWGQGTLV<br>TVSSGGGGSGGGGSGGGGSQTVVTQEPSLTVSPGGTVTLTCGSSTGAVTSGNYPNWVQQKPG<br>QAPRGLIGGTKFLAPGTPARFSGSLLGGKAALTLSGVQPEDEAEYYCVLWYSNRWVFGGGTK<br>LTVLPGGGGSDAHKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECFLQHKDDNPNLPR<br>LVRPEVDVMCTAFHDNEETFLKKYLYEIARRHPYFYAPELLFFAKRYKAAFTECCQAADKAA<br>CLLPKLDELRDEGKASSAKQRLKCASLQKFGERAFKAWAVARLSQRFPKAEFAEVSKLVTDL<br>TKVHTECCHGDLLECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLAKTYETTLEKCCA<br>AADPHECYAKVFDEFKPLVEEPQNLIKQNCELFEQLGEYKFQNALLVRYTKKVPQVSTPTLV<br>EVSRNLGKVGSKCCKHPEAKRMPCAEDYLSVVLNQLCVLHEKTPVSDRVTKCCTESLVNRRP<br>CFSALEVDETYVPKEFNAETFTFHADICTLSEKERQIKKQTALVELVKHKPKATKEQLKAVM<br>DDFAAFVEKCCKADDKETCFAEEGKKLVAASQAALGLHHHHHH |
| 239 | EGF-5/[6] | DLL3-19 xI2C - HALB | bispecific molecule - HALB | QVTLKESGPMLVKPTETLTLTCTVSGFSLSNSRMGVSWIRQPPGRALEWLAHIFSNDGKSYS<br>TSLKSRLTISKDTSKSQVVLTMTNMDPVDTATYYCARYNYDSSGYYYSFFDYWGQGTLVTVS<br>SGGGGSGGGGSGGGGSDIQMTQSPSSLSASVGDRVTITCRASQSISSYLNWYQQKPGKAPKL<br>LIYAASSLQSGVPSRFSGSGSGTDFTLTISSLQPEDFATYYCQQGYSSPFTFGGGTKVEIKS<br>GGGGSEVQLVESGGGLVQPGGSLKLSCAASGFTFNKYAMNWVRQAPGKGLEWVARIRSKYNN<br>YATYYADSVKDRFTISRDDSKNTAYLQMNNLKTEDTAVYYCVRHGNFGNSYISYWAYWGQGT<br>LVTVSSGGGGSGGGGSGGGGSQTVVTQEPSLTVSPGGTVTLTCGSSTGAVTSGNYPNWVQQK<br>PGQAPRGLIGGTKFLAPGTPARFSGSLLGGKAALTLSGVQPEDEAEYYCVLWYSNRWVFGGG<br>TKLTVLPGGGGSDAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNECFLQHKDDNPNL<br>PRLVRPEVDVMCTAFHDNEETFLKKYLYEIARRHPYFYAPELLFFAKRYKAAFTECCQAADK<br>AACLLPKLDELRDEGKASSAKQRLKCASLQKFGERAFKAWAVARLSQRFPKAEFAEVSKLVT<br>DLTKVHTECCHGDLLECADDRADLAKYICENQDSISSKLKECCEKPLLEKSHCIAEVENDEM<br>PADLPSLAADFVESKDVCKNYAEAKDVFLGMFLYEYARRHPDYSVVLLLRLAKTYETTLEKC<br>CAAADPHECYAKVFDEFKPLVEEPQNLIKQNCELFEQLGEYKFQNALLVRYTKKVPQVSTPT<br>LVEVSRNLGKVGSKCCKHPEAKRMPCAEDYLSVVLNQLCVLHEKTPVSDRVTKCCTESLVNR<br>RPCFSALEVDETYVPKEFNAETFTFHADICTLSEKERQIKKQTALVELVKHKPKATKEQLKA<br>VMDDFAAFVEKCCKADDKETCFAEEGKKLVAASQAALGLHHHHHH |
| 240 | EGF-5/[6] | DLL3-20 xI2C - HALB | bispecific molecule — HALB | QVTLKESGPVLVKPTETLTLTCTVSGFSLSNARMGVSWLRQPPGKALEWLAHIFSTDEKSYS<br>TSLKSRLTISKDTSKSQVVLTMTNMDPVDTATYYCARYYYDSSGYYYSFFDYWGQGTLVTVS<br>SGGGGSGGGGSGGGGSDIQMTQSPSSLSASVGDRVTITCRASQSIRSYLNWYQQKPGKAPKL<br>LIYGASNLQSGVPSRFSGSGSGTDFTLTISSLQPEDFATYYCQQSYSSPFTFGGGTKVEIKS<br>GGGGSEVQLVESGGGLVQPGGSLKLSCAASGFTFNKYAMNWVRQAPGKGLEWVARIRSKYNN |

TABLE 18-continued

| SEQ ID NO | DLL3-epi-tope | Desig-nation | Format / Source | Amino acid sequence |
|---|---|---|---|---|
| | | | | YATYYADSVKDRFTISRDDSKNTAYLQMNNLKTEDTAVYYCVRHGNFGNSYISYWAYWGQGT<br>LVTVSSGGGGSGGGGSGGGGSQTVVTQEPSLTVSPGGTVTLTCGSSTGAVTSGNYPNWVQQK<br>PGQAPRGLIGGTKFLAPGTPARFSGSLLGGKAALTLSGVQPEDEAEYYCVLWYSNRWVFGGG<br>TKLTVLPGGGGSDAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNECFLQHKDDNPNL<br>PRLVRPEVDVMCTAFHDNEETFLKKYLYEIARRHPYFYAPELLFFAKRYKAAFTECCQAADK<br>AACLLPKLDELRDEGKASSAKQRLKCASLQKFGERAFKAWAVARLSQRFPKAEFAEVSKLVT<br>DLTKVHTECCHGDLLECADDRADLAKYICENQDSISSKLKECCEKPLLEKSHCIAEVENDEM<br>PADLPSLAADFVESKDVCKNYAEAKDVFLGMFLYEYARRHPDYSVVLLLRLAKTYETTLEKC<br>CAAADPHECYAKVFDEFKPLVEEPQNLIKQNCELFEQLGEYKFQNALLVRYTKKVPQVSTPT<br>LVEVSRNLGKVGSKCCKHPEAKRMPCAEDYLSVVLNQLCVLHEKTPVSDRVTKCCTESLVNR<br>RPCFSALEVDETYVPKEFNAETFTFHADICTLSEKERQIKKQTALVELVKHKPKATKEQLKA<br>VMDDFAAFVEKCCKADDKETCFAEEGKKLVAASQAALGLHHHHHH |
| 241 | EGF-5/[6] | DLL3-21 xI2C - HALB | bispecific molecule — HALB | QVQLVQSGAEVKKPGASVKVSCKASGYAFTSYYIHWVRQAPGQGLEWMGIINPSGGSKSYAQ<br>KFRGRVTMTRDTSTSTVYMELSSLTSEDTAVYYCARSMSTVTSDAFDIWGQGTMVTVSSGGG<br>GSGGGGSGGGGSDIQMTQSPSSLSASVGDRVTITCRASQSISNYLNWYQQKPGKAPKLLIYA<br>ASSLQSGVPSRFSGSGSGTEFTLTISSLQPEDFATYYCQQSYSAPLTFGGGTKVDIKSGGGG<br>SEVQLVESGGGLVQPGGSLKLSCAASGFTFNKYAMNWVRQAPGKGLEWVARIRSKYNNYATY<br>YADSVKDRFTISRDDSKNTAYLQMNNLKTEDTAVYYCVRHGNFGNSYISYWAYWGQGTLVTV<br>SSGGGGSGGGGSGGGGSQTVVTQEPSLTVSPGGTVTLTCGSSTGAVTSGNYPNWVQQKPGQA<br>PRGLIGGTKFLAPGTPARFSGSLLGGKAALTLSGVQPEDEAEYYCVLWYSNRWVFGGGTKLT<br>VLPGGGGSDAHKSEVAHRFKDLGEENFKALVLIAFAQYLQQCPFEDHVKLVNEVTEFAKTCV<br>ADESAENCDKSLHTLFGDKLCTVATLRETYGEMADCCAKQEPERNECFLQHKDDNPNLPRLV<br>RPEVDVMCTAFHDNEETFLKKYLYEIARRHPYFYAPELLFFAKRYKAAFTECCQAADKAACL<br>LPKLDELRDEGKASSAKQRLKCASLQKFGERAFKAWAVARLSQRFPKAEFAEVSKLVTDLTK<br>VHTECCHGDLLECADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKTYETTLEKCCAAA<br>DPHECYAKVFDEFKPLVEEPQNLIKQNCELFEQLGEYKFQNALLVRYTKKVPQVSTPTLVEV<br>SRNLGKVGSKCCKHPEAKRMPCAEDYLSVVLNQLCVLHEKTPVSDRVTKCCTESLVNRRPCF<br>SALEVDETYVPKEFNAETFTFHADICTLSEKERQIKKQTALVELVKHKPKATKEQLKAVMDD<br>FAAFVEKCCKADDKETCFAEEGKKLVAASQAALGLHHHHHH |
| 242 | EGF-3 | DLL3-4 xF12Q - HALB | bispecific molecule - HALB | QVQLQESGPGLVKPSETLSLTCTVSGGSISSYYWSWIRQPPGKGLEWIGYVYYSGTTNYNPS<br>LKSRVTISVDTSKNQFSLKLSSVTAADTAVYYCASIAVTGFYFDYWGQGTLVTVSSGGGGSG<br>GGGSGGGGSEIVLTQSPGTLSLSPGERVTLSCRASQRVNNNYLAWYQQRPGQAPRLLIYGAS<br>SRATGIPDRFSGSGSGTDFTLTISRLEPEDFAVYYCQQYDRSPLTFGGGTKLEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 243 | EGF-3 | DLL3-5 xF12Q - HALB | bispecific molecule-HALB | QVQLQESGPGLVKPSETLSLTCTVSGGSISSYYWSWIRQPPGKGLEWIGYIYYSGRTNYYPS<br>LKSRVTISIDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKLEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 244 | EGF-3 | DLL3-6 xF12Q - HALB | bispecific molecule - HALB | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLRLSCAASGFTFNSYAMNWVRQAPGKGLEWVARIRSKYNNYATYYA |

TABLE 18-continued

| SEQ ID NO | DLL3-epitope | Designation | Format / Source | Amino acid sequence |
|---|---|---|---|---|
| | | | | DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 245 | EGF-3 | DLL3-7 xF12Q - HALB | bispecific molecule-HALB | QVQLQESGPGLVKPSQTLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 246 | EGF-3 | DLL3-8 xF12Q - HALB | bispecific molecule - HALB | QVQLQEWGPGLVKPSETLSLTCTVSGASISSFYWSWIRQPPGKGLEWIGYIYYSGTTNYNPS<br>LKSRVTISVDTSKNQLSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVDIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 247 | EGF-3 | DLL3-9 xF12Q - HALB | bispecific molecule-HALB | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGESATLSCRASQSVNKNYLAWYQQKPGQAPRLLIYGAS<br>SRATGIPDRFSGSGSGTDFTLTISRLEPEDFAVYYCQQYDRSPLTFGGGTRLEIKSGGGGSE<br>VQLVESGGGLVQPGGSLRLSCAASGFTFNSYAMNWVRQAPGKGLEWVARIRSKYNNYATYYA<br>DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 248 | EGF-3 | DLL3-10 xF12Q - HALB | bispecific molecule - HALB | QVQLQESGPGLVKPSQTLSLTCTVSGGSISSYYWSWIRQPPGKGLEWIGYIFYNGITNYNPS<br>LKSRVTISLDTSKNQFSLKLSSVTAADTAKYYCARIHSGSFSFDYWDQGTLVTVSSGGGGSG<br>GGGSGGGGSEIVMTQSPGTLSLSPGERATLSCRASQSVSRGYLAWYQQKPGQAPRLLIYGAS<br>SRATDIPDRFSGSGSGTDFTLTISRLEPEDFAVYYCQQYDTSPITFGQGTKVEIKSGGGGSE<br>VQLVESGGGLVQPGGSLRLSCAASGFTFNSYAMNWVRQAPGKGLEWVARIRSKYNNYATYYA |

TABLE 18-continued

| SEQ ID NO | DLL3-epi-tope | Desig-nation | Format / Source | Amino acid sequence |
|---|---|---|---|---|
| | | | | DSVKGRFTISRDDSKNTAYLQMNSLKTEDTAVYYCVRHGNFGNSYVSWWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>PGGGGSDAHKSEVAHRFKDLGEENFKALVLIAFAQYLQQCPFEDHVKLVNEVTEFAKTCVAD<br>ESAENCDKSLHTLFGDKLCTVATLRETYGEMADCCAKQEPERNECFLQHKDDNPNLPRLVRP<br>EVDVMCTAFHDNEETFLKKYLYEIARRHPYFYAPELLFFAKRYKAAFTECCQAADKAACLLP<br>KLDELRDEGKASSAKQRLKCASLQKFGERAFKAWAVARLSQRFPKAEFAEVSKLVTDLTKVH<br>TECCHGDLLECADDRADLAKYICENQDSISSKLKECCEKPLLEKSHCIAEVENDEMPADLPS<br>LAADFVESKDVCKNYAEAKDVFLGMFLYEYARRHPDYSVVLLLRLAKTYETTLEKCCAAADP<br>HECYAKVFDEFKPLVEEPQNLIKQNCELFEQLGEYKFQNALLVRYTKKVPQVSTPTLVEVSR<br>NLGKVGSKCCKHPEAKRMPCAEDYLSVVLNQLCVLHEKTPVSDRVTKCCTESLVNRRPCFSA<br>LEVDETYVPKEFNAETFTFHADICTLSEKERQIKKQTALVELVKHKPKATKEQLKAVMDDFA<br>AFVEKCCKADDKETCFAEEGKKLVAASQAALGLHHHHHH |
| 249 | EGF-4 | DLL3-13 xF12Q - HALB | bispecific molecule - HALB | QVQLVQSGAEVKKPGASVKVSCKASGYTFTSYYMHWVRQAPGQGLEWMGIINPSDGSTNYAQ<br>NFQGRVTMTRDTSTNTVYMELSSLRSEDTAVYYCARGGNSAFYSYYDMDVWGQGTTVTVSSG<br>GGGSGGGGSGGGGSDVVMTQSPLSLPVTLGQPASISCRSSQSLVYRDGNTYLSWFQQRPGQS<br>PRRLIYKVSNWQSGVPDRFSGSGSGTDFTLKISRVEAEDVGVYFCMQGTHWPPTFGQGTKVE<br>IKSGGGGSEVQLVESGGGLVQPGGSLRLSCAASGFTFNSYAMNWVRQAPGKGLEWVARIRSK<br>YNNYATYYADSVKGRFTISRDDSKNTAYLQMNSLKTEDTAVYYCVRHGNFGNSYVSWWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLPGGGGSDAHKSEVAHRFKDLGEENFKALVLIAFAQYLQQCPFEDHVKLVNEVT<br>EFAKTCVADESAENCDKSLHTLFGDKLCTVATLRETYGEMADCCAKQEPERNECFLQHKDDN<br>PNLPRLVRPEVDVMCTAFHDNEETFLKKYLYEIARRHPYFYAPELLFFAKRYKAAFTECCQA<br>ADKAACLLPKLDELRDEGKASSAKQRLKCASLQKFGERAFKAWAVARLSQRFPKAEFAEVSK<br>LVTDLTKVHTECCHGDLLECADDRADLAKYICENQDSISSKLKECCEKPLLEKSHCIAEVEN<br>DEMPADLPSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRYTKKVPQVS<br>TPTLVEVSRNLGKVGSKCCKHPEAKRMPCAEDYLSVVLNQLCVLHEKTPVSDRVTKCCTESL<br>VNRRPCFSALEVDETYVPKEFNAETFTFHADICTLSEKERQIKKQTALVELVKHKPKATKEQ<br>LKAVMDDFAAFVEKCCKADDKETCFAEEGKKLVAASQAALGLHHHHHH |
| 250 | EGF-4 | DLL3-14 xF12Q - HALB | bispecific molecule - HALB | QVQLVQSGAEVKKPGASVKVSCKASGYTFTNYYMHWVRQAPGLGLEWMGIINPSDGSTSYAQ<br>KFQGRVTMTRDTSTNTVYMELSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGQGTKVE<br>IKSGGGGSEVQLVESGGGLVQPGGSLRLSCAASGFTFNSYAMNWVRQAPGKGLEWVARIRSK<br>YNNYATYYADSVKGRFTISRDDSKNTAYLQMNSLKTEDTAVYYCVRHGNFGNSYVSWWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLPGGGGSDAHKSEVAHRFKDLGEENFKALVLIAFAQYLQQCPFEDHVKLVNEVT<br>EFAKTCVADESAENCDKSLHTLFGDKLCTVATLRETYGEMADCCAKQEPERNECFLQHKDDN<br>PNLPRLVRPEVDVMCTAFHDNEETFLKKYLYEIARRHPYFYAPELLFFAKRYKAAFTECCQA<br>ADKAACLLPKLDELRDEGKASSAKQRLKCASLQKFGERAFKAWAVARLSQRFPKAEFAEVSK<br>LVTDLTKVHTECCHGDLLECADDRADLAKYICENQDSISSKLKECCEKPLLEKSHCIAEVEN<br>DEMPADLPSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRYTKKVPQVS<br>TPTLVEVSRNLGKVGSKCCKHPEAKRMPCAEDYLSVVLNQLCVLHEKTPVSDRVTKCCTESL<br>VNRRPCFSALEVDETYVPKEFNAETFTFHADICTLSEKERQIKKQTALVELVKHKPKATKEQ<br>LKAVMDDFAAFVEKCCKADDKETCFAEEGKKLVAASQAALGLHHHHHH |
| 251 | EGF-4 | DLL3-15 xF12Q - HALB | bispecific molecule-HALB | QVQLVQSGAEVKKPGASVKVSCKASGYTFTGYYIHWVRQAPGQGLEWMGIINPSDGSTSYGQ<br>NFQGRVTMTRDTSTNTVYMDLSSLRSEDTAVYYCARGGNSAFYSYYDMDVWGQGTTVTVSSG<br>GGGSGGGGSGGGGSDVVMTQSPLSLPVTLGQPASISCRSSQSLAYRDGNTYLSWFQQRPGQS<br>PRRLIYKVSNWQSGVPDRFSGSGSGTDFTLKISRVEAEDVGVYFCMQGTHWPPTFGQGTKVE<br>IKSGGGGSEVQLVESGGGLVQPGGSLRLSCAASGFTFNSYAMNWVRQAPGKGLEWVARIRSK<br>YNNYATYYADSVKGRFTISRDDSKNTAYLQMNSLKTEDTAVYYCVRHGNFGNSYVSWWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLPGGGGSDAHKSEVAHRFKDLGEENFKALVLIAFAQYLQQCPFEDHVKLVNEVT<br>EFAKTCVADESAENCDKSLHTLFGDKLCTVATLRETYGEMADCCAKQEPERNECFLQHKDDN<br>PNLPRLVRPEVDVMCTAFHDNEETFLKKYLYEIARRHPYFYAPELLFFAKRYKAAFTECCQA<br>ADKAACLLPKLDELRDEGKASSAKQRLKCASLQKFGERAFKAWAVARLSQRFPKAEFAEVSK<br>LVTDLTKVHTECCHGDLLECADDRADLAKYICENQDSISSKLKECCEKPLLEKSHCIAEVEN<br>DEMPADLPSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRYTKKVPQVS<br>TPTLVEVSRNLGKVGSKCCKHPEAKRMPCAEDYLSVVLNQLCVLHEKTPVSDRVTKCCTESL<br>VNRRPCFSALEVDETYVPKEFNAETFTFHADICTLSEKERQIKKQTALVELVKHKPKATKEQ<br>LKAVMDDFAAFVEKCCKADDKETCFAEEGKKLVAASQAALGLHHHHHH |
| 252 | — | Human DLL3 | human | MVSPRMSGLLSQTVILALIFLPQTRPAGVFELQIHSFGPGPGPGAPRSPCSARLPCRLFFRV<br>CLKPGLSEEAAESPCALGAALSARGPVYTEQPGAPAPDLPLPDGLLQVPFRDAWPGTFSFII<br>ETWREELGDQIGGPAWSLLARVAGRRRLAAGGPWARDIQRAGAWELRFSYRARCEPPAVGTA<br>CTRLCRPRSAPSRCGPGLRPCAPLEDECEAPLVCRAGCSPEHGFCEQPGECRCLEGWTGPLC<br>TVPVSTSSCLSPRGPSSATTGCLVPGPGPCDGNPCANGGSCSETPRSFECTCPRGFYGLRCE |

TABLE 18-continued

| SEQ ID NO | DLL3-epi-tope | Desig-nation | Format / Source | Amino acid sequence |
|---|---|---|---|---|
| | | | | VSGVTCADGPCFNGGLCVGGADPDSAYICHCPPGFQGSNCEKRVDRCSLQPCRNGGLCLDLG<br>HALRCRCRAGFAGPRCEHDLDDCAGRACANGGTCVEGGGAHRCSCALGFGGRDCRERADPCA<br>ARPCAHGGRCYAHFSGLVCACAPGYMGARCEFPVHPDGASALPAAPPGLRPGDPQRYLLPPA<br>LGLLVAAGVAGAALLLVHVRRRGHSQDAGSRLLAGTPEPSVHALPDALNNLRTQEGSGDGPS<br>SSVDWNRPEDVDPQGIYVISAPSIYAREVATPLFPPLHTGRAGQRQHLLFPYPSSILSVK |
| 253 | — | Human DLL3 ECD | human | MVSPRMSGLLSQTVILALIFLPQTRPAGVFELQIHSFGPGPGPGAPRSPCSARLPCRLFFRV<br>CLKPGLSEEAAESPCALGAALSARGPVYTEQPGAPAPDLPLPDGLLQVPFRDAWPGTFSFII<br>ETWREELGDQIGGPAWSLLARVAGRRRLAAGGPWARDIQRAGAWELRFSYRARCEPPAVGTA<br>CTRLCRPRSAPSRCGPGLRPCAPLEDECEAPLVCRAGCSPEHGFCEQPGECRCLEGWTGPLC<br>TVPVSTSSCLSPRGPSSATTGCLVPGPGPCDGNPCANGGSCSETPRSFECTCPRGFYGLRCE<br>VSGVTCADGPCFNGGLCVGGADPDSAYICHCPPGFQGSNCEKRVDRCSLQPCRNGGLCLDLG<br>HALRCRCRAGFAGPRCEHDLDDCAGRACANGGTCVEGGGAHRCSCALGFGGRDCRERADPCA<br>ARPCAHGGRCYAHFSGLVCACAPGYMGARCEFPVHPDGASALPAAPPGLRPGDPQRYL |
| 254 | — | Hu DLL3 N-term. | human | MVSPRMSGLLSQTVILALIFLPQTRPAGVFELQIHSFGPGPGPGAPRSPCSARLPCRLFFRV<br>CLKPGLSEEAAESPCALGAALSARGPVYTEQPGAPAPDLPLPDGLLQVPFRDAWPGTFSFII<br>ETWREELGDQIGGPAWSLLARVAGRRRLAAGGPWARDIQRAGAWELRFSYR |
| 255 | — | Hu DLL3 DSL dom | human | ARCEPPAVGTACTRLCRPRSAPSRCGPGLRPCAPLEDECE |
| 256 | — | Hu DLL3 EGF-1 | human | APLVCRAGCSPEHGFCEQPGECRCLEGWTGPLCT |
| 257 | — | Hu DLL3 EGF-2 | human | GPGPCDGNPCANGGSCSETPRSFECTCPRGFYGLRCE |
| 258 | — | Hu DLL3 EGF-3 | human | SGVTCADGPCFNGGLCVGGADPDSAYICHCPPGFQGSNCE |
| 259 | — | Hu DLL3 EGF-4 | human | RVDRCSLQPCRNGGLCLDLGHALRCRCRAGFAGPRCE |
| 260 | — | Hu DLL3 EGF-3 + 4 | h uman | SGVTCADGPCFNGGLCVGGADPDSAYICHCPPGFQGSNCEKRVDRCSLQPCRNGGLCLDLGH<br>ALRCRCRAGFAGPRCE |
| 261 | — | Hu DLL3 EGF-5 | human | DLDDCAGRACANGGTCVEGGGAHRCSCALGFGGRDCR |
| 262 | — | Hu DLL3 EGF-6 | human | RADPCAARPCAHGGRCYAHFSGLVCACAPGYMGARCE |
| 263 | — | Human DLL3 ECD × EpCAM | artificial | MVSPRMSGLLSQTVILALIFLPQTRPAGVFELQIHSFGPGPGPGAPRSPCSARLPCRLFFRV<br>CLKPGLSEEAAESPCALGAALSARGPVYTEQPGAPAPDLPLPDGLLQVPFRDAWPGTFSFII<br>ETWREELGDQIGGPAWSLLARVAGRRRLAAGGPWARDIQRAGAWELRFSYRARCEPPAVGTA<br>CTRLCRPRSAPSRCGPGLRPCAPLEDECEAPLVCRAGCSPEHGFCEQPGECRCLEGWTGPLC<br>TVPVSTSSCLSPRGPSSATTGCLVPGPGPCDGNPCANGGSCSETPRSFECTCPRGFYGLRCE<br>VSGVTCADGPCFNGGLCVGGADPDSAYICHCPPGFQGSNCEKRVDRCSLQPCRNGGLCLDLG<br>HALRCRCRAGFAGPRCEHDLDDCAGRACANGGTCVEGGGAHRCSCALGFGGRDCRERADPCA<br>ARPCAHGGRCYAHFSGLVCACAPGYMGARCEFPVHPDGASALPAAPPGLRPGDPQRYLSGGG<br>GSGAGVIAVIVVVVIAIVAGIVVLVISRKKRMAKYEKAEIKEMGEMHRELNA |
| 264 | — | V5 × hu DLL3-DSL × EpCAM | artificial | MGWSCIILFLVATATGVHSGKPIPNPLLGLDSTSGARCEPPAVGTACTRLCRPRSAPSRCGP<br>GLRPCAPLEDECEAPLVCRAGCSPEHGFCEQPGECRCLEGWTGPLCTVPVSTSSCLSPRGPS<br>SATTGCLVPGPGPCDGNPCANGGSCSETPRSFECTCPRGFYGLRCEVSGVTCADGPCFNGGL<br>CVGGADPDSAYICHCPPGFQGSNCEKRVDRCSLQPCRNGGLCLDLGHALRCRCRAGFAGPRC<br>EHDLDDCAGRACANGGTCVEGGGAHRCSCALGFGGRDCRERADPCAARPCAHGGRCYAHFSG<br>LVCACAPGYMGARCEFPVHPDGASALPAAPPGLRPGDPQRYLSGGGGSGAGVIAVIVVVVIA<br>IVAGIVVLVISRKKRMAKYEKAEIKEMGEMHRELNA |
| 265 | — | V5 × hu DLL3-EGF1 × EpCAM | artificial | MGWSCIILFLVATATGVHSGKPIPNPLLGLDSTSGAPLVCRAGCSPEHGFCEQPGECRCLEG<br>WTGPLCTVPVSTSSCLSPRGPSSATTGCLVPGPGPCDGNPCANGGSCSETPRSFECTCPRGF<br>YGLRCEVSGVTCADGPCFNGGLCVGGADPDSAYICHCPPGFQGSNCEKRVDRCSLQPCRNGG<br>LCLDLGHALRCRCRAGFAGPRCEHDLDDCAGRACANGGTCVEGGGAHRCSCALGFGGRDCRE<br>RADPCAARPCAHGGRCYAHFSGLVCACAPGYMGARCEFPVHPDGASALPAAPPGLRPGDPQR<br>YLSGGGGSGAGVIAVIVVVVIAIVAGIVVLVISRKKRMAKYEKAEIKEMGEMHRELNA |
| 266 | — | V5 × hu DLL3-EGF2 × EpCAM | artificial | MGWSCIILFLVATATGVHSGKPIPNPLLGLDSTSGGPGPCDGNPCANGGSCSETPRSFECTC<br>PRGFYGLRCEVSGVTCADGPCFNGGLCVGGADPDSAYICHCPPGFQGSNCEKRVDRCSLQPC<br>RNGGLCLDLGHALRCRCRAGFAGPRCEHDLDDCAGRACANGGTCVEGGGAHRCSCALGFGGR<br>DCRERADPCAARPCAHGGRCYAHFSGLVCACAPGYMGARCEFPVHPDGASALPAAPPGLRPG<br>DPQRYLSGGGGSGAGVIAVIVVVVIAIVAGIVVLVISRKKRMAKYEKAEIKEMGEMHRELNA |

TABLE 18-continued

| SEQ ID NO | DLL3-epi-tope | Desig-nation | Format / Source | Amino acid sequence |
|---|---|---|---|---|
| 267 | — | V5 × hu DLL3-EGF3 × EpCAM | artificial | MGWSCIILFLVATATGVHSGKPIPNPLLGLDSTSGSGVTCADGPCFNGGLCVGGADPDSAYICHCPPGFQGSNCEKRVDRCSLQPCRNGGLCLDLGHALRCRCRAGFAGPRCEHDLDDCAGRACANGGTCVEGGGAHRCSCALGFGGRDCRERADPCAARPCAHGGRCYAHFSGLVCACAPGYMGARCEFPVHPDGASALPAAPPGLRPGDPQRYLSGGGGSGAGVIAVIVVVVIAIVAGIVVLVISRKKRMAKYEKAEIKEMGEMHRELNA |
| 268 | — | V5 × hu DLL3-EGF4 × EpCAM | artificial | MGWSCIILFLVATATGVHSGKPIPNPLLGLDSTSGRVDRCSLQPCRNGGLCLDLGHALRCRCRAGFAGPRCEHDLDDCAGRACANGGTCVEGGGAHRCSCALGFGGRDCRERADPCAARPCAHGGRCYAHFSGLVCACAPGYMGARCEFPVHPDGASALPAAPPGLRPGDPQRYLSGGGGSGAGVIAVIVVVVIAIVAGIVVLVISRKKRMAKYEKAEIKEMGEMHRELNA |
| 269 | — | V5 × hu DLL3-EGF5 × EpCAM | artificial | MGWSCIILFLVATATGVHSGKPIPNPLLGLDSTSGDLDDCAGRACANGGTCVEGGGAHRCSCALGFGGRDCRERADPCAARPCAHGGRCYAHFSGLVCACAPGYMGARCEFPVHPDGASALPAAPPGLRPGDPQRYLSGGGGSGAGVIAVIVVVVIAIVAGIVVLVISRKKRMAKYEKAEIKEMGEMHRELNA |
| 270 | — | V5 × hu DLL3-EGF6 × EpCAM | artificial | MGWSCIILFLVATATGVHSGKPIPNPLLGLDSTSGRADPCAARPCAHGGRCYAHFSGLVCACAPGYMGARCEFPVHPDGASALPAAPPGLRPGDPQRYLSGGGGSGAGVIAVIVVVVIAIVAGIVVLVISRKKRMAKYEKAEIKEMGEMHRELNA |
| 271 | — | Macaque DLL3 | cyno | MVSPRMSRLLSQTVILALIFIPQARPAGVFELQIHSFGPGPGPGAPRSPCSARGPCRLFFRVCLKPGLSEEAAESPCALGAALSARGPVYTEQPEAPAPDLPLPNGLLQVPFRDAWPGTFSLIIETWREELGDQIGGPAWSLLARVTRRRRLAAGGPWARDIQRAGAWELRFSYRARCELPAVGTACTRLCRPRSAPSRCGPGLRPCAPLEDECEAPPVCRAGCSLEHGFCEQPGECRCLEGWTGPLCMVPASTSSCLGLRGPSSATTGCLVPGPGPCDGNPCANGGSCSETPGSFECTCPRGFYGLRCEVSGVTCADGPCFNGGLCVGGADPDSAYICHCPPGFQGSNCEKRVDRCSLQPCRNGGLCLDLGHALRCRCRAGFAGPRCEHNLDDCAGRACANGGTCVEGGGAHRCSCALGFGGRDCRERADPCAARPCAHGGRCYAHFSGLVCACAPGYMGSRCEFPVHPDGVSALPAAPPGLRPGDPQRYLLPPALGLLVAAGVAGAALLLVHVRRRGHAQDAGSRLLAGTPEPSVHALPDALNNQRTQEGPGDVPSSSVDWNRPEDVDSRGIYVISAPSIYAREA |
| 272 | — | Macaque DLL3 ECD | cyno | MVSPRMSRLLSQTVILALIFIPQARPAGVFELQIHSFGPGPGPGAPRSPCSARGPCRLFFRVCLKPGLSEEAAESPCALGAALSARGPVYTEQPEAPAPDLPLPNGLLQVPFRDAWPGTFSLIIETWREELGDQIGGPAWSLLARVTRRRRLAAGGPWARDIQRAGAWELRFSYRARCELPAVGTACTRLCRPRSAPSRCGPGLRPCAPLEDECEAPPVCRAGCSLEHGFCEQPGECRCLEGWTGPLCMVPASTSSCLGLRGPSSATTGCLVPGPGPCDGNPCANGGSCSETPGSFECTCPRGFYGLRCEVSGVTCADGPCFNGGLCVGGADPDSAYICHCPPGFQGSNCEKRVDRCSLQPCRNGGLCLDLGHALRCRCRAGFAGPRCEHNLDDCAGRACANGGTCVEGGGAHRCSCALGFGGRDCRERADPCAARPCAHGGRCYAHFSGLVCACAPGYMGSRCEFPVHPDGVSALPAAPPGLRPGDPQRYL |
| 273 | — | Ma DLL3 N-term. | cyno | MVSPRMSRLLSQTVILALIFIPQARPAGVFELQIHSFGPGPGPGAPRSPCSARGPCRLFFRVCLKPGLSEEAAESPCALGAALSARGPVYTEQPEAPAPDLPLPNGLLQVPFRDAWPGTFSLIIETWREELGDQIGGPAWSLLARVTRRRRLAAGGPWARDIQRAGAWELRFSYR |
| 274 | — | Ma DLL3 DSL dom. | cyno | ARCELPAVGTACTRLCRPRSAPSRCGPGLRPCAPLEDECE |
| 275 | — | Ma DLL3 EGF-1 | cyno | APPVCRAGCSLEHGFCEQPGECRCLEGWTGPLCM |
| 276 | — | Ma DLL3 EGF-2 | cyno | GPGPCDGNPCANGGSCSETPGSFECTCPRGFYGLRCE |
| 277 | — | Ma DLL3 EGF-3 | cyno | SGVTCADGPCFNGGLCVGGADPDSAYICHCPPGFQGSNCE |
| 278 | — | Ma DLL3 EGF-4 | cyno | RVDRCSLQPCRNGGLCLDLGHALRCRCRAGFAGPRCE |
| 279 | — | Ma DLL3 EGF-3 + 4 | cyno | SGVTCADGPCFNGGLCVGGADPDSAYICHCPPGFQGSNCEKRVDRCSLQPCRNGGLCLDLGHALRCRCRAGFAGPRCE |
| 280 | — | Ma DLL3 EGF-5 | cyno | NLDDCAGRACANGGTCVEGGGAHRCSCALGFGGRDCR |
| 281 | — | Ma DLL3 EGF-6 | cyno | RADPCAARPCAHGGRCYAHFSGLVCACAPGYMGSRCE |
| 282 | — | Ma DLL3 ECD × EpCAM | artificial | MVSPRMSRLLSQTVILALIFIPQARPAGVFELQIHSFGPGPGPGAPRSPCSARGPCRLFFRVCLKPGLSEEAAESPCALGAALSARGPVYTEQPEAPAPDLPLPNGLLQVPFRDAWPGTFSLIIETWREELGDQIGGPAWSLLARVTRRRRLAAGGPWARDIQRAGAWELRFSYRARCELPAVGTACTRLCRPRSAPSRCGPGLRPCAPLEDECEAPPVCRAGCSLEHGFCEQPGECRCLEGWTGPLCMVPASTSSCLGLRGPSSATTGCLVPGPGPCDGNPCANGGSCSETPGSFECTCPRGFYGLRCEVSGVTCADGPCFNGGLCVGGADPDSAYICHCPPGFQGSNCEKRVDRCSLQPCRNGGLCLDLG |

TABLE 18-continued

| SEQ ID NO | DLL3-epi-tope | Desig-nation | Format / Source | Amino acid sequence |
|---|---|---|---|---|
| | | | | HALRCRCRAGFAGPRCEHNLDDCAGRACANGGTCVEGGGAHRCSCALGFGGRDCRERADPCA ARPCAHGGRCYAHFSGLVCACAPGYMGSRCEFPVHPDGVSALPAAPPGLRPGDPQRYLSGGG GSGAGVIAVIVVVVIAIVAGIVVLVISRKKRMAKYEKAEIKEMGEMHRELNA |
| 283 | — | Human DLL1 | human | MGSRCALALAVLSALLCQVWSSGVFELKLQEFVNKKGLLGNRNCCRGGAGPPPCACRTFFRV CLKHYQASVSPEPPCTYGSAVTPVLGVDSFSLPDGGGADSAFSNPIRFPFGFTWPGTFSLII EALHTDSPDDLATENPERLISRLATQRHLTVGEEWSQDLHSSGRTDLKYSYRFVCDEHYYGE GCSVFCRPRDDAFGHFTCGERGEKVCNPGWKGPYCTEPICLPGCDEQHGFCDKPGECKCRVG WQGRYCDECIRYPGCLHGTCQQPWQCNCQEGWGGLFCNQDLNYCTHHKPCKNGATCTNTGQG SYTCSCRPGYTGATCELGIDECDPSPCKNGGSCTDLENSYSCTCPPGFYGKICELSAMTCAD GPCFNGGRCSDSPDGGYSCRCPVGYSGFNCEKKIDYCSSSPCSNGAKCVDLGDAYLCRCQAG FSGRHCDDNVDDCASSPCANGGTCRDGVNDFSCTCPPGYTGRNCSAPVSRCEHAPCHNGATC HERGHRYVCECARGYGGPNCQFLLPELPPGPAVVDLTEKLEGQGGPFPWVAVCAGVILVLML LLGCAAVVVCVRLRLQKHRPPADPCRGETETMNNLANCQREKDISVSIIGATQIKNTNKKAD FHGDHSADKNGFKARYPAVDYNLVQDLKGDDTAVRDAHSKRDTKCQPQGSSGEEKGTPTTLR GGEASERKRPDSGCSTSKDTKYQSVYVISEEKDECVIATEV |
| 284 | — | Human DLL4 | human | MAAASRSASGWALLLLVALWQQRAAGSGVFQLQLQEFINERGVLASGRPCEPGCRTFFRVCL KHFQAVVSPGPCTFGTVSTPVLGTNSFAVRDDSSGGGRNPLQLPFNFTWPGTFSLIIEAWHA PGDDLRPEALPPDALISKIAIQGSLAVGQNWLLDEQTSTLTRLRYSYRVICSDNYYGDNCSR LCKKRNDHFGHYVCQPDGNLSCLPGWTGEYCQQPICLSGCHEQNGYCSKPAECLCRPGWQGR LCNECIPHNGCRHGTCSTPWQCTCDEGWGGLFCDQDLNYCTHHSPCKNGATCSNSGQRSYTC TCRPGYTGVDCELELSECDSNPCRNGGSCKDQEDGYHCLCPPGYYGLHCEHSTLSCADSPCF NGGSCRERNQGANYACECPPNFTGSNCEKKVDRCTSNPCANGGQCLNRGPSRMCRCRPGFTG TYCELHVSDCARNPCAHGGTCHDLENGLMCTCPAGFSGRRCEVRTSIDACASSPCFNRATCY TDLSTDTFVCNCPYGFVGSRCEFPVGLPPSFPWVAVSLGVGLAVLLVLLGMVAVAVRQLRLR RPDDGSREAMNNLSDFQKDNLIPAAQLKNTNQKKELEVDCGLDKSNCGKQQNHTLDYNLAPG PLGRGTMPGKFPHSDKSLGEKAPLRLHSEKPECRISAICSPRDSMYQSVCLISEERNECVIA TEV |
| 285 | — | linker 1 | artificial | GGGG |
| 286 | — | linker 2 | artificial | GGGGS |
| 287 | — | linker 3 | artificial | GGGGQ |
| 288 | — | linker 4 | artificial | SGGGGS |
| 289 | — | linker 5 | artificial | PGGGGS |
| 290 | — | linker 6 | artificial | PGGDGS |
| 291 | — | linker 7 | artificial | GGGGSGGGS |
| 292 | — | linker 8 | artificial | GGGGSGGGGS |
| 293 | — | linker 9 | artificial | GGGGSGGGGSGGGGS |
| 294 | — | Hexa-his | artificial | HHHHHH |
| 295 | — | Ab156 | artificial | RDWDFDVFGGGTPVGG |
| 296 | — | linear FcRn BP | artificial | QRFVTGHFGGLXPANG |
| 297 | — | linear FcRn BP-Y | artificial | QRFVTGHFGGLYPANG |
| 298 | — | linear FcRn BP-H | artificial | QRFVTGHFGGLHPANG |
| 299 | | core FcRn BP-H | artificial | TGHFGGLHP |
| 300 | FcRn | cyclic BP-H | artificial | QRFCTGHFGGLHPCNG |
| 301 | — | HALB | human | DAHKSEVAHRFKDLGEENFKALVLIAFAQYLQQCPFEDHVKLVNEVTEFAKTCVADESAENC DKSLHTLFGDKLCTVATLRETYGEMADCCAKQEPERNECFLQHKDDNPNLPRLVRPEVDVMC TAFHDNEETFLKKYLYEIARRHPYFYAPELLFFAKRYKAAFTECCQAADKAACLLPKLDELR DEGKASSAKQRLKCASLQKFGERAFKAWAVARLSQRFPKAEFAEVSKLVTDLTKVHTECCHG DLLECADDRADLAKYICENQDSISSKLKECCEKPLLEKSHCIAEVENDEMPADLPSLAADFV ESKDVCKNYAEAKDVFLGMFLYEYARRHPDYSVVLLLRLAKTYETTLEKCCAAADPHECYAK |

TABLE 18-continued

| SEQ ID NO | DLL3-epitope | Designation | Format / Source | Amino acid sequence |
|---|---|---|---|---|
| | | | | VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGKKLVAASQAALGL |
| 302 | — | HALB variant 1 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAGTFTFHADICTLSEKERQIKKQTALVELVKHKPKATKEQLKAAMDDFAAFVEKC<br>CKADDKETCFAEEGKKLVAASQAALGL |
| 303 | — | HALB variant 2 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGPKLVAASQAALGL |
| 304 | — | HALB variant 3 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDDFAAFVEKC<br>CKADDKETCFAEEGPHLVAASKAALGL |
| 305 | — | HALB variant 4 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALGVDET<br>YVPKEFNAETFTFHADICTLSEKERQIKKQTALVELVKHKPKATKEQLKAVMDKFAAFVEKC<br>CKADDKETCFAEEGPKLVAASQAALGL |
| 306 | — | HALB variant 5 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDKFAAFVEKC<br>CKADDKETCFAEEGPKLVAASQAALGL |
| 307 | — | HALB variant 6 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDKFAAFVEKC<br>CKADDKETCFAEEGPHLVAASQAALGL |
| 308 | — | HALB variant 7 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV |

TABLE 18-continued

| SEQ ID NO | DLL3-epi-tope | Desig-nation | Format / Source | Amino acid sequence |
|---|---|---|---|---|
| | | | | ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGPHLVAASKAALGL |
| 309 | — | HALB variant 8 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDKFAAFVEKC<br>CKADDKETCFAEEGPKLVAASKAALGL |
| 310 | — | HALB variant 9 | artificial | DAHKSEVAHRFKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDDFAAFVEKC<br>CKADDKETCFAEEGPKLVAASKAALGL |
| 311 | — | HALB variant 10 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGKKLVAASQAALGL |
| 312 | — | HALB variant 11 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAGTFTFHADICTLSEKERQIKKQTALVELVKHKPKATKEQLKAAMDDFAAFVEKC<br>CKADDKETCFAEEGKKLVAASQAALGL |
| 313 | — | HALB variant 12 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGPKLVAASQAALGL |
| 314 | — | HALB variant 13 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDDFAAFVEKC<br>CKADDKETCFAEEGPHLVAASKAALGL |
| 315 | — | HALB variant 14 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG |

TABLE 18-continued

| SEQ ID NO | DLL3-epi-tope | Desig-nation | Format / Source | Amino acid sequence |
|---|---|---|---|---|
| | | | | DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALGVDET<br>YVPKEFNAETFTFHADICTLSEKERQIKKQTALVELVKHKPKATKEQLKAVMDKFAAFVEKC<br>CKADDKETCFAEEGPKLVAASQAALGL |
| 316 | — | HALB variant 15 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDKFAAFVEKC<br>CKADDKETCFAEEGPKLVAASQAALGL |
| 317 | — | HALB variant 16 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDKFAAFVEKC<br>CKADDKETCFAEEGPHLVAASQAALGL |
| 318 | — | HALB variant 17 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGPHLVAASKAALGL |
| 319 | — | HALB variant 18 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDKFAAFVEKC<br>CKADDKETCFAEEGPKLVAASKAALGL |
| 320 | — | HALB variant 19 | artificial | DAHKSEVAHRFKDLGEENFKALVLIAFAQYLQQSPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDDFAAFVEKC<br>CKADDKETCFAEEGPKLVAASKAALGL |
| 321 | — | HALB variant 20 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGKKLVAASQAALGL |

TABLE 18-continued

| SEQ ID NO | DLL3-epi-tope | Desig-nation | Format / Source | Amino acid sequence |
|---|---|---|---|---|
| 322 | — | HALB variant 21 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAGTFTFHADICTLSEKERQIKKQTALVELVKHKPKATKEQLKAAMDDFAAFVEKC<br>CKADDKETCFAEEGKKLVAASQAALGL |
| 323 | — | HALB variant 22 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGPKLVAASQAALGL |
| 324 | — | HALB variant 23 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDDFAAFVEKC<br>CKADDKETCFAEEGPHLVAASKAALGL |
| 325 | — | HALB variant 24 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALGVDET<br>YVPKEFNAETFTFHADICTLSEKERQIKKQTALVELVKHKPKATKEQLKAVMDKFAAFVEKC<br>CKADDKETCFAEEGPKLVAASQAALGL |
| 326 | — | HALB variant 25 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDKFAAFVEKC<br>CKADDKETCFAEEGPKLVAASQAALGL |
| 327 | — | HALB variant 26 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDKFAAFVEKC<br>CKADDKETCFAEEGPHLVAASQAALGL |
| 328 | — | HALB variant 27 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG |

TABLE 18-continued

| SEQ ID NO | DLL3-epi-tope | Desig-nation | Format / Source | Amino acid sequence |
|---|---|---|---|---|
| | | | | SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDDFAAFVEKC<br>CKADDKETCFAEEGPHLVAASKAALGL |
| 329 | — | HALB variant 28 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALEVDET<br>YVPKEFNAETFTFHADICTLSEKERQIKKQTALVELVKHKPKATKEQLKAVMDKFAAFVEKC<br>CKADDKETCFAEEGPKLVAASKAALGL |
| 330 | — | HALB variant 29 | artificial | DAHKSEVAHRFKDLGEENFKALVLIAFAQYLQQAPFEDHVKLVNEVTEFAKTCVADESAENC<br>DKSLHTLFGDKLCTVATLRETYGEMADCCAKQEPERNECFLQHKDDNPNLPRLVRPEVDVMC<br>TAFHDNEETFLKKYLYEIARRHPYFYAPELLFFAKRYKAAFTECCQAADKAACLLPKLDELR<br>DEGKASSAKQRLKCASLQKFGERAFKAWAVARLSQRFPKAEFAEVSKLVTDLTKVHTECCHG<br>DLLECADDRADLAKYICENQDSISSKLKECCEKPLLEKSHCIAEVENDEMPADLPSLAADFV<br>ESKDVCKNYAEAKDVFLGMFLYEYARRHPDYSVVLLLRLAKTYETTLEKCCAAADPHECYAK<br>VFDEFKPLVEEPQNLIKQNCELFEQLGEYKFQNALLVRYTKKVPQVSTPTLVEVSRNLGKVG<br>SKCCKHPEAKRMPCAEDYLSVVLNQLCVLHEKTPVSDRVTKCCTESLVNRRPCFSALDVDET<br>YVPKEFNAETFTFHADICTLSEKERQIKKQTALVELVKHKPKATKEQLKAVMDDFAAFVEKC<br>CKADDKETCFAEEGPKLVAASKAALGL |
| 331 | — | Cross body 1 HC | artificial | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKPCEEQYGSTYRCV<br>SVLTVLHQDWLNGKEYKCKVSNKALPAPIEKTISKAKGQPREPQVYTLPPSREEMTKNQVSL<br>TCLVKGFYPSDIAVEWESNGQPENNYDTTPPVLDSDGSFFLYSDLTVDKSRWQQGNVFSCSV<br>MHEALHNHYTQKSLSLSPGK |
| 332 | — | Cross body 1 LC | artificial | GQPKAAPSVTLFPPSSEELQANKATLVCLISDFYPGAVTVAWKADSSPVKAGVETTTPSKQS<br>NNKYAASSYLSLTPEQWKSHRSYSCQVTHEGSTVEKTVAPTECSDKTHTCPPCPAPELLGGP<br>SVFLFPPKPKDTLMISRTPEVTCVVVDVSHEDPEVKFNWYVDGVEVHNAKTKPCEEQYGSTY<br>RCVSVLTVLHQDWLNGKEYKCKVSNKALPAPIEKTISKAKGQPREPQVYTLPPSRKEMTKNQ<br>VSLTCLVKGFYPSDIAVEWESNGQPENNYKTTPPVLKSDGSFFLYSKLTVDKSRWQQGNVFS<br>CSVMHEALHNHYTQKSLSLSPGK |
| 333 | — | Cross body 2 HC | artificial | ASTKGPSVFPLAPCSRSTSESTAALGCLVKDYFPEPVTVSWNSGALTSGVHTFPAVLQSSGL<br>YSLSSVVTVPSSNFGTQTYTCNVDHKPSNTKVDKTVEPKSSDKTHTCPPCPAPEAAGGPSVF<br>LFPPKPKDTLMISRTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPSREEMTKNQVSL<br>TCLVKGFYPSDIAVEWESNGQPENNYDTTPPVLDSDGSFFLYSDLTVDKSRWQQGNVFSCSV<br>MHEALHNHYTQKSLSLSPGK |
| 334 | — | Cross body 2 LC | artificial | GQPKAAPSVTLFPPSSEELQANKATLVCLISDFYPGAVTVAWKADSSPVKAGVETTTPSKQS<br>NNKYAASSYLSLTPEQWKSHRSYSCQVTHEGSTVEKTVAPTECSEPKSSDKTHTCPPCPAPE<br>AAGGPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLPPSRKE<br>MTKNQVSLTCLVKGFYPSDIAVEWESNGQPENNYKTTPPVLKSDGSFFLYSKLTVDKSRWQQ<br>GNVFSCSVMHEALHNHYTQKSLSLSPGK |
| 335 | — | Hetero-Fc binder Fc | artificial | DKTHTCPPCPAPELLGGPSVFLFPPKPKDTLMISRTPEVTCVVVDVSHEDPEVKFNWYVDGV<br>EVHNAKTKPCEEQYGSTYRCVSVLTVLHQDWLNGKEYKCKVSNKALPAPIEKTISKAKGQPR<br>EPQVYTLPPSRKEMTKNQVSLTCLVKGFYPSDIAVEWESNGQPENNYKTTPPVLKSDGSFFL<br>YSKLTVDKSRWQQGNVFSCSVMHEALHNHYTQKSLSLSPGK |
| 336 | — | Hetero-Fc partner Fc | artificial | DKTHTCPPCPAPELLGGPSVFLFPPKPKDTLMISRTPEVTCVVVDVSHEDPEVKFNWYVDGV<br>EVHNAKTKPCEEQYGSTYRCVSVLTVLHQDWLNGKEYKCKVSNKALPAPIEKTISKAKGQPR<br>EPQVYTLPPSREEMTKNQVSLTCLVKGFYPSDIAVEWESNGQPENNYDTTPPVLDSDGSFFL<br>YSDLTVDKSRWQQGNVFSCSVMHEALHNHYTQKSLSLSPGK |
| 337 | — | Maxi-body 1 target Fc | artificial | EPKSSDKTHTCPPCPAPELLGGPSVFLFPPKPKDTLMISRTPEVTCVVVDVSHEDPEVKFNW<br>YVDGVEVHNAKTKPCEEQYGSTYRCVSVLTVLHQDWLNGKEYKCKVSNKALPAPIEKTISKA<br>KGQPREPQVYTLPPSRKEMTKNQVSLTCLVKGFYPSDIAVEWESNGQPENNYKTTPPVLKSD<br>GSFFLYSKLTVDKSRWQQGNVFSCSVMHEALHNHYTQKSLSLSPGK |
| 338 | — | Maxi-body 1 CD3 Fc | artificial | EPKSSDKTHTCPPCPAPELLGGPSVFLFPPKPKDTLMISRTPEVTCVVVDVSHEDPEVKFNW<br>YVDGVEVHNAKTKPCEEQYGSTYRCVSVLTVLHQDWLNGKEYKCKVSNKALPAPIEKTISKA<br>KGQPREPQVYTLPPSREEMTKNQVSLTCLVKGFYPSDIAVEWESNGQPENNYDTTPPVLDSD<br>GSFFLYSDLTVDKSRWQQGNVFSCSVMHEALHNHYTQKSLSLSPGK |

TABLE 18-continued

| SEQ ID NO | DLL3-epitope | Designation | Format / Source | Amino acid sequence |
|---|---|---|---|---|
| 339 | — | Maxi-body 2 target Fc | artificial | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRKEMTKNQVSLTCLVKGFYPSDIAVEWESNGQPENNYKTTPPVLKSDGSFFLYSKLTVDKSRWQQGNVFSCSVMHEALHNHYTQKSLSLSPGK |
| 340 | — | Maxi-body 2 CD3 Fc | artificial | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYDTTPPVLDSDGSFFLYSDLTVDKSRWQQGNVFSCSVMHEALHNHYTQKSLSLSPGK |
| 341 | — | Mono Fc | artificial | APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVTTLPPSREEMTKNQVSLTCLVKGFYPSDIAVEWESNGQPENNYDTTPPVLDSDGSFFLYSDLTVDKSRWQQGNVFSCSVMHEALHNHYTQKSLSLSPGK |
| 342 | — | CDR-L1 of F6A | artificial | GSSTGAVTSGYYPN |
| 343 | | CDR-L2 of F6A | artificial | GTKFLAP |
| 344 | | CDR-L3 of F6A | artificial | ALWYSNRWV |
| 345 | | CDR-H1 of F6A | artificial | IYAMN |
| 346 | | CDR-H2 of F6A | artificial | RIRSKYNNYATYYADSVKS |
| 347 | | CDR-H3 of F6A | artificial | HGNFGNSYVSFFAY |
| 348 | | VH of F6A | artificial | EVQLVESGGGLVQPGGSLKLSCAASGFTFNIYAMNWVRQAPGKGLEWVARIRSKYNNYATYYADSVKSRFTISRDDSKNTAYLQMNNLKTEDTAVYYCVRHGNFGNSYVSFFAYWGQGTLVTVSS |
| 349 | | VL of F6A | artificial | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 350 | | VH-VL of F6A | artificial | EVQLVESGGGLVQPGGSLKLSCAASGFTFNIYAMNWVRQAPGKGLEWVARIRSKYNNYATYYADSVKSRFTISRDDSKNTAYLQMNNLKTEDTAVYYCVRHGNFGNSYVSFFAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 351 | | CDR-L1 of H2C | artificial | GSSTGAVTSGYYPN |
| 352 | | CDR-L2 of H2C | artificial | GTKFLAP |
| 353 | | CDR-L3 of H2C | artificial | ALWYSNRWV |
| 354 | | CDR-H1 of H2C | artificial | KYAMN |
| 355 | | CDR-H2 of H2C | artificial | RIRSKYNNYATYYADSVKD |
| 356 | | CDR-H3 of H2C | artificial | HGNFGNSYISYWAY |
| 357 | | VH of H2C | artificial | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS |
| 358 | | VL of H2C | artificial | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |

TABLE 18-continued

| SEQ ID NO | DLL3-epi- tope | Desig- nation | Format / Source | Amino acid sequence |
|---|---|---|---|---|
| 359 | | VH-VL of H2C | artificial | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 360 | | CDR-L1 of H1E | artificial | GSSTGAVTSGYYPN |
| 361 | | CDR-L2 of H1E | artificial | GTKFLAP |
| 362 | | CDR-L3 of H1E | artificial | ALWYSNRWV |
| 363 | | CDR-H1 of H1E | artificial | SYAMN |
| 364 | | CDR-H2 of H1E | artificial | RIRSKYNNYATYYADSVKG |
| 365 | | CDR-H3 of H1E | artificial | HGNFGNSYLSFWAY |
| 366 | | VH of H1E | artificial | EVQLVESGGGLEQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYLSFWAYWGQGTLVTVSS |
| 367 | | VL of H1E | artificial | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 368 | | VH-VL of H1E | artificial | EVQLVESGGGLEQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYLSFWAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 369 | | CDR-L1 of G4H | artificial | GSSTGAVTSGYYPN |
| 370 | | CDR-L2 of G4H | artificial | GTKFLAP |
| 371 | | CDR-L3 of G4H | artificial | ALWYSNRWV |
| 372 | | CDR-H1 of G4H | artificial | RYAMN |
| 373 | | CDR-H2 of G4H | artificial | RIRSKYNNYATYYADSVKG |
| 374 | | CDR-H3 of G4H | artificial | HGNFGNSYLSYFAY |
| 375 | | VH of G4H | artificial | EVQLVESGGGLVQPGGSLKLSCAASGFTFNRYAMNWVRQAPGKGLEWVARIRSKYNNYATYYADSVKGRFTISRDDSKNTAYLQMNNLKTEDTAVYYCVRHGNFGNSYLSYFAYWGQGTLVTVSS |
| 376 | | VL of G4H | artificial | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 377 | | VH-VL of G4H | artificial | EVQLVESGGGLVQPGGSLKLSCAASGFTFNRYAMNWVRQAPGKGLEWVARIRSKYNNYATYYADSVKGRFTISRDDSKNTAYLQMNNLKTEDTAVYYCVRHGNFGNSYLSYFAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 378 | | CDR-L1 of A2J | artificial | RSSTGAVTSGYYPN |
| 379 | | CDR-L2 of A2J | artificial | ATDMRPS |

TABLE 18-continued

| SEQ ID NO | DLL3-epi-tope | Desig-nation | Format / Source | Amino acid sequence |
|---|---|---|---|---|
| 380 | | CDR-L3 of A2J | artificial | ALWYSNRWV |
| 381 | | CDR-H1 of A2J | artificial | VYAMN |
| 382 | | CDR-H2 of A2J | artificial | RIRSKYNNYATYYADSVKK |
| 383 | | CDR-H3 of A2J | artificial | HGNFGNSYLSWWAY |
| 384 | | VH of A2J | artificial | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYLSWWAYWGQGTLVTVSS |
| 385 | | VL of A2J | artificial | QTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 386 | | VH-VL of A2J | artificial | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYLSWWAYWGQGTLVTVSSGGGGSGGGGSGGGGSQTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 387 | | CDR-L1 of E1L | artificial | GSSTGAVTSGYYPN |
| 388 | | CDR-L2 of E1L | artificial | GTKFLAP |
| 389 | | CDR-L3 of E1L | artificial | ALWYSNRWV |
| 390 | | CDR-H1 of E1L | artificial | KYAMN |
| 391 | | CDR-H2 of E1L | artificial | RIRSKYNNYATYYADSVKS |
| 392 | | CDR-H3 of E1L | artificial | HGNFGNSYTSYYAY |
| 393 | | VH of E1L | artificial | EVQLVESGGGLVQPGGSLKLSCAASGFTFNKYAMNWVRQAPGKGLEWVARIRSKYNNYATYYADSVKSRFTISRDDSKNTAYLQMNNLKTEDTAVYYCVRHGNFGNSYTSYYAYWGQGTLVTVSS |
| 394 | | VL of E1L | artificial | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 395 | | VH-VL of E1L | artificial | EVQLVESGGGLVQPGGSLKLSCAASGFTFNKYAMNWVRQAPGKGLEWVARIRSKYNNYATYYADSVKSRFTISRDDSKNTAYLQMNNLKTEDTAVYYCVRHGNFGNSYTSYYAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 396 | | CDR-L1 of E2M | artificial | RSSTGAVTSGYYPN |
| 397 | | CDR-L2 of E2M | artificial | ATDMRPS |
| 398 | | CDR-L3 of E2M | artificial | ALWYSNRWV |
| 399 | | CDR-H1 of E2M | artificial | GYAMN |
| 400 | | CDR-H2 of E2M | artificial | RIRSKYNNYATYYADSVKE |
| 401 | | CDR-H3 of E2M | artificial | HRNFGNSYLSWFAY |

TABLE 18-continued

| SEQ ID NO | DLL3-epi-tope | Desig-nation | Format / Source | Amino acid sequence |
|---|---|---|---|---|
| 402 | | VH of E2M | artificial | EVQLVESGGGLVQPGGSLKLSCAASGFTFNGYAMNWVRQAPGKGLEWVARIRSKYNNYATYYADSVKERFTISRDDSKNTAYLQMNNLKTEDTAVYYCVRHRNFGNSYLSWFAYWGQGTLVTVSS |
| 403 | | VL of E2M | artificial | QTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 404 | | VH-VL of E2M | artificial | EVQLVESGGGLVQPGGSLKLSCAASGFTFNGYAMNWVRQAPGKGLEWVARIRSKYNNYATYYADSVKERFTISRDDSKNTAYLQMNNLKTEDTAVYYCVRHRNFGNSYLSWFAYWGQGTLVTVSSGGGGSGGGGSGGGGSQTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 405 | | CDR-L1 of F7O | artificial | GSSTGAVTSGYYPN |
| 406 | | CDR-L2 of F7O | artificial | GTKFLAP |
| 407 | | CDR-L3 of F7O | artificial | ALWYSNRWV |
| 408 | | CDR-H1 of F7O | artificial | VYAMN |
| 409 | | CDR-H2 of F7O | artificial | RIRSKYNNYATYYADSVKK |
| 410 | | CDR-H3 of F7O | artificial | HGNFGNSYISWWAY |
| 411 | | VH of F7O | artificial | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYISWWAYWGQGTLVTVSS |
| 412 | | VL of F7O | artificial | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 413 | | VH-VL of F7O | artificial | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYISWWAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 414 | | CDR-L1 of F12Q | artificial | GSSTGAVTSGNYPN |
| 415 | | CDR-L2 of F12Q | artificial | GTKFLAP |
| 416 | | CDR-L3 of F12Q | artificial | VLWYSNRWV |
| 417 | | CDR-H1 of F12Q | artificial | SYAMN |
| 418 | | CDR-H2 of F12Q | artificial | RIRSKYNNYATYYADSVKG |
| 419 | | CDR-H3 of F12Q | artificial | HGNFGNSYVSWWAY |
| 420 | | VH of F12Q | artificial | EVQLVESGGGLVQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYVSWWAYWGQGTLVTVSS |
| 421 | | VL of F12Q | artificial | QTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 422 | | VH-VL of F12Q | artificial | EVQLVESGGGLVQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYVSWWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |

TABLE 18-continued

| SEQ ID NO | DLL3-epi-tope | Desig-nation | Format / Source | Amino acid sequence |
|---|---|---|---|---|
| 423 | | CDR-L1 of I2C | artificial | GSSTGAVTSGNYPN |
| 424 | | CDR-L2 of I2C | artificial | GTKFLAP |
| 425 | | CDR-L3 of I2C | artificial | VLWYSNRWV |
| 426 | | CDR-H1 of I2C | artificial | KYAMN |
| 427 | | CDR-H2 of I2C | artificial | RIRSKYNNYATYYADSVKD |
| 428 | | CDR-H3 of I2C | artificial | HGNFGNSYISYWAY |
| 429 | | VH of I2C | artificial | EVQLVESGGGLVQPGGSLKLSCAASGFTFNKYAMNWVRQAPGKGLEWVARIRSKYNNYATYY ADSVKDRFTISRDDSKNTAYLQMNNLKTEDTAVYYCVRHGNFGNSYISYWAYWGQGTLVTVS S |
| 430 | | VL of I2C | artificial | QTVVTQEPSLTVSPGGTVTLTCGSSTGAVTSGNYPNWVQQKPGQAPRGLIGGTKFLAPGTPA RFSGSLLGGKAALTLSGVQPEDEAEYYCVLWYSNRWVFGGGTKLTVL |
| 431 | | VH-VL of I2C | artificial | EVQLVESGGGLVQPGGSLKLSCAASGFTFNKYAMNWVRQAPGKGLEWVARIRSKYNNYATYY ADSVKDRFTISRDDSKNTAYLQMNNLKTEDTAVYYCVRHGNFGNSYISYWAYWGQGTLVTVS SGGGGSGGGGSGGGGSQTVVTQEPSLTVSPGGTVTLTCGSSTGAVTSGNYPNWVQQKPGQAP RGLIGGTKFLAPGTPARFSGSLLGGKAALTLSGVQPEDEAEYYCVLWYSNRWVFGGGTKLTV L |
| 432 | | VH of F12q | artificial | EVQLVESGGGLVQPGGSLRLSCAASGFTFNSYAMNWVRQAPGKGLEWVARIRSKYNNYATYY ADSVKGRFTISRDDSKNTAYLQMNSLKTEDTAVYYCVRHGNFGNSYVSWWAYWGQGTLVTVS S |
| 433 | | VL of F12q | artificial | QTVVTQEPSLTVSPGGTVTLTCGSSTGAVTSGNYPNWVQQKPGQAPRGLIGGTKFLAPGTPA RFSGSLLGGKAALTLSGVQPEDEAEYYCVLWYSNRWVFGGGTKLTVL |
| 434 | | VH VL of F12q | artificial | EVQLVESGGGLVQPGGSLRLSCAASGFTFNSYAMNWVRQAPGKGLEWVARIRSKYNNYATYY ADSVKGRFTISRDDSKNTAYLQMNSLKTEDTAVYYCVRHGNFGNSYVSWWAYWGQGTLVTVS SGGGGSGGGGSGGGGSQTVVTQEPSLTVSPGGTVTLTCGSSTGAVTSGNYPNWVQQKPGQAP RGLIGGTKFLAPGTPARFSGSLLGGKAALTLSGVQPEDEAEYYCVLWYSNRWVFGGGTKLTV L |
| 435 | | DLL3-4-001 (G44C) | VH | QVQLQESGPGLVKPSETLSLTCTVSGGSISSYYWSWIRQPPGKCLEWIGYVYYSGTTNYNPS LKSRVTISVDTSKNQFSLKLSSVTAADTAVYYCASIAVTGFYFDYWGQGTLVTVSS |
| 436 | | DLL3-4-001 (G234C) | VL | EIVLTQSPGTLSLSPGERVTLSCRASQRVNNNYLAWYQQRPGQAPRLLIYGASSRATGIPDR FSGSGSGTDFTLTISRLEPEDFAVYYCQQYDRSPLTFGCGTKLEIK |
| 437 | | DLL3-4-001 (G44C-G243C) | scFv | QVQLQESGPGLVKPSETLSLTCTVSGGSISSYYWSWIRQPPGKCLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGCGTKLEIK |
| 438 | | DLL3-4-001 (CC) xI2C | bispecific molecule | QVQLQESGPGLVKPSETLSLTCTVSGGSISSYYWSWIRQPPGKCLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGCGTKLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 439 | | DLL3-14-D55E | VH-CDR2 | IINPSEGSTSYAQKFQG |
| 440 | | DLL3-14-G56A | VH-CDR2 | IINPSDASTSYAQKFQG |
| 441 | | DLL3-14-D171E | VL-CDR1 | RSSQSLVYREGNTYLS |

TABLE 18-continued

| SEQ ID NO | DLL3-epi-tope | Desig-nation | Format / Source | Amino acid sequence |
|---|---|---|---|---|
| 442 | | DLL3-14 -G172A | VL-CDR1 | RSSQSLVYRDANTYLS |
| 443 | | DLL3-14 -N173Q | VL-CDR1 | RSSQSLVYRDGQTYLS |
| 444 | | DLL3-14 -T174A | VL-CDR1 | RSSQSLVYRDGNAYLS |
| 445 | | DLL3-14 -L43Q | VH | QVQLVQSGAEVKKPGASVKVSCKASGYTFTNYYMHWVRQAPGQGLEWMGIINPSDGSTSYAQ KFQGRVTMTRDTSTNTVYMDLSSLRSEDTAVYYCARGGNSAFYSYYDMDVWGQGTTVTVSS |
| 446 | | DLL3-14 -D55E | VH | QVQLVQSGAEVKKPGASVKVSCKASGYTFTNYYMHWVRQAPGLGLEWMGIINPSEGSTSYAQ KFQGRVTMTRDTSTNTVYMDLSSLRSEDTAVYYCARGGNSAFYSYYDMDVWGQGTTVTVSS |
| 447 | | DLL3-14 -G56A | VH | QVQLVQSGAEVKKPGASVKVSCKASGYTFTNYYMHWVRQAPGLGLEWMGIINPSDASTSYAQ KFQGRVTMTRDTSTNTVYMDLSSLRSEDTAVYYCARGGNSAFYSYYDMDVWGQGTTVTVSS |
| 448 | | DLL3-14 -L43Q-D55E | VH | QVQLVQSGAEVKKPGASVKVSCKASGYTFTNYYMHWVRQAPGQGLEWMGIINPSEGSTSYAQ KFQGRVTMTRDTSTNTVYMDLSSLRSEDTAVYYCARGGNSAFYSYYDMDVWGQGTTVTVSS |
| 449 | | DLL3-14 -L43Q-G56A | VH | QVQLVQSGAEVKKPGASVKVSCKASGYTFTNYYMHWVRQAPGQGLEWMGIINPSDASTSYAQ KFQGRVTMTRDTSTNTVYMDLSSLRSEDTAVYYCARGGNSAFYSYYDMDVWGQGTTVTVS |
| 450 | | DLL3-14 -G44C | VH | QVQLVQSGAEVKKPGASVKVSCKASGYTFTNYYMHWVRQAPGLCLEWMGIINPSDGSTSYAQ KFQGRVTMTRDTSTNTVYMDLSSLRSEDTAVYYCARGGNSAFYSYYDMDVWGQGTTVTVSS |
| 451 | | DLL3-14 -L43Q-G44C | VH | QVQLVQSGAEVKKPGASVKVSCKASGYTFTNYYMHWVRQAPGQCLEWMGIINPSDGSTSYAQ KFQGRVTMTRDTSTNTVYMDLSSLRSEDTAVYYCARGGNSAFYSYYDMDVWGQGTTVTVSS |
| 452 | | DLL3-14 -G44C-D55E | VH | QVQLVQSGAEVKKPGASVKVSCKASGYTFTNYYMHWVRQAPGLCLEWMGIINPSEGSTSYAQ KFQGRVTMTRDTSTNTVYMDLSSLRSEDTAVYYCARGGNSAFYSYYDMDVWGQGTTVTVSS |
| 453 | | DLL3-14 -G44C-G56A | VH | QVQLVQSGAEVKKPGASVKVSCKASGYTFTNYYMHWVRQAPGLCLEWMGIINPSDASTSYAQ KFQGRVTMTRDTSTNTVYMDLSSLRSEDTAVYYCARGGNSAFYSYYDMDVWGQGTTVTVSS |
| 454 | | DLL3-14 -L43Q-G44C-D55E | VH | QVQLVQSGAEVKKPGASVKVSCKASGYTFTNYYMHWVRQAPGQCLEWMGIINPSEGSTSYAQ KFQGRVTMTRDTSTNTVYMDLSSLRSEDTAVYYCARGGNSAFYSYYDMDVWGQGTTVTVSS |
| 455 | | DLL3-14 -L43Q-G44C-G56A | VH | QVQLVQSGAEVKKPGASVKVSCKASGYTFTNYYMHWVRQAPGQCLEWMGIINPSDASTSYAQ KFQGRVTMTRDTSTNTVYMDLSSLRSEDTAVYYCARGGNSAFYSYYDMDVWGQGTTVTVSS |
| 456 | | DLL3-14 -D171E | VL | DVVMTQTPLSLPVTLGQPASISCRSSQSLVYREGNTYLSWFQQRPGQSPRRLIYKVSNWQSG VPDRFSGGGSGTDFTLKISRVEAEDVGVYYCMQGTHWPPTFGQGTKVEIK |
| 457 | | DLL3-14 -G172A | VL | DVVMTQTPLSLPVTLGQPASISCRSSQSLVYRDANTYLSWFQQRPGQSPRRLIYKVSNWQSG VPDRFSGGGSGTDFTLKISRVEAEDVGVYYCMQGTHWPPTFGQGTKVEIK |
| 458 | | DLL3-14 -N173Q | VL | DVVMTQTPLSLPVTLGQPASISCRSSQSLVYRDGQTYLSWFQQRPGQSPRRLIYKVSNWQSG VPDRFSGGGSGTDFTLKISRVEAEDVGVYYCMQGTHWPPTFGQGTKVEIK |
| 459 | | DLL3-14 -T174A | VL | DVVMTQTPLSLPVTLGQPASISCRSSQSLVYRDGNAYLSWFQQRPGQSPRRLIYKVSNWQSG VPDRFSGGGSGTDFTLKISRVEAEDVGVYYCMQGTHWPPTFGQGTKVEIK |
| 460 | | DLL3-14 -G208S | VL | DVVMTQTPLSLPVTLGQPASISCRSSQSLVYRDGNTYLSWFQQRPGQSPRRLIYKVSNWQSG VPDRFSGSGSGTDFTLKISRVEAEDVGVYYCMQGTHWPPTFGQGTKVEIK |
| 461 | | DLL3-14 -D171E-G208S | VL | DVVMTQTPLSLPVTLGQPASISCRSSQSLVYREGNTYLSWFQQRPGQSPRRLIYKVSNWQSG VPDRFSGSGSGTDFTLKISRVEAEDVGVYYCMQGTHWPPTFGQGTKVEIK |
| 462 | | DLL3-14 G172A-G208S | VL | DVVMTQTPLSLPVTLGQPASISCRSSQSLVYRDANTYLSWFQQRPGQSPRRLIYKVSNWQSG VPDRFSGSGSGTDFTLKISRVEAEDVGVYYCMQGTHWPPTFGQGTKVEIK |

TABLE 18-continued

| SEQ ID NO | DLL3-epi-tope | Desig-nation | Format / Source | Amino acid sequence |
|---|---|---|---|---|
| 463 | | DLL3-14 -Q243C | VL | DVVMTQTPLSLPVTLGQPASISCRSSQSLVYRDGNTYLSWFQQRPGQSPRRLIYKVSNWQSG VPDRFSGGGSGTDFTLKISRVEAEDVGVYYCMQGTHWPPTFGCGTKVEIK |
| 464 | | DLL3-14 -D171E-Q243C | VL | DVVMTQTPLSLPVTLGQPASISCRSSQSLVYREGNTYLSWFQQRPGQSPRRLIYKVSNWQSG VPDRFSGGGSGTDFTLKISRVEAEDVGVYYCMQGTHWPPTFGCGTKVEIK |
| 465 | | DLL3-14 -G172A-Q243C | VL | DVVMTQTPLSLPVTLGQPASISCRSSQSLVYRDANTYLSWFQQRPGQSPRRLIYKVSNWQSG VPDRFSGGGSGTDFTLKISRVEAEDVGVYYCMQGTHWPPTFGCGTKVEIK |
| 466 | | DLL3-14 -N173Q Q243C | VL | DVVMTQTPLSLPVTLGQPASISCRSSQSLVYRDGQTYLSWFQQRPGQSPRRLIYKVSNWQSG VPDRFSGGGSGTDFTLKISRVEAEDVGVYYCMQGTHWPPTFGCGTKVEIK |
| 467 | | DLL3-14 -T174A-Q243C | VL | DVVMTQTPLSLPVTLGQPASISCRSSQSLVYRDGNAYLSWFQQRPGQSPRRLIYKVSNWQSG VPDRFSGGGSGTDFTLKISRVEAEDVGVYYCMQGTHWPPTFGCGTKVEIK |
| 468 | | DLL3-14 -G208S-Q243C | VL | DVVMTQTPLSLPVTLGQPASISCRSSQSLVYRDGNTYLSWFQQRPGQSPRRLIYKVSNWQSG VPDRFSGSGSGTDFTLKISRVEAEDVGVYYCMQGTHWPPTFGCGTKVEIK |
| 469 | | DLL3-14 -D171E-G208S-Q243C | VL | DVVMTQTPLSLPVTLGQPASISCRSSQSLVYREGNTYLSWFQQRPGQSPRRLIYKVSNWQSG VPDRFSGSGSGTDFTLKISRVEAEDVGVYYCMQGTHWPPTFGCGTKVEIK |
| 470 | | DLL3-14 -G172A-G208S-Q243C | VL | DVVMTQTPLSLPVTLGQPASISCRSSQSLVYRDANTYLSWFQQRPGQSPRRLIYKVSNWQSG VPDRFSGSGSGTDFTLKISRVEAEDVGVYYCMQGTHWPPTFGCGTKVEIK |
| 471 | | DLL3-14 -001 | scFv | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYREGNTYLSWFQQRPGQS PRRLIYKVSNWQSGVPDRFSGGGSGTDFTLKISRVEAEDVGVYYCMQGTHWPPTFGQGTKVE IK |
| 472 | | DLL3-14 -002 | scFv | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDANTYLSWFQQRPGQS PRRLIYKVSNWQSGVPDRFSGGGSGTDFTLKISRVEAEDVGVYYCMQGTHWPPTFGQGTKVE IK |
| 473 | | DLL3-14 -003 | scFv | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGQTYLSWFQQRPGQS PRRLIYKVSNWQSGVPDRFSGGGSGTDFTLKISRVEAEDVGVYYCMQGTHWPPTFGQGTKVE IK |
| 474 | | DLL3-14 -004 | scFv | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNAYLSWFQQRPGQS PRRLIYKVSNWQSGVPDRFSGGGSGTDFTLKISRVEAEDVGVYYCMQGTHWPPTFGQGTKVE IK |
| 475 | | DLL3-14 -005 | scFv | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGSGSGTDFTLKISRVEAEDVGVYYCMQGTHWPPTFGQGTKVE IK |
| 476 | | DLL3-14 -006 | scFv | QVQLVQSGAEVKKPGASVKVSCKASGYTFTNYYMHWVRQAPGQGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGGGSGTDFTLKISRVEAEDVGVYYCMQGTHWPPTFGQGTKVE IK |
| 477 | | DLL3-14 -007 | scFv | QVQLVQSGAEVKKPGASVKVSCKASGYTFTNYYMHWVRQAPGLGLEWMGIINPSEGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGGGSGTDFTLKISRVEAEDVGVYYCMQGTHWPPTFGQGTKVE IK |

TABLE 18-continued

| SEQ ID NO | DLL3-epitope | Designation | Format / Source | Amino acid sequence |
|---|---|---|---|---|
| 478 | | DLL3-14-008 | scFv | QVQLVQSGAEVKKPGASVKVSCKASGYTFTNYYMHWVRQAPGLGLEWMGIINPSDASTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGQGTKVEIK |
| 479 | | DLL3-14-009 | scFv | QVQLVQSGAEVKKPGASVKVSCKASGYTFTNYYMHWVRQAPGQGLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGSGSGTDFTLKISRVEAEDVGVYYCMQGTHWPPTFGQGTKVEIK |
| 480 | | DLL3-14-010 | scFv | QVQLVQSGAEVKKPGASVKVSCKASGYTFTNYYMHWVRQAPGQGLEWMGIINPSEGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYREGNTYLSWFQQRPGQSPRRLIYKVSNWQSGVPDRFSGSGSGTDFTLKISRVEAEDVGVYYCMQGTHWPPTFGQGTKVEIK |
| 481 | | DLL3-14-011 | scFv | QVQLVQSGAEVKKPGASVKVSCKASGYTFTNYYMHWVRQAPGQGLEWMGIINPSDASTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDANTYLSWFQQRPGQSPRRLIYKVSNWQSGVPDRFSGSGSGTDFTLKISRVEAEDVGVYYCMQGTHWPPTFGQGTKVEIK |
| 482 | | DLL3-14-012 (CC) | scFv | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGCGTKVEIK |
| 483 | | DLL3-14-013 | scFv | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYREGNTYLSWFQQRPGQSPRRLIYKVSNWQSGVPDRFSGGGSGTDFTLKISRVEAEDVGVYYCMQGTHWPPTFGCGTKVEIK |
| 484 | | DLL3-14-014 | scFv | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDANTYLSWFQQRPGQSPRRLIYKVSNWQSGVPDRFSGGGSGTDFTLKISRVEAEDVGVYYCMQGTHWPPTFGCGTKVEIK |
| 485 | | DLL3-14-015 | scFv | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGQTYLSWFQQRPGQSPRRLIYKVSNWQSGVPDRFSGGGSGTDFTLKISRVEAEDVGVYYCMQGTHWPPTFGCGTKVEIK |
| 486 | | DLL3-14-016 | scFv | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNAYLSWFQQRPGQSPRRLIYKVSNWQSGVPDRFSGGGSGTDFTLKISRVEAEDVGVYYCMQGTHWPPTFGCGTKVEIK |
| 487 | | DLL3-14-017 | scFv | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGSGSGTDFTLKISRVEAEDVGVYYCMQGTHWPPTFGCGTKVEIK |
| 488 | | DLL3-14-018 | scFv | QVQLVQSGAEVKKPGASVKVSCKASGYTFTNYYMHWVRQAPGQCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGCGTKVEIK |
| 489 | | DLL3-14-019 | scFv | QVQLVQSGAEVKKPGASVKVSCKASGYTFTNYYMHWVRQAPGLCLEWMGIINPSEGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGCGTKVEIK |

TABLE 18-continued

| SEQ ID NO | DLL3-epi-tope | Desig-nation | Format / Source | Amino acid sequence |
|---|---|---|---|---|
| 490 | | DLL3-14 -020 | scFv | QVQLVQSGAEVKKPGASVKVSCKASGYTFTNYYMHWVRQAPGLCLEWMGIINPSDASTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGGGSGTDFTLKISRVEAEDVGVYYCMQGTHWPPTFGCGTKVE IK |
| 491 | | DLL3-14 -021 | scFv | QVQLVQSGAEVKKPGASVKVSCKASGYTFTNYYMHWVRQAPGQCLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGSGSGTDFTLKISRVEAEDVGVYYCMQGTHWPPTFGCGTKVE IK |
| 492 | | DLL3-14 -022 | scFv | QVQLVQSGAEVKKPGASVKVSCKASGYTFTNYYMHWVRQAPGQCLEWMGIINPSEGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYREGNTYLSWFQQRPGQS PRRLIYKVSNWQSGVPDRFSGSGSGTDFTLKISRVEAEDVGVYYCMQGTHWPPTFGCGTKVE IK |
| 493 | | DLL3-14 -023 | scFv | QVQLVQSGAEVKKPGASVKVSCKASGYTFTNYYMHWVRQAPGQCLEWMGIINPSDASTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDANTYLSWFQQRPGQS PRRLIYKVSNWQSGVPDRFSGSGSGTDFTLKISRVEAEDVGVYYCMQGTHWPPTFGCGTKVE IK |
| 494 | | DLL3-14 -001 xI2C | bispecific molecule | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYREGNTYLSWFQQRPGQS PRRLIYKVSNWQSGVPDRFSGGGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 495 | | DLL3-14 -002 xI2C | bispecific molecule | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDANTYLSWFQQRPGQS PRRLIYKVSNWQSGVPDRFSGGGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 496 | | DLL3-14 -003 xI2C | bispecific molecule | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGQTYLSWFQQRPGQS PRRLIYKVSNWQSGVPDRFSGGGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 497 | | DLL3-14 -004 xI2C | bispecific molecule | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNAYLSWFQQRPGQS PRRLIYKVSNWQSGVPDRFSGGGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 498 | | DLL3-14 -005 xI2C | bispecific molecule | QVQLVQSGAEVKKPGASVKVSCKASGYTFTNYYMHWVRQAPGLGLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGSGSGTDFTLKISRVEAEDVGVYYCMQGTHWPPTFGQGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |

TABLE 18-continued

| SEQ ID NO | DLL3-epi-tope | Desig-nation | Format / Source | Amino acid sequence |
|---|---|---|---|---|
| 499 | | DLL3-14 -006x12C | bispecific molecule | QVQLVQSGAEVKKPGASVKVSCKASGYTFTNYYMHWVRQAPGQGLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 500 | | DLL3-14 -007 xI2C | bispecific molecule | QVQLVQSGAEVKKPGASVKVSCKASGYTFTNYYMHWVRQAPGLGLEWMGIINPSEGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 501 | | DLL3-14 -008 xI2C | bispecific molecule | QVQLVQSGAEVKKPGASVKVSCKASGYTFTNYYMHWVRQAPGLGLEWMGIINPSDASTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 502 | | DLL3-14 -009 xI2C | bispecific molecule | QVQLVQSGAEVKKPGASVKVSCKASGYTFTNYYMHWVRQAPGQGLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGSGSGTDFTLKISRVEAEDVGVYYCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 503 | | DLL3-14 -010 xI2C | bispecific molecule | QVQLVQSGAEVKKPGASVKVSCKASGYTFTNYYMHWVRQAPGQGLEWMGIINPSEGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYREGNTYLSWFQQRPGQSPRRLIYKVSNWQSGVPDRFSGSGSGTDFTLKISRVEAEDVGVYYCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 504 | | DLL3-14 -011 xI2C | bispecific molecule | QVQLVQSGAEVKKPGASVKVSCKASGYTFTNYYMHWVRQAPGQGLEWMGIINPSDASTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDANTYLSWFQQRPGQSPRRLIYKVSNWQSGVPDRFSGSGSGTDFTLKISRVEAEDVGVYYCMQGTHWPPTFGQGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 505 | | DLL3-14 -012 (CC) xI2C | bispecific molecule | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYRDGNTYLSWFQQRPGQSPRRLIYKVSNWQSGVPDRFSGGGSGTDFTLKISRVEAEDVGVYYCMQGTHWPPTFGCGTKVEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 506 | | DLL3-14 -013 xI2C | bispecific molecule | QVQLVQSGAEVKKPGASVKVSCKASGYTFTNYYMHWVRQAPGLCLEWMGIINPSDGSTSYAQKFQGRVTMTRDTSTNTVYMDLSSLRSEDTAVYYCARGGNSAFYSYYDMDVWGQGTTVTVSSGGGGSGGGGSGGGGSDVVMTQTPLSLPVTLGQPASISCRSSQSLVYREGNTYLSWFQQRPGQSPRRLIYKVSNWQSGVPDRFSGGGSGTDFTLKISRVEAEDVGVYYCMQGTHWPPTFGCGTKVEIKSGGGGSEVQLVESGGGLVQPGGSLKLSCAASGFTFNKYAMNWVRQAPGKGLEWVARIRSK |

TABLE 18-continued

| SEQ ID NO | DLL3-epi-tope | Desig-nation | Format / Source | Amino acid sequence |
|---|---|---|---|---|
| | | | | YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 507 | | DLL3-14 -014 xI2C | bispecific molecule | QVQLVQSGAEVKKPGASVKVSCKASGYTFTNYYMHWVRQAPGLCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDANTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 508 | | DLL3-14 -015 xI2C | bispecific molecule | QVQLVQSGAEVKKPGASVKVSCKASGYTFTNYYMHWVRQAPGLCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGQTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 509 | | DLL3-14 -016 xI2C | bispecific molecule | QVQLVQSGAEVKKPGASVKVSCKASGYTFTNYYMHWVRQAPGLCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNAYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 510 | | DLL3-14 -017 xI2C | bispecific molecule | QVQLVQSGAEVKKPGASVKVSCKASGYTFTNYYMHWVRQAPGLCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGSGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 511 | | DLL3-14 -018 xI2C | bispecific molecule | QVQLVQSGAEVKKPGASVKVSCKASGYTFTNYYMHWVRQAPGQCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 512 | | DLL3-14 -019 xI2C | bispecific molecule | QVQLVQSGAEVKKPGASVKVSCKASGYTFTNYYMHWVRQAPGLCLEWMGIINPSEGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |
| 513 | | DLL3-14 -020 xI2C | bispecific molecule | QVQLVQSGAEVKKPGASVKVSCKASGYTFTNYYMHWVRQAPGLCLEWMGIINPSDASTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVL |

TABLE 18-continued

| SEQ ID NO | DLL3-epi-tope | Desig-nation | Format / Source | Amino acid sequence |
|---|---|---|---|---|
| 514 | | DLL3-14 -021 xI2C | bispecific molecule | QVQLVQSGAEVKKPGASVKVSCKASGYTFTNYYMHWVRQAPGQCLEWMGIINPSDGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDGNTYLSWFQQRPGQS PRRLIYKVSNWQSGVPDRFSGSGSGTDFTLKISRVEAEDVGVYYCMQGTHWPPTFGCGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 515 | | DLL3-14 -022 xI2C | bispecific molecule | QVQLVQSGAEVKKPGASVKVSCKASGYTFTNYYMHWVRQAPGQCLEWMGIINPSEGSTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYREGNTYLSWFQQRPGQS PRRLIYKVSNWQSGVPDRFSGSGSGTDFTLKISRVEAEDVGVYYCMQGTHWPPTFGCGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 516 | | DLL3-14 -023 xI2C | bispecific molecule | QVQLVQSGAEVKKPGASVKVSCKASGYTFTNYYMHWVRQAPGQCLEWMGIINPSDASTSYAQ KFQGRVTMTRDTSTNTVYMDLSSLRSEDTAVYYCARGGNSAFYSYYDMDVWGQGTTVTVSSG GGGSGGGGSGGGGSDVVMTQTPLSLPVTLGQPASISCRSSQSLVYRDANTYLSWFQQRPGQS PRRLIYKVSNWQSGVPDRFSGSGSGTDFTLKISRVEAEDVGVYYCMQGTHWPPTFGCGTKVE IKSGGGGSEVQLVESGGGLVQPGGSLKLSCAASGFTFNKYAMNWVRQAPGKGLEWVARIRSK YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVL |
| 517 | | DLL3-4 xI2C - scFc | bispecific HLE molecule | QVQLQESGPGLVKPSETLSLTCTVSGGSISSYYWSWIRQPPGKGLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGGGTKLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL GGGGDKTHTCPPCPAPELLGGPSVFLFPPKPKDTLMISRTPEVTCVVVDVSHEDPEVKFNWY VDGVEVHNAKTKPCEEQYGSTYRCVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGKGGGGSGGGGSGGGGSGG GGSGGGGSGGGGSDKTHTCPPCPAPELLGGPSVFLFPPKPKDTLMISRTPEVTCVVVDVSHE DPEVKFNWYVDGVEVHNAKTKPCEEQYGSTYRCVSVLTVLHQDWLNGKEYKCKVSNKALPAP IEKTISKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGK |
| 518 | | DLL3-4 xI2C - scFc_del GK | bispecific HLE molecule | QVQLQESGPGLVKPSETLSLTCTVSGGSISSYYWSWIRQPPGKGLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGGGTKLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL GGGGDKTHTCPPCPAPELLGGPSVFLFPPKPKDTLMISRTPEVTCVVVDVSHEDPEVKFNWY VDGVEVHNAKTKPCEEQYGSTYRCVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGGGGSGGGGSGGGGSGGGG SGGGGSGGGGSDKTHTCPPCPAPELLGGPSVFLFPPKPKDTLMISRTPEVTCVVVDVSHEDP EVKFNWYVDGVEVHNAKTKPCEEQYGSTYRCVSVLTVLHQDWLNGKEYKCKVSNKALPAPIE KTISKAKGQPREPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSPGK |
| 519 | | DLL3-4-001 (CC) xI2C - scFc | bispecific HLE molecule | QVQLQESGPGLVKPSETLSLTCTVSGGSISSYYWSWIRQPPGKCLEWIGYVYYSGTTNYNPS LKSRVTISVDTSKNQFSLKLSSVTAADTAVYYCASIAVTGFYFDYWGQGTLVTVSSGGGGSG GGGSGGGGSEIVLTQSPGTLSLSPGERVTLSCRASQRVNNNYLAWYQQRPGQAPRLLIYGAS SRATGIPDRFSGSGSGTDFTLTISRLEPEDFAVYYCQQYDRSPLTFGCGTKLEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL GGGGDKTHTCPPCPAPELLGGPSVFLFPPKPKDTLMISRTPEVTCVVVDVSHEDPEVKFNWY VDGVEVHNAKTKPCEEQYGSTYRCVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLDSDG |

TABLE 18-continued

| SEQ ID NO | DLL3-epi-tope | Desig-nation | Format / Source | Amino acid sequence |
|---|---|---|---|---|
| | | | | SFFLYSKLTVDKSRWQQGNVFSCSVMHEALHNHYTQKSLSLSPGKGGGGSGGGGSGGGGSGG<br>GGSGGGGSGGGGSDKTHTCPPCPAPELLGGPSVFLFPPKPKDTLMISRTPEVTCVVVDVSHE<br>DPEVKFNWYVDGVEVHNAKTKPCEEQYGSTYRCVSVLTVLHQDWLNGKEYKCKVSNKALPAP<br>IEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |
| 520 | | DLL3-4-001 (CC) xI2C - scFc _delGK | bispecific HLE molecule | QVQLQESGPGLVKPSETLSLTCTVSGGSISSYYWSWIRQPPGKCLEWIGYVYYSGTTNYNPS<br>LKSRVTISVDTSKNQFSLKLSSVTAADTAVYYCASIAVTGFYFDYWGQGTLVTVSSGGGGSG<br>GGGSGGGGSEIVLTQSPGTLSLSPGERVTLSCRASQRVNNNYLAWYQQRPGQAPRLLIYGAS<br>SRATGIPDRFSGSGSGTDFTLTISRLEPEDFAVYYCQQYDRSPLTFGCGTKLEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>GGGGDKTHTCPPCPAPELLGGPSVFLFPPKPKDTLMISRTPEVTCVVVDVSHEDPEVKFNWY<br>VDGVEVHNAKTKPCEEQYGSTYRCVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGGGGSGGGGSGGGGSGGGG<br>SGGGGSGGGGSDKTHTCPPCPAPELLGGPSVFLFPPKPKDTLMISRTPEVTCVVVDVSHEDP<br>EVKFNWYVDGVEVHNAKTKPCEEQYGSTYRCVSVLTVLHQDWLNGKEYKCKVSNKALPAPIE<br>KTISKAKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 521 | | DLL3-6 xI2C - scFc | bispecific HLE molecule | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>GGGGDKTHTCPPCPAPELLGGPSVFLFPPKPKDTLMISRTPEVTCVVVDVSHEDPEVKFNWY<br>VDGVEVHNAKTKPCEEQYGSTYRCVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGKGGGGSGGGGSGGGGSGG<br>GGSGGGGSGGGGSDKTHTCPPCPAPELLGGPSVFLFPPKPKDTLMISRTPEVTCVVVDVSHE<br>DPEVKFNWYVDGVEVHNAKTKPCEEQYGSTYRCVSVLTVLHQDWLNGKEYKCKVSNKALPAP<br>IEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |
| 522 | | DLL3-6 xI2C - scFc_del GK | bispecific HLE molecule | QVQLQESGPGLVKPSETLSLTCTVSGASISSFYWSWIRQPPGKGLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGGGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>GGGGDKTHTCPPCPAPELLGGPSVFLFPPKPKDTLMISRTPEVTCVVVDVSHEDPEVKFNWY<br>VDGVEVHNAKTKPCEEQYGSTYRCVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGGGGSGGGGSGGGGSGGGG<br>SGGGGSGGGGSDKTHTCPPCPAPELLGGPSVFLFPPKPKDTLMISRTPEVTCVVVDVSHEDP<br>EVKFNWYVDGVEVHNAKTKPCEEQYGSTYRCVSVLTVLHQDWLNGKEYKCKVSNKALPAPIE<br>KTISKAKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 523 | | DLL3-6-001 (CC) xI2C - scFc | bispecific HLE molecule | QVQLQESGPGLVKPSETLSLTCTVSGASISSFYWSWIRQPPGKCLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGCGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>GGGGDKTHTCPPCPAPELLGGPSVFLFPPKPKDTLMISRTPEVTCVVVDVSHEDPEVKFNWY<br>VDGVEVHNAKTKPCEEQYGSTYRCVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGKGGGGSGGGGSGGGGSGG<br>GGSGGGGSGGGGSDKTHTCPPCPAPELLGGPSVFLFPPKPKDTLMISRTPEVTCVVVDVSHE<br>DPEVKFNWYVDGVEVHNAKTKPCEEQYGSTYRCVSVLTVLHQDWLNGKEYKCKVSNKALPAP<br>IEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |

TABLE 18-continued

| SEQ ID NO | DLL3-epi-tope | Desig-nation | Format / Source | Amino acid sequence |
|---|---|---|---|---|
| 524 | | DLL3-6-001 (CC) xI2C - scFc_del GK | bispecific HEL molecule | QVQLQESGPGLVKPSETLSLTCTVSGASISSFYWSWIRQPPGKCLEWIGYIYYSGTTNYNPS<br>LKSRVTISVDTSKNQFSLKLSSVTAADTAVYYCARIAVAGFFFDYWGQGTLVTVSSGGGGSG<br>GGGSGGGGSEIVLTQSPGTLSLSPGERATLSCRASQSVNKNYLAWYQQKPGQAPRLLIYGAS<br>SRATGIPDRFSGSGSGTDFTLTISRLEPEDFAVYYCQQYDRSPLTFGCGTKVEIKSGGGGSE<br>VQLVESGGGLVQPGGSLKLSCAASGFTFNKYAMNWVRQAPGKGLEWVARIRSKYNNYATYYA<br>DSVKDRFTISRDDSKNTAYLQMNNLKTEDTAVYYCVRHGNFGNSYISYWAYWGQGTLVTVSS<br>GGGGSGGGGSGGGGSQTVVTQEPSLTVSPGGTVTLTCGSSTGAVTSGNYPNWVQQKPGQAPR<br>GLIGGTKFLAPGTPARFSGSLLGGKAALTLSGVQPEDEAEYYCVLWYSNRWVFGGGTKLTVL<br>GGGGDKTHTCPPCPAPELLGGPSVFLFPPKPKDTLMISRTPEVTCVVVDVSHEDPEVKFNWY<br>VDGVEVHNAKTKPCEEQYGSTYRCVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGGGGSGGGGSGGGGSGGGG<br>SGGGGSGGGGSDKTHTCPPCPAPELLGGPSVFLFPPKPKDTLMISRTPEVTCVVVDVSHEDP<br>EVKFNWYVDGVEVHNAKTKPCEEQYGSTYRCVSVLTVLHQDWLNGKEYKCKVSNKALPAPIE<br>KTISKAKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 525 | | DLL3-14 xI2C - scFc | bispecific HLE molecule | QVQLVQSGAEVKKPGASVKVSCKASGYTFTNYYMHWVRQAPGLGLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGQGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLGGGGDKTHTCPPCPAPELLGGPSVFLFPPKPKDTLMISRTPEVTCVVVDVSHE<br>DPEVKFNWYVDGVEVHNAKTKPCEEQYGSTYRCVSVLTVLHQDWLNGKEYKCKVSNKALPAP<br>IEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGKGGGGSGGG<br>GSGGGGSGGGGSGGGGSGGGGSDKTHTCPPCPAPELLGGPSVFLFPPKPKDTLMISRTPEVT<br>CVVVDVSHEDPEVKFNWYVDGVEVHNAKTKPCEEQYGSTYRCVSVLTVLHQDWLNGKEYKCK<br>VSNKALPAPIEKTISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHNHYTQKSLSLSPG<br>K |
| 526 | | DLL3-14 xI2C - scFc_del GK | bispecific HLE molecule | QVQLVQSGAEVKKPGASVKVSCKASGYTFTNYYMHWVRQAPGLGLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGQGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLGGGGDKTHTCPPCPAPELLGGPSVFLFPPKPKDTLMISRTPEVTCVVVDVSHE<br>DPEVKFNWYVDGVEVHNAKTKPCEEQYGSTYRCVSVLTVLHQDWLNGKEYKCKVSNKALPAP<br>IEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGGGGSGGGGS<br>GGGGSGGGGSGGGGSGGGGSDKTHTCPPCPAPELLGGPSVFLFPPKPKDTLMISRTPEVTCV<br>VVDVSHEDPEVKFNWYVDGVEVHNAKTKPCEEQYGSTYRCVSVLTVLHQDWLNGKEYKCKVS<br>NKALPAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLSPGK |
| 527 | | DLL3-14 -012 (CC) xI2C - scFc | bispecific HLE molecule | QVQLVQSGAEVKKPGASVKVSCKASGYTFTNYYMHWVRQAPGLCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK<br>YNNYATYYADSVKDRFTISRDDSKNTAYLQMNNLKTEDTAVYYCVRHGNFGNSYISYWAYWG<br>QGTLVTVSSGGGGSGGGGSGGGGSQTVVTQEPSLTVSPGGTVTLTCGSSTGAVTSGNYPNWV<br>QQKPGQAPRGLIGGTKFLAPGTPARFSGSLLGGKAALTLSGVQPEDEAEYYCVLWYSNRWVF<br>GGGTKLTVLGGGGDKTHTCPPCPAPELLGGPSVFLFPPKPKDTLMISRTPEVTCVVVDVSHE<br>DPEVKFNWYVDGVEVHNAKTKPCEEQYGSTYRCVSVLTVLHQDWLNGKEYKCKVSNKALPAP<br>IEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGKGGGGSGGG<br>GSGGGGSGGGGSGGGGSGGGGSDKTHTCPPCPAPELLGGPSVFLFPPKPKDTLMISRTPEVT<br>CVVVDVSHEDPEVKFNWYVDGVEVHNAKTKPCEEQYGSTYRCVSVLTVLHQDWLNGKEYKCK<br>VSNKALPAPIEKTISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHNHYTQKSLSLSPG<br>K |
| 528 | | DLL3-14 -012 (CC) xI2C - scFc_del GK | bispecific HLE molecule | QVQLVQSGAEVKKPGASVKVSCKASGYTFTNYYMHWVRQAPGLCLEWMGIINPSDGSTSYAQ<br>KFQGRVTMTRDTSTNTVYMDLSSLRSEDTAVYYCARGGNSAFYSYYDMDVWGQGTTVTVSSG<br>GGGSGGGGSGGGGSDVVMTQTPLSLPVTLGQPASISCRSSQSLVYRDGNTYLSWFQQRPGQS<br>PRRLIYKVSNWQSGVPDRFSGGGSGTDFTLKISRVEAEDVGVYYCMQGTHWPPTFGCGTKVE<br>IKSGGGGSEVQLVESGGGLVQPGGSLKLSCAASGFTFNKYAMNWVRQAPGKGLEWVARIRSK |

TABLE 18-continued

| SEQ ID NO | DLL3-epi-tope | Desig-nation | Format / Source | Amino acid sequence |
|---|---|---|---|---|
| | | | | YNNYATYYADSVKDRFTISRDDSKNTAYLQMNNLKTEDTAVYYCVRHGNFGNSYISYWAYWG QGTLVTVSSGGGGSGGGGSGGGGSQTVVTQEPSLTVSPGGTVTLTCGSSTGAVTSGNYPNWV QQKPGQAPRGLIGGTKFLAPGTPARFSGSLLGGKAALTLSGVQPEDEAEYYCVLWYSNRWVF GGGTKLTVLGGGGDKTHTCPPCPAPELLGGPSVFLFPPKPKDTLMISRTPEVTCVVVDVSHE DPEVKFNWYVDGVEVHNAKTKPCEEQYGSTYRCVSVLTVLHQDWLNGKEYKCKVSNKALPAP IEKTISKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGGGGSGGGGS GGGGSGGGGSGGGGSGGGGSDKTHTCPPCPAPELLGGPSVFLFPPKPKDTLMISRTPEVTCV VVDVSHEDPEVKFNWYVDGVEVHNAKTKPCEEQYGSTYRCVSVLTVLHQDWLNGKEYKCKVS NKALPAPIEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 529 | | DLL3-6-001 (CC) | VH | QVQLQESGPGLVKPSETLSLTCTVSGASISSFYWSWIRQPPGKCLEWIGYIYYSGTTNYNPS LKSRVTISVDTSKNQFSLKLSSVTAADTAVYYCARIAVAGFFFDYWGQGTLVTVSS |
| 530 | | DLL3-6-001 (CC) | VL | EIVLTQSPGTLSLSPGERATLSCRASQSVNKNYLAWYQQKPGQAPRLLIYGASSRATGIPDR FSGSGSGTDFTLTISRLEPEDFAVYYCQQYDRSPLTFGCGTKVEIK |
| 531 | | DLL3-6-001 (CC) | scFv | QVQLQESGPGLVKPSETLSLTCTVSGASISSFYWSWIRQPPGKCLEWIGYIYYSGTTNYNPS LKSRVTISVDTSKNQFSLKLSSVTAADTAVYYCARIAVAGFFFDYWGQGTLVTVSSGGGGSG GGGSGGGGSEIVLTQSPGTLSLSPGERATLSCRASQSVNKNYLAWYQQKPGQAPRLLIYGAS SRATGIPDRFSGSGSGTDFTLTISRLEPEDFAVYYCQQYDRSPLTFGCGTKVEIK |
| 532 | | DLL3-6-001 (CC) xI2C | bispecific molecule | QVQLQESGPGLVKPSETLSLTCTVSGASISSFYWSWIRQPPGKCLEWIGYIYYSGTTNYNPS LKSRVTISVDTSKNQFSLKLSSVTAADTAVYYCARIAVAGFFFDYWGQGTLVTVSSGGGGSG GGGSGGGGSEIVLTQSPGTLSLSPGERATLSCRASQSVNKNYLAWYQQKPGQAPRLLIYGAS SRATGIPDRFSGSGSGTDFTLTISRLEPEDFAVYYCQQYDRSPLTFGCGTKVEIKSGGGGSE VQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWYSNRWVFGGGTKLTVL |
| 533 | | Fc monomer-1 +c/-g | | DKTHTCPPCPAPELLGGPSVFLFPPKPKDTLMISRTPEVTCVVVDVSHEDPEVKFNWYVDGV EVHNAKTKPCEEQYGSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 534 | | Fc monomer-2 +c/-g/ delGK | | DKTHTCPPCPAPELLGGPSVFLFPPKPKDTLMISRTPEVTCVVVDVSHEDPEVKFNWYVDGV EVHNAKTKPCEEQYGSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSP |
| 535 | | Fc monomer-3 -c/+g | | DKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 536 | | Fc monomer-4 -c/-g/ delGK | | DKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSP |
| 537 | | Fc monomer-5 -c/-g | | DKTHTCPPCPAPELLGGPSVFLFPPKPKDTLMISRTPEVTCVVVDVSHEDPEVKFNWYVDGV EVHNAKTKPREEQYGSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 538 | | Fc monomer-6 -c/-g/ delGK | | DKTHTCPPCPAPELLGGPSVFLFPPKPKDTLMISRTPEVTCVVVDVSHEDPEVKFNWYVDGV EVHNAKTKPREEQYGSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSP |
| 539 | | Fc monomer-7 +c/+g | | DKTHTCPPCPAPELLGGPSVFLFPPKPKDTLMISRTPEVTCVVVDVSHEDPEVKFNWYVDGV EVHNAKTKPCEEQYNSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 540 | | Fc monomer-8 +c/+g/ delGK | | DKTHTCPPCPAPELLGGPSVFLFPPKPKDTLMISRTPEVTCVVVDVSHEDPEVKFNWYVDGV EVHNAKTKPCEEQYNSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSP |

TABLE 18-continued

| SEQ ID NO | DLL3-epi-tope | Desig-nation | Format / Source | Amino acid sequence |
|---|---|---|---|---|
| 541 | | scFc-1 | | DKTHTCPPCPAPELLGGPSVFLFPPKPKDTLMISRTPEVTCVVVDVSHEDPEVKFNWYVDGV EVHNAKTKPCEEQYGSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGKGGGGSGGGGSGGGGSGGGGSG GGGSGGGGSDKTHTCPPCPAPELLGGPSVFLFPPKPKDTLMISRTPEVTCVVVDVSHEDPEV KFNWYVDGVEVHNAKTKPCEEQYGSTYRCVSVLTVLHQDWLNGKEYKCKVSNKALPAPIEKT ISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 542 | | scFc-2 | | DKTHTCPPCPAPELLGGPSVFLFPPKPKDTLMISRTPEVTCVVVDVSHEDPEVKFNWYVDGV EVHNAKTKPCEEQYGSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGGGGSGGGGSGGGGSGGGGSGGG GSGGGGSDKTHTCPPCPAPELLGGPSVFLFPPKPKDTLMISRTPEVTCVVVDVSHEDPEVKF NWYVDGVEVHNAKTKPCEEQYGSTYRCVSVLTVLHQDWLNGKEYKCKVSNKALPAPIEKTIS KAKGQPREPQVYTLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSP |
| 543 | | scFc-3 | | DKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGKGGGGSGGGGSGGGGSGGGGSG GGGSGGGGSDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKT ISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 544 | | scFc-4 | | DKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGGGGSGGGGSGGGGSGGGGSGGG GSGGGGSDKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSP |
| 545 | | scFc-5 | | DKTHTCPPCPAPELLGGPSVFLFPPKPKDTLMISRTPEVTCVVVDVSHEDPEVKFNWYVDGV EVHNAKTKPREEQYGSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGKGGGGSGGGGSGGGGSGGGGSG GGGSGGGGSDKTHTCPPCPAPELLGGPSVFLFPPKPKDTLMISRTPEVTCVVVDVSHEDPEV KFNWYVDGVEVHNAKTKPREEQYGSTYRVVSVLTVLHQDWLNGKEYKCKVSNKALPAPIEKT ISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 546 | | scFc-6 | | DKTHTCPPCPAPELLGGPSVFLFPPKPKDTLMISRTPEVTCVVVDVSHEDPEVKFNWYVDGV EVHNAKTKPREEQYGSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGGGGSGGGGSGGGGSGGGGSGGG GSGGGGSDKTHTCPPCPAPELLGGPSVFLFPPKPKDTLMISRTPEVTCVVVDVSHEDPEVKF NWYVDGVEVHNAKTKPREEQYGSTYRVVSVLTVLHQDWLNGKEYKCKVSNKALPAPIEKTIS KAKGQPREPQVYTLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSP |
| 547 | | scFc-7 | | DKTHTCPPCPAPELLGGPSVFLFPPKPKDTLMISRTPEVTCVVVDVSHEDPEVKFNWYVDGV EVHNAKTKPCEEQYNSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGKGGGGSGGGGSGGGGSGGGGSG GGGSGGGGSDKTHTCPPCPAPELLGGPSVFLFPPKPKDTLMISRTPEVTCVVVDVSHEDPEV KFNWYVDGVEVHNAKTKPCEEQYNSTYRCVSVLTVLHQDWLNGKEYKCKVSNKALPAPIEKT ISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 548 | | scFc-8 | | DKTHTCPPCPAPELLGGPSVFLFPPKPKDTLMISRTPEVTCVVVDVSHEDPEVKFNWYVDGV EVHNAKTKPCEEQYNSTYRCVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGGGGSGGGGSGGGGSGGGGSGGG GSGGGGSDKTHTCPPCPAPELLGGPSVFLFPPKPKDTLMISRTPEVTCVVVDVSHEDPEVKF NWYVDGVEVHNAKTKPCEEQYNSTYRCVSVLTVLHQDWLNGKEYKCKVSNKALPAPIEKTIS KAKGQPREPQVYTLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSP |
| 549 | | $(G_4S)_4$ linker | | GGGGSGGGGSGGGGSGGGGS |

TABLE 18-continued

| SEQ ID NO | DLL3-epitope | Designation | Format / Source | Amino acid sequence |
|---|---|---|---|---|
| 550 | | $(G_4S)_5$ linker | | GGGGSGGGGSGGGGSGGGGSGGGGS |
| 551 | | $(G_4S)_6$ linker | | GGGGSGGGGSGGGGSGGGGSGGGGSGGGGS |
| 552 | | $(G_4S)_7$ linker | | GGGGSGGGGSGGGGSGGGGSGGGGSGGGGSGGGGS |
| 553 | | $(G_4S)_8$ linker | | GGGGSGGGGSGGGGSGGGGSGGGGSGGGGSGGGGSGGGGS |
| 554 | | DLL3-22 | bispecific molecule | QVQLQESGPGLVKPSETLSLTCTVSGDSISSYYWTWIRQPPGKGLEWIGYIYYSGTTNYNPS LKSRVTISVDTSKSQFSLKLSSVTAADTAVYYCASIAVRGFFFDYWGQGTLVTVSSGGGGSG GGGSGGGGSEIVLTQSPGTLSLSPGERATLSCRASQSVSSSYLAWYQQKPGQAPRLLIYGAS TRATGIPDRFSGSGSGTDFTLTISRLEPEDFAVYYCQQYGTSPLTFGGGTKVEIKRSGGGGS EVQLVESGGGLVQPGGSLKLSCAASGFTFNKYAMNWVRQAPGKGLEWVARIRSKYNNYATYY ADSVKDRFTISRDDSKNTAYLQMNNLKTEDTAVYYCVRHGNFGNSYISYWAYWGQGTLVTVS SGGGGSGGGGSGGGGSQTVVTQEPSLTVSPGGTVTLTCGSSTGAVTSGNYPNWVQQKPGQAP RGLIGGTKFLAPGTPARFSGSLLGGKAALTLSGVQPEDEAEYYCVLWYSNRWVFGGGTKLTV LHHHHHH |

SEQUENCE LISTING

```
Sequence total quantity: 577
SEQ ID NO: 1            moltype = AA  length = 5
FEATURE                 Location/Qualifiers
REGION                  1..5
                        note = Synthetic peptide
source                  1..5
                        mol_type = protein
                        organism = synthetic construct
SEQUENCE: 1
DYGIH                                                                5

SEQ ID NO: 2            moltype = AA  length = 17
FEATURE                 Location/Qualifiers
REGION                  1..17
                        note = Synthetic peptide
source                  1..17
                        mol_type = protein
                        organism = synthetic construct
SEQUENCE: 2
VISYHGSNKY YARSVKG                                                   17

SEQ ID NO: 3            moltype = AA  length = 8
FEATURE                 Location/Qualifiers
REGION                  1..8
                        note = Synthetic peptide
source                  1..8
                        mol_type = protein
                        organism = synthetic construct
SEQUENCE: 3
EIPFGMDV                                                             8

SEQ ID NO: 4            moltype = AA  length = 16
FEATURE                 Location/Qualifiers
REGION                  1..16
                        note = Synthetic peptide
source                  1..16
                        mol_type = protein
                        organism = synthetic construct
SEQUENCE: 4
RSSQSLLHSD GYNYLD                                                    16

SEQ ID NO: 5            moltype = AA  length = 7
FEATURE                 Location/Qualifiers
REGION                  1..7
                        note = Synthetic peptide
source                  1..7
```

```
                        mol_type = protein
                        organism = synthetic construct
SEQUENCE: 5
LGSNRAS                                                         7

SEQ ID NO: 6            moltype = AA  length = 9
FEATURE                 Location/Qualifiers
REGION                  1..9
                        note = Synthetic peptide
source                  1..9
                        mol_type = protein
                        organism = synthetic construct
SEQUENCE: 6
MQALQTPLT                                                       9

SEQ ID NO: 7            moltype = AA  length = 117
FEATURE                 Location/Qualifiers
REGION                  1..117
                        note = Synthetic peptide
source                  1..117
                        mol_type = protein
                        organism = synthetic construct
SEQUENCE: 7
QVQLVESGGG VVQSGRSLRL SCAASGFTFS DYGIHWVRQA PGKGLEWVAV ISYHGSNKYY  60
ARSVKGRFTV SRDNSKNTLY LQMNSLRAED TAVYYCAREI PFGMDVWGQG TTVTVSS     117

SEQ ID NO: 8            moltype = AA  length = 112
FEATURE                 Location/Qualifiers
REGION                  1..112
                        note = Synthetic peptide
source                  1..112
                        mol_type = protein
                        organism = synthetic construct
SEQUENCE: 8
DIVMTQTPLS LPVTPGEPAS ISCRSSQSLL HSDGYNYLDW YLQKPGQSPQ LLIYLGSNRA  60
SGVPDRFSGS GSGTDFTLTI SRVEAEDVGV YYCMQALQTP LTFGGGTKVD IK          112

SEQ ID NO: 9            moltype = AA  length = 244
FEATURE                 Location/Qualifiers
REGION                  1..244
                        note = Synthetic peptide
source                  1..244
                        mol_type = protein
                        organism = synthetic construct
SEQUENCE: 9
QVQLVESGGG VVQSGRSLRL SCAASGFTFS DYGIHWVRQA PGKGLEWVAV ISYHGSNKYY  60
ARSVKGRFTV SRDNSKNTLY LQMNSLRAED TAVYYCAREI PFGMDVWGQG TTVTVSSGGG  120
GSGGGGSGGG GSDIVMTQTP LSLPVTPGEP ASISCRSSQS LLHSDGYNYL DWYLQKPGQS  180
PQLLIYLGSN RASGVPDRFS GSGSGTDFTL TISRVEAEDV GVYYCMQALQ TPLTFGGGTK  240
VDIK                                                            244

SEQ ID NO: 10           moltype = AA  length = 499
FEATURE                 Location/Qualifiers
REGION                  1..499
                        note = Synthetic peptide
source                  1..499
                        mol_type = protein
                        organism = synthetic construct
SEQUENCE: 10
QVQLVESGGG VVQSGRSLRL SCAASGFTFS DYGIHWVRQA PGKGLEWVAV ISYHGSNKYY  60
ARSVKGRFTV SRDNSKNTLY LQMNSLRAED TAVYYCAREI PFGMDVWGQG TTVTVSSGGG  120
GSGGGGSGGG GSDIVMTQTP LSLPVTPGEP ASISCRSSQS LLHSDGYNYL DWYLQKPGQS  180
PQLLIYLGSN RASGVPDRFS GSGSGTDFTL TISRVEAEDV GVYYCMQALQ TPLTFGGGTK  240
VDIKSGGGGS EVQLVESGGG LVQPGGSLKL SCAASGFTFN KYAMNWVRQA PGKGLEWVAR  300
IRSKYNNYAT YYADSVKDRF TISRDDSKNT AYLQMNNLKT EDTAVYYCVR HGNFGNSYIS  360
YWAYWGQGTL VTVSSGGGGS GGGGSGGGGS QTVVTQEPSL TVSPGGTVTL TCGSSTGAVT  420
SGNYPNWVQQ KPGQAPRGLI GGTKFLAPGT PARFSGSLLG GKAALTLSGV QPEDEAEYYC  480
VLWYSNRWVF GGGTKLTVL                                            499

SEQ ID NO: 11           moltype = AA  length = 5
FEATURE                 Location/Qualifiers
REGION                  1..5
                        note = Synthetic peptide
source                  1..5
                        mol_type = protein
                        organism = synthetic construct
SEQUENCE: 11
GYYMH                                                           5
```

```
SEQ ID NO: 12          moltype = AA  length = 17
FEATURE                Location/Qualifiers
REGION                 1..17
                       note = Synthetic peptide
source                 1..17
                       mol_type = protein
                       organism = synthetic construct
SEQUENCE: 12
WINPNSGDTN YAQKFQG                                                17

SEQ ID NO: 13          moltype = AA  length = 12
FEATURE                Location/Qualifiers
REGION                 1..12
                       note = Synthetic peptide
source                 1..12
                       mol_type = protein
                       organism = synthetic construct
SEQUENCE: 13
DANIAALDAF EI                                                     12

SEQ ID NO: 14          moltype = AA  length = 11
FEATURE                Location/Qualifiers
REGION                 1..11
                       note = Synthetic peptide
source                 1..11
                       mol_type = protein
                       organism = synthetic construct
SEQUENCE: 14
RASQSISSYL N                                                      11

SEQ ID NO: 15          moltype = AA  length = 7
FEATURE                Location/Qualifiers
REGION                 1..7
                       note = Synthetic peptide
source                 1..7
                       mol_type = protein
                       organism = synthetic construct
SEQUENCE: 15
AASSLQS                                                           7

SEQ ID NO: 16          moltype = AA  length = 9
FEATURE                Location/Qualifiers
REGION                 1..9
                       note = Synthetic peptide
source                 1..9
                       mol_type = protein
                       organism = synthetic construct
SEQUENCE: 16
QQSYSTPLT                                                         9

SEQ ID NO: 17          moltype = AA  length = 121
FEATURE                Location/Qualifiers
REGION                 1..121
                       note = Synthetic peptide
source                 1..121
                       mol_type = protein
                       organism = synthetic construct
SEQUENCE: 17
QVQLVQSGAE VKKPGASVKV SCKASGYTFT GYYMHWVRQA PGQGLEWMGW INPNSGDTNY  60
AQKFQGRVTM TRDTSISTAY MELSRLTSDD TAVYYCARDA NIAALDAFEI WGQGTMVTVS  120
S                                                                 121

SEQ ID NO: 18          moltype = AA  length = 107
FEATURE                Location/Qualifiers
REGION                 1..107
                       note = Synthetic peptide
source                 1..107
                       mol_type = protein
                       organism = synthetic construct
SEQUENCE: 18
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIK               107

SEQ ID NO: 19          moltype = AA  length = 243
FEATURE                Location/Qualifiers
REGION                 1..243
                       note = Synthetic peptide
source                 1..243
                       mol_type = protein
```

```
                         organism = synthetic construct
SEQUENCE: 19
QVQLVQSGAE VKKPGASVKV SCKASGYTFT GYYMHWVRQA PGQGLEWMGW INPNSGDTNY  60
AQKFQGRVTM TRDTSISTAY MELSRLTSDD TAVYYCARDA NIAALDAFEI WGQGTMVTVS  120
SGGGGSGGGG SGGGGSDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIK                                                               243

SEQ ID NO: 20            moltype = AA  length = 498
FEATURE                  Location/Qualifiers
REGION                   1..498
                         note = Synthetic peptide
source                   1..498
                         mol_type = protein
                         organism = synthetic construct
SEQUENCE: 20
QVQLVQSGAE VKKPGASVKV SCKASGYTFT GYYMHWVRQA PGQGLEWMGW INPNSGDTNY  60
AQKFQGRVTM TRDTSISTAY MELSRLTSDD TAVYYCARDA NIAALDAFEI WGQGTMVTVS  120
SGGGGSGGGG SGGGGSDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIKSGGGGSE VQLVESGGGL VQPGGSLKLS CAASGFTFNK YAMNWVRQAP GKGLEWVARI  300
RSKYNNYATY YADSVKDRFT ISRDDSKNTA YLQMNNLKTE DTAVYYCVRH GNFGNSYISY  360
WAYWGQGTLV TVSSGGGGSG GGGSGGGGSQ TVVTQEPSLT VSPGGTVTLT CGSSTGAVTS  420
GNYPNWVQQK PGQAPRGLIG GTKFLAPGTP ARFSGSLLGG KAALTLSGVQ PEDEAEYYCV  480
LWYSNRWVFG GGTKLTVL                                               498

SEQ ID NO: 21            moltype = AA  length = 5
FEATURE                  Location/Qualifiers
REGION                   1..5
                         note = Synthetic peptide
source                   1..5
                         mol_type = protein
                         organism = synthetic construct
SEQUENCE: 21
SYGMH                                                             5

SEQ ID NO: 22            moltype = AA  length = 17
FEATURE                  Location/Qualifiers
REGION                   1..17
                         note = Synthetic peptide
source                   1..17
                         mol_type = protein
                         organism = synthetic construct
SEQUENCE: 22
VISYHGRDTY YARSVKG                                                17

SEQ ID NO: 23            moltype = AA  length = 15
FEATURE                  Location/Qualifiers
REGION                   1..15
                         note = Synthetic peptide
source                   1..15
                         mol_type = protein
                         organism = synthetic construct
SEQUENCE: 23
DGATVTSYYY SGMDV                                                  15

SEQ ID NO: 24            moltype = AA  length = 11
FEATURE                  Location/Qualifiers
REGION                   1..11
                         note = Synthetic peptide
source                   1..11
                         mol_type = protein
                         organism = synthetic construct
SEQUENCE: 24
RASQGISNYL A                                                      11

SEQ ID NO: 25            moltype = AA  length = 7
FEATURE                  Location/Qualifiers
REGION                   1..7
                         note = Synthetic peptide
source                   1..7
                         mol_type = protein
                         organism = synthetic construct
SEQUENCE: 25
LASSLQS                                                           7

SEQ ID NO: 26            moltype = AA  length = 9
FEATURE                  Location/Qualifiers
REGION                   1..9
```

```
                         note = Synthetic peptide
source                   1..9
                         mol_type = protein
                         organism = synthetic construct
SEQUENCE: 26
QQYNFYPFT                                                        9

SEQ ID NO: 27            moltype = AA  length = 125
FEATURE                  Location/Qualifiers
REGION                   1..125
                         note = Synthetic peptide
source                   1..125
                         mol_type = protein
                         organism = synthetic construct
SEQUENCE: 27
QVQLVESGGG VVQPGRSLRL SCAASGFTFS SYGMHWVRQA PGKGLEWVAV ISYHGRDTYY  60
ARSVKGRFTI SRDNSKNTLY LHMNSLRAED TAVYYCARDG ATVTSYYYSG MDVWGQGTTV  120
TVSSK                                                            125

SEQ ID NO: 28            moltype = AA  length = 107
FEATURE                  Location/Qualifiers
REGION                   1..107
                         note = Synthetic peptide
source                   1..107
                         mol_type = protein
                         organism = synthetic construct
SEQUENCE: 28
DIQMTQSPSS LSASVGDRVT ITCRASQGIS NYLAWFQQKP GKAPKSLIYL ASSLQSGVPS  60
KFSGSGSGTD FTLTISSLQP EDFATYYCQQ YNFYPFTFGP GTKVDIK              107

SEQ ID NO: 29            moltype = AA  length = 246
FEATURE                  Location/Qualifiers
REGION                   1..246
                         note = Synthetic peptide
source                   1..246
                         mol_type = protein
                         organism = synthetic construct
SEQUENCE: 29
QVQLVESGGG VVQPGRSLRL SCAASGFTFS SYGMHWVRQA PGKGLEWVAV ISYHGRDTYY  60
ARSVKGRFTI SRDNSKNTLY LHMNSLRAED TAVYYCARDG ATVTSYYYSG MDVWGQGTTV  120
TVSSGGGGSG GGGSGGGGSD IQMTQSPSSL SASVGDRVTI TCRASQGISN YLAWFQQKPG  180
KAPKSLIYLA SSLQSGVPSK FSGSGSGTDF TLTISSLQPE DFATYYCQQY NFYPFTFGPG  240
TKVDIK                                                           246

SEQ ID NO: 30            moltype = AA  length = 501
FEATURE                  Location/Qualifiers
REGION                   1..501
                         note = Synthetic peptide
source                   1..501
                         mol_type = protein
                         organism = synthetic construct
SEQUENCE: 30
QVQLVESGGG VVQPGRSLRL SCAASGFTFS SYGMHWVRQA PGKGLEWVAV ISYHGRDTYY  60
ARSVKGRFTI SRDNSKNTLY LHMNSLRAED TAVYYCARDG ATVTSYYYSG MDVWGQGTTV  120
TVSSGGGGSG GGGSGGGGSD IQMTQSPSSL SASVGDRVTI TCRASQGISN YLAWFQQKPG  180
KAPKSLIYLA SSLQSGVPSK FSGSGSGTDF TLTISSLQPE DFATYYCQQY NFYPFTFGPG  240
TKVDIKSGGG GSEVQLVESG GGLVQPGGSL KLSCAASGFT FNKYAMNWVR QAPGKGLEWV  300
ARIRSKYNNY ATYYADSVKD RFTISRDDSK NTAYLQMNNL KTEDTAVYYC VRHGNFGNSY  360
ISYWAYWGQG TLVTVSSGGG GSGGGGSGGG GSQTVVTQEP SLTVSPGGTV TLTCGSSTGA  420
VTSGNYPNWV QQKPGQAPRG LIGGTKFLAP GTPARFSGSL LGGKAALTLS GVQPEDEAEY  480
YCVLWYSNRW VFGGGTKLTV L                                          501

SEQ ID NO: 31            moltype = AA  length = 5
FEATURE                  Location/Qualifiers
REGION                   1..5
                         note = Synthetic peptide
source                   1..5
                         mol_type = protein
                         organism = synthetic construct
SEQUENCE: 31
SYYWS                                                            5

SEQ ID NO: 32            moltype = AA  length = 16
FEATURE                  Location/Qualifiers
REGION                   1..16
                         note = Synthetic peptide
source                   1..16
                         mol_type = protein
                         organism = synthetic construct
```

```
SEQUENCE: 32
YVYYSGTTNY NPSLKS                                              16

SEQ ID NO: 33           moltype = AA  length = 10
FEATURE                 Location/Qualifiers
REGION                  1..10
                        note = Synthetic peptide
source                  1..10
                        mol_type = protein
                        organism = synthetic construct
SEQUENCE: 33
IAVTGFYFDY                                                     10

SEQ ID NO: 34           moltype = AA  length = 12
FEATURE                 Location/Qualifiers
REGION                  1..12
                        note = Synthetic peptide
source                  1..12
                        mol_type = protein
                        organism = synthetic construct
SEQUENCE: 34
RASQRVNNNY LA                                                  12

SEQ ID NO: 35           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 35
GASSRAT                                                        7

SEQ ID NO: 36           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 36
QQYDRSPLT                                                      9

SEQ ID NO: 37           moltype = AA  length = 118
FEATURE                 Location/Qualifiers
REGION                  1..118
                        note = Synthetic peptide
source                  1..118
                        mol_type = protein
                        organism = synthetic construct
SEQUENCE: 37
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSS    118

SEQ ID NO: 38           moltype = AA  length = 108
FEATURE                 Location/Qualifiers
REGION                  1..108
                        note = Synthetic peptide
source                  1..108
                        mol_type = protein
                        organism = synthetic construct
SEQUENCE: 38
EIVLTQSPGT LSLSPGERVT LSCRASQRVN NNYLAWYQQR PGQAPRLLIY GASSRATGIP  60
DRFSGSGSGT DFTLTISRLE PEDFAVYYCQ QYDRSPLTFG GGTKLEIK            108

SEQ ID NO: 39           moltype = AA  length = 241
FEATURE                 Location/Qualifiers
REGION                  1..241
                        note = Synthetic peptide
source                  1..241
                        mol_type = protein
                        organism = synthetic construct
SEQUENCE: 39
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGGGTKLEI  240
K                                                              241
```

```
SEQ ID NO: 40          moltype = AA  length = 496
FEATURE                Location/Qualifiers
REGION                 1..496
                       note = Synthetic peptide
source                 1..496
                       mol_type = protein
                       organism = synthetic construct
SEQUENCE: 40
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 41          moltype = AA  length = 5
FEATURE                Location/Qualifiers
REGION                 1..5
                       note = Synthetic peptide
source                 1..5
                       mol_type = protein
                       organism = synthetic construct
SEQUENCE: 41
SYYWS                                                             5

SEQ ID NO: 42          moltype = AA  length = 16
FEATURE                Location/Qualifiers
REGION                 1..16
                       note = Synthetic peptide
source                 1..16
                       mol_type = protein
                       organism = synthetic construct
SEQUENCE: 42
YIYYSGRTNY YPSLKS                                                 16

SEQ ID NO: 43          moltype = AA  length = 10
FEATURE                Location/Qualifiers
REGION                 1..10
                       note = Synthetic peptide
source                 1..10
                       mol_type = protein
                       organism = synthetic construct
SEQUENCE: 43
IAVAGFFFDY                                                        10

SEQ ID NO: 44          moltype = AA  length = 12
FEATURE                Location/Qualifiers
REGION                 1..12
                       note = Synthetic peptide
source                 1..12
                       mol_type = protein
                       organism = synthetic construct
SEQUENCE: 44
RASQSVNKNY LA                                                     12

SEQ ID NO: 45          moltype = AA  length = 7
FEATURE                Location/Qualifiers
REGION                 1..7
                       note = Synthetic peptide
source                 1..7
                       mol_type = protein
                       organism = synthetic construct
SEQUENCE: 45
GASSRAT                                                           7

SEQ ID NO: 46          moltype = AA  length = 9
FEATURE                Location/Qualifiers
REGION                 1..9
                       note = Synthetic peptide
source                 1..9
                       mol_type = protein
                       organism = synthetic construct
SEQUENCE: 46
QQYDRSPLT                                                         9

SEQ ID NO: 47          moltype = AA  length = 118
```

```
FEATURE                 Location/Qualifiers
REGION                  1..118
                        note = Synthetic peptide
source                  1..118
                        mol_type = protein
                        organism = synthetic construct
SEQUENCE: 47
QVQLQESGPG LVKPSETLSL TCTVSGGSIS SYYWSWIRQP PGKGLEWIGY IYYSGRTNYY  60
PSLKSRVTIS IDTSKNQFSL KLSSVTAADT AVYYCARIAV AGFFFDYWGQ GTLVTVSS    118

SEQ ID NO: 48           moltype = AA  length = 108
FEATURE                 Location/Qualifiers
REGION                  1..108
                        note = Synthetic peptide
source                  1..108
                        mol_type = protein
                        organism = synthetic construct
SEQUENCE: 48
EIVLTQSPGT LSLSPGERAT LSCRASQSVN KNYLAWYQQK PGQAPRLLIY GASSRATGIP  60
DRFSGSGSGT DFTLTISRLE PEDFAVYYCQ QYDRSPLTFG GGTKLEIK               108

SEQ ID NO: 49           moltype = AA  length = 241
FEATURE                 Location/Qualifiers
REGION                  1..241
                        note = Synthetic peptide
source                  1..241
                        mol_type = protein
                        organism = synthetic construct
SEQUENCE: 49
QVQLQESGPG LVKPSETLSL TCTVSGGSIS SYYWSWIRQP PGKGLEWIGY IYYSGRTNYY  60
PSLKSRVTIS IDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKLEI  240
K                                                                  241

SEQ ID NO: 50           moltype = AA  length = 496
FEATURE                 Location/Qualifiers
REGION                  1..496
                        note = Synthetic peptide
source                  1..496
                        mol_type = protein
                        organism = synthetic construct
SEQUENCE: 50
QVQLQESGPG LVKPSETLSL TCTVSGGSIS SYYWSWIRQP PGKGLEWIGY IYYSGRTNYY  60
PSLKSRVTIS IDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 51           moltype = AA  length = 5
FEATURE                 Location/Qualifiers
REGION                  1..5
                        note = Synthetic peptide
source                  1..5
                        mol_type = protein
                        organism = synthetic construct
SEQUENCE: 51
SFYWS                                                              5

SEQ ID NO: 52           moltype = AA  length = 16
FEATURE                 Location/Qualifiers
REGION                  1..16
                        note = Synthetic peptide
source                  1..16
                        mol_type = protein
                        organism = synthetic construct
SEQUENCE: 52
YIYYSGTTNY NPSLKS                                                  16

SEQ ID NO: 53           moltype = AA  length = 10
FEATURE                 Location/Qualifiers
REGION                  1..10
                        note = Synthetic peptide
source                  1..10
                        mol_type = protein
```

```
                        organism = synthetic construct
SEQUENCE: 53
IAVAGFFFDY                                                  10

SEQ ID NO: 54           moltype = AA  length = 12
FEATURE                 Location/Qualifiers
REGION                  1..12
                        note = Synthetic peptide
source                  1..12
                        mol_type = protein
                        organism = synthetic construct
SEQUENCE: 54
RASQSVNKNY LA                                               12

SEQ ID NO: 55           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 55
GASSRAT                                                     7

SEQ ID NO: 56           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 56
QQYDRSPLT                                                   9

SEQ ID NO: 57           moltype = AA  length = 118
FEATURE                 Location/Qualifiers
REGION                  1..118
                        note = Synthetic peptide
source                  1..118
                        mol_type = protein
                        organism = synthetic construct
SEQUENCE: 57
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSS    118

SEQ ID NO: 58           moltype = AA  length = 108
FEATURE                 Location/Qualifiers
REGION                  1..108
                        note = Synthetic peptide
source                  1..108
                        mol_type = protein
                        organism = synthetic construct
SEQUENCE: 58
EIVLTQSPGT LSLSPGERAT LSCRASQSVN KNYLAWYQQK PGQAPRLLIY GASSRATGIP  60
DRFSGSGSGT DFTLTISRLE PEDFAVYYCQ QYDRSPLTFG GGTKVEIK               108

SEQ ID NO: 59           moltype = AA  length = 241
FEATURE                 Location/Qualifiers
REGION                  1..241
                        note = Synthetic peptide
source                  1..241
                        mol_type = protein
                        organism = synthetic construct
SEQUENCE: 59
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
K                                                                  241

SEQ ID NO: 60           moltype = AA  length = 496
FEATURE                 Location/Qualifiers
REGION                  1..496
                        note = Synthetic peptide
source                  1..496
                        mol_type = protein
                        organism = synthetic construct
SEQUENCE: 60
QVQLQESGPG LVKPSETLSL TCTVSGASIS SFYWSWIRQP PGKGLEWIGY IYYSGTTNYN  60
```

-continued

```
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 61          moltype = AA  length = 5
FEATURE                Location/Qualifiers
REGION                 1..5
                       note = Synthetic peptide
source                 1..5
                       mol_type = protein
                       organism = synthetic construct
SEQUENCE: 61
SFYWS                                                             5

SEQ ID NO: 62          moltype = AA  length = 16
FEATURE                Location/Qualifiers
REGION                 1..16
                       note = Synthetic peptide
source                 1..16
                       mol_type = protein
                       organism = synthetic construct
SEQUENCE: 62
YIYYSGTTNY NPSLKS                                                 16

SEQ ID NO: 63          moltype = AA  length = 10
FEATURE                Location/Qualifiers
REGION                 1..10
                       note = Synthetic peptide
source                 1..10
                       mol_type = protein
                       organism = synthetic construct
SEQUENCE: 63
IAVAGFFFDY                                                        10

SEQ ID NO: 64          moltype = AA  length = 12
FEATURE                Location/Qualifiers
REGION                 1..12
                       note = Synthetic peptide
source                 1..12
                       mol_type = protein
                       organism = synthetic construct
SEQUENCE: 64
RASQSVNKNY LA                                                     12

SEQ ID NO: 65          moltype = AA  length = 7
FEATURE                Location/Qualifiers
REGION                 1..7
                       note = Synthetic peptide
source                 1..7
                       mol_type = protein
                       organism = synthetic construct
SEQUENCE: 65
GASSRAT                                                           7

SEQ ID NO: 66          moltype = AA  length = 9
FEATURE                Location/Qualifiers
REGION                 1..9
                       note = Synthetic peptide
source                 1..9
                       mol_type = protein
                       organism = synthetic construct
SEQUENCE: 66
QQYDRSPLT                                                         9

SEQ ID NO: 67          moltype = AA  length = 118
FEATURE                Location/Qualifiers
REGION                 1..118
                       note = Synthetic peptide
source                 1..118
                       mol_type = protein
                       organism = synthetic construct
SEQUENCE: 67
QVQLQESGPG LVKPSQTLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSS    118
```

```
SEQ ID NO: 68          moltype = AA  length = 108
FEATURE                Location/Qualifiers
REGION                 1..108
                       note = Synthetic peptide
source                 1..108
                       mol_type = protein
                       organism = synthetic construct
SEQUENCE: 68
EIVLTQSPGT LSLSPGERAT LSCRASQSVN KNYLAWYQQK PGQAPRLLIY GASSRATGIP  60
DRFSGSGSGT DFTLTISRLE PEDFAVYYCQ QYDRSPLTFG GGTKVEIK              108

SEQ ID NO: 69          moltype = AA  length = 241
FEATURE                Location/Qualifiers
REGION                 1..241
                       note = Synthetic peptide
source                 1..241
                       mol_type = protein
                       organism = synthetic construct
SEQUENCE: 69
QVQLQESGPG LVKPSQTLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
K                                                                  241

SEQ ID NO: 70          moltype = AA  length = 496
FEATURE                Location/Qualifiers
REGION                 1..496
                       note = Synthetic peptide
source                 1..496
                       mol_type = protein
                       organism = synthetic construct
SEQUENCE: 70
QVQLQESGPG LVKPSQTLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 71          moltype = AA  length = 5
FEATURE                Location/Qualifiers
REGION                 1..5
                       note = Synthetic peptide
source                 1..5
                       mol_type = protein
                       organism = synthetic construct
SEQUENCE: 71
SFYWS                                                              5

SEQ ID NO: 72          moltype = AA  length = 16
FEATURE                Location/Qualifiers
REGION                 1..16
                       note = Synthetic peptide
source                 1..16
                       mol_type = protein
                       organism = synthetic construct
SEQUENCE: 72
YIYYSGTTNY NPSLKS                                                  16

SEQ ID NO: 73          moltype = AA  length = 10
FEATURE                Location/Qualifiers
REGION                 1..10
                       note = Synthetic peptide
source                 1..10
                       mol_type = protein
                       organism = synthetic construct
SEQUENCE: 73
IAVAGFFFDY                                                         10

SEQ ID NO: 74          moltype = AA  length = 12
FEATURE                Location/Qualifiers
REGION                 1..12
                       note = Synthetic peptide
source                 1..12
```

```
                        mol_type = protein
                        organism = synthetic construct
SEQUENCE: 74
RASQSVNKNY LA                                                  12

SEQ ID NO: 75           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 75
GASSRAT                                                        7

SEQ ID NO: 76           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 76
QQYDRSPLT                                                      9

SEQ ID NO: 77           moltype = AA  length = 119
FEATURE                 Location/Qualifiers
REGION                  1..119
                        note = Synthetic peptide
source                  1..119
                        mol_type = protein
                        organism = synthetic construct
SEQUENCE: 77
QVQLQEWGPG LVKPSETLSL TCTVSGASIS SFYWSWIRQP PGKGLEWIGY IYYSGTTNYN  60
PSLKSRVTIS VDTSKNQLSL KLSSVTAADT AVYYCARIAV AGFFFDYWGQ GTLVTVSSK   119

SEQ ID NO: 78           moltype = AA  length = 108
FEATURE                 Location/Qualifiers
REGION                  1..108
                        note = Synthetic peptide
source                  1..108
                        mol_type = protein
                        organism = synthetic construct
SEQUENCE: 78
EIVLTQSPGT LSLSPGERAT LSCRASQSVN KNYLAWYQQK PGQAPRLLIY GASSRATGIP  60
DRFSGSGSGT DFTLTISRLE PEDFAVYYCQ QYDRSPLTFG GGTKVDIK               108

SEQ ID NO: 79           moltype = AA  length = 241
FEATURE                 Location/Qualifiers
REGION                  1..241
                        note = Synthetic peptide
source                  1..241
                        mol_type = protein
                        organism = synthetic construct
SEQUENCE: 79
QVQLQEWGPG LVKPSETLSL TCTVSGASIS SFYWSWIRQP PGKGLEWIGY IYYSGTTNYN  60
PSLKSRVTIS VDTSKNQLSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVDI  240
K                                                              241

SEQ ID NO: 80           moltype = AA  length = 496
FEATURE                 Location/Qualifiers
REGION                  1..496
                        note = Synthetic peptide
source                  1..496
                        mol_type = protein
                        organism = synthetic construct
SEQUENCE: 80
QVQLQEWGPG LVKPSETLSL TCTVSGASIS SFYWSWIRQP PGKGLEWIGY IYYSGTTNYN  60
PSLKSRVTIS VDTSKNQLSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVDI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                              496
```

```
SEQ ID NO: 81           moltype = AA  length = 5
FEATURE                 Location/Qualifiers
REGION                  1..5
                        note = Synthetic peptide
source                  1..5
                        mol_type = protein
                        organism = synthetic construct
SEQUENCE: 81
SFYWS                                                          5

SEQ ID NO: 82           moltype = AA  length = 16
FEATURE                 Location/Qualifiers
REGION                  1..16
                        note = Synthetic peptide
source                  1..16
                        mol_type = protein
                        organism = synthetic construct
SEQUENCE: 82
YIYYSGTTNY NPSLKS                                              16

SEQ ID NO: 83           moltype = AA  length = 10
FEATURE                 Location/Qualifiers
REGION                  1..10
                        note = Synthetic peptide
source                  1..10
                        mol_type = protein
                        organism = synthetic construct
SEQUENCE: 83
IAVAGFFFDY                                                     10

SEQ ID NO: 84           moltype = AA  length = 12
FEATURE                 Location/Qualifiers
REGION                  1..12
                        note = Synthetic peptide
source                  1..12
                        mol_type = protein
                        organism = synthetic construct
SEQUENCE: 84
RASQSVNKNY LA                                                  12

SEQ ID NO: 85           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 85
GASSRAT                                                        7

SEQ ID NO: 86           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 86
QQYDRSPLT                                                      9

SEQ ID NO: 87           moltype = AA  length = 118
FEATURE                 Location/Qualifiers
REGION                  1..118
                        note = Synthetic peptide
source                  1..118
                        mol_type = protein
                        organism = synthetic construct
SEQUENCE: 87
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSS    118

SEQ ID NO: 88           moltype = AA  length = 108
FEATURE                 Location/Qualifiers
REGION                  1..108
                        note = Synthetic peptide
source                  1..108
                        mol_type = protein
                        organism = synthetic construct
SEQUENCE: 88
```

```
EIVLTQSPGT LSLSPGESAT LSCRASQSVN KNYLAWYQQK PGQAPRLLIY GASSRATGIP  60
DRFSGSGSGT DFTLTISRLE PEDFAVYYCQ QYDRSPLTFG GGTRLEIK               108

SEQ ID NO: 89          moltype = AA  length = 241
FEATURE                Location/Qualifiers
REGION                 1..241
                       note = Synthetic peptide
source                 1..241
                       mol_type = protein
                       organism = synthetic construct
SEQUENCE: 89
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE SATLSCRASQ SVNKNYLAWY QQKPGQAPRL  180
LIYGASSRAT GIPDRFSGSG SGTDFTLTIS RLEPEDFAVY YCQQYDRSPL TFGGGTRLEI  240
K                                                                  241

SEQ ID NO: 90          moltype = AA  length = 496
FEATURE                Location/Qualifiers
REGION                 1..496
                       note = Synthetic peptide
source                 1..496
                       mol_type = protein
                       organism = synthetic construct
SEQUENCE: 90
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE SATLSCRASQ SVNKNYLAWY QQKPGQAPRL  180
LIYGASSRAT GIPDRFSGSG SGTDFTLTIS RLEPEDFAVY YCQQYDRSPL TFGGGTRLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 91          moltype = AA  length = 5
FEATURE                Location/Qualifiers
REGION                 1..5
                       note = Synthetic peptide
source                 1..5
                       mol_type = protein
                       organism = synthetic construct
SEQUENCE: 91
SYYWS                                                              5

SEQ ID NO: 92          moltype = AA  length = 16
FEATURE                Location/Qualifiers
REGION                 1..16
                       note = Synthetic peptide
source                 1..16
                       mol_type = protein
                       organism = synthetic construct
SEQUENCE: 92
YIFYNGITNY NPSLKS                                                  16

SEQ ID NO: 93          moltype = AA  length = 10
FEATURE                Location/Qualifiers
REGION                 1..10
                       note = Synthetic peptide
source                 1..10
                       mol_type = protein
                       organism = synthetic construct
SEQUENCE: 93
IHSGSFSFDY                                                         10

SEQ ID NO: 94          moltype = AA  length = 12
FEATURE                Location/Qualifiers
REGION                 1..12
                       note = Synthetic peptide
source                 1..12
                       mol_type = protein
                       organism = synthetic construct
SEQUENCE: 94
RASQSVSRGY LA                                                      12

SEQ ID NO: 95          moltype = AA  length = 7
FEATURE                Location/Qualifiers
REGION                 1..7
                       note = Synthetic peptide
```

```
source                1..7
                      mol_type = protein
                      organism = synthetic construct
SEQUENCE: 95
GASSRAT                                                            7

SEQ ID NO: 96         moltype = AA  length = 9
FEATURE               Location/Qualifiers
REGION                1..9
                      note = Synthetic peptide
source                1..9
                      mol_type = protein
                      organism = synthetic construct
SEQUENCE: 96
QQYDTSPIT                                                          9

SEQ ID NO: 97         moltype = AA  length = 118
FEATURE               Location/Qualifiers
REGION                1..118
                      note = Synthetic peptide
source                1..118
                      mol_type = protein
                      organism = synthetic construct
SEQUENCE: 97
QVQLQESGPG LVKPSQTLSL TCTVSGGSIS SYYWSWIRQP PGKGLEWIGY IFYNGITNYN  60
PSLKSRVTIS LDTSKNQFSL KLSSVTAADT AKYYCARIHS GSFSFDYWDQ GTLVTVSS    118

SEQ ID NO: 98         moltype = AA  length = 108
FEATURE               Location/Qualifiers
REGION                1..108
                      note = Synthetic peptide
source                1..108
                      mol_type = protein
                      organism = synthetic construct
SEQUENCE: 98
EIVMTQSPGT LSLSPGERAT LSCRASQSVS RGYLAWYQQK PGQAPRLLIY GASSRATDIP  60
DRFSGSGSGT DFTLTISRLE PEDFAVYYCQ QYDTSPITFG QGTKVEIK               108

SEQ ID NO: 99         moltype = AA  length = 241
FEATURE               Location/Qualifiers
REGION                1..241
                      note = Synthetic peptide
source                1..241
                      mol_type = protein
                      organism = synthetic construct
SEQUENCE: 99
QVQLQESGPG LVKPSQTLSL TCTVSGGSIS SYYWSWIRQP PGKGLEWIGY IFYNGITNYN  60
PSLKSRVTIS LDTSKNQFSL KLSSVTAADT AKYYCARIHS GSFSFDYWDQ GTLVTVSSGG  120
GGSGGGGSGG GGSEIVMTQS PGTLSLSPGE RATLSCRASQ SVSRGYLAWY QQKPGQAPRL  180
LIYGASSRAT DIPDRFSGSG SGTDFTLTIS RLEPEDFAVY YCQQYDTSPI TFGQGTKVEI  240
K                                                                  241

SEQ ID NO: 100        moltype = AA  length = 496
FEATURE               Location/Qualifiers
REGION                1..496
                      note = Synthetic peptide
source                1..496
                      mol_type = protein
                      organism = synthetic construct
SEQUENCE: 100
QVQLQESGPG LVKPSQTLSL TCTVSGGSIS SYYWSWIRQP PGKGLEWIGY IFYNGITNYN  60
PSLKSRVTIS LDTSKNQFSL KLSSVTAADT AKYYCARIHS GSFSFDYWDQ GTLVTVSSGG  120
GGSGGGGSGG GGSEIVMTQS PGTLSLSPGE RATLSCRASQ SVSRGYLAWY QQKPGQAPRL  180
LIYGASSRAT DIPDRFSGSG SGTDFTLTIS RLEPEDFAVY YCQQYDTSPI TFGQGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 101        moltype = AA  length = 5
FEATURE               Location/Qualifiers
REGION                1..5
                      note = Synthetic peptide
source                1..5
                      mol_type = protein
                      organism = synthetic construct
SEQUENCE: 101
NAGMS                                                              5
```

```
SEQ ID NO: 102          moltype = AA  length = 19
FEATURE                 Location/Qualifiers
REGION                  1..19
                        note = Synthetic peptide
source                  1..19
                        mol_type = protein
                        organism = synthetic construct
SEQUENCE: 102
RIKNKIDGGT TDFAAPVKG                                                19

SEQ ID NO: 103          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 103
RGWYGDYFDY                                                          10

SEQ ID NO: 104          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 104
RSSQSLLHSN GYNYLD                                                   16

SEQ ID NO: 105          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 105
LGSNRAS                                                             7

SEQ ID NO: 106          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 106
MQALQTPFT                                                           9

SEQ ID NO: 107          moltype = AA  length = 121
FEATURE                 Location/Qualifiers
REGION                  1..121
                        note = Synthetic peptide
source                  1..121
                        mol_type = protein
                        organism = synthetic construct
SEQUENCE: 107
EVQLVESGGG LVKPGGSLRL SCAASGFIFN NAGMSWVRQA PGKGLEWVGR IKNKIDGGTT  60
DFAAPVKGRF TISRDDSKNT LYLQMNSLKA EDTAVYYCTA RGWYGDYFDY WGQGTLVTVS  120
S                                                                   121

SEQ ID NO: 108          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 108
DIVMTQTPLS LPVTPGEPAS ISCRSSQSLL HSNGYNYLDW YLQKPGQSPQ LLIYLGSNRA  60
SGVPDRFSGS GSGTDFTLKI SRVEAEDVGI YYCMQALQTP FTFGPGTKVE IK          112

SEQ ID NO: 109          moltype = AA  length = 248
FEATURE                 Location/Qualifiers
REGION                  1..248
                        note = Synthetic peptide
source                  1..248
```

```
                        mol_type = protein
                        organism = synthetic construct
SEQUENCE: 109
EVQLVESGGG LVKPGGSLRL SCAASGFIFN NAGMSWVRQA PGKGLEWVGR IKNKIDGGTT  60
DFAAPVKGRF TISRDDSKNT LYLQMNSLKA EDTAVYYCTA RGWYGDYFDY WGQGTLVTVS  120
SGGGGSGGGG SGGGGSDIVM TQTPLSLPVT PGEPASISCR SSQSLLHSNG YNYLDWYLQK  180
PGQSPQLLIY LGSNRASGVP DRFSGSGSGT DFTLKISRVE AEDVGIYYCM QALQTPFTFG  240
PGTKVEIK                                                          248

SEQ ID NO: 110          moltype = AA  length = 503
FEATURE                 Location/Qualifiers
REGION                  1..503
                        note = Synthetic peptide
source                  1..503
                        mol_type = protein
                        organism = synthetic construct
SEQUENCE: 110
EVQLVESGGG LVKPGGSLRL SCAASGFIFN NAGMSWVRQA PGKGLEWVGR IKNKIDGGTT  60
DFAAPVKGRF TISRDDSKNT LYLQMNSLKA EDTAVYYCTA RGWYGDYFDY WGQGTLVTVS  120
SGGGGSGGGG SGGGGSDIVM TQTPLSLPVT PGEPASISCR SSQSLLHSNG YNYLDWYLQK  180
PGQSPQLLIY LGSNRASGVP DRFSGSGSGT DFTLKISRVE AEDVGIYYCM QALQTPFTFG  240
PGTKVEIKSG GGGSEVQLVE SGGGLVQPGG SLKLSCAASG FTFNKYAMNW VRQAPGKGLE  300
WVARIRSKYN NYATYYADSV KDRFTISRDD SKNTAYLQMN NLKTEDTAVY YCVRHGNFGN  360
SYISYWAYWG QGTLVTVSSG GGGSGGGGSG GGGSQTVVTQ EPSLTVSPGG TVTLTCGSST  420
GAVTSGNYPN WVQQKPGQAP RGLIGGTKFL APGTPARFSG SLLGGKAALT LSGVQPEDEA  480
EYYCVLWYSN RWVFGGGTKL TVL                                         503

SEQ ID NO: 111          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 111
SYDIH                                                             5

SEQ ID NO: 112          moltype = AA  length = 17
FEATURE                 Location/Qualifiers
REGION                  1..17
                        note = Synthetic peptide
source                  1..17
                        mol_type = protein
                        organism = synthetic construct
SEQUENCE: 112
VISSHGSNKN YARSVKG                                                17

SEQ ID NO: 113          moltype = AA  length = 18
FEATURE                 Location/Qualifiers
REGION                  1..18
                        note = Synthetic peptide
source                  1..18
                        mol_type = protein
                        organism = synthetic construct
SEQUENCE: 113
DGYSGNDPFY YYYHGMDV                                               18

SEQ ID NO: 114          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 114
RASQSISSYL N                                                      11

SEQ ID NO: 115          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 115
AASSLQS                                                           7

SEQ ID NO: 116          moltype = AA  length = 9
FEATURE                 Location/Qualifiers
```

```
REGION                  1..9
                        note = Synthetic peptide
source                  1..9
                        mol_type = protein
                        organism = synthetic construct
SEQUENCE: 116
QQSFTTPLT                                                                 9

SEQ ID NO: 117          moltype = AA  length = 127
FEATURE                 Location/Qualifiers
REGION                  1..127
                        note = Synthetic peptide
source                  1..127
                        mol_type = protein
                        organism = synthetic construct
SEQUENCE: 117
QVQLVESGGG VVQPGRSLRL SCAASGFSFS SYDIHWVRQA PGKGLEWVAV ISSHGSNKNY  60
ARSVKGRFTI SRDNSKNTLY LQMNSLKAED TAVYYCARDG YSGNDPFYYY YHGMDVWGQG  120
TTVTVSS                                                           127

SEQ ID NO: 118          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 118
DIQMTQSPSS LSASVGDRVT ITCRASQSIS SYLNWYQQKP GKAPKLLIYA ASSLQSGVPS  60
RFSGSGSGTD FSLTISSLQP EDFATYYCQQ SFTTPLTFGG GTKVEIK               107

SEQ ID NO: 119          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 119
QVQLVESGGG VVQPGRSLRL SCAASGFSFS SYDIHWVRQA PGKGLEWVAV ISSHGSNKNY  60
ARSVKGRFTI SRDNSKNTLY LQMNSLKAED TAVYYCARDG YSGNDPFYYY YHGMDVWGQG  120
TTVTVSSGGG GSGGGGSGGG GSDIQMTQSP SSLSASVGDR VTITCRASQS ISSYLNWYQQ  180
KPGKAPKLLI YAASSLQSGV PSRFSGSGSG TDFSLTISSL QPEDFATYYC QQSFTTPLTF  240
GGGTKVEIK                                                         249

SEQ ID NO: 120          moltype = AA  length = 504
FEATURE                 Location/Qualifiers
REGION                  1..504
                        note = Synthetic peptide
source                  1..504
                        mol_type = protein
                        organism = synthetic construct
SEQUENCE: 120
QVQLVESGGG VVQPGRSLRL SCAASGFSFS SYDIHWVRQA PGKGLEWVAV ISSHGSNKNY  60
ARSVKGRFTI SRDNSKNTLY LQMNSLKAED TAVYYCARDG YSGNDPFYYY YHGMDVWGQG  120
TTVTVSSGGG GSGGGGSGGG GSDIQMTQSP SSLSASVGDR VTITCRASQS ISSYLNWYQQ  180
KPGKAPKLLI YAASSLQSGV PSRFSGSGSG TDFSLTISSL QPEDFATYYC QQSFTTPLTF  240
GGGTKVEIKS GGGGSEVQLV ESGGGLVQPG GSLKLSCAAS GFTFNKYAMN WVRQAPGKGL  300
EWVARIRSKY NNYATYYADS VKDRFTISRD DSKNTAYLQM NNLKTEDTAV YYCVRHGNFG  360
NSYISYWAYW GQGTLVTVSS GGGGSGGGGS GGGGSQTVVT QEPSLTVSPG GTVTLTCGSS  420
TGAVTSGNYP NWVQQKPGQA PRGLIGGTKF LAPGTPARFS GSLLGGKAAL TLSGVQPEDE  480
AEYYCVLWYS NRWVFGGGTK LTVL                                        504

SEQ ID NO: 121          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 121
SYYMH                                                             5

SEQ ID NO: 122          moltype = AA  length = 17
FEATURE                 Location/Qualifiers
REGION                  1..17
                        note = Synthetic peptide
source                  1..17
                        mol_type = protein
```

```
                        organism = synthetic construct
SEQUENCE: 122
IINPSDGSTN YAQNFQG                                              17

SEQ ID NO: 123          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 123
GGNSAFYSYY DMDV                                                 14

SEQ ID NO: 124          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 124
RSSQSLVYRD GNTYLS                                               16

SEQ ID NO: 125          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 125
KVSNWQS                                                         7

SEQ ID NO: 126          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 126
MQGTHWPPT                                                       9

SEQ ID NO: 127          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 127
QVQLVQSGAE VKKPGASVKV SCKASGYTFT SYYMHWVRQA PGQGLEWMGI INPSDGSTNY  60
AQNFQGRVTM TRDTSTNTVY MELSSLRSED TAVYYCARGG NSAFYSYYDM DVWGQGTTVT  120
VSS                                                             123

SEQ ID NO: 128          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 128
DVVMTQSPLS LPVTLGQPAS ISCRSSQSLV YRDGNTYLSW FQQRPGQSPR RLIYKVSNWQ  60
SGVPDRFSGS GSGTDFTLKI SRVEAEDVGV YFCMQGTHWP PTFGQGTKVE IK        112

SEQ ID NO: 129          moltype = AA  length = 250
FEATURE                 Location/Qualifiers
REGION                  1..250
                        note = Synthetic peptide
source                  1..250
                        mol_type = protein
                        organism = synthetic construct
SEQUENCE: 129
QVQLVQSGAE VKKPGASVKV SCKASGYTFT SYYMHWVRQA PGQGLEWMGI INPSDGSTNY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYKVSNWQSG VPDRFSGSGS GTDFTLKISR VEAEDVGVYF CMQGTHWPPT  240
```

```
FGQGTKVEIK                                                 250

SEQ ID NO: 130          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 130
QVQLVQSGAE VKKPGASVKV SCKASGYTFT SYYMHWVRQA PGQGLEWMGI INPSDGSTNY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                505

SEQ ID NO: 131          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 131
NYYMH                                                      5

SEQ ID NO: 132          moltype = AA  length = 17
FEATURE                 Location/Qualifiers
REGION                  1..17
                        note = Synthetic peptide
source                  1..17
                        mol_type = protein
                        organism = synthetic construct
SEQUENCE: 132
IINPSDGSTS YAQKFQG                                         17

SEQ ID NO: 133          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 133
GGNSAFYSYY DMDV                                            14

SEQ ID NO: 134          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 134
RSSQSLVYRD GNTYLS                                          16

SEQ ID NO: 135          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 135
KVSNWQS                                                    7

SEQ ID NO: 136          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 136
MQGTHWPPT                                                  9
```

```
SEQ ID NO: 137          moltype = AA  length = 123
FEATURE                Location/Qualifiers
REGION                 1..123
                       note = Synthetic peptide
source                 1..123
                       mol_type = protein
                       organism = synthetic construct
SEQUENCE: 137
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSS                                                                123

SEQ ID NO: 138          moltype = AA  length = 112
FEATURE                Location/Qualifiers
REGION                 1..112
                       note = Synthetic peptide
source                 1..112
                       mol_type = protein
                       organism = synthetic construct
SEQUENCE: 138
DVVMTQTPLS LPVTLGQPAS ISCRSSQSLV YRDGNTYLSW FQQRPGQSPR RLIYKVSNWQ  60
SGVPDRFSGG GSGTDFTLKI SRVEAEDVGV YYCMQGTHWP PTFGQGTKVE IK          112

SEQ ID NO: 139          moltype = AA  length = 250
FEATURE                Location/Qualifiers
REGION                 1..250
                       note = Synthetic peptide
source                 1..250
                       mol_type = protein
                       organism = synthetic construct
SEQUENCE: 139
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 140          moltype = AA  length = 505
FEATURE                Location/Qualifiers
REGION                 1..505
                       note = Synthetic peptide
source                 1..505
                       mol_type = protein
                       organism = synthetic construct
SEQUENCE: 140
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 141          moltype = AA  length = 5
FEATURE                Location/Qualifiers
REGION                 1..5
                       note = Synthetic peptide
source                 1..5
                       mol_type = protein
                       organism = synthetic construct
SEQUENCE: 141
GYYIH                                                              5

SEQ ID NO: 142          moltype = AA  length = 17
FEATURE                Location/Qualifiers
REGION                 1..17
                       note = Synthetic peptide
source                 1..17
                       mol_type = protein
                       organism = synthetic construct
SEQUENCE: 142
IINPSDGSTS YGQNFQG                                                 17

SEQ ID NO: 143          moltype = AA  length = 14
FEATURE                Location/Qualifiers
REGION                 1..14
```

```
                        note = Synthetic peptide
source                  1..14
                        mol_type = protein
                        organism = synthetic construct
SEQUENCE: 143
GGNSAFYSYY DMDV                                                  14

SEQ ID NO: 144          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 144
RSSQSLAYRD GNTYLS                                                16

SEQ ID NO: 145          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 145
KVSNWQS                                                          7

SEQ ID NO: 146          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 146
MQGTHWPPT                                                        9

SEQ ID NO: 147          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 147
QVQLVQSGAE VKKPGASVKV SCKASGYTFT GYYIHWVRQA PGQGLEWMGI INPSDGSTSY  60
GQNFQGRVTM TRDTSTNTVY MELSSLRSED TAVYYCARGG NSAFYSYYDM DVWGQGTTVT  120
VSS                                                              123

SEQ ID NO: 148          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 148
DVVMTQSPLS LPVTLGQPAS ISCRSSQSLA YRDGNTYLSW FQQRPGQSPR RLIYKVSNWQ  60
SGVPDRFSGS GSGTDFTLKI SRVEAEDVGV YFCMQGTHWP PTFGQGTKVE IK          112

SEQ ID NO: 149          moltype = AA  length = 250
FEATURE                 Location/Qualifiers
REGION                  1..250
                        note = Synthetic peptide
source                  1..250
                        mol_type = protein
                        organism = synthetic construct
SEQUENCE: 149
QVQLVQSGAE VKKPGASVKV SCKASGYTFT GYYIHWVRQA PGQGLEWMGI INPSDGSTSY  60
GQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLAYR DGNTYLSWFQ  180
QRPGQSPRRL IYKVSNWQSG VPDRFSGSGS GTDFTLKISR VEAEDVGVYF CMQGTHWPPT  240
FGQGTKVEIK                                                       250

SEQ ID NO: 150          moltype = AA  length = 505
FEATURE                 Location/Qualifiers
REGION                  1..505
                        note = Synthetic peptide
source                  1..505
```

```
                         mol_type = protein
                         organism = synthetic construct
SEQUENCE: 150
QVQLVQSGAE VKKPGASVKV SCKASGYTFT GYYIHWVRQA PGQGLEWMGI INPSDGSTSY  60
GQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLAYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 151           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 151
GHYMH                                                             5

SEQ ID NO: 152           moltype = AA  length = 17
FEATURE                  Location/Qualifiers
REGION                   1..17
                         note = Synthetic peptide
source                   1..17
                         mol_type = protein
                         organism = synthetic construct
SEQUENCE: 152
IINPSDGSTN YAQKFQG                                                17

SEQ ID NO: 153           moltype = AA  length = 14
FEATURE                  Location/Qualifiers
REGION                   1..14
                         note = Synthetic peptide
source                   1..14
                         mol_type = protein
                         organism = synthetic construct
SEQUENCE: 153
GTTVVHYSYY DMDV                                                   14

SEQ ID NO: 154           moltype = AA  length = 16
FEATURE                  Location/Qualifiers
REGION                   1..16
                         note = Synthetic peptide
source                   1..16
                         mol_type = protein
                         organism = synthetic construct
SEQUENCE: 154
RSSQSLVYRD GNTYLT                                                 16

SEQ ID NO: 155           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 155
KVSNWQS                                                           7

SEQ ID NO: 156           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 156
MQGTHWPPT                                                         9

SEQ ID NO: 157           moltype = AA  length = 123
FEATURE                  Location/Qualifiers
REGION                   1..123
                         note = Synthetic peptide
source                   1..123
                         mol_type = protein
```

```
                        organism = synthetic construct
SEQUENCE: 157
QVQLVQSGAE VKKPGASVKV SCKASGYTFT GHYMHWVRQA PGQGLEWMGI INPSDGSTNY  60
AQKFQGRVTM TRDTSTSTVY MELRSLRSED TAVYYCTRGT TVVHYSYYDM DVWGQGTTVT  120
VSS                                                               123

SEQ ID NO: 158          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 158
DVVMTQTPLS LPVTLGQPAS ISCRSSQSLV YRDGNTYLTW FQQRPGQSPR RLIYKVSNWQ  60
SGVPDRFSGS GSGTDFTLKI SRVEAEDVGV YYCMQGTHWP PTFGGGTKVE IK          112

SEQ ID NO: 159          moltype = AA  length = 250
FEATURE                 Location/Qualifiers
REGION                  1..250
                        note = Synthetic peptide
source                  1..250
                        mol_type = protein
                        organism = synthetic construct
SEQUENCE: 159
QVQLVQSGAE VKKPGASVKV SCKASGYTFT GHYMHWVRQA PGQGLEWMGI INPSDGSTNY  60
AQKFQGRVTM TRDTSTSTVY MELRSLRSED TAVYYCTRGT TVVHYSYYDM DVWGQGTTVT  120
VSSGGGGSGG GGSGGGGSDV VMTQTPLSLP VTLGQPASIS CRSSQSLVYR DGNTYLTWFQ  180
QRPGQSPRRL IYKVSNWQSG VPDRFSGSGS GTDFTLKISR VEAEDVGVYY CMQGTHWPPT  240
FGGGTKVEIK                                                        250

SEQ ID NO: 160          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 160
QVQLVQSGAE VKKPGASVKV SCKASGYTFT GHYMHWVRQA PGQGLEWMGI INPSDGSTNY  60
AQKFQGRVTM TRDTSTSTVY MELRSLRSED TAVYYCTRGT TVVHYSYYDM DVWGQGTTVT  120
VSSGGGGSGG GGSGGGGSDV VMTQTPLSLP VTLGQPASIS CRSSQSLVYR DGNTYLTWFQ  180
QRPGQSPRRL IYKVSNWQSG VPDRFSGSGS GTDFTLKISR VEAEDVGVYY CMQGTHWPPT  240
FGGGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 161          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 161
NYFMH                                                             5

SEQ ID NO: 162          moltype = AA  length = 17
FEATURE                 Location/Qualifiers
REGION                  1..17
                        note = Synthetic peptide
source                  1..17
                        mol_type = protein
                        organism = synthetic construct
SEQUENCE: 162
IINPSDGSTS YAQNFQG                                                17

SEQ ID NO: 163          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 163
GGNSAFYSYY DMDV                                                   14
```

```
SEQ ID NO: 164         moltype = AA  length = 16
FEATURE                Location/Qualifiers
REGION                 1..16
                       note = Synthetic peptide
source                 1..16
                       mol_type = protein
                       organism = synthetic construct
SEQUENCE: 164
RSSQSLVYRD GNTYLS                                                  16

SEQ ID NO: 165         moltype = AA  length = 7
FEATURE                Location/Qualifiers
REGION                 1..7
                       note = Synthetic peptide
source                 1..7
                       mol_type = protein
                       organism = synthetic construct
SEQUENCE: 165
RVSNWQS                                                            7

SEQ ID NO: 166         moltype = AA  length = 9
FEATURE                Location/Qualifiers
REGION                 1..9
                       note = Synthetic peptide
source                 1..9
                       mol_type = protein
                       organism = synthetic construct
SEQUENCE: 166
MQGTYWPPT                                                          9

SEQ ID NO: 167         moltype = AA  length = 123
FEATURE                Location/Qualifiers
REGION                 1..123
                       note = Synthetic peptide
source                 1..123
                       mol_type = protein
                       organism = synthetic construct
SEQUENCE: 167
QVQLVQSGAE VKKPGASVKV SCKASGYTFT NYFMHWVRQA PGLGLEWMGI INPSDGSTSY  60
AQNFQGRVTM TRDTSTNTVY MELSSLRSED TAVYYCARGG NSAFYSYYDM DVWGQGTTVT  120
VSS                                                                123

SEQ ID NO: 168         moltype = AA  length = 112
FEATURE                Location/Qualifiers
REGION                 1..112
                       note = Synthetic peptide
source                 1..112
                       mol_type = protein
                       organism = synthetic construct
SEQUENCE: 168
DVVMTQSPLS LPVTLGQPAS ISCRSSQSLV YRDGNTYLSW FQQRPGQSPR RLIYRVSNWQ  60
SGVPDRFSGS GSGTDFTLKI SRVEAEDVGV YFCMQGTYWP PTFGQGTKVD IK          112

SEQ ID NO: 169         moltype = AA  length = 250
FEATURE                Location/Qualifiers
REGION                 1..250
                       note = Synthetic peptide
source                 1..250
                       mol_type = protein
                       organism = synthetic construct
SEQUENCE: 169
QVQLVQSGAE VKKPGASVKV SCKASGYTFT NYFMHWVRQA PGLGLEWMGI INPSDGSTSY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYRVSNWQSG VPDRFSGSGS GTDFTLKISR VEAEDVGVYF CMQGTYWPPT  240
FGQGTKVDIK                                                         250

SEQ ID NO: 170         moltype = AA  length = 505
FEATURE                Location/Qualifiers
REGION                 1..505
                       note = Synthetic peptide
source                 1..505
                       mol_type = protein
                       organism = synthetic construct
SEQUENCE: 170
QVQLVQSGAE VKKPGASVKV SCKASGYTFT NYFMHWVRQA PGLGLEWMGI INPSDGSTSY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYRVSNWQSG VPDRFSGSGS GTDFTLKISR VEAEDVGVYF CMQGTYWPPT  240
```

```
FGQGTKVDIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 171         moltype = AA  length = 5
FEATURE                Location/Qualifiers
REGION                 1..5
                       note = Synthetic peptide
source                 1..5
                       mol_type = protein
                       organism = synthetic construct
SEQUENCE: 171
NYGMH                                                              5

SEQ ID NO: 172         moltype = AA  length = 17
FEATURE                Location/Qualifiers
REGION                 1..17
                       note = Synthetic peptide
source                 1..17
                       mol_type = protein
                       organism = synthetic construct
SEQUENCE: 172
VISHHGSSKY YARSVKG                                                 17

SEQ ID NO: 173         moltype = AA  length = 9
FEATURE                Location/Qualifiers
REGION                 1..9
                       note = Synthetic peptide
source                 1..9
                       mol_type = protein
                       organism = synthetic construct
SEQUENCE: 173
DWWELVFDY                                                          9

SEQ ID NO: 174         moltype = AA  length = 16
FEATURE                Location/Qualifiers
REGION                 1..16
                       note = Synthetic peptide
source                 1..16
                       mol_type = protein
                       organism = synthetic construct
SEQUENCE: 174
KSSQSLLHSD GKTFLY                                                  16

SEQ ID NO: 175         moltype = AA  length = 7
FEATURE                Location/Qualifiers
REGION                 1..7
                       note = Synthetic peptide
source                 1..7
                       mol_type = protein
                       organism = synthetic construct
SEQUENCE: 175
EVSNRFS                                                            7

SEQ ID NO: 176         moltype = AA  length = 9
FEATURE                Location/Qualifiers
REGION                 1..9
                       note = Synthetic peptide
source                 1..9
                       mol_type = protein
                       organism = synthetic construct
SEQUENCE: 176
LQGIHLPFT                                                          9

SEQ ID NO: 177         moltype = AA  length = 118
FEATURE                Location/Qualifiers
REGION                 1..118
                       note = Synthetic peptide
source                 1..118
                       mol_type = protein
                       organism = synthetic construct
SEQUENCE: 177
QVQLVESGGG AVQPGRSLRL SCAASGFTFS NYGMHWVRQA PGKGLEWVAV ISHHGSSKYY  60
ARSVKGRFTI SRDNSKNTLY LEMNSLRAED TAVYYCARDW WELVFDYWGQ GTLVTVSS    118

SEQ ID NO: 178         moltype = AA  length = 112
FEATURE                Location/Qualifiers
```

```
REGION                  1..112
                        note = Synthetic peptide
source                  1..112
                        mol_type = protein
                        organism = synthetic construct
SEQUENCE: 178
DIVMTQTPLS LSVTPGQPAS ISCKSSQSLL HSDGKTFLYW YLQKPGQPPQ LLIYEVSNRF  60
SGVPDRFSGS GSGTDFTLKI SRVEAEDVGV YYCLQGIHLP FTFGPGTKVE IK          112

SEQ ID NO: 179          moltype = AA  length = 245
FEATURE                 Location/Qualifiers
REGION                  1..245
                        note = Synthetic peptide
source                  1..245
                        mol_type = protein
                        organism = synthetic construct
SEQUENCE: 179
QVQLVESGGG AVQPGRSLRL SCAASGFTFS NYGMHWVRQA PGKGLEWVAV ISHHGSSKYY  60
ARSVKGRFTI SRDNSKNTLY LEMNSLRAED TAVYYCARDW WELVFDYWGQ GTLVTVSSGG  120
GGSGGGGSGG GGSDIVMTQT PLSLSVTPGQ PASISCKSSQ SLLHSDGKTF LYWYLQKPGQ  180
PPQLLIYEVS NRFSGVPDRF SGSGSGTDFT LKISRVEAED VGVYYCLQGI HLPFTFGPGT  240
KVEIK                                                              245

SEQ ID NO: 180          moltype = AA  length = 500
FEATURE                 Location/Qualifiers
REGION                  1..500
                        note = Synthetic peptide
source                  1..500
                        mol_type = protein
                        organism = synthetic construct
SEQUENCE: 180
QVQLVESGGG AVQPGRSLRL SCAASGFTFS NYGMHWVRQA PGKGLEWVAV ISHHGSSKYY  60
ARSVKGRFTI SRDNSKNTLY LEMNSLRAED TAVYYCARDW WELVFDYWGQ GTLVTVSSGG  120
GGSGGGGSGG GGSDIVMTQT PLSLSVTPGQ PASISCKSSQ SLLHSDGKTF LYWYLQKPGQ  180
PPQLLIYEVS NRFSGVPDRF SGSGSGTDFT LKISRVEAED VGVYYCLQGI HLPFTFGPGT  240
KVEIKSGGGG SEVQLVESGG GLVQPGGSLK LSCAASGFTF NKYAMNWVRQ APGKGLEWVA  300
RIRSKYNNYA TYYADSVKDR FTISRDDSKN TAYLQMNNLK TEDTAVYYCV RHGNFGNSYI  360
SYWAYWGQGT LVTVSSGGGG SGGGGSGGGG SQTVVTQEPS LTVSPGGTVT LTCGSSTGAV  420
TSGNYPNWVQ QKPGQAPRGL IGGTKFLAPG TPARFSGSLL GGKAALTLSG VQPEDEAEYY  480
CVLWYSNRWV FGGGTKLTVL                                              500

SEQ ID NO: 181          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 181
NSRMGVS                                                            7

SEQ ID NO: 182          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 182
HIFSNDGKSY STSLKS                                                  16

SEQ ID NO: 183          moltype = AA  length = 15
FEATURE                 Location/Qualifiers
REGION                  1..15
                        note = Synthetic peptide
source                  1..15
                        mol_type = protein
                        organism = synthetic construct
SEQUENCE: 183
YNYDSSGYYY SFFDY                                                   15

SEQ ID NO: 184          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 184
```

```
RASQSISSYL N                                                    11

SEQ ID NO: 185          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 185
AASSLQS                                                         7

SEQ ID NO: 186          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 186
QQGYSSPFT                                                       9

SEQ ID NO: 187          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 187
QVTLKESGPM LVKPTETLTL TCTVSGFSLS NSRMGVSWIR QPPGRALEWL AHIFSNDGKS  60
YSTSLKSRLT ISKDTSKSQV VLTMTNMDPV DTATYYCARY NYDSSGYYYS FFDYWGQGTL  120
VTVSS                                                           125

SEQ ID NO: 188          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 188
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ GYSSPFTFGG GTKVEIK             107

SEQ ID NO: 189          moltype = AA  length = 247
FEATURE                 Location/Qualifiers
REGION                  1..247
                        note = Synthetic peptide
source                  1..247
                        mol_type = protein
                        organism = synthetic construct
SEQUENCE: 189
QVTLKESGPM LVKPTETLTL TCTVSGFSLS NSRMGVSWIR QPPGRALEWL AHIFSNDGKS  60
YSTSLKSRLT ISKDTSKSQV VLTMTNMDPV DTATYYCARY NYDSSGYYYS FFDYWGQGTL  120
VTVSSGGGGS GGGGSGGGGS DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ GYSSPFTFGG  240
GTKVEIK                                                         247

SEQ ID NO: 190          moltype = AA  length = 502
FEATURE                 Location/Qualifiers
REGION                  1..502
                        note = Synthetic peptide
source                  1..502
                        mol_type = protein
                        organism = synthetic construct
SEQUENCE: 190
QVTLKESGPM LVKPTETLTL TCTVSGFSLS NSRMGVSWIR QPPGRALEWL AHIFSNDGKS  60
YSTSLKSRLT ISKDTSKSQV VLTMTNMDPV DTATYYCARY NYDSSGYYYS FFDYWGQGTL  120
VTVSSGGGGS GGGGSGGGGS DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ GYSSPFTFGG  240
GTKVEIKSGG GGSEVQLVES GGGLVQPGGS LKLSCAASGF TFNKYAMNWV RQAPGKGLEW  300
VARIRSKYNN YATYYADSVK DRFTISRDDS KNTAYLQMNN LKTEDTAVYY CVRHGNFGNS  360
YISYWAYWGQ GTLVTVSSGG GGSGGGGSGG GGSQTVVTQE PSLTVSPGGT VTLTCGSSTG  420
AVTSGNYPNW VQQKPGQAPR GLIGGTKFLA PGTPARFSGS LLGGKAALTL SGVQPEDEAE  480
YYCVLWYSNR WVFGGGTKLT VL                                        502

SEQ ID NO: 191          moltype = AA  length = 7
FEATURE                 Location/Qualifiers
```

```
REGION                1..7
                      note = Synthetic peptide
source                1..7
                      mol_type = protein
                      organism = synthetic construct
SEQUENCE: 191
NARMGVS                                                              7

SEQ ID NO: 192        moltype = AA  length = 16
FEATURE               Location/Qualifiers
REGION                1..16
                      note = Synthetic peptide
source                1..16
                      mol_type = protein
                      organism = synthetic construct
SEQUENCE: 192
HIFSTDEKSY STSLKS                                                    16

SEQ ID NO: 193        moltype = AA  length = 15
FEATURE               Location/Qualifiers
REGION                1..15
                      note = Synthetic peptide
source                1..15
                      mol_type = protein
                      organism = synthetic construct
SEQUENCE: 193
YYYDSSGYYY SFFDY                                                     15

SEQ ID NO: 194        moltype = AA  length = 11
FEATURE               Location/Qualifiers
REGION                1..11
                      note = Synthetic peptide
source                1..11
                      mol_type = protein
                      organism = synthetic construct
SEQUENCE: 194
RASQSIRSYL N                                                         11

SEQ ID NO: 195        moltype = AA  length = 7
FEATURE               Location/Qualifiers
REGION                1..7
                      note = Synthetic peptide
source                1..7
                      mol_type = protein
                      organism = synthetic construct
SEQUENCE: 195
GASNLQS                                                              7

SEQ ID NO: 196        moltype = AA  length = 9
FEATURE               Location/Qualifiers
REGION                1..9
                      note = Synthetic peptide
source                1..9
                      mol_type = protein
                      organism = synthetic construct
SEQUENCE: 196
QQSYSSPFT                                                            9

SEQ ID NO: 197        moltype = AA  length = 125
FEATURE               Location/Qualifiers
REGION                1..125
                      note = Synthetic peptide
source                1..125
                      mol_type = protein
                      organism = synthetic construct
SEQUENCE: 197
QVTLKESGPV LVKPTETLTL TCTVSGFSLS NARMGVSWLR QPPGKALEWL AHIFSTDEKS  60
YSTSLKSRLT ISKDTSKSQV VLTMTNMDPV DTATYYCARY YYDSSGYYYS FFDYWGQGTL  120
VTVSS                                                                125

SEQ ID NO: 198        moltype = AA  length = 107
FEATURE               Location/Qualifiers
REGION                1..107
                      note = Synthetic peptide
source                1..107
                      mol_type = protein
                      organism = synthetic construct
SEQUENCE: 198
DIQMTQSPSS LSASVGDRVT ITCRASQSIR SYLNWYQQKP GKAPKLLIYG ASNLQSGVPS  60
```

```
RFSGSGSGTD FTLTISSLQP EDFATYYCQQ SYSSPFTFGG GTKVEIK                 107

SEQ ID NO: 199         moltype = AA  length = 247
FEATURE                Location/Qualifiers
REGION                 1..247
                       note = Synthetic peptide
source                 1..247
                       mol_type = protein
                       organism = synthetic construct
SEQUENCE: 199
QVTLKESGPV LVKPTETLTL TCTVSGFSLS NARMGVSWLR QPPGKALEWL AHIFSTDEKS  60
YSTSLKSRLT ISKDTSKSQV VLTMTNMDPV DTATYYCARY YYDSSGYYYS FFDYWGQGTL  120
VTVSSGGGGS GGGGSGGGGS DIQMTQSPSS LSASVGDRVT ITCRASQSIR SYLNWYQQKP  180
GKAPKLLIYG ASNLQSGVPS RFSGSGSGTD FTLTISSLQP EDFATYYCQQ SYSSPFTFGG  240
GTKVEIK                                                             247

SEQ ID NO: 200         moltype = AA  length = 502
FEATURE                Location/Qualifiers
REGION                 1..502
                       note = Synthetic peptide
source                 1..502
                       mol_type = protein
                       organism = synthetic construct
SEQUENCE: 200
QVTLKESGPV LVKPTETLTL TCTVSGFSLS NARMGVSWLR QPPGKALEWL AHIFSTDEKS  60
YSTSLKSRLT ISKDTSKSQV VLTMTNMDPV DTATYYCARY YYDSSGYYYS FFDYWGQGTL  120
VTVSSGGGGS GGGGSGGGGS DIQMTQSPSS LSASVGDRVT ITCRASQSIR SYLNWYQQKP  180
GKAPKLLIYG ASNLQSGVPS RFSGSGSGTD FTLTISSLQP EDFATYYCQQ SYSSPFTFGG  240
GTKVEIKSGG GGSEVQLVES GGGLVQPGGS LKLSCAASGF TFNKYAMNWV RQAPGKGLEW  300
VARIRSKYNN YATYYADSVK DRFTISRDDS KNTAYLQMNN LKTEDTAVYY CVRHGNFGNS  360
YISYWAYWGQ GTLVTVSSGG GGSGGGGSGG GGSQTVVTQE PSLTVSPGGT VTLTCGSSTG  420
AVTSGNYPNW VQQKPGQAPR GLIGGTKFLA PGTPARFSGS LLGGKAALTL SGVQPEDEAE  480
YYCVLWYSNR WVFGGGTKLT VL                                            502

SEQ ID NO: 201         moltype = AA  length = 5
FEATURE                Location/Qualifiers
REGION                 1..5
                       note = Synthetic peptide
source                 1..5
                       mol_type = protein
                       organism = synthetic construct
SEQUENCE: 201
SYYIH                                                               5

SEQ ID NO: 202         moltype = AA  length = 17
FEATURE                Location/Qualifiers
REGION                 1..17
                       note = Synthetic peptide
source                 1..17
                       mol_type = protein
                       organism = synthetic construct
SEQUENCE: 202
IINPSGGSKS YAQKFRG                                                  17

SEQ ID NO: 203         moltype = AA  length = 12
FEATURE                Location/Qualifiers
REGION                 1..12
                       note = Synthetic peptide
source                 1..12
                       mol_type = protein
                       organism = synthetic construct
SEQUENCE: 203
SMSTVTSDAF DI                                                       12

SEQ ID NO: 204         moltype = AA  length = 11
FEATURE                Location/Qualifiers
REGION                 1..11
                       note = Synthetic peptide
source                 1..11
                       mol_type = protein
                       organism = synthetic construct
SEQUENCE: 204
RASQSISNYL N                                                        11

SEQ ID NO: 205         moltype = AA  length = 7
FEATURE                Location/Qualifiers
REGION                 1..7
                       note = Synthetic peptide
source                 1..7
```

```
                        mol_type = protein
                        organism = synthetic construct
SEQUENCE: 205
AASSLQS                                                                 7

SEQ ID NO: 206          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 206
QQSYSAPLT                                                               9

SEQ ID NO: 207          moltype = AA  length = 121
FEATURE                 Location/Qualifiers
REGION                  1..121
                        note = Synthetic peptide
source                  1..121
                        mol_type = protein
                        organism = synthetic construct
SEQUENCE: 207
QVQLVQSGAE VKKPGASVKV SCKASGYAFT SYYIHWVRQA PGQGLEWMGI INPSGGSKSY  60
AQKFRGRVTM TRDTSTSTVY MELSSLTSED TAVYYCARSM STVTSDAFDI WGQGTMVTVS  120
S                                                                   121

SEQ ID NO: 208          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 208
DIQMTQSPSS LSASVGDRVT ITCRASQSIS NYLNWYQQKP GKAPKLLIYA ASSLQSGVPS  60
RFSGSGSGTE FTLTISSLQP EDFATYYCQQ SYSAPLTFGG GTKVDIK                 107

SEQ ID NO: 209          moltype = AA  length = 243
FEATURE                 Location/Qualifiers
REGION                  1..243
                        note = Synthetic peptide
source                  1..243
                        mol_type = protein
                        organism = synthetic construct
SEQUENCE: 209
QVQLVQSGAE VKKPGASVKV SCKASGYAFT SYYIHWVRQA PGQGLEWMGI INPSGGSKSY  60
AQKFRGRVTM TRDTSTSTVY MELSSLTSED TAVYYCARSM STVTSDAFDI WGQGTMVTVS  120
SGGGGSGGGG SGGGGSDIQM TQSPSSLSAS VGDRVTITCR ASQSISNYLN WYQQKPGKAP  180
KLLIYAASSL QSGVPSRFSG SGSGTEFTLT ISSLQPEDFA TYYCQQSYSA PLTFGGGTKV  240
DIK                                                                 243

SEQ ID NO: 210          moltype = AA  length = 498
FEATURE                 Location/Qualifiers
REGION                  1..498
                        note = Synthetic peptide
source                  1..498
                        mol_type = protein
                        organism = synthetic construct
SEQUENCE: 210
QVQLVQSGAE VKKPGASVKV SCKASGYAFT SYYIHWVRQA PGQGLEWMGI INPSGGSKSY  60
AQKFRGRVTM TRDTSTSTVY MELSSLTSED TAVYYCARSM STVTSDAFDI WGQGTMVTVS  120
SGGGGSGGGG SGGGGSDIQM TQSPSSLSAS VGDRVTITCR ASQSISNYLN WYQQKPGKAP  180
KLLIYAASSL QSGVPSRFSG SGSGTEFTLT ISSLQPEDFA TYYCQQSYSA PLTFGGGTKV  240
DIKSGGGGSE VQLVESGGGL VQPGGSLKLS CAASGFTFNK YAMNWVRQAP GKGLEWVARI  300
RSKYNNYATY YADSVKDRFT ISRDDSKNTA YLQMNNLKTE DTAVYYCVRH GNFGNSYISY  360
WAYWGQGTLV TVSSGGGGSG GGGSGGGGSQ TVVTQEPSLT VSPGGTVTLT CGSSTGAVTS  420
GNYPNWVQQK PGQAPRGLIG GTKFLAPGTP ARFSGSLLGG KAALTLSGVQ PEDEAEYYCV  480
LWYSNRWVFG GGTKLTVL                                                 498

SEQ ID NO: 211          moltype = AA  length = 496
FEATURE                 Location/Qualifiers
REGION                  1..496
                        note = Synthetic peptide
source                  1..496
                        mol_type = protein
                        organism = synthetic construct
SEQUENCE: 211
QVQLQESGPG LVKPSETLSL TCTVSGGSIS SYYWSWIRQP PGKGLEWIGY VYYSGTTNYN  60
```

```
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 212         moltype = AA  length = 496
FEATURE                Location/Qualifiers
REGION                 1..496
                       note = Synthetic peptide
source                 1..496
                       mol_type = protein
                       organism = synthetic construct
SEQUENCE: 212
QVQLQESGPG LVKPSETLSL TCTVSGGSIS SYYWSWIRQP PGKGLEWIGY IYYSGRTNYY  60
PSLKSRVTIS IDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 213         moltype = AA  length = 496
FEATURE                Location/Qualifiers
REGION                 1..496
                       note = Synthetic peptide
source                 1..496
                       mol_type = protein
                       organism = synthetic construct
SEQUENCE: 213
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 214         moltype = AA  length = 496
FEATURE                Location/Qualifiers
REGION                 1..496
                       note = Synthetic peptide
source                 1..496
                       mol_type = protein
                       organism = synthetic construct
SEQUENCE: 214
QVQLQESGPG LVKPSQTLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 215         moltype = AA  length = 496
FEATURE                Location/Qualifiers
REGION                 1..496
                       note = Synthetic peptide
source                 1..496
                       mol_type = protein
                       organism = synthetic construct
SEQUENCE: 215
QVQLQEWGPG LVKPSETLSL TCTVSGASIS SFYWSWIRQP PGKGLEWIGY IYYSGTTNYN  60
PSLKSRVTIS VDTSKNQLSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVDI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
```

```
YSNRWVFGGG TKLTVL                                                  496

SEQ ID NO: 216         moltype = AA  length = 496
FEATURE                Location/Qualifiers
REGION                 1..496
                       note = Synthetic peptide
source                 1..496
                       mol_type = protein
                       organism = synthetic construct
SEQUENCE: 216
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE SATLSCRASQ SVNKNYLAWY QQKPGQAPRL  180
LIYGASSRAT GIPDRFSGSG SGTDFTLTIS RLEPEDFAVY YCQQYDRSPL TFGGGTRLEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 217         moltype = AA  length = 496
FEATURE                Location/Qualifiers
REGION                 1..496
                       note = Synthetic peptide
source                 1..496
                       mol_type = protein
                       organism = synthetic construct
SEQUENCE: 217
QVQLQESGPG LVKPSQTLSL TCTVSGGSIS SYYWSWIRQP PGKGLEWIGY IFYNGITNYN  60
PSLKSRVTIS LDTSKNQFSL KLSSVTAADT AKYYCARIHS GSFSFDYWDQ GTLVTVSSGG  120
GGSGGGGSGG GGSEIVMTQS PGTLSLSPGE RATLSCRASQ SVSRGYLAWY QQKPGQAPRL  180
LIYGASSRAT DIPDRFSGSG SGTDFTLTIS RLEPEDFAVY YCQQYDTSPI TFGQGTKVEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 218         moltype = AA  length = 505
FEATURE                Location/Qualifiers
REGION                 1..505
                       note = Synthetic peptide
source                 1..505
                       mol_type = protein
                       organism = synthetic construct
SEQUENCE: 218
QVQLVQSGAE VKKPGASVKV SCKASGYTFT SYYMHWVRQA PGQGLEWMGI INPSDGSTNY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLRLSCAA SGFTFNSYAM NWVRQAPGKG  300
LEWVARIRSK YNNYATYYAD SVKGRFTISR DDSKNTAYLQ MNSLKTEDTA VYYCVRHGNF  360
GNSYVSWWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 219         moltype = AA  length = 505
FEATURE                Location/Qualifiers
REGION                 1..505
                       note = Synthetic peptide
source                 1..505
                       mol_type = protein
                       organism = synthetic construct
SEQUENCE: 219
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLRLSCAA SGFTFNSYAM NWVRQAPGKG  300
LEWVARIRSK YNNYATYYAD SVKGRFTISR DDSKNTAYLQ MNSLKTEDTA VYYCVRHGNF  360
GNSYVSWWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 220         moltype = AA  length = 505
FEATURE                Location/Qualifiers
REGION                 1..505
                       note = Synthetic peptide
source                 1..505
```

```
                         mol_type = protein
                         organism = synthetic construct
SEQUENCE: 220
QVQLVQSGAE VKKPGASVKV SCKASGYTFT GYYIHWVRQA PGQGLEWMGI INPSDGSTSY  60
GQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLAYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLRLSCAA SGFTFNSYAM NWVRQAPGKG  300
LEWVARIRSK YNNYATYYAD SVKGRFTISR DDSKNTAYLQ MNSLKTEDTA VYYCVRHGNF  360
GNSYVSWWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                      505

SEQ ID NO: 221           moltype = AA  length = 1096
FEATURE                  Location/Qualifiers
REGION                   1..1096
                         note = Synthetic peptide
source                   1..1096
                         mol_type = protein
                         organism = synthetic construct
SEQUENCE: 221
QVQLVESGGG VVQSGRSLRL SCAASGFTFS DYGIHWVRQA PGKGLEWVAV ISYHGSNKYY  60
ARSVKGRFTV SRDNSKNTLY LQMNSLRAED TAVYYCAREI PFGMDVWGQG TTVTVSSGGG  120
GSGGGGSGGG GSDIVMTQTP LSLPVTPGEP ASISCRSSQS LLHSDGYNYL DWYLQKPGQS  180
PQLLIYLGSN RASGVPDRFS GSGSGTDFTL TISRVEAEDV GVYYCMQALQ TPLTFGGGTK  240
VDIKSGGGGS EVQLVESGGG LVQPGGSLKL SCAASGFTFN KYAMNWVRQA PGKGLEWVAR  300
IRSKYNNYAT YYADSVKDRF TISRDDSKNT AYLQMNNLKT EDTAVYYCVR HGNFGNSYIS  360
YWAYWGQGTL VTVSSGGGGS GGGGSGGGGS QTVVTQEPSL TVSPGGTVTL TCGSSTGAVT  420
SGNYPNWVQQ KPGQAPRGLI GGTKFLAPGT PARFSGSLLG GKAALTLSGV QPEDEAEYYC  480
VLWYSNRWVF GGGTKLTVLP GGGGSDAHKS EVAHRFKDLG EENFKALVLI AFAQYLQQCP  540
FEDHVKLVNE VTEFAKTCVA DESAENCDKS LHTLFGDKLC TVATLRETYG EMADCCAKQE  600
PERNECFLQH KDDNPNLPRL VRPEVDVMCT AFHDNEETFL KKYLYEIARR HPYFYAPELL  660
FFAKRYKAAF TECCQAADKA ACLLPKLDEL RDEGKASSAK QRLKCASLQK FGERAFKAWA  720
VARLSQRFPK AEFAEVSKLV TDLTKVHTEC CHGDLLECAD DRADLAKYIC ENQDSISSKL  780
KECCEKPLLE KSHCIAEVEN DEMPADLPSL AADFVESKDV CKNYAEAKDV FLGMFLYEYA  840
RRHPDYSVVL LLRLAKTYET TLEKCCAAAD PHECYAKVFD EFKPLVEEPQ NLIKQNCELF  900
EQLGEYKFQN ALLVRYTKKV PQVSTPTLVE VSRNLGKVGS KCCKHPEAKR MPCAEDYLSV  960
VLNQLCVLHE KTPVSDRVTK CCTESLVNRR PCFSALEVDE TYVPKEFNAG TFTFHADICT  1020
LSEKERQIKK QTALVELVKH KPKATKEQLK AAMDDFAAFV EKCCKADDKE TCFAEEGKKL  1080
VAASQAALGL HHHHHH                                                1096

SEQ ID NO: 222           moltype = AA  length = 1095
FEATURE                  Location/Qualifiers
REGION                   1..1095
                         note = Synthetic peptide
source                   1..1095
                         mol_type = protein
                         organism = synthetic construct
SEQUENCE: 222
QVQLVQSGAE VKKPGASVKV SCKASGYTFT GYYMHWVRQA PGQGLEWMGW INPNSGDTNY  60
AQKFQGRVTM TRDTSISTAY MELSRLTSDD TAVYYCARDA NIAALDAFEI WGQGTMVTVS  120
SGGGGSGGGG SGGGGSDIQM TQSPSSLSAS VGDRVTITCR ASQSISSYLN WYQQKPGKAP  180
KLLIYAASSL QSGVPSRFSG SGSGTDFTLT ISSLQPEDFA TYYCQQSYST PLTFGGGTKV  240
EIKSGGGGSE VQLVESGGGL VQPGGSLKLS CAASGFTFNK YAMNWVRQAP GKGLEWVARI  300
RSKYNNYATY YADSVKDRFT ISRDDSKNTA YLQMNNLKTE DTAVYYCVRH GNFGNSYISY  360
WAYWGQGTLV TVSSGGGGSG GGGSGGGGSQ TVVTQEPSLT VSPGGTVTLT CGSSTGAVTS  420
GNYPNWVQQK PGQAPRGLIG GTKFLAPGTP ARFSGSLLGG KAALTLSGVQ PEDEAEYYCV  480
LWYSNRWVFG GGTKLTVLPG GGGSDAHKSE VAHRFKDLGE ENFKALVLIA FAQYLQQCPF  540
EDHVKLVNEV TEFAKTCVAD ESAENCDKSL HTLFGDKLCT VATLRETYGE MADCCAKQEP  600
ERNECFLQHK DDNPNLPRLV RPEVDVMCTA FHDNEETFLK KYLYEIARRH PYFYAPELLF  660
FAKRYKAAFT ECCQAADKAA CLLPKLDELR DEGKASSAKQ RLKCASLQKF GERAFKAWAV  720
ARLSQRFPKA EFAEVSKLVT DLTKVHTECC HGDLLECADD RADLAKYICE NQDSISSKLK  780
ECCEKPLLEK SHCIAEVEND EMPADLPSLA ADFVESKDVC KNYAEAKDVF LGMFLYEYAR  840
RHPDYSVVLL LRLAKTYETT LEKCCAAADP HECYAKVFDE FKPLVEEPQN LIKQNCELFE  900
QLGEYKFQNA LLVRYTKKVP QVSTPTLVEV SRNLGKVGSK CCKHPEAKRM PCAEDYLSVV  960
LNQLCVLHEK TPVSDRVTKC CTESLVNRRP CFSALEVDET YVPKEFNAGT FTFHADICTL  1020
SEKERQIKKQ TALVELVKHK PKATKEQLKA AMDDFAAFVE KCCKADDKET CFAEEGKKLV  1080
AASQAALGLH HHHH                                                  1095

SEQ ID NO: 223           moltype = AA  length = 1098
FEATURE                  Location/Qualifiers
REGION                   1..1098
                         note = Synthetic peptide
source                   1..1098
                         mol_type = protein
                         organism = synthetic construct
SEQUENCE: 223
QVQLVESGGG VVQPGRSLRL SCAASGFTFS SYGMHWVRQA PGKGLEWVAV ISYHGRDTYY  60
ARSVKGRFTI SRDNSKNTLY LHMNSLRAED TAVYYCARDG ATVTSYYYSG MDVWGQGTTV  120
```

-continued

```
TVSSGGGGSG GGGSGGGGSD IQMTQSPSSL SASVGDRVTI TCRASQGISN YLAWFQQKPG  180
KAPKSLIYLA SSLQSGVPSK FSGSGSGTDF TLTISSLQPE DFATYYCQQY NFYPFTFGPG  240
TKVDIKSGGG GSEVQLVESG GGLVQPGGSL KLSCAASGFT FNKYAMNWVR QAPGKGLEWV  300
ARIRSKYNNY ATYYADSVKD RFTISRDDSK NTAYLQMNNL KTEDTAVYYC VRHGNFGNSY  360
ISYWAYWGQG TLVTVSSGGG GSGGGGSGGG GSQTVVTQEP SLTVSPGGTV TLTCGSSTGA  420
VTSGNYPNWV QQKPGQAPRG LIGGTKFLAP GTPARFSGSL LGGKAALTLS GVQPEDEAEY  480
YCVLWYSNRW VFGGGTKLTV LPGGGGSDAH KSEVAHRFKD LGEENFKALV LIAFAQYLQQ  540
CPFEDHVKLV NEVTEFAKTC VADESAENCD KSLHTLFGDK LCTVATLRET YGEMADCCAK  600
QEPERNECFL QHKDDNPNLP RLVRPEVDVM CTAFHDNEET FLKKYLYEIA RRHPYFYAPE  660
LLFFAKRYKA AFTECCQAAD KAACLLPKLD ELRDEGKASS AKQRLKCASL QKFGERAFKA  720
WAVARLSQRF PKAEFAEVSK LVTDLTKVHT ECCHGDLLEC ADDRADLAKY ICENQDSISS  780
KLKECCEKPL LEKSHCIAEV ENDEMPADLP SLAADFVESK DVCKNYAEAK DVFLGMFLYE  840
YARRHPDYSV VLLLRLAKTY ETTLEKCCAA ADPHECYAKV FDEFKPLVEE PQNLIKQNCE  900
LFEQLGEYKF QNALLVRYTK KVPQVSTPTL VEVSRNLGKV GSKCCKHPEA KRMPCAEDYL  960
SVVLNQLCVL HEKTPVSDRV TKCCTESLVN RRPCFSALEV DETYVPKEFN AETFTFHADI  1020
CTLSEKERQI KKQTALVELV KHKPKATKEQ LKAVMDDFAA FVEKCCKADD KETCFAEEGK  1080
KLVAASQAAL GLHHHHHH                                              1098

SEQ ID NO: 224         moltype = AA  length = 1093
FEATURE                Location/Qualifiers
REGION                 1..1093
                       note = Synthetic peptide
source                 1..1093
                       mol_type = protein
                       organism = synthetic construct
SEQUENCE: 224
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093

SEQ ID NO: 225         moltype = AA  length = 1093
FEATURE                Location/Qualifiers
REGION                 1..1093
                       note = Synthetic peptide
source                 1..1093
                       mol_type = protein
                       organism = synthetic construct
SEQUENCE: 225
QVQLQESGPG LVKPSETLSL TCTVSGGSIS SYYWSWIRQP PGKGLEWIGY IYYSGRTNYY  60
PSLKSRVTIS IDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093

SEQ ID NO: 226         moltype = AA  length = 1093
FEATURE                Location/Qualifiers
REGION                 1..1093
                       note = Synthetic peptide
source                 1..1093
```

```
                        mol_type = protein
                        organism = synthetic construct
SEQUENCE: 226
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093

SEQ ID NO: 227          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 227
QVQLQESGPG LVKPSQTLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093

SEQ ID NO: 228          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 228
QVQLQEWGPG LVKPSETLSL TCTVSGASIS SFYWSWIRQP PGKGLEWIGY IYYSGTTNYN  60
PSLKSRVTIS VDTSKNQLSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVDI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093
```

```
SEQ ID NO: 229         moltype = AA  length = 1093
FEATURE                Location/Qualifiers
REGION                 1..1093
                       note = Synthetic peptide
source                 1..1093
                       mol_type = protein
                       organism = synthetic construct
SEQUENCE: 229
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE SATLSCRASQ SVNKNYLAWY QQKPGQAPRL  180
LIYGASSRAT GIPDRFSGSG SGTDFTLTIS RLEPEDFAVY YCQQYDRSPL TFGGGTRLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093

SEQ ID NO: 230         moltype = AA  length = 1093
FEATURE                Location/Qualifiers
REGION                 1..1093
                       note = Synthetic peptide
source                 1..1093
                       mol_type = protein
                       organism = synthetic construct
SEQUENCE: 230
QVQLQESGPG LVKPSQTLSL TCTVSGGSIS SYYWSWIRQP PGKGLEWIGY IFYNGITNYN  60
PSLKSRVTIS LDTSKNQFSL KLSSVTAADT AKYYCARIHS GSFSFDYWDQ GTLVTVSSGG  120
GGSGGGGSGG GGSEIVMTQS PGTLSLSPGE RATLSCRASQ SVSRGYLAWY QQKPGQAPRL  180
LIYGASSRAT DIPDRFSGSG SGTDFTLTIS RLEPEDFAVY YCQQYDTSPI TFGQGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                   1093

SEQ ID NO: 231         moltype = AA  length = 1100
FEATURE                Location/Qualifiers
REGION                 1..1100
                       note = Synthetic peptide
source                 1..1100
                       mol_type = protein
                       organism = synthetic construct
SEQUENCE: 231
EVQLVESGGG LVKPGGSLRL SCAASGFIFN NAGMSWVRQA PGKGLEWVGR IKNKIDGGTT  60
DFAAPVKGRF TISRDDSKNT LYLQMNSLKA EDTAVYYCTA RGWYGDYFDY WGQGTLVTVS  120
SGGGGSGGGG SGGGGSDIVM TQTPLSLPVT PGEPASISCR SSQSLLHSNG YNYLDWYLQK  180
PGQSPQLLIY LGSNRASGVP DRFSGSGSGT DFTLKISRVE AEDVGIYYCM QALQTPFTFG  240
PGTKVEIKSG GGGSEVQLVE SGGGLVQPGG SLKLSCAASG FTFNKYAMNW VRQAPGKGLE  300
WVARIRSKYN NYATYYADSV KDRFTISRDD SKNTAYLQMN NLKTEDTAVY YCVRHGNFGN  360
SYISYWAYWG QGTLVTVSSG GGGSGGGGSG GGGSQTVVTQ EPSLTVSPGG TVTLTCGSST  420
GAVTSGNYPN WVQQKPGQAP RGLIGGTKFL APGTPARFSG SLLGGKAALT LSGVQPEDEA  480
EYYCVLWYSN RWVFGGGTKL TVLPGGGGSD AHKSEVAHRF KDLGEENFKA LVLIAFAQYL  540
QQCPFEDHVK LVNEVTEFAK TCVADESAEN CDKSLHTLFG DKLCTVATLR ETYGEMADCC  600
AKQEPERNEC FLQHKDDNPN LPRLVRPEVD VMCTAFHDNE ETFLKKYLYE IARRHPYFYA  660
PELLFFAKRY KAAFTECCQA ADKAACLLPK LDELRDEGKA SSAKQRLKCA SLQKFGERAF  720
KAWAVARLSQ RFPKAEFAEV SKLVTDLTKV HTECCHGDLL ECADDRADLA KYICENQDSI  780
SSKLKECCEK PLLEKSHCIA EVENDEMPAD LPSLAADFVE SKDVCKNYAE AKDVFLGMFL  840
YEYARRHPDY SVVLLLRLAK TYETTLEKCC AAADPHECYA KVFDEFKPLV EEPQNLIKQN  900
```

```
CELFEQLGEY KFQNALLVRY TKKVPQVSTP TLVEVSRNLG KVGSKCCKHP EAKRMPCAED  960
YLSVVLNQLC VLHEKTPVSD RVTKCCTESL VNRRPCFSAL EVDETYVPKE FNAETFTFHA  1020
DICTLSEKER QIKKQTALVE LVKHKPKATK EQLKAVMDDF AAFVEKCCKA DDKETCFAEE  1080
GKKLVAASQA ALGLHHHHHH                                             1100

SEQ ID NO: 232          moltype = AA  length = 1101
FEATURE                 Location/Qualifiers
REGION                  1..1101
                        note = Synthetic peptide
source                  1..1101
                        mol_type = protein
                        organism = synthetic construct
SEQUENCE: 232
QVQLVESGGG VVQPGRSLRL SCAASGFSFS SYDIHWVRQA PGKGLEWVAV ISSHGSNKNY  60
ARSVKGRFTI SRDNSKNTLY LQMNSLKAED TAVYYCARDG YSGNDPFYYY YHGMDVWGQG  120
TTVTVSSGGG GSGGGGSGGG GSDIQMTQSP SSLSASVGDR VTITCRASQS ISSYLNWYQQ  180
KPGKAPKLLI YAASSLQSGV PSRFSGSGSG TDFSLTISSL QPEDFATYYC QQSFTTPLTF  240
GGGTKVEIKS GGGGSEVQLV ESGGGLVQPG GSLKLSCAAS GFTFNKYAMN WVRQAPGKGL  300
EWVARIRSKY NNYATYYADS VKDRFTISRD DSKNTAYLQM NNLKTEDTAV YYCVRHGNFG  360
NSYISYWAYW GQGTLVTVSS GGGGSGGGGS GGGGSQTVVT QEPSLTVSPG GTVTLTCGSS  420
TGAVTSGNYP NWVQQKPGQA PRGLIGGTKF LAPGTPARFS GSLLGGKAAL TLSGVQPEDE  480
AEYYCVLWYS NRWVFGGGTK LTVLPGGGGS DAHKSEVAHR FKDLGEENFK ALVLIAFAQY  540
LQQCPFEDHV KLVNEVTEFA KTCVADESAE NCDKSLHTLF GDKLCTVATL RETYGEMADC  600
CAKQEPERNE CFLQHKDDNP NLPRLVRPEV DVMCTAFHDN EETFLKKYLY EIARRHPYFY  660
APELLFFAKR YKAAFTECCQ AADKAACLLP KLDELRDEGK ASSAKQRLKC ASLQKFGERA  720
FKAWAVARLS QRFPKAEFAE VSKLVTDLTK VHTECCHGDL LECADDRADL AKYICENQDS  780
ISSKLKECCE KPLLEKSHCI AEVENDEMPA DLPSLAADFV ESKDVCKNYA EAKDVFLGMF  840
LYEYARRHPD YSVVLLLRLA KTYETTLEKC CAAADPHECY AKVFDEFKPL VEEPQNLIKQ  900
NCELFEQLGE YKFQNALLVR YTKKVPQVST PTLVEVSRNL GKVGSKCCKH PEAKRMPCAE  960
DYLSVVLNQL CVLHEKTPVS DRVTKCCTES LVNRRPCFSA LEVDETYVPK EFNAETFTFH  1020
ADICTLSEKE RQIKKQTALV ELVKHKPKAT KEQLKAVMDD FAAFVEKCCK ADDKETCFAE  1080
EGKKLVAASQ AALGLHHHHH H                                           1101

SEQ ID NO: 233          moltype = AA  length = 1102
FEATURE                 Location/Qualifiers
REGION                  1..1102
                        note = Synthetic peptide
source                  1..1102
                        mol_type = protein
                        organism = synthetic construct
SEQUENCE: 233
QVQLVQSGAE VKKPGASVKV SCKASGYTFT SYYMHWVRQA PGQGLEWMGI INPSDGSTNY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 234          moltype = AA  length = 1102
FEATURE                 Location/Qualifiers
REGION                  1..1102
                        note = Synthetic peptide
source                  1..1102
                        mol_type = protein
                        organism = synthetic construct
SEQUENCE: 234
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
```

```
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 235         moltype = AA  length = 1102
FEATURE                Location/Qualifiers
REGION                 1..1102
                       note = Synthetic peptide
source                 1..1102
                       mol_type = protein
                       organism = synthetic construct
SEQUENCE: 235
QVQLVQSGAE VKKPGASVKV SCKASGYTFT GYYIHWVRQA PGQGLEWMGI INPSDGSTSY  60
GQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLAYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 236         moltype = AA  length = 1102
FEATURE                Location/Qualifiers
REGION                 1..1102
                       note = Synthetic peptide
source                 1..1102
                       mol_type = protein
                       organism = synthetic construct
SEQUENCE: 236
QVQLVQSGAE VKKPGASVKV SCKASGYTFT GHYMHWVRQA PGQGLEWMGI INPSDGSTNY  60
AQKFQGRVTM TRDTSTSTVY MELRSLRSED TAVYYCTRGT TVVHYSYYDM DVWGQGTTVT  120
VSSGGGGSGG GGSGGGGSDV VMTQTPLSLP VTLGQPASIS CRSSQSLVYR DGNTYLTWFQ  180
QRPGQSPRRL IYKVSNWQSG VPDRFSGSGS GTDFTLKISR VEAEDVGVYY CMQGTHWPPT  240
FGGGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 237         moltype = AA  length = 1102
FEATURE                Location/Qualifiers
REGION                 1..1102
                       note = Synthetic peptide
source                 1..1102
                       mol_type = protein
                       organism = synthetic construct
SEQUENCE: 237
QVQLVQSGAE VKKPGASVKV SCKASGYTFT NYFMHWVRQA PGLGLEWMGI INPSDGSTSY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYRVSNWQSG VPDRFSGSGS GTDFTLKISR VEAEDVGVYF CMQGTYWPPT  240
FGQGTKVDIK SGGGGSEVQL VESGGGLVQP GGSLKLSCAA SGFTFNKYAM NWVRQAPGKG  300
```

```
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 238         moltype = AA  length = 1097
FEATURE                Location/Qualifiers
REGION                 1..1097
                       note = Synthetic peptide
source                 1..1097
                       mol_type = protein
                       organism = synthetic construct
SEQUENCE: 238
QVQLVESGGG AVQPGRSLRL SCAASGFTFS NYGMHWVRQA PGKGLEWVAV ISHHGSSKYY  60
ARSVKGRFTI SRDNSKNTLY LEMNSLRAED TAVYYCARDW WELVFDYWGQ GTLVTVSSGG  120
GGSGGGGSGG GGSDIVMTQT PLSLSVTPGQ PASISCKSSQ SLLHSDGKTF LYWYLQKPGQ  180
PPQLLIYEVS NRFSGVPDRF SGSGSGTDFT LKISRVEAED VGVYYCLQGI HLPFTFGPGT  240
KVEIKSGGGG SEVQLVESGG GLVQPGGSLK LSCAASGFTF NKYAMNWVRQ APGKGLEWVA  300
RIRSKYNNYA TYYADSVKDR FTISRDDSKN TAYLQMNNLK TEDTAVYYCV RHGNFGNSYI  360
SYWAYWGQGT LVTVSSGGGG SGGGGSGGGG SQTVVTQEPS LTVSPGGTVT LTCGSSTGAV  420
TSGNYPNWVQ QKPGQAPRGL IGGTKFLAPG TPARFSGSLL GGKAALTLSG VQPEDEAEYY  480
CVLWYSNRWV FGGGTKLTVL PGGGGSDAHK SEVAHRFKDL GEENFKALVL IAFAQYLQQC  540
PFEDHVKLVN EVTEFAKTCV ADESAENCDK SLHTLFGDKL CTVATLRETY GEMADCCAKQ  600
EPERNECFLQ HKDDNPNLPR LVRPEVDVMC TAFHDNEETF LKKYLYEIAR RHPYFYAPEL  660
LFFAKRYKAA FTECCQAADK AACLLPKLDE LRDEGKASSA KQRLKCASLQ KFGERAFKAW  720
AVARLSQRFP KAEFAEVSKL VTDLTKVHTE CCHGDLLECA DDRADLAKYI CENQDSISSK  780
LKECCEKPLL EKSHCIAEVE NDEMPADLPS LAADFVESKD VCKNYAEAKD VFLGMFLYEY  840
ARRHPDYSVV LLLRLAKTYE TTLEKCCAAA DPHECYAKVF DEFKPLVEEP QNLIKQNCEL  900
FEQLGEYKFQ NALLVRYTKK VPQVSTPTLV EVSRNLGKVG SKCCKHPEAK RMPCAEDYLS  960
VVLNQLCVLH EKTPVSDRVT KCCTESLVNR RPCFSALEVD ETYVPKEFNA ETFTFHADIC  1020
TLSEKERQIK KQTALVELVK HKPKATKEQL KAVMDDFAAF VEKCCKADDK ETCFAEEGKK  1080
LVAASQAALG LHHHHHH                                                1097

SEQ ID NO: 239         moltype = AA  length = 1099
FEATURE                Location/Qualifiers
REGION                 1..1099
                       note = Synthetic peptide
source                 1..1099
                       mol_type = protein
                       organism = synthetic construct
SEQUENCE: 239
QVTLKESGPM LVKPTETLTL TCTVSGFSLS NSRMGVSWIR QPPGRALEWL AHIFSNDGKS  60
YSTSLKSRLT ISKDTSKSQV VLTMTNMDPV DTATYYCARY NYDSSGYYYS FFDYWGQGTL  120
VTVSSGGGGS GGGGSGGGGS DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ GYSSPFTFGG  240
GTKVEIKSGG GGSEVQLVES GGGLVQPGGS LKLSCAASGF TFNKYAMNWV RQAPGKGLEW  300
VARIRSKYNN YATYYADSVK DRFTISRDDS KNTAYLQMNN LKTEDTAVYY CVRHGNFGNS  360
YISYWAYWGQ GTLVTVSSGG GGSGGGGSGG GGSQTVVTQE PSLTVSPGGT VTLTCGSSTG  420
AVTSGNYPNW VQQKPGQAPR GLIGGTKFLA PGTPARFSGS LLGGKAALTL SGVQPEDEAE  480
YYCVLWYSNR WVFGGGTKLT VLPGGGGSDA HKSEVAHRFK DLGEENFKAL VLIAFAQYLQ  540
QCPFEDHVKL VNEVTEFAKT CVADESAENC DKSLHTLFGD KLCTVATLRE TYGEMADCCA  600
KQEPERNECF LQHKDDNPNL PRLVRPEVDV MCTAFHDNEE TFLKKYLYEI ARRHPYFYAP  660
ELLFFAKRYK AAFTECCQAA DKAACLLPKL DELRDEGKAS SAKQRLKCAS LQKFGERAFK  720
AWAVARLSQR FPKAEFAEVS KLVTDLTKVH TECCHGDLLE CADDRADLAK YICENQDSIS  780
SKLKECCEKP LLEKSHCIAE VENDEMPADL PSLAADFVES KDVCKNYAEA KDVFLGMFLY  840
EYARRHPDYS VVLLLRLAKT YETTLEKCCA AADPHECYAK VFDEFKPLVE EPQNLIKQNC  900
ELFEQLGEYK FQNALLVRYT KKVPQVSTPT LVEVSRNLGK VGSKCCKHPE AKRMPCAEDY  960
LSVVLNQLCV LHEKTPVSDR VTKCCTESLV NRRPCFSALE VDETYVPKEF NAETFTFHAD  1020
ICTLSEKERQ IKKQTALVEL VKHKPKATKE QLKAVMDDFA AFVEKCCKAD DKETCFAEEG  1080
KKLVAASQAA LGLHHHHHH                                              1099

SEQ ID NO: 240         moltype = AA  length = 1099
FEATURE                Location/Qualifiers
REGION                 1..1099
                       note = Synthetic peptide
source                 1..1099
                       mol_type = protein
                       organism = synthetic construct
SEQUENCE: 240
```

```
QVTLKESGPV LVKPTETLTL TCTVSGFSLS NARMGVSWLR QPPGKALEWL AHIFSTDEKS  60
YSTSLKSRLT ISKDTSKSQV VLTMTNMDPV DTATYYCARY YYDSSGYYYS FFDYWGQGTL  120
VTVSSGGGGS GGGGSGGGGS DIQMTQSPSS LSASVGDRVT ITCRASQSIR SYLNWYQQKP  180
GKAPKLLIYG ASNLQSGVPS RFSGSGSGTD FTLTISSLQP EDFATYYCQQ SYSSPFTFGG  240
GTKVEIKSGG GGSEVQLVES GGGLVQPGGS LKLSCAASGF TFNKYAMNWV RQAPGKGLEW  300
VARIRSKYNN YATYYADSVK DRFTISRDDS KNTAYLQMNN LKTEDTAVYY CVRHGNFGNS  360
YISYWAYWGQ GTLVTVSSGG GGSGGGGSGG GGSQTVVTQE PSLTVSPGGT VTLTCGSSTG  420
AVTSGNYPNW VQQKPGQAPR GLIGGTKFLA PGTPARFSGS LLGGKAALTL SGVQPEDEAE  480
YYCVLWYSNR WVFGGGTKLT VLPGGGGSDA HKSEVAHRFK DLGEENFKAL VLIAFAQYLQ  540
QCPFEDHVKL VNEVTEFAKT CVADESAENC DKSLHTLFGD KLCTVATLRE TYGEMADCCA  600
KQEPERNECF LQHKDDNPNL PRLVRPEVDV MCTAFHDNEE TFLKKYLYEI ARRHPYFYAP  660
ELLFFAKRYK AAFTECCQAA DKAACLLPKL DELRDEGKAS SAKQRLKCAS LQKFGERAFK  720
AWAVARLSQR FPKAEFAEVS KLVTDLTKVH TECCHGDLLE CADDRADLAK YICENQDSIS  780
SKLKECCEKP LLEKSHCIAE VENDEMPADL PSLAADFVES KDVCKNYAEA KDVFLGMFLY  840
EYARRHPDYS VVLLLRLAKT YETTLEKCCA AADPHECYAK VFDEFKPLVE EPQNLIKQNC  900
ELFEQLGEYK FQNALLVRYT KKVPQVSTPT LVEVSRNLGK VGSKCCKHPE AKRMPCAEDY  960
LSVVLNQLCV LHEKTPVSDR VTKCCTESLV NRRPCFSALE VDETYVPKEF NAETFTFHAD  1020
ICTLSEKERQ IKKQTALVEL VKHKPKATKE QLKAVMDDFA AFVEKCCKAD DKETCFAEEG  1080
KKLVAASQAA LGLHHHHHH                                              1099

SEQ ID NO: 241          moltype = AA  length = 1095
FEATURE                 Location/Qualifiers
REGION                  1..1095
                        note = Synthetic peptide
source                  1..1095
                        mol_type = protein
                        organism = synthetic construct
SEQUENCE: 241
QVQLVQSGAE VKKPGASVKV SCKASGYAFT SYYIHWVRQA PGQGLEWMGI INPSGGSKSY  60
AQKFRGRVTM TRDTSTSTVY MELSSLTSED TAVYYCARSM STVTSDAFDI WGQGTMVTVS  120
SGGGGSGGGG SGGGGSDIQM TQSPSSLSAS VGDRVTITCR ASQSISNYLN WYQQKPGKAP  180
KLLIYAASSL QSGVPSRFSG SGSGTEFTLT ISSLQPEDFA TYYCQQSYSA PLTFGGGTKV  240
DIKSGGGGSE VQLVESGGGL VQPGGSLKLS CAASGFTFNK YAMNWVRQAP GKGLEWVARI  300
RSKYNNYATY YADSVKDRFT ISRDDSKNTA YLQMNNLKTE DTAVYYCVRH GNFGNSYISY  360
WAYWGQGTLV TVSSGGGGSG GGGSGGGGSQ TVVTQEPSLT VSPGGTVTLT CGSSTGAVTS  420
GNYPNWVQQK PGQAPRGLIG GTKFLAPGTP ARFSGSLLGG KAALTLSGVQ PEDEAEYYCV  480
LWYSNRWVFG GGTKLTVLPG GGGSDAHKSE VAHRFKDLGE ENFKALVLIA FAQYLQQCPF  540
EDHVKLVNEV TEFAKTCVAD ESAENCDKSL HTLFGDKLCT VATLRETYGE MADCCAKQEP  600
ERNECFLQHK DDNPNLPRLV RPEVDVMCTA FHDNEETFLK KYLYEIARRH PYFYAPELLF  660
FAKRYKAAFT ECCQAADKAA CLLPKLDELR DEGKASSAKQ RLKCASLQKF GERAFKAWAV  720
ARLSQRFPKA EFAEVSKLVT DLTKVHTECC HGDLLECADD RADLAKYICE NQDSISSKLK  780
ECCEKPLLEK SHCIAEVEND EMPADLPSLA ADFVESKDVC KNYAEAKDVF LGMFLYEYAR  840
RHPDYSVVLL LRLAKTYETT LEKCCAAADP HECYAKVFDE FKPLVEEPQN LIKQNCELFE  900
QLGEYKFQNA LLVRYTKKVP QVSTPTLVEV SRNLGKVGSK CCKHPEAKRM PCAEDYLSVV  960
LNQLCVLHEK TPVSDRVTKC CTESLVNRRP CFSALEVDET YVPKEFNAET FTFHADICTL  1020
SEKERQIKKQ TALVELVKHK PKATKEQLKA VMDDFAAFVE KCCKADDKET CFAEEGKKLV  1080
AASQAALGLH HHHHH                                                  1095

SEQ ID NO: 242          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 242
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                    1093

SEQ ID NO: 243          moltype = AA  length = 1093
FEATURE                 Location/Qualifiers
REGION                  1..1093
```

```
                        note = Synthetic peptide
source                  1..1093
                        mol_type = protein
                        organism = synthetic construct
SEQUENCE: 243
QVQLQESGPG LVKPSETLSL TCTVSGGSIS SYYWSWIRQP PGKGLEWIGY IYYSGRTNYY  60
PSLKSRVTIS IDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                    1093

SEQ ID NO: 244          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 244
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                    1093

SEQ ID NO: 245          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 245
QVQLQESGPG LVKPSQTLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
```

```
SQAALGLHHH HHH                                                  1093

SEQ ID NO: 246          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 246
QVQLQEWGPG LVKPSETLSL TCTVSGASIS SFYWSWIRQP PGKGLEWIGY IYYSGTTNYN  60
PSLKSRVTIS VDTSKNQLSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVDI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                  1093

SEQ ID NO: 247          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 247
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE SATLSCRASQ SVNKNYLAWY QQKPGQAPRL  180
LIYGASSRAT GIPDRFSGSG SGTDFTLTIS RLEPEDFAVY YCQQYDRSPL TFGGGTRLEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                  1093

SEQ ID NO: 248          moltype = AA  length = 1093
FEATURE                 Location/Qualifiers
REGION                  1..1093
                        note = Synthetic peptide
source                  1..1093
                        mol_type = protein
                        organism = synthetic construct
SEQUENCE: 248
QVQLQESGPG LVKPSQTLSL TCTVSGGSIS SYYWSWIRQP PGKGLEWIGY IFYNGITNYN  60
PSLKSRVTIS LDTSKNQFSL KLSSVTAADT AKYYCARIHS GSFSFDYWDQ GTLVTVSSGG  120
GGSGGGGSGG GGSEIVMTQS PGTLSLSPGE RATLSCRASQ SVSRGYLAWY QQKPGQAPRL  180
LIYGASSRAT DIPDRFSGSG SGTDFTLTIS RLEPEDFAVY YCQQYDTSPI TFGQGTKVEI  240
KSGGGGSEVQ LVESGGGLVQ PGGSLRLSCA ASGFTFNSYA MNWVRQAPGK GLEWVARIRS  300
KYNNYATYYA DSVKGRFTIS RDDSKNTAYL QMNSLKTEDT AVYYCVRHGN FGNSYVSWWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLPGGG GSDAHKSEVA HRFKDLGEEN FKALVLIAFA QYLQQCPFED  540
HVKLVNEVTE FAKTCVADES AENCDKSLHT LFGDKLCTVA TLRETYGEMA DCCAKQEPER  600
NECFLQHKDD NPNLPRLVRP EVDVMCTAFH DNEETFLKKY LYEIARRHPY FYAPELLFFA  660
KRYKAAFTEC CQAADKAACL LPKLDELRDE GKASSAKQRL KCASLQKFGE RAFKAWAVAR  720
LSQRFPKAEF AEVSKLVTDL TKVHTECCHG DLLECADDRA DLAKYICENQ DSISSKLKEC  780
```

```
CEKPLLEKSH CIAEVENDEM PADLPSLAAD FVESKDVCKN YAEAKDVFLG MFLYEYARRH  840
PDYSVVLLLR LAKTYETTLE KCCAAADPHE CYAKVFDEFK PLVEEPQNLI KQNCELFEQL  900
GEYKFQNALL VRYTKKVPQV STPTLVEVSR NLGKVGSKCC KHPEAKRMPC AEDYLSVVLN  960
QLCVLHEKTP VSDRVTKCCT ESLVNRRPCF SALEVDETYV PKEFNAETFT FHADICTLSE  1020
KERQIKKQTA LVELVKHKPK ATKEQLKAVM DDFAAFVEKC CKADDKETCF AEEGKKLVAA  1080
SQAALGLHHH HHH                                                    1093

SEQ ID NO: 249          moltype = AA  length = 1102
FEATURE                 Location/Qualifiers
REGION                  1..1102
                        note = Synthetic peptide
source                  1..1102
                        mol_type = protein
                        organism = synthetic construct
SEQUENCE: 249
QVQLVQSGAE VKKPGASVKV SCKASGYTFT SYYMHWVRQA PGQGLEWMGI INPSDGSTNY  60
AQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLVYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLRLSCAA SGFTFNSYAM NWVRQAPGKG  300
LEWVARIRSK YNNYATYYAD SVKGRFTISR DDSKNTAYLQ MNSLKTEDTA VYYCVRHGNF  360
GNSYVSWWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 250          moltype = AA  length = 1102
FEATURE                 Location/Qualifiers
REGION                  1..1102
                        note = Synthetic peptide
source                  1..1102
                        mol_type = protein
                        organism = synthetic construct
SEQUENCE: 250
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLRLSCAA SGFTFNSYAM NWVRQAPGKG  300
LEWVARIRSK YNNYATYYAD SVKGRFTISR DDSKNTAYLQ MNSLKTEDTA VYYCVRHGNF  360
GNSYVSWWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 251          moltype = AA  length = 1102
FEATURE                 Location/Qualifiers
source                  1..1102
                        mol_type = protein
                        organism = Homo sapiens
SEQUENCE: 251
QVQLVQSGAE VKKPGASVKV SCKASGYTFT GYYIHWVRQA PGQGLEWMGI INPSDGSTSY  60
GQNFQGRVTM TRDTSTNTVY MELSSLRSED TAVYYCARGG NSAFYSYYDM DVWGQGTTVT  120
VSSGGGGSGG GGSGGGGSDV VMTQSPLSLP VTLGQPASIS CRSSQSLAYR DGNTYLSWFQ  180
QRPGQSPRRL IYKVSNWQSG VPDRFSGSGS GTDFTLKISR VEAEDVGVYF CMQGTHWPPT  240
FGQGTKVEIK SGGGGSEVQL VESGGGLVQP GGSLRLSCAA SGFTFNSYAM NWVRQAPGKG  300
LEWVARIRSK YNNYATYYAD SVKGRFTISR DDSKNTAYLQ MNSLKTEDTA VYYCVRHGNF  360
GNSYVSWWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLPGGGG SDAHKSEVAH RFKDLGEENF KALVLIAFAQ  540
YLQQCPFEDH VKLVNEVTEF AKTCVADESA ENCDKSLHTL FGDKLCTVAT LRETYGEMAD  600
```

```
CCAKQEPERN ECFLQHKDDN PNLPRLVRPE VDVMCTAFHD NEETFLKKYL YEIARRHPYF  660
YAPELLFFAK RYKAAFTECC QAADKAACLL PKLDELRDEG KASSAKQRLK CASLQKFGER  720
AFKAWAVARL SQRFPKAEFA EVSKLVTDLT KVHTECCHGD LLECADDRAD LAKYICENQD  780
SISSKLKECC EKPLLEKSHC IAEVENDEMP ADLPSLAADF VESKDVCKNY AEAKDVFLGM  840
FLYEYARRHP DYSVVLLLRL AKTYETTLEK CCAAADPHEC YAKVFDEFKP LVEEPQNLIK  900
QNCELFEQLG EYKFQNALLV RYTKKVPQVS TPTLVEVSRN LGKVGSKCCK HPEAKRMPCA  960
EDYLSVVLNQ LCVLHEKTPV SDRVTKCCTE SLVNRRPCFS ALEVDETYVP KEFNAETFTF  1020
HADICTLSEK ERQIKKQTAL VELVKHKPKA TKEQLKAVMD DFAAFVEKCC KADDKETCFA  1080
EEGKKLVAAS QAALGLHHHH HH                                          1102

SEQ ID NO: 252          moltype = AA  length = 618
FEATURE                 Location/Qualifiers
source                  1..618
                        mol_type = protein
                        organism = Homo sapiens
SEQUENCE: 252
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYRARCEP  180
PAVGTACTRL CRPRSAPSRC GPGLRPCAPL EDECEAPLVC RAGCSPEHGF CEQPGECRCL  240
EGWTGPLCTV PVSTSSCLSP RGPSSATTGC LVPGPGPCDG NPCANGGSCS ETPRSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH DLDDCAGRAC ANGGTCVEGG GAHRCSCALG  420
FGGRDCRERA DPCAARPCAH GGRCYAHFSG LVCACAPGYM GARCEFPVHP DGASALPAAP  480
PGLRPGDPQR YLLPPALGLL VAAGVAGAAL LLVHVRRRGH SQDAGSRLLA GTPEPSVHAL  540
PDALNNLRTQ EGSGDGPSSS VDWNRPEDVD PQGIYVISAP SIYAREVATP LFPPLHTGRA  600
GQRQHLLFPY PSSILSVK                                               618

SEQ ID NO: 253          moltype = AA  length = 492
FEATURE                 Location/Qualifiers
source                  1..492
                        mol_type = protein
                        organism = Homo sapiens
SEQUENCE: 253
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYRARCEP  180
PAVGTACTRL CRPRSAPSRC GPGLRPCAPL EDECEAPLVC RAGCSPEHGF CEQPGECRCL  240
EGWTGPLCTV PVSTSSCLSP RGPSSATTGC LVPGPGPCDG NPCANGGSCS ETPRSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH DLDDCAGRAC ANGGTCVEGG GAHRCSCALG  420
FGGRDCRERA DPCAARPCAH GGRCYAHFSG LVCACAPGYM GARCEFPVHP DGASALPAAP  480
PGLRPGDPQR YL                                                     492

SEQ ID NO: 254          moltype = AA  length = 175
FEATURE                 Location/Qualifiers
source                  1..175
                        mol_type = protein
                        organism = Homo sapiens
SEQUENCE: 254
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYR       175

SEQ ID NO: 255          moltype = AA  length = 40
FEATURE                 Location/Qualifiers
source                  1..40
                        mol_type = protein
                        organism = Homo sapiens
SEQUENCE: 255
ARCEPPAVGT ACTRLCRPRS APSRCGPGLR PCAPLEDECE                       40

SEQ ID NO: 256          moltype = AA  length = 34
FEATURE                 Location/Qualifiers
source                  1..34
                        mol_type = protein
                        organism = Homo sapiens
SEQUENCE: 256
APLVCRAGCS PEHGFCEQPG ECRCLEGWTG PLCT                             34

SEQ ID NO: 257          moltype = AA  length = 37
FEATURE                 Location/Qualifiers
source                  1..37
                        mol_type = protein
                        organism = Homo sapiens
SEQUENCE: 257
GPGPCDGNPC ANGGSCSETP RSFECTCPRG FYGLRCE                          37

SEQ ID NO: 258          moltype = AA  length = 40
```

```
FEATURE                Location/Qualifiers
source                 1..40
                       mol_type = protein
                       organism = Homo sapiens
SEQUENCE: 258
SGVTCADGPC FNGGLCVGGA DPDSAYICHC PPGFQGSNCE                        40

SEQ ID NO: 259         moltype = AA  length = 37
FEATURE                Location/Qualifiers
source                 1..37
                       mol_type = protein
                       organism = Homo sapiens
SEQUENCE: 259
RVDRCSLQPC RNGGLCLDLG HALRCRCRAG FAGPRCE                           37

SEQ ID NO: 260         moltype = AA  length = 78
FEATURE                Location/Qualifiers
source                 1..78
                       mol_type = protein
                       organism = Homo sapiens
SEQUENCE: 260
SGVTCADGPC FNGGLCVGGA DPDSAYICHC PPGFQGSNCE KRVDRCSLQP CRNGGLCLDL  60
GHALRCRCRA GFAGPRCE                                                78

SEQ ID NO: 261         moltype = AA  length = 37
FEATURE                Location/Qualifiers
source                 1..37
                       mol_type = protein
                       organism = Homo sapiens
SEQUENCE: 261
DLDDCAGRAC ANGGTCVEGG GAHRCSCALG FGGRDCR                           37

SEQ ID NO: 262         moltype = AA  length = 37
FEATURE                Location/Qualifiers
source                 1..37
                       mol_type = protein
                       organism = Homo sapiens
SEQUENCE: 262
RADPCAARPC AHGGRCYAHF SGLVCACAPG YMGARCE                           37

SEQ ID NO: 263         moltype = AA  length = 548
FEATURE                Location/Qualifiers
REGION                 1..548
                       note = Synthetic peptide
source                 1..548
                       mol_type = protein
                       organism = synthetic construct
SEQUENCE: 263
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYRARCEP  180
PAVGTACTRL CRPRSAPSRC GPGLRPCAPL EDECEAPLVC RAGCSPEHGF CEQPGECRCL  240
EGWTGPLCTV PVSTSSCLSP RGPSSATTGC LVPGPGPCDG NPCANGGSCS ETPRSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH DLDDCAGRAC ANGGTCVEGG GAHRCSCALG  420
FGGRDCRERA DPCAARPCAH GGRCYAHFSG LVCACAPGYM GARCEFPVHP DGASALPAAP  480
PGLRPGDPQR YLSGGGGSGA GVIAVIVVVV IAIVAGIVVL VISRKKRMAK YEKAEIKEMG  540
EMHRELNA                                                           548

SEQ ID NO: 264         moltype = AA  length = 408
FEATURE                Location/Qualifiers
REGION                 1..408
                       note = Synthetic peptide
source                 1..408
                       mol_type = protein
                       organism = synthetic construct
SEQUENCE: 264
MGWSCIILFL VATATGVHSG KPIPNPLLGL DSTSGARCEP PAVGTACTRL CRPRSAPSRC  60
GPGLRPCAPL EDECEAPLVC RAGCSPEHGF CEQPGECRCL EGWTGPLCTV PVSTSSCLSP  120
RGPSSATTGC LVPGPGPCDG NPCANGGSCS ETPRSFECTC PRGFYGLRCE VSGVTCADGP  180
CFNGGLCVGG ADPDSAYICH CPPGFQGSNC EKRVDRCSLQ PCRNGGLCLD LGHALRCRCR  240
AGFAGPRCEH DLDDCAGRAC ANGGTCVEGG GAHRCSCALG FGGRDCRERA DPCAARPCAH  300
GGRCYAHFSG LVCACAPGYM GARCEFPVHP DGASALPAAP PGLRPGDPQR YLSGGGGSGA  360
GVIAVIVVVV IAIVAGIVVL VISRKKRMAK YEKAEIKEMG EMHRELNA               408

SEQ ID NO: 265         moltype = AA  length = 368
FEATURE                Location/Qualifiers
REGION                 1..368
                       note = Synthetic peptide
```

```
source                1..368
                      mol_type = protein
                      organism = synthetic construct
SEQUENCE: 265
MGWSCIILFL VATATGVHSG KPIPNPLLGL DSTSGAPLVC RAGCSPEHGF CEQPGECRCL  60
EGWTGPLCTV PVSTSSCLSP RGPSSATTGC LVPGPGPCDG NPCANGGSCS ETPRSFECTC  120
PRGFYGLRCE VSGVTCADGP CFNGGLCVGG ADPDSAYICH CPPGFQGSNC EKRVDRCSLQ  180
PCRNGGLCLD LGHALRCRCR AGFAGPRCEH DLDDCAGRAC ANGGTCVEGG GAHRCSCALG  240
FGGRDCRERA DPCAARPCAH GGRCYAHFSG LVCACAPGYM GARCEFPVHP DGASALPAAP  300
PGLRPGDPQR YLSGGGGSGA GVIAVIVVVV IAIVAGIVVL VISRKKRMAK YEKAEIKEMG  360
EMHRELNA                                                          368

SEQ ID NO: 266        moltype = AA  length = 310
FEATURE               Location/Qualifiers
REGION                1..310
                      note = Synthetic peptide
source                1..310
                      mol_type = protein
                      organism = synthetic construct
SEQUENCE: 266
MGWSCIILFL VATATGVHSG KPIPNPLLGL DSTSGGPGPC DGNPCANGGS CSETPRSFEC  60
TCPRGFYGLR CEVSGVTCAD GPCFNGGLCV GGADPDSAYI CHCPPGFQGS NCEKRVDRCS  120
LQPCRNGGLC LDLGHALRCR CRAGFAGPRC EHDLDDCAGR ACANGGTCVE GGGAHRCSCA  180
LGFGGRDCRE RADPCAARPC AHGGRCYAHF SGLVCACAPG YMGARCEFPV HPDGASALPA  240
APPGLRPGDP QRYLSGGGGS GAGVIAVIVV VVIAIVAGIV VLVISRKKRM AKYEKAEIKE  300
MGEMHRELNA                                                        310

SEQ ID NO: 267        moltype = AA  length = 272
FEATURE               Location/Qualifiers
REGION                1..272
                      note = Synthetic peptide
source                1..272
                      mol_type = protein
                      organism = synthetic construct
SEQUENCE: 267
MGWSCIILFL VATATGVHSG KPIPNPLLGL DSTSGSGVTC ADGPCFNGGL CVGGADPDSA  60
YICHCPPGFQ GSNCEKRVDR CSLQPCRNGG LCLDLGHALR CRCRAGFAGP RCEHDLDDCA  120
GRACANGGTC VEGGGAHRCS CALGFGGRDC RERADPCAAR PCAHGGRCYA HFSGLVCACA  180
PGYMGARCEF PVHPDGASAL PAAPPGLRPG DPQRYLSGGG GSGAGVIAVI VVVVIAIVAG  240
IVVLVISRKK RMAKYEKAEI KEMGEMHREL NA                               272

SEQ ID NO: 268        moltype = AA  length = 231
FEATURE               Location/Qualifiers
REGION                1..231
                      note = Synthetic peptide
source                1..231
                      mol_type = protein
                      organism = synthetic construct
SEQUENCE: 268
MGWSCIILFL VATATGVHSG KPIPNPLLGL DSTSGRVDRC SLQPCRNGGL CLDLGHALRC  60
RCRAGFAGPR CEHDLDDCAG RACANGGTCV EGGGAHRCSC ALGFGGRDCR ERADPCAARP  120
CAHGGRCYAH FSGLVCACAP GYMGARCEFP VHPDGASALP AAPPGLRPGD PQRYLSGGGG  180
SGAGVIAVIV VVVIAIVAGI VVLVISRKKR MAKYEKAEIK EMGEMHRELN A          231

SEQ ID NO: 269        moltype = AA  length = 193
FEATURE               Location/Qualifiers
REGION                1..193
                      note = Synthetic peptide
source                1..193
                      mol_type = protein
                      organism = synthetic construct
SEQUENCE: 269
MGWSCIILFL VATATGVHSG KPIPNPLLGL DSTSGDLDDC AGRACANGGT CVEGGGAHRC  60
SCALGFGGRD CRERADPCAA RPCAHGGRCY AHFSGLVCAC APGYMGARCE FPVHPDGASA  120
LPAAPPGLRP GDPQRYLSGG GGSGAGVIAV IVVVVIAIVA GIVVLVISRK KRMAKYEKAE  180
IKEMGEMHRE LNA                                                    193

SEQ ID NO: 270        moltype = AA  length = 155
FEATURE               Location/Qualifiers
REGION                1..155
                      note = Synthetic peptide
source                1..155
                      mol_type = protein
                      organism = synthetic construct
SEQUENCE: 270
MGWSCIILFL VATATGVHSG KPIPNPLLGL DSTSGRADPC AARPCAHGGR CYAHFSGLVC  60
ACAPGYMGAR CEFPVHPDGA SALPAAPPGL RPGDPQRYLS GGGGSGAGVI AVIVVVVIAI  120
VAGIVVLVIS RKKRMAKYEK AEIKEMGEMH RELNA                            155
```

```
SEQ ID NO: 271         moltype = AA  length = 587
FEATURE                Location/Qualifiers
source                 1..587
                       mol_type = protein
                       organism = Macaca fascicularis
SEQUENCE: 271
MVSPRMSRLL SQTVILALIF IPQARPAGVF ELQIHSFGPG PGPGAPRSPC SARGPCRLFF  60
RVCLKPGLSE EAAESPCALG AALSARGPVY TEQPEAPAPD LPLPNGLLQV PFRDAWPGTF  120
SLIIETWREE LGDQIGGPAW SLLARVTRRR RLAAGGPWAR DIQRAGAWEL RFSYRARCEL  180
PAVGTACTRL CRPRSAPSRC GPGLRPCAPL EDECEAPPVC RAGCSLEHGF CEQPGECRCL  240
EGWTGPLCMV PASTSSCLGL RGPSSATTGC LVPGPGPCDG NPCANGGSCS ETPGSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH NLDDCAGRAC ANGGTCVEGG GAHRCSCALG  420
FGGRDCRERA DPCAARPCAH GGRCYAHFSG LVCACAPGYM GSRCEFPVHP DGVSALPAAP  480
PGLRPGDPQR YLLPPALGLL VAAGVAGAAL LLVHVRRRGH AQDAGSRLLA GTPEPSVHAL  540
PDALNNQRTQ EGPGDVPSSS VDWNRPEDVD SRGIYVISAP SIYAREA                587

SEQ ID NO: 272         moltype = AA  length = 492
FEATURE                Location/Qualifiers
source                 1..492
                       mol_type = protein
                       organism = Macaca fascicularis
SEQUENCE: 272
MVSPRMSRLL SQTVILALIF IPQARPAGVF ELQIHSFGPG PGPGAPRSPC SARGPCRLFF  60
RVCLKPGLSE EAAESPCALG AALSARGPVY TEQPEAPAPD LPLPNGLLQV PFRDAWPGTF  120
SLIIETWREE LGDQIGGPAW SLLARVTRRR RLAAGGPWAR DIQRAGAWEL RFSYRARCEL  180
PAVGTACTRL CRPRSAPSRC GPGLRPCAPL EDECEAPPVC RAGCSLEHGF CEQPGECRCL  240
EGWTGPLCMV PASTSSCLGL RGPSSATTGC LVPGPGPCDG NPCANGGSCS ETPGSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH NLDDCAGRAC ANGGTCVEGG GAHRCSCALG  420
FGGRDCRERA DPCAARPCAH GGRCYAHFSG LVCACAPGYM GSRCEFPVHP DGVSALPAAP  480
PGLRPGDPQR YL                                                      492

SEQ ID NO: 273         moltype = AA  length = 175
FEATURE                Location/Qualifiers
source                 1..175
                       mol_type = protein
                       organism = Macaca fascicularis
SEQUENCE: 273
MVSPRMSRLL SQTVILALIF IPQARPAGVF ELQIHSFGPG PGPGAPRSPC SARGPCRLFF  60
RVCLKPGLSE EAAESPCALG AALSARGPVY TEQPEAPAPD LPLPNGLLQV PFRDAWPGTF  120
SLIIETWREE LGDQIGGPAW SLLARVTRRR RLAAGGPWAR DIQRAGAWEL RFSYR       175

SEQ ID NO: 274         moltype = AA  length = 40
FEATURE                Location/Qualifiers
source                 1..40
                       mol_type = protein
                       organism = Macaca fascicularis
SEQUENCE: 274
ARCELPAVGT ACTRLCRPRS APSRCGPGLR PCAPLEDECE                        40

SEQ ID NO: 275         moltype = AA  length = 34
FEATURE                Location/Qualifiers
source                 1..34
                       mol_type = protein
                       organism = Macaca fascicularis
SEQUENCE: 275
APPVCRAGCS LEHGFCEQPG ECRCLEGWTG PLCM                              34

SEQ ID NO: 276         moltype = AA  length = 37
FEATURE                Location/Qualifiers
source                 1..37
                       mol_type = protein
                       organism = Macaca fascicularis
SEQUENCE: 276
GPGPCDGNPC ANGGSCSETP GSFECTCPRG FYGLRCE                           37

SEQ ID NO: 277         moltype = AA  length = 40
FEATURE                Location/Qualifiers
source                 1..40
                       mol_type = protein
                       organism = Macaca fascicularis
SEQUENCE: 277
SGVTCADGPC FNGGLCVGGA DPDSAYICHC PPGFQGSNCE                        40

SEQ ID NO: 278         moltype = AA  length = 37
FEATURE                Location/Qualifiers
source                 1..37
                       mol_type = protein
```

```
                        organism = Macaca fascicularis
SEQUENCE: 278
RVDRCSLQPC RNGGLCLDLG HALRCRCRAG FAGPRCE                     37

SEQ ID NO: 279          moltype = AA  length = 78
FEATURE                 Location/Qualifiers
source                  1..78
                        mol_type = protein
                        organism = Macaca fascicularis
SEQUENCE: 279
SGVTCADGPC FNGGLCVGGA DPDSAYICHC PPGFQGSNCE KRVDRCSLQP CRNGGLCLDL  60
GHALRCRCRA GFAGPRCE                                                 78

SEQ ID NO: 280          moltype = AA  length = 37
FEATURE                 Location/Qualifiers
source                  1..37
                        mol_type = protein
                        organism = Macaca fascicularis
SEQUENCE: 280
NLDDCAGRAC ANGGTCVEGG GAHRCSCALG FGGRDCR                     37

SEQ ID NO: 281          moltype = AA  length = 37
FEATURE                 Location/Qualifiers
source                  1..37
                        mol_type = protein
                        organism = Macaca fascicularis
SEQUENCE: 281
RADPCAARPC AHGGRCYAHF SGLVCACAPG YMGSRCE                     37

SEQ ID NO: 282          moltype = AA  length = 548
FEATURE                 Location/Qualifiers
REGION                  1..548
                        note = Synthetic peptide
source                  1..548
                        mol_type = protein
                        organism = synthetic construct
SEQUENCE: 282
MVSPRMSRLL SQTVILALIF IPQARPAGVF ELQIHSFGPG PGPGAPRSPC SARGPCRLFF  60
RVCLKPGLSE EAAESPCALG AALSARGPVY TEQPEAPAPD LPLPNGLLQV PFRDAWPGTF  120
SLIIETWREE LGDQIGGPAW SLLARVTRRR RLAAGGPWAR DIQRAGAWEL RFSYRARCEL  180
PAVGTACTRL CRPRSAPSRC GPGLRPCAPL EDECEAPPVC RAGCSLEHGF CEQPGECRCL  240
EGWTGPLCMV PASTSSCLGL RGPSSATTGC LVPGPGPCDG NPCANGGSCS ETPGSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH NLDDCAGRAC ANGGTCVEGG GAHRCSCALG  420
FGGRDCRERA DPCAARPCAH GGRCYAHFSG LVCACAPGYM GSRCEFPVHP DGVSALPAAP  480
PGLRPGDPQR YLSGGGGSGA GVIAVIVVVV IAIVAGIVVL VISRKKRMAK YEKAEIKEMG  540
EMHRELNA                                                            548

SEQ ID NO: 283          moltype = AA  length = 723
FEATURE                 Location/Qualifiers
source                  1..723
                        mol_type = protein
                        organism = Homo sapiens
SEQUENCE: 283
MGSRCALALA VLSALLCQVW SSGVFELKLQ EFVNKKGLLG NRNCCRGGAG PPPCACRTFF  60
RVCLKHYQAS VSPEPPCTYG SAVTPVLGVD SFSLPDGGGA DSAFSNPIRF PFGFTWPGTF  120
SLIIEALHTD SPDDLATENP ERLISRLATQ RHLTVGEEWS QDLHSSGRTD LKYSYRFVCD  180
EHYYGEGCSV FCRPRDDAFG HFTCGERGEK VCNPGWKGPY CTEPICLPGC DEQHGFCDKP  240
GECKCRVGWQ GRYCDECIRY PGCLHGTCQQ PWQCNCQEGW GGLFCNQDLN YCTHHKPCKN  300
GATCTNTGQG SYTCSCRPGY TGATCELGID ECDPSPCKNG GSCTDLENSY SCTCPPGFYG  360
KICELSAMTC ADGPCFNGGR CSDSPDGGYS CRCPVGYSGF NCEKKIDYCS SSPCSNGAKC  420
VDLGDAYLCR CQAGFSGRHC DDNVDDCASS PCANGGTCRD GVNDFSCTCP PGYTGRNCSA  480
PVSRCEHAPC HNGATCHERG HRYVCECARG YGGPNCQFLL PELPPGPAVV DLTEKLEGQG  540
GPFPWVAVCA GVILVLMLLL GCAAVVVCVR LRLQKHRPPA DPCRGETETM NNLANCQREK  600
DISVSIIGAT QIKNTNKKAD FHGDHSADKN GFKARYPAVD YNLVQDLKGD DTAVRDAHSK  660
RDTKCQPQGS SGEEKGTPTT LRGGEASERK RPDSGCSTSK DTKYQSVYVI SEEKDECVIA  720
TEV                                                                 723

SEQ ID NO: 284          moltype = AA  length = 685
FEATURE                 Location/Qualifiers
source                  1..685
                        mol_type = protein
                        organism = Homo sapiens
SEQUENCE: 284
MAAASRSASG WALLLLVALW QQRAAGSGVF QLQLQEFINE RGVLASGRPC EPGCRTFFRV  60
CLKHFQAVVS PGPCTFGTVS TPVLGTNSFA VRDDSSGGGR NPLQLPFNFT WPGTFSLIIE  120
AWHAPGDDLR PEALPPDALI SKIAIQGSLA VGQNWLLDEQ TSTLTRLRYS YRVICSDNYY  180
GDNCSRLCKK RNDHFGHYVC QPDGNLSCLP GWTGEYCQQP ICLSGCHEQN GYCSKPAECL  240
CRPGWQGRLC NECIPHNGCR HGTCSTPWQC TCDEGWGGLF CDQDLNYCTH HSPCKNGATC  300
```

```
SNSGQRSYTC TCRPGYTGVD CELELSECDS NPCRNGGSCK DQEDGYHCLC PPGYYGLHCE  360
HSTLSCADSP CFNGGSCRER NQGANYACEC PPNFTGSNCE KKVDRCTSNP CANGGQCLNR  420
GPSRMCRCRP GFTGTYCELH VSDCARNPCA HGGTCHDLEN GLMCTCPAGF SGRRCEVRTS  480
IDACASSPCF NRATCYTDLS TDTFVCNCPY GFVGSRCEFP VGLPPSFPWV AVSLGVGLAV  540
LLVLLGMVAV AVRQLRLRRP DDGSREAMNN LSDFQKDNLI PAAQLKNTNQ KKELEVDCGL  600
DKSNCGKQQN HTLDYNLAPG PLGRGTMPGK FPHSDKSLGE KAPLRLHSEK PECRISAICS  660
PRDSMYQSVC LISEERNECV IATEV                                        685

SEQ ID NO: 285          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 285
GGGG                                                               4

SEQ ID NO: 286          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 286
GGGGS                                                              5

SEQ ID NO: 287          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 287
GGGGQ                                                              5

SEQ ID NO: 288          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 288
SGGGGS                                                             6

SEQ ID NO: 289          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 289
PGGGGS                                                             6

SEQ ID NO: 290          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 290
PGGDGS                                                             6

SEQ ID NO: 291          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 291
GGGGSGGGS                                                          9

SEQ ID NO: 292          moltype = AA  length = 10
```

```
FEATURE                Location/Qualifiers
REGION                 1..10
                       note = Synthetic peptide
source                 1..10
                       mol_type = protein
                       organism = synthetic construct
SEQUENCE: 292
GGGGSGGGGS                                                                 10

SEQ ID NO: 293         moltype = AA  length = 15
FEATURE                Location/Qualifiers
REGION                 1..15
                       note = Synthetic peptide
source                 1..15
                       mol_type = protein
                       organism = synthetic construct
SEQUENCE: 293
GGGGSGGGGS GGGGS                                                           15

SEQ ID NO: 294         moltype = AA  length = 6
FEATURE                Location/Qualifiers
REGION                 1..6
                       note = Synthetic peptide
source                 1..6
                       mol_type = protein
                       organism = synthetic construct
SEQUENCE: 294
HHHHHH                                                                     6

SEQ ID NO: 295         moltype = AA  length = 16
FEATURE                Location/Qualifiers
REGION                 1..16
                       note = Synthetic peptide
source                 1..16
                       mol_type = protein
                       organism = synthetic construct
SEQUENCE: 295
RDWDFDVFGG GTPVGG                                                          16

SEQ ID NO: 296         moltype = AA  length = 16
FEATURE                Location/Qualifiers
REGION                 1..16
                       note = Synthetic peptide
SITE                   12
                       note = misc_feature - Xaa can be any naturally occurring
                        amino acid
source                 1..16
                       mol_type = protein
                       organism = synthetic construct
SEQUENCE: 296
QRFVTGHFGG LXPANG                                                          16

SEQ ID NO: 297         moltype = AA  length = 16
FEATURE                Location/Qualifiers
REGION                 1..16
                       note = Synthetic peptide
source                 1..16
                       mol_type = protein
                       organism = synthetic construct
SEQUENCE: 297
QRFVTGHFGG LYPANG                                                          16

SEQ ID NO: 298         moltype = AA  length = 16
FEATURE                Location/Qualifiers
REGION                 1..16
                       note = Synthetic peptide
source                 1..16
                       mol_type = protein
                       organism = synthetic construct
SEQUENCE: 298
QRFVTGHFGG LHPANG                                                          16

SEQ ID NO: 299         moltype = AA  length = 9
FEATURE                Location/Qualifiers
REGION                 1..9
                       note = Synthetic peptide
source                 1..9
                       mol_type = protein
                       organism = synthetic construct
```

```
SEQUENCE: 299
TGHFGGLHP                                                        9

SEQ ID NO: 300          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 300
QRFCTGHFGG LHPCNG                                                16

SEQ ID NO: 301          moltype = AA  length = 585
FEATURE                 Location/Qualifiers
source                  1..585
                        mol_type = protein
                        organism = Homo sapiens
SEQUENCE: 301
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 302          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 302
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAGTFTFH ADICTLSEKE RQIKKQTALV ELVKHKPKAT  540
KEQLKAAMDD FAAFVEKCCK ADDKETCFAE EGKKLVAASQ AALGL                  585

SEQ ID NO: 303          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 303
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGPKLVAASQ AALGL                  585

SEQ ID NO: 304          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 304
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
```

```
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDD FAAFVEKCCK ADDKETCFAE EGPHLVAASK AALGL                   585

SEQ ID NO: 305         moltype = AA  length = 585
FEATURE                Location/Qualifiers
REGION                 1..585
                       note = Synthetic peptide
source                 1..585
                       mol_type = protein
                       organism = synthetic construct
SEQUENCE: 305
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LGVDETYVPK EFNAETFTFH ADICTLSEKE RQIKKQTALV ELVKHKPKAT  540
KEQLKAVMDK FAAFVEKCCK ADDKETCFAE EGPKLVAASQ AALGL                   585

SEQ ID NO: 306         moltype = AA  length = 585
FEATURE                Location/Qualifiers
REGION                 1..585
                       note = Synthetic peptide
source                 1..585
                       mol_type = protein
                       organism = synthetic construct
SEQUENCE: 306
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDK FAAFVEKCCK ADDKETCFAE EGPKLVAASQ AALGL                   585

SEQ ID NO: 307         moltype = AA  length = 585
FEATURE                Location/Qualifiers
REGION                 1..585
                       note = Synthetic peptide
source                 1..585
                       mol_type = protein
                       organism = synthetic construct
SEQUENCE: 307
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDK FAAFVEKCCK ADDKETCFAE EGPHLVAASQ AALGL                   585

SEQ ID NO: 308         moltype = AA  length = 585
FEATURE                Location/Qualifiers
REGION                 1..585
                       note = Synthetic peptide
source                 1..585
                       mol_type = protein
                       organism = synthetic construct
SEQUENCE: 308
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
```

```
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGPHLVAASK AALGL                  585

SEQ ID NO: 309          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 309
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDK FAAFVEKCCK ADDKETCFAE EGPKLVAASK AALGL                  585

SEQ ID NO: 310          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 310
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDD FAAFVEKCCK ADDKETCFAE EGPKLVAASK AALGL                  585

SEQ ID NO: 311          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 311
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 312          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 312
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAGTFTFH ADICTLSEKE RQIKKQTALV ELVKHKPKAT  540
```

```
KEQLKAAMDD FAAFVEKCCK ADDKETCFAE EGKKLVAASQ AALGL                585

SEQ ID NO: 313          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 313
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGPKLVAASQ AALGL                585

SEQ ID NO: 314          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 314
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDD FAAFVEKCCK ADDKETCFAE EGPHLVAASK AALGL                585

SEQ ID NO: 315          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 315
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LGVDETYVPK EFNAETFTFH ADICTLSEKE RQIKKQTALV ELVKHKPKAT  540
KEQLKAVMDK FAAFVEKCCK ADDKETCFAE EGPKLVAASQ AALGL                585

SEQ ID NO: 316          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 316
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDK FAAFVEKCCK ADDKETCFAE EGPKLVAASQ AALGL                585

SEQ ID NO: 317          moltype = AA  length = 585
```

```
FEATURE                Location/Qualifiers
REGION                 1..585
                       note = Synthetic peptide
source                 1..585
                       mol_type = protein
                       organism = synthetic construct
SEQUENCE: 317
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDK FAAFVEKCCK ADDKETCFAE EGPHLVAASQ AALGL                585

SEQ ID NO: 318         moltype = AA  length = 585
FEATURE                Location/Qualifiers
REGION                 1..585
                       note = Synthetic peptide
source                 1..585
                       mol_type = protein
                       organism = synthetic construct
SEQUENCE: 318
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGPHLVAASK AALGL                585

SEQ ID NO: 319         moltype = AA  length = 585
FEATURE                Location/Qualifiers
REGION                 1..585
                       note = Synthetic peptide
source                 1..585
                       mol_type = protein
                       organism = synthetic construct
SEQUENCE: 319
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDK FAAFVEKCCK ADDKETCFAE EGPKLVAASK AALGL                585

SEQ ID NO: 320         moltype = AA  length = 585
FEATURE                Location/Qualifiers
REGION                 1..585
                       note = Synthetic peptide
source                 1..585
                       mol_type = protein
                       organism = synthetic construct
SEQUENCE: 320
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDD FAAFVEKCCK ADDKETCFAE EGPKLVAASK AALGL                585

SEQ ID NO: 321         moltype = AA  length = 585
FEATURE                Location/Qualifiers
REGION                 1..585
                       note = Synthetic peptide
```

```
source                  1..585
                        mol_type = protein
                        organism = synthetic construct
SEQUENCE: 321
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 322          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 322
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAGTFTFH ADICTLSEKE RQIKKQTALV ELVKHKPKAT  540
KEQLKAAMDD FAAFVEKCCK ADDKETCFAE EGKKLVAASQ AALGL                  585

SEQ ID NO: 323          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 323
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGPKLVAASQ AALGL                  585

SEQ ID NO: 324          moltype = AA  length = 585
FEATURE                 Location/Qualifiers
REGION                  1..585
                        note = Synthetic peptide
source                  1..585
                        mol_type = protein
                        organism = synthetic construct
SEQUENCE: 324
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDD FAAFVEKCCK ADDKETCFAE EGPHLVAASK AALGL                  585

SEQ ID NO: 325          moltype = AA  length = 585
FEATURE                 Location/Qualifiers
REGION                  1..585
                        note = Synthetic peptide
source                  1..585
                        mol_type = protein
                        organism = synthetic construct
```

```
SEQUENCE: 325
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LGVDETYVPK EFNAETFTFH ADICTLSEKE RQIKKQTALV ELVKHKPKAT  540
KEQLKAVMDK FAAFVEKCCK ADDKETCFAE EGPKLVAASQ AALGL                  585

SEQ ID NO: 326         moltype = AA  length = 585
FEATURE                Location/Qualifiers
REGION                 1..585
                       note = Synthetic peptide
source                 1..585
                       mol_type = protein
                       organism = synthetic construct
SEQUENCE: 326
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDK FAAFVEKCCK ADDKETCFAE EGPKLVAASQ AALGL                  585

SEQ ID NO: 327         moltype = AA  length = 585
FEATURE                Location/Qualifiers
REGION                 1..585
                       note = Synthetic peptide
source                 1..585
                       mol_type = protein
                       organism = synthetic construct
SEQUENCE: 327
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDK FAAFVEKCCK ADDKETCFAE EGPHLVAASQ AALGL                  585

SEQ ID NO: 328         moltype = AA  length = 585
FEATURE                Location/Qualifiers
REGION                 1..585
                       note = Synthetic peptide
source                 1..585
                       mol_type = protein
                       organism = synthetic construct
SEQUENCE: 328
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGPHLVAASK AALGL                  585

SEQ ID NO: 329         moltype = AA  length = 585
FEATURE                Location/Qualifiers
REGION                 1..585
                       note = Synthetic peptide
source                 1..585
                       mol_type = protein
                       organism = synthetic construct
SEQUENCE: 329
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
```

```
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDK FAAFVEKCCK ADDKETCFAE EGPKLVAASK AALGL                  585

SEQ ID NO: 330         moltype = AA  length = 585
FEATURE                Location/Qualifiers
REGION                 1..585
                       note = Synthetic peptide
source                 1..585
                       mol_type = protein
                       organism = synthetic construct
SEQUENCE: 330
DAHKSEVAHR FKDLGEENFK ALVLIAFAQY LQQAPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LDVDETYVPK EFNAETFTFH ADICTLSEKE RQIKKQTALV ELVKHKPKAT  540
KEQLKAVMDD FAAFVEKCCK ADDKETCFAE EGPKLVAASK AALGL                  585

SEQ ID NO: 331         moltype = AA  length = 330
FEATURE                Location/Qualifiers
REGION                 1..330
                       note = Synthetic peptide
source                 1..330
                       mol_type = protein
                       organism = synthetic construct
SEQUENCE: 331
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPCEEQYG  180
STYRCVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYDTTPPV LDSDGSFFLY SDLTVDKSRW  300
QQGNVFSCSV MHEALHNHYT QKSLSLSPGK                                  330

SEQ ID NO: 332         moltype = AA  length = 333
FEATURE                Location/Qualifiers
REGION                 1..333
                       note = Synthetic peptide
source                 1..333
                       mol_type = protein
                       organism = synthetic construct
SEQUENCE: 332
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECSDKTH TCPPCPAPEL  120
LGGPSVFLFP PKPKDTLMIS RTPEVTCVVV DVSHEDPEVK FNWYVDGVEV HNAKTKPCEE  180
QYGSTYRCVS VLTVLHQDWL NGKEYKCKVS NKALPAPIEK TISKAKGQPR EPQVYTLPPS  240
RKEMTKNQVS LTCLVKGFYP SDIAVEWESN GQPENNYKTT PPVLKSDGSF FLYSKLTVDK  300
SRWQQGNVFS CSVMHEALHN HYTQKSLSLS PGK                               333

SEQ ID NO: 333         moltype = AA  length = 330
FEATURE                Location/Qualifiers
REGION                 1..330
                       note = Synthetic peptide
source                 1..330
                       mol_type = protein
                       organism = synthetic construct
SEQUENCE: 333
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVEP KSSDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYDTTPPV LDSDGSFFLY SDLTVDKSRW  300
QQGNVFSCSV MHEALHNHYT QKSLSLSPGK                                  330

SEQ ID NO: 334         moltype = AA  length = 338
FEATURE                Location/Qualifiers
REGION                 1..338
                       note = Synthetic peptide
source                 1..338
                       mol_type = protein
```

```
                         organism = synthetic construct
SEQUENCE: 334
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECSEPKS SDKTHTCPPC  120
PAPEAAGGPS VFLFPPKPKD TLMISRTPEV TCVVVDVSHE DPEVKFNWYV DGVEVHNAKT  180
KPREEQYNST YRVVSVLTVL HQDWLNGKEY KCKVSNKALP APIEKTISKA KGQPREPQVY  240
TLPPSRKEMT KNQVSLTCLV KGFYPSDIAV EWESNGQPEN NYKTTPPVLK SDGSFFLYSK  300
LTVDKSRWQQ GNVFSCSVMH EALHNHYTQK SLSLSPGK                         338

SEQ ID NO: 335           moltype = AA  length = 227
FEATURE                  Location/Qualifiers
REGION                   1..227
                         note = Synthetic peptide
source                   1..227
                         mol_type = protein
                         organism = synthetic construct
SEQUENCE: 335
DKTHTCPPCP APELLGGPSV FLFPPKPKDT LMISRTPEVT CVVVDVSHED PEVKFNWYVD  60
GVEVHNAKTK PCEEQYGSTY RCVSVLTVLH QDWLNGKEYK CKVSNKALPA PIEKTISKAK  120
GQPREPQVYT LPPSRKEMTK NQVSLTCLVK GFYPSDIAVE WESNGQPENN YKTTPPVLKS  180
DGSFFLYSKL TVDKSRWQQG NVFSCSVMHE ALHNHYTQKS LSLSPGK                227

SEQ ID NO: 336           moltype = AA  length = 227
FEATURE                  Location/Qualifiers
REGION                   1..227
                         note = Synthetic peptide
source                   1..227
                         mol_type = protein
                         organism = synthetic construct
SEQUENCE: 336
DKTHTCPPCP APELLGGPSV FLFPPKPKDT LMISRTPEVT CVVVDVSHED PEVKFNWYVD  60
GVEVHNAKTK PCEEQYGSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YDTTPPVLDS  180
DGSFFLYSDL TVDKSRWQQG NVFSCSVMHE ALHNHYTQKS LSLSPGK                227

SEQ ID NO: 337           moltype = AA  length = 232
FEATURE                  Location/Qualifiers
REGION                   1..232
                         note = Synthetic peptide
source                   1..232
                         mol_type = protein
                         organism = synthetic construct
SEQUENCE: 337
EPKSSDKTHT CPPCPAPELL GGPSVFLFPP KPKDTLMISR TPEVTCVVVD VSHEDPEVKF  60
NWYVDGVEVH NAKTKPCEEQ YGSTYRCVSV LTVLHQDWLN GKEYKCKVSN KALPAPIEKT  120
ISKAKGQPRE PQVYTLPPSR KEMTKNQVSL TCLVKGFYPS DIAVEWESNG QPENNYKTTP  180
PVLKSDGSFF LYSKLTVDKS RWQQGNVFSC SVMHEALHNH YTQKSLSLSP GK          232

SEQ ID NO: 338           moltype = AA  length = 232
FEATURE                  Location/Qualifiers
REGION                   1..232
                         note = Synthetic peptide
source                   1..232
                         mol_type = protein
                         organism = synthetic construct
SEQUENCE: 338
EPKSSDKTHT CPPCPAPELL GGPSVFLFPP KPKDTLMISR TPEVTCVVVD VSHEDPEVKF  60
NWYVDGVEVH NAKTKPCEEQ YGSTYRCVSV LTVLHQDWLN GKEYKCKVSN KALPAPIEKT  120
ISKAKGQPRE PQVYTLPPSR EEMTKNQVSL TCLVKGFYPS DIAVEWESNG QPENNYDTTP  180
PVLDSDGSFF LYSDLTVDKS RWQQGNVFSC SVMHEALHNH YTQKSLSLSP GK          232

SEQ ID NO: 339           moltype = AA  length = 232
FEATURE                  Location/Qualifiers
REGION                   1..232
                         note = Synthetic peptide
source                   1..232
                         mol_type = protein
                         organism = synthetic construct
SEQUENCE: 339
EPKSSDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR KEMTKNQVSL TCLVKGFYPS DIAVEWESNG QPENNYKTTP  180
PVLKSDGSFF LYSKLTVDKS RWQQGNVFSC SVMHEALHNH YTQKSLSLSP GK          232

SEQ ID NO: 340           moltype = AA  length = 232
FEATURE                  Location/Qualifiers
REGION                   1..232
                         note = Synthetic peptide
source                   1..232
```

```
                         mol_type = protein
                         organism = synthetic construct
SEQUENCE: 340
EPKSSDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYDTTP  180
PVLDSDGSFF LYSDLTVDKS RWQQGNVFSC SVMHEALHNH YTQKSLSLSP GK          232

SEQ ID NO: 341           moltype = AA  length = 217
FEATURE                  Location/Qualifiers
REGION                   1..217
                         note = Synthetic peptide
source                   1..217
                         mol_type = protein
                         organism = synthetic construct
SEQUENCE: 341
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVTT  120
LPPSREEMTK NQVSLTCLVK GFYPSDIAVE WESNGQPENN YDTTPPVLDS DGSFFLYSDL  180
TVDKSRWQQG NVFSCSVMHE ALHNHYTQKS LSLSPGK                           217

SEQ ID NO: 342           moltype = AA  length = 14
FEATURE                  Location/Qualifiers
REGION                   1..14
                         note = Synthetic peptide
source                   1..14
                         mol_type = protein
                         organism = synthetic construct
SEQUENCE: 342
GSSTGAVTSG YYPN                                                    14

SEQ ID NO: 343           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 343
GTKFLAP                                                            7

SEQ ID NO: 344           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 344
ALWYSNRWV                                                          9

SEQ ID NO: 345           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 345
IYAMN                                                              5

SEQ ID NO: 346           moltype = AA  length = 19
FEATURE                  Location/Qualifiers
REGION                   1..19
                         note = Synthetic peptide
source                   1..19
                         mol_type = protein
                         organism = synthetic construct
SEQUENCE: 346
RIRSKYNNYA TYYADSVKS                                               19

SEQ ID NO: 347           moltype = AA  length = 14
FEATURE                  Location/Qualifiers
REGION                   1..14
                         note = Synthetic peptide
source                   1..14
                         mol_type = protein
                         organism = synthetic construct
SEQUENCE: 347
```

```
HGNFGNSYVS FFAY                                                   14

SEQ ID NO: 348          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 348
EVQLVESGGG LVQPGGSLKL SCAASGFTFN IYAMNWVRQA PGKGLEWVAR IRSKYNNYAT  60
YYADSVKSRF TISRDDSKNT AYLQMNNLKT EDTAVYYCVR HGNFGNSYVS FFAYWGQGTL  120
VTVSS                                                             125

SEQ ID NO: 349          moltype = AA  length = 109
FEATURE                 Location/Qualifiers
REGION                  1..109
                        note = Synthetic peptide
source                  1..109
                        mol_type = protein
                        organism = synthetic construct
SEQUENCE: 349
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL             109

SEQ ID NO: 350          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 350
EVQLVESGGG LVQPGGSLKL SCAASGFTFN IYAMNWVRQA PGKGLEWVAR IRSKYNNYAT  60
YYADSVKSRF TISRDDSKNT AYLQMNNLKT EDTAVYYCVR HGNFGNSYVS FFAYWGQGTL  120
VTVSSGGGGS GGGGSGGGGS QTVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                         249

SEQ ID NO: 351          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 351
GSSTGAVTSG YYPN                                                   14

SEQ ID NO: 352          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 352
GTKFLAP                                                           7

SEQ ID NO: 353          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 353
ALWYSNRWV                                                         9

SEQ ID NO: 354          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 354
KYAMN                                                             5
```

```
SEQ ID NO: 355         moltype = AA  length = 19
FEATURE                Location/Qualifiers
REGION                 1..19
                       note = Synthetic peptide
source                 1..19
                       mol_type = protein
                       organism = synthetic construct
SEQUENCE: 355
RIRSKYNNYA TYYADSVKD                                              19

SEQ ID NO: 356         moltype = AA  length = 14
FEATURE                Location/Qualifiers
REGION                 1..14
                       note = Synthetic peptide
source                 1..14
                       mol_type = protein
                       organism = synthetic construct
SEQUENCE: 356
HGNFGNSYIS YWAY                                                   14

SEQ ID NO: 357         moltype = AA  length = 125
FEATURE                Location/Qualifiers
REGION                 1..125
                       note = Synthetic peptide
source                 1..125
                       mol_type = protein
                       organism = synthetic construct
SEQUENCE: 357
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSS                                                             125

SEQ ID NO: 358         moltype = AA  length = 109
FEATURE                Location/Qualifiers
REGION                 1..109
                       note = Synthetic peptide
source                 1..109
                       mol_type = protein
                       organism = synthetic construct
SEQUENCE: 358
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL              109

SEQ ID NO: 359         moltype = AA  length = 249
FEATURE                Location/Qualifiers
REGION                 1..249
                       note = Synthetic peptide
source                 1..249
                       mol_type = protein
                       organism = synthetic construct
SEQUENCE: 359
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                         249

SEQ ID NO: 360         moltype = AA  length = 14
FEATURE                Location/Qualifiers
REGION                 1..14
                       note = Synthetic peptide
source                 1..14
                       mol_type = protein
                       organism = synthetic construct
SEQUENCE: 360
GSSTGAVTSG YYPN                                                   14

SEQ ID NO: 361         moltype = AA  length = 7
FEATURE                Location/Qualifiers
REGION                 1..7
                       note = Synthetic peptide
source                 1..7
                       mol_type = protein
                       organism = synthetic construct
SEQUENCE: 361
GTKFLAP                                                           7

SEQ ID NO: 362         moltype = AA  length = 9
FEATURE                Location/Qualifiers
```

```
REGION                  1..9
                        note = Synthetic peptide
source                  1..9
                        mol_type = protein
                        organism = synthetic construct
SEQUENCE: 362
ALWYSNRWV                                                          9

SEQ ID NO: 363          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 363
SYAMN                                                              5

SEQ ID NO: 364          moltype = AA  length = 19
FEATURE                 Location/Qualifiers
REGION                  1..19
                        note = Synthetic peptide
source                  1..19
                        mol_type = protein
                        organism = synthetic construct
SEQUENCE: 364
RIRSKYNNYA TYYADSVKG                                               19

SEQ ID NO: 365          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 365
HGNFGNSYLS FWAY                                                    14

SEQ ID NO: 366          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 366
EVQLVESGGG LEQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYLS FWAYWGQGTL  120
VTVSS                                                              125

SEQ ID NO: 367          moltype = AA  length = 109
FEATURE                 Location/Qualifiers
REGION                  1..109
                        note = Synthetic peptide
source                  1..109
                        mol_type = protein
                        organism = synthetic construct
SEQUENCE: 367
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL              109

SEQ ID NO: 368          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 368
EVQLVESGGG LEQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYLS FWAYWGQGTL  120
VTVSSGGGGS GGGGSGGGGS QTVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 369          moltype = AA  length = 14
FEATURE                 Location/Qualifiers
REGION                  1..14
                        note = Synthetic peptide
```

```
source                  1..14
                        mol_type = protein
                        organism = synthetic construct
SEQUENCE: 369
GSSTGAVTSG YYPN                                                  14

SEQ ID NO: 370          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 370
GTKFLAP                                                          7

SEQ ID NO: 371          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 371
ALWYSNRWV                                                        9

SEQ ID NO: 372          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 372
RYAMN                                                            5

SEQ ID NO: 373          moltype = AA  length = 19
FEATURE                 Location/Qualifiers
REGION                  1..19
                        note = Synthetic peptide
source                  1..19
                        mol_type = protein
                        organism = synthetic construct
SEQUENCE: 373
RIRSKYNNYA TYYADSVKG                                             19

SEQ ID NO: 374          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 374
HGNFGNSYLS YFAY                                                  14

SEQ ID NO: 375          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 375
EVQLVESGGG LVQPGGSLKL SCAASGFTFN RYAMNWVRQA PGKGLEWVAR IRSKYNNYAT  60
YYADSVKGRF TISRDDSKNT AYLQMNNLKT EDTAVYYCVR HGNFGNSYLS YFAYWGQGTL  120
VTVSS                                                            125

SEQ ID NO: 376          moltype = AA  length = 109
FEATURE                 Location/Qualifiers
REGION                  1..109
                        note = Synthetic peptide
source                  1..109
                        mol_type = protein
                        organism = synthetic construct
SEQUENCE: 376
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL            109
```

```
SEQ ID NO: 377          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 377
EVQLVESGGG LVQPGGSLKL SCAASGFTFN RYAMNWVRQA PGKGLEWVAR IRSKYNNYAT  60
YYADSVKGRF TISRDDSKNT AYLQMNNLKT EDTAVYYCVR HGNFGNSYLS YFAYWGQGTL  120
VTVSSGGGGS GGGGSGGGGS QTVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 378          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 378
RSSTGAVTSG YYPN                                                    14

SEQ ID NO: 379          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 379
ATDMRPS                                                            7

SEQ ID NO: 380          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 380
ALWYSNRWV                                                          9

SEQ ID NO: 381          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 381
VYAMN                                                              5

SEQ ID NO: 382          moltype = AA  length = 19
FEATURE                 Location/Qualifiers
REGION                  1..19
                        note = Synthetic peptide
source                  1..19
                        mol_type = protein
                        organism = synthetic construct
SEQUENCE: 382
RIRSKYNNYA TYYADSVKK                                               19

SEQ ID NO: 383          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 383
HGNFGNSYLS WWAY                                                    14

SEQ ID NO: 384          moltype = AA  length = 125
FEATURE                 Location/Qualifiers
REGION                  1..125
                        note = Synthetic peptide
source                  1..125
```

```
                         mol_type = protein
                         organism = synthetic construct
SEQUENCE: 384
EVQLVESGGG LVQPGGSLKL SCAASGFTFN VYAMNWVRQA PGKGLEWVAR IRSKYNNYAT  60
YYADSVKKRF TISRDDSKNT AYLQMNNLKT EDTAVYYCVR HGNFGNSYLS WWAYWGQGTL  120
VTVSS                                                              125

SEQ ID NO: 385           moltype = AA  length = 109
FEATURE                  Location/Qualifiers
REGION                   1..109
                         note = Synthetic peptide
source                   1..109
                         mol_type = protein
                         organism = synthetic construct
SEQUENCE: 385
QTVVTQEPSL TVSPGGTVTL TCRSSTGAVT SGYYPNWVQQ KPGQAPRGLI GATDMRPSGT  60
PARFSGSLLG GKAALTLSGV QPEDEAEYYC ALWYSNRWVF GGGTKLTVL             109

SEQ ID NO: 386           moltype = AA  length = 249
FEATURE                  Location/Qualifiers
REGION                   1..249
                         note = Synthetic peptide
source                   1..249
                         mol_type = protein
                         organism = synthetic construct
SEQUENCE: 386
EVQLVESGGG LVQPGGSLKL SCAASGFTFN VYAMNWVRQA PGKGLEWVAR IRSKYNNYAT  60
YYADSVKKRF TISRDDSKNT AYLQMNNLKT EDTAVYYCVR HGNFGNSYLS WWAYWGQGTL  120
VTVSSGGGGS GGGGSGGGGS QTVVTQEPSL TVSPGGTVTL TCRSSTGAVT SGYYPNWVQQ  180
KPGQAPRGLI GATDMRPSGT PARFSGSLLG GKAALTLSGV QPEDEAEYYC ALWYSNRWVF  240
GGGTKLTVL                                                          249

SEQ ID NO: 387           moltype = AA  length = 14
FEATURE                  Location/Qualifiers
REGION                   1..14
                         note = Synthetic peptide
source                   1..14
                         mol_type = protein
                         organism = synthetic construct
SEQUENCE: 387
GSSTGAVTSG YYPN                                                    14

SEQ ID NO: 388           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 388
GTKFLAP                                                            7

SEQ ID NO: 389           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 389
ALWYSNRWV                                                          9

SEQ ID NO: 390           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 390
KYAMN                                                              5

SEQ ID NO: 391           moltype = AA  length = 19
FEATURE                  Location/Qualifiers
REGION                   1..19
                         note = Synthetic peptide
source                   1..19
                         mol_type = protein
                         organism = synthetic construct
```

```
SEQUENCE: 391
RIRSKYNNYA TYYADSVKS                                        19

SEQ ID NO: 392         moltype = AA  length = 14
FEATURE                Location/Qualifiers
REGION                 1..14
                       note = Synthetic peptide
source                 1..14
                       mol_type = protein
                       organism = synthetic construct
SEQUENCE: 392
HGNFGNSYTS YYAY                                             14

SEQ ID NO: 393         moltype = AA  length = 125
FEATURE                Location/Qualifiers
REGION                 1..125
                       note = Synthetic peptide
source                 1..125
                       mol_type = protein
                       organism = synthetic construct
SEQUENCE: 393
EVQLVESGGG LVQPGGSLKL SCAASGFTFN KYAMNWVRQA PGKGLEWVAR IRSKYNNYAT  60
YYADSVKSRF TISRDDSKNT AYLQMNNLKT EDTAVYYCVR HGNFGNSYTS YYAYWGQGTL  120
VTVSS                                                       125

SEQ ID NO: 394         moltype = AA  length = 109
FEATURE                Location/Qualifiers
REGION                 1..109
                       note = Synthetic peptide
source                 1..109
                       mol_type = protein
                       organism = synthetic construct
SEQUENCE: 394
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL           109

SEQ ID NO: 395         moltype = AA  length = 249
FEATURE                Location/Qualifiers
REGION                 1..249
                       note = Synthetic peptide
source                 1..249
                       mol_type = protein
                       organism = synthetic construct
SEQUENCE: 395
EVQLVESGGG LVQPGGSLKL SCAASGFTFN KYAMNWVRQA PGKGLEWVAR IRSKYNNYAT  60
YYADSVKSRF TISRDDSKNT AYLQMNNLKT EDTAVYYCVR HGNFGNSYTS YYAYWGQGTL  120
VTVSSGGGGS GGGGSGGGGS QTVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                   249

SEQ ID NO: 396         moltype = AA  length = 14
FEATURE                Location/Qualifiers
REGION                 1..14
                       note = Synthetic peptide
source                 1..14
                       mol_type = protein
                       organism = synthetic construct
SEQUENCE: 396
RSSTGAVTSG YYPN                                             14

SEQ ID NO: 397         moltype = AA  length = 7
FEATURE                Location/Qualifiers
REGION                 1..7
                       note = Synthetic peptide
source                 1..7
                       mol_type = protein
                       organism = synthetic construct
SEQUENCE: 397
ATDMRPS                                                     7

SEQ ID NO: 398         moltype = AA  length = 9
FEATURE                Location/Qualifiers
REGION                 1..9
                       note = Synthetic peptide
source                 1..9
                       mol_type = protein
                       organism = synthetic construct
SEQUENCE: 398
ALWYSNRWV                                                   9
```

```
SEQ ID NO: 399         moltype = AA  length = 5
FEATURE                Location/Qualifiers
REGION                 1..5
                       note = Synthetic peptide
source                 1..5
                       mol_type = protein
                       organism = synthetic construct
SEQUENCE: 399
GYAMN                                                              5

SEQ ID NO: 400         moltype = AA  length = 19
FEATURE                Location/Qualifiers
REGION                 1..19
                       note = Synthetic peptide
source                 1..19
                       mol_type = protein
                       organism = synthetic construct
SEQUENCE: 400
RIRSKYNNYA TYYADSVKE                                               19

SEQ ID NO: 401         moltype = AA  length = 14
FEATURE                Location/Qualifiers
REGION                 1..14
                       note = Synthetic peptide
source                 1..14
                       mol_type = protein
                       organism = synthetic construct
SEQUENCE: 401
HRNFGNSYLS WFAY                                                    14

SEQ ID NO: 402         moltype = AA  length = 125
FEATURE                Location/Qualifiers
REGION                 1..125
                       note = Synthetic peptide
source                 1..125
                       mol_type = protein
                       organism = synthetic construct
SEQUENCE: 402
EVQLVESGGG LVQPGGSLKL SCAASGFTFN GYAMNWVRQA PGKGLEWVAR IRSKYNNYAT  60
YYADSVKERF TISRDDSKNT AYLQMNNLKT EDTAVYYCVR HRNFGNSYLS WFAYWGQGTL  120
VTVSS                                                              125

SEQ ID NO: 403         moltype = AA  length = 109
FEATURE                Location/Qualifiers
REGION                 1..109
                       note = Synthetic peptide
source                 1..109
                       mol_type = protein
                       organism = synthetic construct
SEQUENCE: 403
QTVVTQEPSL TVSPGGTVTL TCRSSTGAVT SGYYPNWVQQ KPGQAPRGLI GATDMRPSGT  60
PARFSGSLLG GKAALTLSGV QPEDEAEYYC ALWYSNRWVF GGGTKLTVL              109

SEQ ID NO: 404         moltype = AA  length = 249
FEATURE                Location/Qualifiers
REGION                 1..249
                       note = Synthetic peptide
source                 1..249
                       mol_type = protein
                       organism = synthetic construct
SEQUENCE: 404
EVQLVESGGG LVQPGGSLKL SCAASGFTFN GYAMNWVRQA PGKGLEWVAR IRSKYNNYAT  60
YYADSVKERF TISRDDSKNT AYLQMNNLKT EDTAVYYCVR HRNFGNSYLS WFAYWGQGTL  120
VTVSSGGGGS GGGGSGGGGS QTVVTQEPSL TVSPGGTVTL TCRSSTGAVT SGYYPNWVQQ  180
KPGQAPRGLI GATDMRPSGT PARFSGSLLG GKAALTLSGV QPEDEAEYYC ALWYSNRWVF  240
GGGTKLTVL                                                          249

SEQ ID NO: 405         moltype = AA  length = 14
FEATURE                Location/Qualifiers
REGION                 1..14
                       note = Synthetic peptide
source                 1..14
                       mol_type = protein
                       organism = synthetic construct
SEQUENCE: 405
GSSTGAVTSG YYPN                                                    14

SEQ ID NO: 406         moltype = AA  length = 7
```

```
FEATURE                Location/Qualifiers
REGION                 1..7
                       note = Synthetic peptide
source                 1..7
                       mol_type = protein
                       organism = synthetic construct
SEQUENCE: 406
GTKFLAP                                                       7

SEQ ID NO: 407         moltype = AA  length = 9
FEATURE                Location/Qualifiers
REGION                 1..9
                       note = Synthetic peptide
source                 1..9
                       mol_type = protein
                       organism = synthetic construct
SEQUENCE: 407
ALWYSNRWV                                                     9

SEQ ID NO: 408         moltype = AA  length = 5
FEATURE                Location/Qualifiers
REGION                 1..5
                       note = Synthetic peptide
source                 1..5
                       mol_type = protein
                       organism = synthetic construct
SEQUENCE: 408
VYAMN                                                         5

SEQ ID NO: 409         moltype = AA  length = 19
FEATURE                Location/Qualifiers
REGION                 1..19
                       note = Synthetic peptide
source                 1..19
                       mol_type = protein
                       organism = synthetic construct
SEQUENCE: 409
RIRSKYNNYA TYYADSVKK                                          19

SEQ ID NO: 410         moltype = AA  length = 14
FEATURE                Location/Qualifiers
REGION                 1..14
                       note = Synthetic peptide
source                 1..14
                       mol_type = protein
                       organism = synthetic construct
SEQUENCE: 410
HGNFGNSYIS WWAY                                               14

SEQ ID NO: 411         moltype = AA  length = 125
FEATURE                Location/Qualifiers
REGION                 1..125
                       note = Synthetic peptide
source                 1..125
                       mol_type = protein
                       organism = synthetic construct
SEQUENCE: 411
EVQLVESGGG LVQPGGSLKL SCAASGFTFN VYAMNWVRQA PGKGLEWVAR IRSKYNNYAT  60
YYADSVKKRF TISRDDSKNT AYLQMNNLKT EDTAVYYCVR HGNFGNSYIS WWAYWGQGTL  120
VTVSS                                                         125

SEQ ID NO: 412         moltype = AA  length = 109
FEATURE                Location/Qualifiers
REGION                 1..109
                       note = Synthetic peptide
source                 1..109
                       mol_type = protein
                       organism = synthetic construct
SEQUENCE: 412
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL             109

SEQ ID NO: 413         moltype = AA  length = 249
FEATURE                Location/Qualifiers
REGION                 1..249
                       note = Synthetic peptide
source                 1..249
                       mol_type = protein
                       organism = synthetic construct
```

```
SEQUENCE: 413
EVQLVESGGG LVQPGGSLKL SCAASGFTFN VYAMNWVRQA PGKGLEWVAR IRSKYNNYAT  60
YYADSVKKRF TISRDDSKNT AYLQMNNLKT EDTAVYYCVR HGNFGNSYIS WWAYWGQGTL  120
VTVSSGGGGS GGGGSGGGGS QTVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 414          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 414
GSSTGAVTSG NYPN                                                    14

SEQ ID NO: 415          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 415
GTKFLAP                                                            7

SEQ ID NO: 416          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 416
VLWYSNRWV                                                          9

SEQ ID NO: 417          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 417
SYAMN                                                              5

SEQ ID NO: 418          moltype = AA  length = 19
FEATURE                 Location/Qualifiers
REGION                  1..19
                        note = Synthetic peptide
source                  1..19
                        mol_type = protein
                        organism = synthetic construct
SEQUENCE: 418
RIRSKYNNYA TYYADSVKG                                               19

SEQ ID NO: 419          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 419
HGNFGNSYVS WWAY                                                    14

SEQ ID NO: 420          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 420
EVQLVESGGG LVQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYVS WWAYWGQGTL  120
VTVSS                                                              125
```

```
SEQ ID NO: 421          moltype = AA  length = 109
FEATURE                 Location/Qualifiers
REGION                  1..109
                        note = Synthetic peptide
source                  1..109
                        mol_type = protein
                        organism = synthetic construct
SEQUENCE: 421
QTVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVL             109

SEQ ID NO: 422          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 422
EVQLVESGGG LVQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYVS WWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                         249

SEQ ID NO: 423          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 423
GSSTGAVTSG NYPN                                                   14

SEQ ID NO: 424          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 424
GTKFLAP                                                           7

SEQ ID NO: 425          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 425
VLWYSNRWV                                                         9

SEQ ID NO: 426          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 426
KYAMN                                                             5

SEQ ID NO: 427          moltype = AA  length = 19
FEATURE                 Location/Qualifiers
REGION                  1..19
                        note = Synthetic peptide
source                  1..19
                        mol_type = protein
                        organism = synthetic construct
SEQUENCE: 427
RIRSKYNNYA TYYADSVKD                                              19

SEQ ID NO: 428          moltype = AA  length = 14
FEATURE                 Location/Qualifiers
REGION                  1..14
                        note = Synthetic peptide
```

```
source                  1..14
                        mol_type = protein
                        organism = synthetic construct
SEQUENCE: 428
HGNFGNSYIS YWAY                                                  14

SEQ ID NO: 429          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 429
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSS                                                            125

SEQ ID NO: 430          moltype = AA  length = 109
FEATURE                 Location/Qualifiers
REGION                  1..109
                        note = Synthetic peptide
source                  1..109
                        mol_type = protein
                        organism = synthetic construct
SEQUENCE: 430
QTVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVL             109

SEQ ID NO: 431          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 431
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                        249

SEQ ID NO: 432          moltype = AA  length = 125
FEATURE                 Location/Qualifiers
REGION                  1..125
                        note = Synthetic peptide
source                  1..125
                        mol_type = protein
                        organism = synthetic construct
SEQUENCE: 432
EVQLVESGGG LVQPGGSLRL SCAASGFTFN SYAMNWVRQA PGKGLEWVAR IRSKYNNYAT  60
YYADSVKGRF TISRDDSKNT AYLQMNSLKT EDTAVYYCVR HGNFGNSYVS WWAYWGQGTL  120
VTVSS                                                            125

SEQ ID NO: 433          moltype = AA  length = 109
FEATURE                 Location/Qualifiers
REGION                  1..109
                        note = Synthetic peptide
source                  1..109
                        mol_type = protein
                        organism = synthetic construct
SEQUENCE: 433
QTVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVL             109

SEQ ID NO: 434          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 434
EVQLVESGGG LVQPGGSLRL SCAASGFTFN SYAMNWVRQA PGKGLEWVAR IRSKYNNYAT  60
YYADSVKGRF TISRDDSKNT AYLQMNSLKT EDTAVYYCVR HGNFGNSYVS WWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                        249
```

```
SEQ ID NO: 435         moltype = AA  length = 118
FEATURE                Location/Qualifiers
REGION                 1..118
                       note = Synthetic peptide
source                 1..118
                       mol_type = protein
                       organism = synthetic construct
SEQUENCE: 435
QVQLQESGPG LVKPSETLSL TCTVSGGSIS SYYWSWIRQP PGKCLEWIGY VYYSGTTNYN  60
PSLKSRVTIS VDTSKNQFSL KLSSVTAADT AVYYCASIAV TGFYFDYWGQ GTLVTVSS    118

SEQ ID NO: 436         moltype = AA  length = 108
FEATURE                Location/Qualifiers
REGION                 1..108
                       note = Synthetic peptide
source                 1..108
                       mol_type = protein
                       organism = synthetic construct
SEQUENCE: 436
EIVLTQSPGT LSLSPGERVT LSCRASQRVN NNYLAWYQQR PGQAPRLLIY GASSRATGIP  60
DRFSGSGSGT DFTLTISRLE PEDFAVYYCQ QYDRSPLTFG CGTKLEIK               108

SEQ ID NO: 437         moltype = AA  length = 241
FEATURE                Location/Qualifiers
REGION                 1..241
                       note = Synthetic peptide
source                 1..241
                       mol_type = protein
                       organism = synthetic construct
SEQUENCE: 437
QVQLQESGPG LVKPSETLSL TCTVSGGSIS SYYWSWIRQP PGKCLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGCGTKLEI  240
K                                                                  241

SEQ ID NO: 438         moltype = AA  length = 496
FEATURE                Location/Qualifiers
REGION                 1..496
                       note = Synthetic peptide
source                 1..496
                       mol_type = protein
                       organism = synthetic construct
SEQUENCE: 438
QVQLQESGPG LVKPSETLSL TCTVSGGSIS SYYWSWIRQP PGKCLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGCGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                  496

SEQ ID NO: 439         moltype = AA  length = 17
FEATURE                Location/Qualifiers
REGION                 1..17
                       note = Synthetic peptide
source                 1..17
                       mol_type = protein
                       organism = synthetic construct
SEQUENCE: 439
IINPSEGSTS YAQKFQG                                                 17

SEQ ID NO: 440         moltype = AA  length = 17
FEATURE                Location/Qualifiers
REGION                 1..17
                       note = Synthetic peptide
source                 1..17
                       mol_type = protein
                       organism = synthetic construct
SEQUENCE: 440
IINPSDASTS YAQKFQG                                                 17

SEQ ID NO: 441         moltype = AA  length = 16
FEATURE                Location/Qualifiers
REGION                 1..16
                       note = Synthetic peptide
```

```
source                  1..16
                        mol_type = protein
                        organism = synthetic construct
SEQUENCE: 441
RSSQSLVYRE GNTYLS                                                16

SEQ ID NO: 442          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 442
RSSQSLVYRD ANTYLS                                                16

SEQ ID NO: 443          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 443
RSSQSLVYRD GQTYLS                                                16

SEQ ID NO: 444          moltype = AA  length = 16
FEATURE                 Location/Qualifiers
REGION                  1..16
                        note = Synthetic peptide
source                  1..16
                        mol_type = protein
                        organism = synthetic construct
SEQUENCE: 444
RSSQSLVYRD GNAYLS                                                16

SEQ ID NO: 445          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 445
QVQLVQSGAE VKKPGASVKV SCKASGYTFT NYYMHWVRQA PGQGLEWMGI INPSDGSTSY  60
AQKFQGRVTM TRDTSTNTVY MDLSSLRSED TAVYYCARGG NSAFYSYYDM DVWGQGTTVT  120
VSS                                                              123

SEQ ID NO: 446          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 446
QVQLVQSGAE VKKPGASVKV SCKASGYTFT NYYMHWVRQA PGLGLEWMGI INPSEGSTSY  60
AQKFQGRVTM TRDTSTNTVY MDLSSLRSED TAVYYCARGG NSAFYSYYDM DVWGQGTTVT  120
VSS                                                              123

SEQ ID NO: 447          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 447
QVQLVQSGAE VKKPGASVKV SCKASGYTFT NYYMHWVRQA PGLGLEWMGI INPSDASTSY  60
AQKFQGRVTM TRDTSTNTVY MDLSSLRSED TAVYYCARGG NSAFYSYYDM DVWGQGTTVT  120
VSS                                                              123

SEQ ID NO: 448          moltype = AA  length = 123
FEATURE                 Location/Qualifiers
REGION                  1..123
                        note = Synthetic peptide
source                  1..123
                        mol_type = protein
                        organism = synthetic construct
```

```
SEQUENCE: 448
QVQLVQSGAE VKKPGASVKV SCKASGYTFT NYYMHWVRQA PGQGLEWMGI INPSEGSTSY  60
AQKFQGRVTM TRDTSTNTVY MDLSSLRSED TAVYYCARGG NSAFYSYYDM DVWGQGTTVT  120
VSS                                                               123

SEQ ID NO: 449          moltype = AA  length = 122
FEATURE                 Location/Qualifiers
REGION                  1..122
                        note = Synthetic peptide
source                  1..122
                        mol_type = protein
                        organism = synthetic construct
SEQUENCE: 449
QVQLVQSGAE VKKPGASVKV SCKASGYTFT NYYMHWVRQA PGQGLEWMGI INPSDASTSY  60
AQKFQGRVTM TRDTSTNTVY MDLSSLRSED TAVYYCARGG NSAFYSYYDM DVWGQGTTVT  120
VS                                                                122

SEQ ID NO: 450          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 450
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSS                                                               123

SEQ ID NO: 451          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 451
QVQLVQSGAE VKKPGASVKV SCKASGYTFT NYYMHWVRQA PGQCLEWMGI INPSDGSTSY  60
AQKFQGRVTM TRDTSTNTVY MDLSSLRSED TAVYYCARGG NSAFYSYYDM DVWGQGTTVT  120
VSS                                                               123

SEQ ID NO: 452          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 452
QVQLVQSGAE VKKPGASVKV SCKASGYTFT NYYMHWVRQA PGLCLEWMGI INPSEGSTSY  60
AQKFQGRVTM TRDTSTNTVY MDLSSLRSED TAVYYCARGG NSAFYSYYDM DVWGQGTTVT  120
VSS                                                               123

SEQ ID NO: 453          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 453
QVQLVQSGAE VKKPGASVKV SCKASGYTFT NYYMHWVRQA PGLCLEWMGI INPSDASTSY  60
AQKFQGRVTM TRDTSTNTVY MDLSSLRSED TAVYYCARGG NSAFYSYYDM DVWGQGTTVT  120
VSS                                                               123

SEQ ID NO: 454          moltype = AA  length = 123
FEATURE                 Location/Qualifiers
REGION                  1..123
                        note = Synthetic peptide
source                  1..123
                        mol_type = protein
                        organism = synthetic construct
SEQUENCE: 454
QVQLVQSGAE VKKPGASVKV SCKASGYTFT NYYMHWVRQA PGQCLEWMGI INPSEGSTSY  60
AQKFQGRVTM TRDTSTNTVY MDLSSLRSED TAVYYCARGG NSAFYSYYDM DVWGQGTTVT  120
VSS                                                               123

SEQ ID NO: 455          moltype = AA  length = 123
FEATURE                 Location/Qualifiers
```

```
REGION                1..123
                      note = Synthetic peptide
source                1..123
                      mol_type = protein
                      organism = synthetic construct
SEQUENCE: 455
QVQLVQSGAE VKKPGASVKV SCKASGYTFT NYYMHWVRQA PGQCLEWMGI INPSDASTSY  60
AQKFQGRVTM TRDTSTNTVY MDLSSLRSED TAVYYCARGG NSAFYSYYDM DVWGQGTTVT  120
VSS                                                               123

SEQ ID NO: 456        moltype = AA  length = 112
FEATURE               Location/Qualifiers
REGION                1..112
                      note = Synthetic peptide
source                1..112
                      mol_type = protein
                      organism = synthetic construct
SEQUENCE: 456
DVVMTQTPLS LPVTLGQPAS ISCRSSQSLV YREGNTYLSW FQQRPGQSPR RLIYKVSNWQ  60
SGVPDRFSGG GSGTDFTLKI SRVEAEDVGV YYCMQGTHWP PTFGQGTKVE IK          112

SEQ ID NO: 457        moltype = AA  length = 112
FEATURE               Location/Qualifiers
REGION                1..112
                      note = Synthetic peptide
source                1..112
                      mol_type = protein
                      organism = synthetic construct
SEQUENCE: 457
DVVMTQTPLS LPVTLGQPAS ISCRSSQSLV YRDANTYLSW FQQRPGQSPR RLIYKVSNWQ  60
SGVPDRFSGG GSGTDFTLKI SRVEAEDVGV YYCMQGTHWP PTFGQGTKVE IK          112

SEQ ID NO: 458        moltype = AA  length = 112
FEATURE               Location/Qualifiers
REGION                1..112
                      note = Synthetic peptide
source                1..112
                      mol_type = protein
                      organism = synthetic construct
SEQUENCE: 458
DVVMTQTPLS LPVTLGQPAS ISCRSSQSLV YRDGQTYLSW FQQRPGQSPR RLIYKVSNWQ  60
SGVPDRFSGG GSGTDFTLKI SRVEAEDVGV YYCMQGTHWP PTFGQGTKVE IK          112

SEQ ID NO: 459        moltype = AA  length = 112
FEATURE               Location/Qualifiers
REGION                1..112
                      note = Synthetic peptide
source                1..112
                      mol_type = protein
                      organism = synthetic construct
SEQUENCE: 459
DVVMTQTPLS LPVTLGQPAS ISCRSSQSLV YRDGNAYLSW FQQRPGQSPR RLIYKVSNWQ  60
SGVPDRFSGG GSGTDFTLKI SRVEAEDVGV YYCMQGTHWP PTFGQGTKVE IK          112

SEQ ID NO: 460        moltype = AA  length = 112
FEATURE               Location/Qualifiers
REGION                1..112
                      note = Synthetic peptide
source                1..112
                      mol_type = protein
                      organism = synthetic construct
SEQUENCE: 460
DVVMTQTPLS LPVTLGQPAS ISCRSSQSLV YRDGNTYLSW FQQRPGQSPR RLIYKVSNWQ  60
SGVPDRFSGS GSGTDFTLKI SRVEAEDVGV YYCMQGTHWP PTFGQGTKVE IK          112

SEQ ID NO: 461        moltype = AA  length = 112
FEATURE               Location/Qualifiers
REGION                1..112
                      note = Synthetic peptide
source                1..112
                      mol_type = protein
                      organism = synthetic construct
SEQUENCE: 461
DVVMTQTPLS LPVTLGQPAS ISCRSSQSLV YREGNTYLSW FQQRPGQSPR RLIYKVSNWQ  60
SGVPDRFSGS GSGTDFTLKI SRVEAEDVGV YYCMQGTHWP PTFGQGTKVE IK          112

SEQ ID NO: 462        moltype = AA  length = 112
FEATURE               Location/Qualifiers
REGION                1..112
```

```
                         note = Synthetic peptide
source                   1..112
                         mol_type = protein
                         organism = synthetic construct
SEQUENCE: 462
DVVMTQTPLS LPVTLGQPAS ISCRSSQSLV YRDANTYLSW FQQRPGQSPR RLIYKVSNWQ  60
SGVPDRFSGS GSGTDFTLKI SRVEAEDVGV YYCMQGTHWP PTFGQGTKVE IK          112

SEQ ID NO: 463           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 463
DVVMTQTPLS LPVTLGQPAS ISCRSSQSLV YRDGNTYLSW FQQRPGQSPR RLIYKVSNWQ  60
SGVPDRFSGG GSGTDFTLKI SRVEAEDVGV YYCMQGTHWP PTFGCGTKVE IK          112

SEQ ID NO: 464           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 464
DVVMTQTPLS LPVTLGQPAS ISCRSSQSLV YREGNTYLSW FQQRPGQSPR RLIYKVSNWQ  60
SGVPDRFSGG GSGTDFTLKI SRVEAEDVGV YYCMQGTHWP PTFGCGTKVE IK          112

SEQ ID NO: 465           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 465
DVVMTQTPLS LPVTLGQPAS ISCRSSQSLV YRDANTYLSW FQQRPGQSPR RLIYKVSNWQ  60
SGVPDRFSGG GSGTDFTLKI SRVEAEDVGV YYCMQGTHWP PTFGCGTKVE IK          112

SEQ ID NO: 466           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 466
DVVMTQTPLS LPVTLGQPAS ISCRSSQSLV YRDGQTYLSW FQQRPGQSPR RLIYKVSNWQ  60
SGVPDRFSGG GSGTDFTLKI SRVEAEDVGV YYCMQGTHWP PTFGCGTKVE IK          112

SEQ ID NO: 467           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 467
DVVMTQTPLS LPVTLGQPAS ISCRSSQSLV YRDGNAYLSW FQQRPGQSPR RLIYKVSNWQ  60
SGVPDRFSGG GSGTDFTLKI SRVEAEDVGV YYCMQGTHWP PTFGCGTKVE IK          112

SEQ ID NO: 468           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 468
DVVMTQTPLS LPVTLGQPAS ISCRSSQSLV YRDGNTYLSW FQQRPGQSPR RLIYKVSNWQ  60
SGVPDRFSGS GSGTDFTLKI SRVEAEDVGV YYCMQGTHWP PTFGCGTKVE IK          112

SEQ ID NO: 469           moltype = AA  length = 112
FEATURE                  Location/Qualifiers
REGION                   1..112
                         note = Synthetic peptide
source                   1..112
```

```
                         mol_type = protein
                         organism = synthetic construct
SEQUENCE: 469
DVVMTQTPLS LPVTLGQPAS ISCRSSQSLV YREGNTYLSW FQQRPGQSPR RLIYKVSNWQ  60
SGVPDRFSGS GSGTDFTLKI SRVEAEDVGV YYCMQGTHWP PTFGCGTKVE IK          112

SEQ ID NO: 470           moltype = AA  length = 112
FEATURE                  Location/Qualifiers
REGION                   1..112
                         note = Synthetic peptide
source                   1..112
                         mol_type = protein
                         organism = synthetic construct
SEQUENCE: 470
DVVMTQTPLS LPVTLGQPAS ISCRSSQSLV YRDANTYLSW FQQRPGQSPR RLIYKVSNWQ  60
SGVPDRFSGS GSGTDFTLKI SRVEAEDVGV YYCMQGTHWP PTFGCGTKVE IK          112

SEQ ID NO: 471           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 471
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 472           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 472
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 473           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 473
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGQTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 474           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 474
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNAYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 475           moltype = AA  length = 250
FEATURE                  Location/Qualifiers
REGION                   1..250
                         note = Synthetic peptide
source                   1..250
                         mol_type = protein
```

```
                         organism = synthetic construct
SEQUENCE: 475
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGQGTKVEIK                                                         250

SEQ ID NO: 476           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 476
QVQLVQSGAE VKKPGASVKV SCKASGYTFT NYYMHWVRQA PGQGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 477           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 477
QVQLVQSGAE VKKPGASVKV SCKASGYTFT NYYMHWVRQA PGLGLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 478           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 478
QVQLVQSGAE VKKPGASVKV SCKASGYTFT NYYMHWVRQA PGLGLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK                                                         250

SEQ ID NO: 479           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 479
QVQLVQSGAE VKKPGASVKV SCKASGYTFT NYYMHWVRQA PGQGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGQGTKVEIK                                                         250

SEQ ID NO: 480           moltype = AA  length = 250
FEATURE                  Location/Qualifiers
REGION                   1..250
                         note = Synthetic peptide
source                   1..250
                         mol_type = protein
                         organism = synthetic construct
SEQUENCE: 480
QVQLVQSGAE VKKPGASVKV SCKASGYTFT NYYMHWVRQA PGQGLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGSGS GTDFTLKISR VEAEDVGVYY CMQGTHWPPT  240
FGQGTKVEIK                                                         250

SEQ ID NO: 481           moltype = AA  length = 250
```

```
FEATURE                Location/Qualifiers
REGION                 1..250
                       note = Synthetic peptide
source                 1..250
                       mol_type = protein
                       organism = synthetic construct
SEQUENCE: 481
QVQLVQSGAE VKKPGASVKV SCKASGYTFT NYYMHWVRQA PGQGLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGSGS GTDFTLKISR VEAEDVGVYY CMQGTHWPPT  240
FGQGTKVEIK                                                        250

SEQ ID NO: 482         moltype = AA  length = 250
FEATURE                Location/Qualifiers
REGION                 1..250
                       note = Synthetic peptide
source                 1..250
                       mol_type = protein
                       organism = synthetic construct
SEQUENCE: 482
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK                                                        250

SEQ ID NO: 483         moltype = AA  length = 250
FEATURE                Location/Qualifiers
REGION                 1..250
                       note = Synthetic peptide
source                 1..250
                       mol_type = protein
                       organism = synthetic construct
SEQUENCE: 483
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGGGS GTDFTLKISR VEAEDVGVYY CMQGTHWPPT  240
FGCGTKVEIK                                                        250

SEQ ID NO: 484         moltype = AA  length = 250
FEATURE                Location/Qualifiers
REGION                 1..250
                       note = Synthetic peptide
source                 1..250
                       mol_type = protein
                       organism = synthetic construct
SEQUENCE: 484
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGGGS GTDFTLKISR VEAEDVGVYY CMQGTHWPPT  240
FGCGTKVEIK                                                        250

SEQ ID NO: 485         moltype = AA  length = 250
FEATURE                Location/Qualifiers
REGION                 1..250
                       note = Synthetic peptide
source                 1..250
                       mol_type = protein
                       organism = synthetic construct
SEQUENCE: 485
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGQTYLSWFQ  180
QRPGQSPRRL IYKVSNWQSG VPDRFSGGGS GTDFTLKISR VEAEDVGVYY CMQGTHWPPT  240
FGCGTKVEIK                                                        250

SEQ ID NO: 486         moltype = AA  length = 250
FEATURE                Location/Qualifiers
REGION                 1..250
                       note = Synthetic peptide
source                 1..250
                       mol_type = protein
                       organism = synthetic construct
SEQUENCE: 486
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
```

```
VSSGGGGSGG GGSGGGGSDV VMTQTPLSLP VTLGQPASIS CRSSQSLVYR DGNAYLSWFQ  180
QRPGQSPRRL IYKVSNWQSG VPDRFSGGGS GTDFTLKISR VEAEDVGVYY CMQGTHWPPT  240
FGCGTKVEIK                                                         250

SEQ ID NO: 487         moltype = AA  length = 250
FEATURE                Location/Qualifiers
REGION                 1..250
                       note = Synthetic peptide
source                 1..250
                       mol_type = protein
                       organism = synthetic construct
SEQUENCE: 487
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGCGTKVEIK                                                         250

SEQ ID NO: 488         moltype = AA  length = 250
FEATURE                Location/Qualifiers
REGION                 1..250
                       note = Synthetic peptide
source                 1..250
                       mol_type = protein
                       organism = synthetic construct
SEQUENCE: 488
QVQLVQSGAE VKKPGASVKV SCKASGYTFT NYYMHWVRQA PGQCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK                                                         250

SEQ ID NO: 489         moltype = AA  length = 250
FEATURE                Location/Qualifiers
REGION                 1..250
                       note = Synthetic peptide
source                 1..250
                       mol_type = protein
                       organism = synthetic construct
SEQUENCE: 489
QVQLVQSGAE VKKPGASVKV SCKASGYTFT NYYMHWVRQA PGLCLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK                                                         250

SEQ ID NO: 490         moltype = AA  length = 250
FEATURE                Location/Qualifiers
REGION                 1..250
                       note = Synthetic peptide
source                 1..250
                       mol_type = protein
                       organism = synthetic construct
SEQUENCE: 490
QVQLVQSGAE VKKPGASVKV SCKASGYTFT NYYMHWVRQA PGLCLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK                                                         250

SEQ ID NO: 491         moltype = AA  length = 250
FEATURE                Location/Qualifiers
REGION                 1..250
                       note = Synthetic peptide
source                 1..250
                       mol_type = protein
                       organism = synthetic construct
SEQUENCE: 491
QVQLVQSGAE VKKPGASVKV SCKASGYTFT NYYMHWVRQA PGQCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGCGTKVEIK                                                         250

SEQ ID NO: 492         moltype = AA  length = 250
FEATURE                Location/Qualifiers
REGION                 1..250
                       note = Synthetic peptide
source                 1..250
```

```
                        mol_type = protein
                        organism = synthetic construct
SEQUENCE: 492
QVQLVQSGAE VKKPGASVKV SCKASGYTFT NYYMHWVRQA PGQCLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGSGS GTDFTLKISR VEAEDVGVYY CMQGTHWPPT  240
FGCGTKVEIK                                                        250

SEQ ID NO: 493          moltype = AA  length = 250
FEATURE                 Location/Qualifiers
REGION                  1..250
                        note = Synthetic peptide
source                  1..250
                        mol_type = protein
                        organism = synthetic construct
SEQUENCE: 493
QVQLVQSGAE VKKPGASVKV SCKASGYTFT NYYMHWVRQA PGQCLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGSGS GTDFTLKISR VEAEDVGVYY CMQGTHWPPT  240
FGCGTKVEIK                                                        250

SEQ ID NO: 494          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 494
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 495          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 495
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 496          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 496
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGQTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 497          moltype = AA  length = 505
FEATURE                 Location/Qualifiers
```

```
REGION                  1..505
                        note = Synthetic peptide
source                  1..505
                        mol_type = protein
                        organism = synthetic construct
SEQUENCE: 497
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNAYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 498          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 498
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 499          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 499
QVQLVQSGAE VKKPGASVKV SCKASGYTFT NYYMHWVRQA PGQGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 500          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 500
QVQLVQSGAE VKKPGASVKV SCKASGYTFT NYYMHWVRQA PGLGLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 501          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 501
QVQLVQSGAE VKKPGASVKV SCKASGYTFT NYYMHWVRQA PGLGLEWMGI INPSDASTSY  60
```

```
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 502          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 502
QVQLVQSGAE VKKPGASVKV SCKASGYTFT NYYMHWVRQA PGQGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 503          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 503
QVQLVQSGAE VKKPGASVKV SCKASGYTFT NYYMHWVRQA PGQGLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGSGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 504          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 504
QVQLVQSGAE VKKPGASVKV SCKASGYTFT NYYMHWVRQA PGQGLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGSGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 505          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 505
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
```

```
EAEYYCVLWY SNRWVFGGGT KLTVL                                     505

SEQ ID NO: 506          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 506
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                     505

SEQ ID NO: 507          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 507
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                     505

SEQ ID NO: 508          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 508
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGQTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                     505

SEQ ID NO: 509          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 509
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNAYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                     505

SEQ ID NO: 510          moltype = AA  length = 505
FEATURE                 Location/Qualifiers
REGION                  1..505
                        note = Synthetic peptide
source                  1..505
```

```
                        mol_type = protein
                        organism = synthetic construct
SEQUENCE: 510
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 511          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 511
QVQLVQSGAE VKKPGASVKV SCKASGYTFT NYYMHWVRQA PGQCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 512          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 512
QVQLVQSGAE VKKPGASVKV SCKASGYTFT NYYMHWVRQA PGLCLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 513          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 513
QVQLVQSGAE VKKPGASVKV SCKASGYTFT NYYMHWVRQA PGLCLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                        505

SEQ ID NO: 514          moltype = AA  length = 505
FEATURE                 Location/Qualifiers
REGION                  1..505
                        note = Synthetic peptide
source                  1..505
                        mol_type = protein
                        organism = synthetic construct
SEQUENCE: 514
QVQLVQSGAE VKKPGASVKV SCKASGYTFT NYYMHWVRQA PGQCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGSGS GTDFTLKISR VEAEDVGVYY CMQGTHWPPT  240
```

```
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 515         moltype = AA  length = 505
FEATURE                Location/Qualifiers
REGION                 1..505
                       note = Synthetic peptide
source                 1..505
                       mol_type = protein
                       organism = synthetic construct
SEQUENCE: 515
QVQLVQSGAE VKKPGASVKV SCKASGYTFT NYYMHWVRQA PGQCLEWMGI INPSEGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR EGNTYLSWFQ  180
QRPGQSPRRL IYKVSNWQSG VPDRFSGSGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 516         moltype = AA  length = 505
FEATURE                Location/Qualifiers
REGION                 1..505
                       note = Synthetic peptide
source                 1..505
                       mol_type = protein
                       organism = synthetic construct
SEQUENCE: 516
QVQLVQSGAE VKKPGASVKV SCKASGYTFT NYYMHWVRQA PGQCLEWMGI INPSDASTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DANTYLSWFQ  180
QRPGQSPRRL IYKVSNWQSG VPDRFSGSGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVL                                       505

SEQ ID NO: 517         moltype = AA  length = 984
FEATURE                Location/Qualifiers
REGION                 1..984
                       note = Synthetic peptide
source                 1..984
                       mol_type = protein
                       organism = synthetic construct
SEQUENCE: 517
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGGGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGKGGG GSGGGGSGGG GSGGGGSGGG GSGGGGSDKT HTCPPCPAPE LLGGPSVFLF  780
PPKPKDTLMI SRTPEVTCVV VDVSHEDPEV KFNWYVDGVE VHNAKTKPCE EQYGSTYRCV  840
SVLTVLHQDW LNGKEYKCKV SNKALPAPIE KTISKAKGQP REPQVYTLPP SREEMTKNQV  900
SLTCLVKGFY PSDIAVEWES NGQPENNYKT TPPVLDSDGS FFLYSKLTVD KSRWQQGNVF  960
SCSVMHEALH NHYTQKSLSL SPGK                                        984

SEQ ID NO: 518         moltype = AA  length = 982
FEATURE                Location/Qualifiers
REGION                 1..982
                       note = Synthetic peptide
source                 1..982
                       mol_type = protein
                       organism = synthetic construct
SEQUENCE: 518
QVQLQESGPG LVKPSETLSL TCTVSGGSIS SYYWSWIRQP PGKGLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
```

```
LIYGASSRAT GIPDRFSGSG SGTDFTLTIS RLEPEDFAVY YCQQYDRSPL TFGGGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGGGGS GGGGSGGGGS GGGGSGGGGS GGGGSDKTHT CPPCPAPELL GGPSVFLFPP  780
KPKDTLMISR TPEVTCVVVD VSHEDPEVKF NWYVDGVEVH NAKTKPCEEQ YGSTYRCVSV  840
LTVLHQDWLN GKEYKCKVSN KALPAPIEKT ISKAKGQPRE PQVYTLPPSR EEMTKNQVSL  900
TCLVKGFYPS DIAVEWESNG QPENNYKTTP PVLDSDGSFF LYSKLTVDKS RWQQGNVFSC  960
SVMHEALHNH YTQKSLSLSP GK                                           982

SEQ ID NO: 519          moltype = AA  length = 984
FEATURE                 Location/Qualifiers
REGION                  1..984
                        note = Synthetic peptide
source                  1..984
                        mol_type = protein
                        organism = synthetic construct
SEQUENCE: 519
QVQLQESGPG LVKPSETLSL TCTVSGGSIS SYYWSWIRQP PGKCLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGCGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGKGGG GSGGGGSGGG GSGGGGSGGG GSGGGGSDKT HTCPPCPAPE LLGGPSVFLF  780
PPKPKDTLMI SRTPEVTCVV VDVSHEDPEV KFNWYVDGVE VHNAKTKPCE EQYGSTYRCV  840
SVLTVLHQDW LNGKEYKCKV SNKALPAPIE KTISKAKGQP REPQVYTLPP SREEMTKNQV  900
SLTCLVKGFY PSDIAVEWES NGQPENNYKT TPPVLDSDGS FFLYSKLTVD KSRWQQGNVF  960
SCSVMHEALH NHYTQKSLSL SPGK                                         984

SEQ ID NO: 520          moltype = AA  length = 982
FEATURE                 Location/Qualifiers
REGION                  1..982
                        note = Synthetic peptide
source                  1..982
                        mol_type = protein
                        organism = synthetic construct
SEQUENCE: 520
QVQLQESGPG LVKPSETLSL TCTVSGGSIS SYYWSWIRQP PGKCLEWIGY VYYSGTTNYN  60
PSLKSRVTIS VDTSKNQFSL KLSSVTAADT AVYYCASIAV TGFYFDYWGQ GTLVTVSSGG  120
GGSGGGGSGG GGSEIVLTQS PGTLSLSPGE RVTLSCRASQ RVNNNYLAWY QQRPGQAPRL  180
LIYGASSRAT GIPDRFSGSG SGTDFTLTIS RLEPEDFAVY YCQQYDRSPL TFGCGTKLEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGGGGS GGGGSGGGGS GGGGSGGGGS GGGGSDKTHT CPPCPAPELL GGPSVFLFPP  780
KPKDTLMISR TPEVTCVVVD VSHEDPEVKF NWYVDGVEVH NAKTKPCEEQ YGSTYRCVSV  840
LTVLHQDWLN GKEYKCKVSN KALPAPIEKT ISKAKGQPRE PQVYTLPPSR EEMTKNQVSL  900
TCLVKGFYPS DIAVEWESNG QPENNYKTTP PVLDSDGSFF LYSKLTVDKS RWQQGNVFSC  960
SVMHEALHNH YTQKSLSLSP GK                                           982

SEQ ID NO: 521          moltype = AA  length = 984
FEATURE                 Location/Qualifiers
REGION                  1..984
                        note = Synthetic peptide
source                  1..984
                        mol_type = protein
                        organism = synthetic construct
SEQUENCE: 521
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
```

-continued

```
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGKGGG GSGGGGSGGG GSGGGGSGGG GSGGGGSDKT HTCPPCPAPE LLGGPSVFLF  780
PPKPKDTLMI SRTPEVTCVV VDVSHEDPEV KFNWYVDGVE VHNAKTKPCE EQYGSTYRCV  840
SVLTVLHQDW LNGKEYKCKV SNKALPAPIE KTISKAKGQP REPQVYTLPP SREEMTKNQV  900
SLTCLVKGFY PSDIAVEWES NGQPENNYKT TPPVLDSDGS FFLYSKLTVD KSRWQQGNVF  960
SCSVMHEALH NHYTQKSLSL SPGK                                       984

SEQ ID NO: 522          moltype = AA  length = 982
FEATURE                 Location/Qualifiers
REGION                  1..982
                        note = Synthetic peptide
source                  1..982
                        mol_type = protein
                        organism = synthetic construct
SEQUENCE: 522
QVQLQESGPG LVKPSETLSL TCTVSGASIS SFYWSWIRQP PGKGLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGGGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGGGGS GGGGSGGGGS GGGGSGGGGS GGGGSDKTHT CPPCPAPELL GGPSVFLFPP  780
KPKDTLMISR TPEVTCVVVD VSHEDPEVKF NWYVDGVEVH NAKTKPCEEQ YGSTYRCVSV  840
LTVLHQDWLN GKEYKCKVSN KALPAPIEKT ISKAKGQPRE PQVYTLPPSR EEMTKNQVSL  900
TCLVKGFYPS DIAVEWESNG QPENNYKTTP PVLDSDGSFF LYSKLTVDKS RWQQGNVFSC  960
SVMHEALHNH YTQKSLSLSP GK                                         982

SEQ ID NO: 523          moltype = AA  length = 984
FEATURE                 Location/Qualifiers
REGION                  1..984
                        note = Synthetic peptide
source                  1..984
                        mol_type = protein
                        organism = synthetic construct
SEQUENCE: 523
QVQLQESGPG LVKPSETLSL TCTVSGASIS SFYWSWIRQP PGKCLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGCGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGKGGG GSGGGGSGGG GSGGGGSGGG GSGGGGSDKT HTCPPCPAPE LLGGPSVFLF  780
PPKPKDTLMI SRTPEVTCVV VDVSHEDPEV KFNWYVDGVE VHNAKTKPCE EQYGSTYRCV  840
SVLTVLHQDW LNGKEYKCKV SNKALPAPIE KTISKAKGQP REPQVYTLPP SREEMTKNQV  900
SLTCLVKGFY PSDIAVEWES NGQPENNYKT TPPVLDSDGS FFLYSKLTVD KSRWQQGNVF  960
SCSVMHEALH NHYTQKSLSL SPGK                                       984

SEQ ID NO: 524          moltype = AA  length = 982
FEATURE                 Location/Qualifiers
REGION                  1..982
                        note = Synthetic peptide
source                  1..982
                        mol_type = protein
                        organism = synthetic construct
SEQUENCE: 524
QVQLQESGPG LVKPSETLSL TCTVSGASIS SFYWSWIRQP PGKCLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGCGTKVEI  240
KSGGGGSEVQ LVESGGGLVQ PGGSLKLSCA ASGFTFNKYA MNWVRQAPGK GLEWVARIRS  300
```

-continued

```
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGGGGS GGGGSGGGGS GGGGSGGGGS GGGGSDKTHT CPPCPAPELL GGPSVFLFPP  780
KPKDTLMISR TPEVTCVVVD VSHEDPEVKF NWYVDGVEVH NAKTKPCEEQ YGSTYRCVSV  840
LTVLHQDWLN GKEYKCKVSN KALPAPIEKT ISKAKGQPRE PQVYTLPPSR EEMTKNQVSL  900
TCLVKGFYPS DIAVEWESNG QPENNYKTTP PVLDSDGSFF LYSKLTVDKS RWQQGNVFSC  960
SVMHEALHNH YTQKSLSLSP GK                                           982

SEQ ID NO: 525          moltype = AA  length = 993
FEATURE                 Location/Qualifiers
REGION                  1..993
                        note = Synthetic peptide
source                  1..993
                        mol_type = protein
                        organism = synthetic construct
SEQUENCE: 525
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLGGGGD KTHTCPPCPA PELLGGPSVF LFPPKPKDTL  540
MISRTPEVTC VVVDVSHEDP EVKFNWYVDG VEVHNAKTKP CEEQYGSTYR CVSVLTVLHQ  600
DWLNGKEYKC KVSNKALPAP IEKTISKAKG QPREPQVYTL PPSREEMTKN QVSLTCLVKG  660
FYPSDIAVEW ESNGQPENNY KTTPPVLDSD GSFFLYSKLT VDKSRWQQGN VFSCSVMHEA  720
LHNHYTQKSL SLSPGKGGGG SGGGGSGGGG SGGGGSGGGG SGGGGSDKTH TCPPCPAPEL  780
LGGPSVFLFP PKPKDTLMIS RTPEVTCVVV DVSHEDPEVK FNWYVDGVEV HNAKTKPCEE  840
QYGSTYRCVS VLTVLHQDWL NGKEYKCKVS NKALPAPIEK TISKAKGQPR EPQVYTLPPS  900
REEMTKNQVS LTCLVKGFYP SDIAVEWESN GQPENNYKTT PPVLDSDGSF FLYSKLTVDK  960
SRWQQGNVFS CSVMHEALHN HYTQKSLSLS PGK                               993

SEQ ID NO: 526          moltype = AA  length = 991
FEATURE                 Location/Qualifiers
REGION                  1..991
                        note = Synthetic peptide
source                  1..991
                        mol_type = protein
                        organism = synthetic construct
SEQUENCE: 526
QVQLVQSGAE VKKPGASVKV SCKASGYTFT NYYMHWVRQA PGLGLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGQGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLGGGGD KTHTCPPCPA PELLGGPSVF LFPPKPKDTL  540
MISRTPEVTC VVVDVSHEDP EVKFNWYVDG VEVHNAKTKP CEEQYGSTYR CVSVLTVLHQ  600
DWLNGKEYKC KVSNKALPAP IEKTISKAKG QPREPQVYTL PPSREEMTKN QVSLTCLVKG  660
FYPSDIAVEW ESNGQPENNY KTTPPVLDSD GSFFLYSKLT VDKSRWQQGN VFSCSVMHEA  720
LHNHYTQKSL SLSPGGGGSG GGGSGGGGSG GGGSGGGGSG GGGSDKTHTC PPCPAPELLG  780
GPSVFLFPPK PKDTLMISRT PEVTCVVVDV SHEDPEVKFN WYVDGVEVHN AKTKPCEEQY  840
GSTYRCVSVL TVLHQDWLNG KEYKCKVSNK ALPAPIEKTI SKAKGQPREP QVYTLPPSRE  900
EMTKNQVSLT CLVKGFYPSD IAVEWESNGQ PENNYKTTPP VLDSDGSFFL YSKLTVDKSR  960
WQQGNVFSCS VMHEALHNHY TQKSLSLSPG K                                 991

SEQ ID NO: 527          moltype = AA  length = 993
FEATURE                 Location/Qualifiers
REGION                  1..993
                        note = Synthetic peptide
source                  1..993
                        mol_type = protein
                        organism = synthetic construct
SEQUENCE: 527
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
```

```
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLGGGGD KTHTCPPCPA PELLGGPSVF LFPPKPKDTL  540
MISRTPEVTC VVVDVSHEDP EVKFNWYVDG VEVHNAKTKP CEEQYGSTYR CVSVLTVLHQ  600
DWLNGKEYKC KVSNKALPAP IEKTISKAKG QPREPQVYTL PPSREEMTKN QVSLTCLVKG  660
FYPSDIAVEW ESNGQPENNY KTTPPVLDSD GSFFLYSKLT VDKSRWQQGN VFSCSVMHEA  720
LHNHYTQKSL SLSPGKGGGG SGGGGSGGGG SGGGGSGGGG SGGGGSDKTH TCPPCPAPEL  780
LGGPSVFLFP PKPKDTLMIS RTPEVTCVVV DVSHEDPEVK FNWYVDGVEV HNAKTKPCEE  840
QYGSTYRCVS VLTVLHQDWL NGKEYKCKVS NKALPAPIEK TISKAKGQPR EPQVYTLPPS  900
REEMTKNQVS LTCLVKGFYP SDIAVEWESN GQPENNYKTT PPVLDSDGSF FLYSKLTVDK  960
SRWQQGNVFS CSVMHEALHN HYTQKSLSLS PGK                               993

SEQ ID NO: 528         moltype = AA  length = 991
FEATURE                Location/Qualifiers
REGION                 1..991
                       note = Synthetic peptide
source                 1..991
                       mol_type = protein
                       organism = synthetic construct
SEQUENCE: 528
QVQLVQSGAE VKKPGASVKV SCKASGYTFT NYYMHWVRQA PGLCLEWMGI INPSDGSTSY  60
AQKFQGRVTM TRDTSTNTVY MDLSSLRSED TAVYYCARGG NSAFYSYYDM DVWGQGTTVT  120
VSSGGGGSGG GGSGGGGSDV VMTQTPLSLP VTLGQPASIS CRSSQSLVYR DGNTYLSWFQ  180
QRPGQSPRRL IYKVSNWQSG VPDRFSGGGS GTDFTLKISR VEAEDVGVYY CMQGTHWPPT  240
FGCGTKVEIK SGGGGSEVQL VESGGGLVQP GGSLKLSCAA SGFTFNKYAM NWVRQAPGKG  300
LEWVARIRSK YNNYATYYAD SVKDRFTISR DDSKNTAYLQ MNNLKTEDTA VYYCVRHGNF  360
GNSYISYWAY WGQGTLVTVS SGGGGSGGGG SGGGGSQTVV TQEPSLTVSP GGTVTLTCGS  420
STGAVTSGNY PNWVQQKPGQ APRGLIGGTK FLAPGTPARF SGSLLGGKAA LTLSGVQPED  480
EAEYYCVLWY SNRWVFGGGT KLTVLGGGGD KTHTCPPCPA PELLGGPSVF LFPPKPKDTL  540
MISRTPEVTC VVVDVSHEDP EVKFNWYVDG VEVHNAKTKP CEEQYGSTYR CVSVLTVLHQ  600
DWLNGKEYKC KVSNKALPAP IEKTISKAKG QPREPQVYTL PPSREEMTKN QVSLTCLVKG  660
FYPSDIAVEW ESNGQPENNY KTTPPVLDSD GSFFLYSKLT VDKSRWQQGN VFSCSVMHEA  720
LHNHYTQKSL SLSPGGGGSG GGGSGGGGSG GGGSGGGGSG GGGSDKTHTC PPCPAPELLG  780
GPSVFLFPPK PKDTLMISRT PEVTCVVVDV SHEDPEVKFN WYVDGVEVHN AKTKPCEEQY  840
GSTYRCVSVL TVLHQDWLNG KEYKCKVSNK ALPAPIEKTI SKAKGQPREP QVYTLPPSRE  900
EMTKNQVSLT CLVKGFYPSD IAVEWESNGQ PENNYKTTPP VLDSDGSFFL YSKLTVDKSR  960
WQQGNVFSCS VMHEALHNHY TQKSLSLSPG K                                 991

SEQ ID NO: 529         moltype = AA  length = 118
FEATURE                Location/Qualifiers
REGION                 1..118
                       note = Synthetic peptide
source                 1..118
                       mol_type = protein
                       organism = synthetic construct
SEQUENCE: 529
QVQLQESGPG LVKPSETLSL TCTVSGASIS SFYWSWIRQP PGKCLEWIGY IYYSGTTNYN  60
PSLKSRVTIS VDTSKNQFSL KLSSVTAADT AVYYCARIAV AGFFFDYWGQ GTLVTVSS    118

SEQ ID NO: 530         moltype = AA  length = 108
FEATURE                Location/Qualifiers
REGION                 1..108
                       note = Synthetic peptide
source                 1..108
                       mol_type = protein
                       organism = synthetic construct
SEQUENCE: 530
EIVLTQSPGT LSLSPGERAT LSCRASQSVN KNYLAWYQQK PGQAPRLLIY GASSRATGIP  60
DRFSGSGSGT DFTLTISRLE PEDFAVYYCQ QYDRSPLTFG CGTKVEIK                108

SEQ ID NO: 531         moltype = AA  length = 241
FEATURE                Location/Qualifiers
REGION                 1..241
                       note = Synthetic peptide
source                 1..241
                       mol_type = protein
                       organism = synthetic construct
SEQUENCE: 531
QVQLQESGPG LVKPSETLSL TCTVSGASIS SFYWSWIRQP PGKCLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGCGTKVEI  240
K                                                                   241

SEQ ID NO: 532         moltype = AA  length = 496
FEATURE                Location/Qualifiers
REGION                 1..496
                       note = Synthetic peptide
source                 1..496
```

```
                         mol_type = protein
                         organism = synthetic construct
SEQUENCE: 532
QVQLQESGPG LVKPSETLSL TCTVSGASIS SFYWSWIRQP PGKCLEWIGY IYYSGTTNYN  60
PSLKSRVTIS VDTSKNQFSL KLSSVTAADT AVYYCARIAV AGFFFDYWGQ GTLVTVSSGG  120
GGSGGGGSGG GGSEIVLTQS PGTLSLSPGE RATLSCRASQ SVNKNYLAWY QQKPGQAPRL  180
LIYGASSRAT GIPDRFSGSG SGTDFTLTIS RLEPEDFAVY YCQQYDRSPL TFGCGTKVEI  240
KSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLKTEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVL                                                 496

SEQ ID NO: 533           moltype = AA  length = 227
FEATURE                  Location/Qualifiers
REGION                   1..227
                         note = Synthetic peptide
source                   1..227
                         mol_type = protein
                         organism = synthetic construct
SEQUENCE: 533
DKTHTCPPCP APELLGGPSV FLFPPKPKDT LMISRTPEVT CVVVDVSHED PEVKFNWYVD  60
GVEVHNAKTK PCEEQYGSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 534           moltype = AA  length = 225
FEATURE                  Location/Qualifiers
REGION                   1..225
                         note = Synthetic peptide
source                   1..225
                         mol_type = protein
                         organism = synthetic construct
SEQUENCE: 534
DKTHTCPPCP APELLGGPSV FLFPPKPKDT LMISRTPEVT CVVVDVSHED PEVKFNWYVD  60
GVEVHNAKTK PCEEQYGSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSP                  225

SEQ ID NO: 535           moltype = AA  length = 227
FEATURE                  Location/Qualifiers
REGION                   1..227
                         note = Synthetic peptide
source                   1..227
                         mol_type = protein
                         organism = synthetic construct
SEQUENCE: 535
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 536           moltype = AA  length = 225
FEATURE                  Location/Qualifiers
REGION                   1..225
                         note = Synthetic peptide
source                   1..225
                         mol_type = protein
                         organism = synthetic construct
SEQUENCE: 536
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSP                  225

SEQ ID NO: 537           moltype = AA  length = 227
FEATURE                  Location/Qualifiers
REGION                   1..227
                         note = Synthetic peptide
source                   1..227
                         mol_type = protein
                         organism = synthetic construct
SEQUENCE: 537
DKTHTCPPCP APELLGGPSV FLFPPKPKDT LMISRTPEVT CVVVDVSHED PEVKFNWYVD  60
GVEVHNAKTK PREEQYGSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 538           moltype = AA  length = 225
```

```
FEATURE                Location/Qualifiers
REGION                 1..225
                       note = Synthetic peptide
source                 1..225
                       mol_type = protein
                       organism = synthetic construct
SEQUENCE: 538
DKTHTCPPCP APELLGGPSV FLFPPKPKDT LMISRTPEVT CVVVDVSHED PEVKFNWYVD  60
GVEVHNAKTK PREEQYGSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSP                  225

SEQ ID NO: 539         moltype = AA  length = 227
FEATURE                Location/Qualifiers
REGION                 1..227
                       note = Synthetic peptide
source                 1..227
                       mol_type = protein
                       organism = synthetic construct
SEQUENCE: 539
DKTHTCPPCP APELLGGPSV FLFPPKPKDT LMISRTPEVT CVVVDVSHED PEVKFNWYVD  60
GVEVHNAKTK PCEEQYNSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 540         moltype = AA  length = 225
FEATURE                Location/Qualifiers
REGION                 1..225
                       note = Synthetic peptide
source                 1..225
                       mol_type = protein
                       organism = synthetic construct
SEQUENCE: 540
DKTHTCPPCP APELLGGPSV FLFPPKPKDT LMISRTPEVT CVVVDVSHED PEVKFNWYVD  60
GVEVHNAKTK PCEEQYNSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSP                  225

SEQ ID NO: 541         moltype = AA  length = 484
FEATURE                Location/Qualifiers
REGION                 1..484
                       note = Synthetic peptide
source                 1..484
                       mol_type = protein
                       organism = synthetic construct
SEQUENCE: 541
DKTHTCPPCP APELLGGPSV FLFPPKPKDT LMISRTPEVT CVVVDVSHED PEVKFNWYVD  60
GVEVHNAKTK PCEEQYGSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSGGGGSGGG GSGGGGSDKT HTCPPCPAPE LLGGPSVFLF PPKPKDTLMI SRTPEVTCVV  300
VDVSHEDPEV KFNWYVDGVE VHNAKTKPCE EQYGSTYRCV SVLTVLHQDW LNGKEYKCKV  360
SNKALPAPIE KTISKAKGQP REPQVYTLPP SREEMTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                               484

SEQ ID NO: 542         moltype = AA  length = 480
FEATURE                Location/Qualifiers
REGION                 1..480
                       note = Synthetic peptide
source                 1..480
                       mol_type = protein
                       organism = synthetic construct
SEQUENCE: 542
DKTHTCPPCP APELLGGPSV FLFPPKPKDT LMISRTPEVT CVVVDVSHED PEVKFNWYVD  60
GVEVHNAKTK PCEEQYGSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGGSGGGGS  240
GGGGSGGGGS GGGGSDKTHT CPPCPAPELL GGPSVFLFPP KPKDTLMISR TPEVTCVVVD  300
VSHEDPEVKF NWYVDGVEVH NAKTKPCEEQ YGSTYRCVSV LTVLHQDWLN GKEYKCKVSN  360
KALPAPIEKT ISKAKGQPRE PQVYTLPPSR EEMTKNQVSL TCLVKGFYPS DIAVEWESNG  420
QPENNYKTTP PVLDSDGSFF LYSKLTVDKS RWQQGNVFSC SVMHEALHNH YTQKSLSLSP  480

SEQ ID NO: 543         moltype = AA  length = 484
FEATURE                Location/Qualifiers
REGION                 1..484
                       note = Synthetic peptide
source                 1..484
                       mol_type = protein
```

```
                        organism = synthetic construct
SEQUENCE: 543
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSGGGGSGGG GSGGGGSDKT HTCPPCPAPE LLGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPAPIE KTISKAKGQP REPQVYTLPP SREEMTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                              484

SEQ ID NO: 544          moltype = AA  length = 480
FEATURE                 Location/Qualifiers
REGION                  1..480
                        note = Synthetic peptide
source                  1..480
                        mol_type = protein
                        organism = synthetic construct
SEQUENCE: 544
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGGSGGGGS  240
GGGGSGGGGS GGGGSDKTHT CPPCPAPELL GGPSVFLFPP KPKDTLMISR TPEVTCVVVD  300
VSHEDPEVKF NWYVDGVEVH NAKTKPREEQ YNSTYRVVSV LTVLHQDWLN GKEYKCKVSN  360
KALPAPIEKT ISKAKGQPRE PQVYTLPPSR EEMTKNQVSL TCLVKGFYPS DIAVEWESNG  420
QPENNYKTTP PVLDSDGSFF LYSKLTVDKS RWQQGNVFSC SVMHEALHNH YTQKSLSLSP  480

SEQ ID NO: 545          moltype = AA  length = 484
FEATURE                 Location/Qualifiers
REGION                  1..484
                        note = Synthetic peptide
source                  1..484
                        mol_type = protein
                        organism = synthetic construct
SEQUENCE: 545
DKTHTCPPCP APELLGGPSV FLFPPKPKDT LMISRTPEVT CVVVDVSHED PEVKFNWYVD  60
GVEVHNAKTK PREEQYGSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSGGGGSGGG GSGGGGSDKT HTCPPCPAPE LLGGPSVFLF PPKPKDTLMI SRTPEVTCVV  300
VDVSHEDPEV KFNWYVDGVE VHNAKTKPRE EQYGSTYRVV SVLTVLHQDW LNGKEYKCKV  360
SNKALPAPIE KTISKAKGQP REPQVYTLPP SREEMTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                              484

SEQ ID NO: 546          moltype = AA  length = 480
FEATURE                 Location/Qualifiers
REGION                  1..480
                        note = Synthetic peptide
source                  1..480
                        mol_type = protein
                        organism = synthetic construct
SEQUENCE: 546
DKTHTCPPCP APELLGGPSV FLFPPKPKDT LMISRTPEVT CVVVDVSHED PEVKFNWYVD  60
GVEVHNAKTK PREEQYGSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGGSGGGGS  240
GGGGSGGGGS GGGGSDKTHT CPPCPAPELL GGPSVFLFPP KPKDTLMISR TPEVTCVVVD  300
VSHEDPEVKF NWYVDGVEVH NAKTKPREEQ YGSTYRVVSV LTVLHQDWLN GKEYKCKVSN  360
KALPAPIEKT ISKAKGQPRE PQVYTLPPSR EEMTKNQVSL TCLVKGFYPS DIAVEWESNG  420
QPENNYKTTP PVLDSDGSFF LYSKLTVDKS RWQQGNVFSC SVMHEALHNH YTQKSLSLSP  480

SEQ ID NO: 547          moltype = AA  length = 484
FEATURE                 Location/Qualifiers
REGION                  1..484
                        note = Synthetic peptide
source                  1..484
                        mol_type = protein
                        organism = synthetic construct
SEQUENCE: 547
DKTHTCPPCP APELLGGPSV FLFPPKPKDT LMISRTPEVT CVVVDVSHED PEVKFNWYVD  60
GVEVHNAKTK PCEEQYNSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSGGGGSGGG GSGGGGSDKT HTCPPCPAPE LLGGPSVFLF PPKPKDTLMI SRTPEVTCVV  300
VDVSHEDPEV KFNWYVDGVE VHNAKTKPCE EQYNSTYRCV SVLTVLHQDW LNGKEYKCKV  360
SNKALPAPIE KTISKAKGQP REPQVYTLPP SREEMTKNQV SLTCLVKGFY PSDIAVEWES  420
```

```
NGQPENNYKT TPPVLDSDGS FFLYSKLTVD KSRWQQGNVF SCSVMHEALH NHYTQKSLSL  480
SPGK                                                               484

SEQ ID NO: 548          moltype = AA  length = 480
FEATURE                 Location/Qualifiers
REGION                  1..480
                        note = Synthetic peptide
source                  1..480
                        mol_type = protein
                        organism = synthetic construct
SEQUENCE: 548
DKTHTCPPCP APELLGGPSV FLFPPKPKDT LMISRTPEVT CVVVDVSHED PEVKFNWYVD  60
GVEVHNAKTK PCEEQYNSTY RCVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGS GGGGSGGGGS  240
GGGGSGGGGS GGGGSDKTHT CPPCPAPELL GGPSVFLFPP KPKDTLMISR TPEVTCVVVD  300
VSHEDPEVKF NWYVDGVEVH NAKTKPCEEQ YNSTYRCVSV LTVLHQDWLN GKEYKCKVSN  360
KALPAPIEKT ISKAKGQPRE PQVYTLPPSR EEMTKNQVSL TCLVKGFYPS DIAVEWESNG  420
QPENNYKTTP PVLDSDGSFF LYSKLTVDKS RWQQGNVFSC SVMHEALHNH YTQKSLSLSP  480

SEQ ID NO: 549          moltype = AA  length = 20
FEATURE                 Location/Qualifiers
REGION                  1..20
                        note = Synthetic peptide
source                  1..20
                        mol_type = protein
                        organism = synthetic construct
SEQUENCE: 549
GGGGSGGGGS GGGGSGGGGS                                              20

SEQ ID NO: 550          moltype = AA  length = 25
FEATURE                 Location/Qualifiers
REGION                  1..25
                        note = Synthetic peptide
source                  1..25
                        mol_type = protein
                        organism = synthetic construct
SEQUENCE: 550
GGGGSGGGGS GGGGSGGGGS GGGGS                                        25

SEQ ID NO: 551          moltype = AA  length = 30
FEATURE                 Location/Qualifiers
REGION                  1..30
                        note = Synthetic peptide
source                  1..30
                        mol_type = protein
                        organism = synthetic construct
SEQUENCE: 551
GGGGSGGGGS GGGGSGGGGS GGGGSGGGGS                                   30

SEQ ID NO: 552          moltype = AA  length = 35
FEATURE                 Location/Qualifiers
REGION                  1..35
                        note = Synthetic peptide
source                  1..35
                        mol_type = protein
                        organism = synthetic construct
SEQUENCE: 552
GGGGSGGGGS GGGGSGGGGS GGGGSGGGGS GGGGS                             35

SEQ ID NO: 553          moltype = AA  length = 40
FEATURE                 Location/Qualifiers
REGION                  1..40
                        note = Synthetic peptide
source                  1..40
                        mol_type = protein
                        organism = synthetic construct
SEQUENCE: 553
GGGGSGGGGS GGGGSGGGGS GGGGSGGGGS GGGGSGGGGS                        40

SEQ ID NO: 554          moltype = AA  length = 503
FEATURE                 Location/Qualifiers
REGION                  1..503
                        note = Synthetic peptide
source                  1..503
                        mol_type = protein
                        organism = synthetic construct
SEQUENCE: 554
QVQLQESGPG LVKPSETLSL TCTVSGDSIS SYYWTWIRQP PGKGLEWIGY IYYSGTTNYN  60
```

-continued

```
PSLKSRVTIS VDTSKSQFSL KLSSVTAADT AVYYCASIAV RGFFFDYWGQ GTLVTVSSGG  120
GGSGGGGSGG GGSEIVLTQS PGTLSLSPGE RATLSCRASQ SVSSSYLAWY QQKPGQAPRL  180
LIYGASTRAT GIPDRFSGSG SGTDFTLTIS RLEPEDFAVY YCQQYGTSPL TFGGGTKVEI  240
KRSGGGGSEV QLVESGGGLV QPGGSLKLSC AASGFTFNKY AMNWVRQAPG KGLEWVARIR  300
SKYNNYATYY ADSVKDRFTI SRDDSKNTAY LQMNNLKTED TAVYYCVRHG NFGNSYISYW  360
AYWGQGTLVT VSSGGGGSGG GGSGGGGSQT VVTQEPSLTV SPGGTVTLTC GSSTGAVTSG  420
NYPNWVQQKP GQAPRGLIGG TKFLAPGTPA RFSGSLLGGK AALTLSGVQP EDEAEYYCVL  480
WYSNRWVFGG GTKLTVLHHH HHH                                          503

SEQ ID NO: 555         moltype = AA  length = 109
FEATURE                Location/Qualifiers
REGION                 1..109
                       note = Synthetic Polypeptide
source                 1..109
                       mol_type = protein
                       organism = synthetic construct
SEQUENCE: 555
ELVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL             109

SEQ ID NO: 556         moltype = AA  length = 109
FEATURE                Location/Qualifiers
REGION                 1..109
                       note = Synthetic Polypeptide
source                 1..109
                       mol_type = protein
                       organism = synthetic construct
SEQUENCE: 556
ELVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL             109

SEQ ID NO: 557         moltype = AA  length = 109
FEATURE                Location/Qualifiers
REGION                 1..109
                       note = Synthetic Polypeptide
source                 1..109
                       mol_type = protein
                       organism = synthetic construct
SEQUENCE: 557
ELVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVL             109

SEQ ID NO: 558         moltype = AA  length = 125
FEATURE                Location/Qualifiers
REGION                 1..125
                       note = Synthetic Polypeptide
source                 1..125
                       mol_type = protein
                       organism = synthetic construct
SEQUENCE: 558
EVQLLESGGG LVQPGGSLKL SCAASGFTFN IYAMNWVRQA PGKGLEWVAR IRSKYNNYAT  60
YYADSVKSRF TISRDDSKNT AYLQMNNLKT EDTAVYYCVR HGNFGNSYVS FFAYWGQGTL  120
VTVSS                                                              125

SEQ ID NO: 559         moltype = AA  length = 125
FEATURE                Location/Qualifiers
REGION                 1..125
                       note = Synthetic Polypeptide
source                 1..125
                       mol_type = protein
                       organism = synthetic construct
SEQUENCE: 559
EVQLLESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSS                                                              125

SEQ ID NO: 560         moltype = AA  length = 125
FEATURE                Location/Qualifiers
REGION                 1..125
                       note = Synthetic Polypeptide
source                 1..125
                       mol_type = protein
                       organism = synthetic construct
SEQUENCE: 560
EVQLLESGGG LEQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYLS FWAYWGQGTL  120
VTVSS                                                              125

SEQ ID NO: 561         moltype = AA  length = 125
```

FEATURE Location/Qualifiers
REGION 1..125
note = Synthetic Polypeptide
source 1..125
mol_type = protein
organism = synthetic construct
SEQUENCE: 561
EVQLLESGGG LVQPGGSLKL SCAASGFTFN RYAMNWVRQA PGKGLEWVAR IRSKYNNYAT 60
YYADSVKGRF TISRDDSKNT AYLQMNNLKT EDTAVYYCVR HGNFGNSYLS YFAYWGQGTL 120
VTVSS 125

SEQ ID NO: 562 moltype = AA length = 125
FEATURE Location/Qualifiers
REGION 1..125
note = Synthetic Polypeptide
source 1..125
mol_type = protein
organism = synthetic construct
SEQUENCE: 562
EVQLLESGGG LVQPGGSLKL SCAASGFTFN VYAMNWVRQA PGKGLEWVAR IRSKYNNYAT 60
YYADSVKKRF TISRDDSKNT AYLQMNNLKT EDTAVYYCVR HGNFGNSYLS WWAYWGQGTL 120
VTVSS 125

SEQ ID NO: 563 moltype = AA length = 125
FEATURE Location/Qualifiers
REGION 1..125
note = Synthetic Polypeptide
source 1..125
mol_type = protein
organism = synthetic construct
SEQUENCE: 563
EVQLLESGGG LVQPGGSLKL SCAASGFTFN KYAMNWVRQA PGKGLEWVAR IRSKYNNYAT 60
YYADSVKSRF TISRDDSKNT AYLQMNNLKT EDTAVYYCVR HGNFGNSYTS YYAYWGQGTL 120
VTVSS 125

SEQ ID NO: 564 moltype = AA length = 125
FEATURE Location/Qualifiers
REGION 1..125
note = Synthetic Polypeptide
source 1..125
mol_type = protein
organism = synthetic construct
SEQUENCE: 564
EVQLLESGGG LVQPGGSLKL SCAASGFTFN GYAMNWVRQA PGKGLEWVAR IRSKYNNYAT 60
YYADSVKERF TISRDDSKNT AYLQMNNLKT EDTAVYYCVR HRNFGNSYLS WFAYWGQGTL 120
VTVSS 125

SEQ ID NO: 565 moltype = AA length = 125
FEATURE Location/Qualifiers
REGION 1..125
note = Synthetic Polypeptide
source 1..125
mol_type = protein
organism = synthetic construct
SEQUENCE: 565
EVQLLESGGG LVQPGGSLKL SCAASGFTFN VYAMNWVRQA PGKGLEWVAR IRSKYNNYAT 60
YYADSVKKRF TISRDDSKNT AYLQMNNLKT EDTAVYYCVR HGNFGNSYIS WWAYWGQGTL 120
VTVSS 125

SEQ ID NO: 566 moltype = AA length = 125
FEATURE Location/Qualifiers
REGION 1..125
note = Synthetic Polypeptide
source 1..125
mol_type = protein
organism = synthetic construct
SEQUENCE: 566
EVQLLESGGG LVQPGGSLKL SCAASGFTFN SYAMNWVRQA PGKGLEWVAR IRSKYNNYAT 60
YYADSVKGRF TISRDDSKNT AYLQMNNLKT EDTAVYYCVR HGNFGNSYVS WWAYWGQGTL 120
VTVSS 125

SEQ ID NO: 567 moltype = AA length = 249
FEATURE Location/Qualifiers
REGION 1..249
note = Synthetic Polypeptide
source 1..249
mol_type = protein
organism = synthetic construct
SEQUENCE: 567

```
EVQLLESGGG LVQPGGSLKL SCAASGFTFN IYAMNWVRQA PGKGLEWVAR IRSKYNNYAT  60
YYADSVKSRF TISRDDSKNT AYLQMNNLKT EDTAVYYCVR HGNFGNSYVS FFAYWGQGTL  120
VTVSSGGGGS GGGGSGGGGS ELVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 568         moltype = AA  length = 249
FEATURE                Location/Qualifiers
REGION                 1..249
                       note = Synthetic Polypeptide
source                 1..249
                       mol_type = protein
                       organism = synthetic construct
SEQUENCE: 568
EVQLLESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS ELVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 569         moltype = AA  length = 249
FEATURE                Location/Qualifiers
REGION                 1..249
                       note = Synthetic Polypeptide
source                 1..249
                       mol_type = protein
                       organism = synthetic construct
SEQUENCE: 569
EVQLLESGGG LEQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYLS FWAYWGQGTL  120
VTVSSGGGGS GGGGSGGGGS ELVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 570         moltype = AA  length = 249
FEATURE                Location/Qualifiers
REGION                 1..249
                       note = Synthetic Polypeptide
source                 1..249
                       mol_type = protein
                       organism = synthetic construct
SEQUENCE: 570
EVQLLESGGG LVQPGGSLKL SCAASGFTFN RYAMNWVRQA PGKGLEWVAR IRSKYNNYAT  60
YYADSVKGRF TISRDDSKNT AYLQMNNLKT EDTAVYYCVR HGNFGNSYLS YFAYWGQGTL  120
VTVSSGGGGS GGGGSGGGGS ELVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 571         moltype = AA  length = 249
FEATURE                Location/Qualifiers
REGION                 1..249
                       note = Synthetic Polypeptide
source                 1..249
                       mol_type = protein
                       organism = synthetic construct
SEQUENCE: 571
EVQLLESGGG LVQPGGSLKL SCAASGFTFN VYAMNWVRQA PGKGLEWVAR IRSKYNNYAT  60
YYADSVKKRF TISRDDSKNT AYLQMNNLKT EDTAVYYCVR HGNFGNSYLS WWAYWGQGTL  120
VTVSSGGGGS GGGGSGGGGS ELVVTQEPSL TVSPGGTVTL TCRSSTGAVT SGYYPNWVQQ  180
KPGQAPRGLI GATDMRPSGT PARFSGSLLG GKAALTLSGV QPEDEAEYYC ALWYSNRWVF  240
GGGTKLTVL                                                          249

SEQ ID NO: 572         moltype = AA  length = 249
FEATURE                Location/Qualifiers
REGION                 1..249
                       note = Synthetic Polypeptide
source                 1..249
                       mol_type = protein
                       organism = synthetic construct
SEQUENCE: 572
EVQLLESGGG LVQPGGSLKL SCAASGFTFN KYAMNWVRQA PGKGLEWVAR IRSKYNNYAT  60
YYADSVKSRF TISRDDSKNT AYLQMNNLKT EDTAVYYCVR HGNFGNSYTS YYAYWGQGTL  120
VTVSSGGGGS GGGGSGGGGS ELVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 573         moltype = AA  length = 249
FEATURE                Location/Qualifiers
REGION                 1..249
```

-continued

```
                        note = Synthetic Polypeptide
source                  1..249
                        mol_type = protein
                        organism = synthetic construct
SEQUENCE: 573
EVQLLESGGG LVQPGGSLKL SCAASGFTFN GYAMNWVRQA PGKGLEWVAR IRSKYNNYAT  60
YYADSVKERF TISRDDSKNT AYLQMNNLKT EDTAVYYCVR HRNFGNSYLS WFAYWGQGTL  120
VTVSSGGGGS GGGGSGGGGS ELVVTQEPSL TVSPGGTVTL TCRSSTGAVT SGYYPNWVQQ  180
KPGQAPRGLI GATDMRPSGT PARFSGSLLG GKAALTLSGV QPEDEAEYYC ALWYSNRWVF  240
GGGTKLTVL                                                          249

SEQ ID NO: 574          moltype = AA  length = 249
FEATURE                 Location/Qualifiers
REGION                  1..249
                        note = Synthetic Polypeptide
source                  1..249
                        mol_type = protein
                        organism = synthetic construct
SEQUENCE: 574
EVQLLESGGG LVQPGGSLKL SCAASGFTFN VYAMNWVRQA PGKGLEWVAR IRSKYNNYAT  60
YYADSVKKRF TISRDDSKNT AYLQMNNLKT EDTAVYYCVR HGNFGNSYIS WWAYWGQGTL  120
VTVSSGGGGS GGGGSGGGGS ELVVTQEPSL TVSPGGTVTL TCGSSTGAVT SGYYPNWVQQ  180
KPGQAPRGLI GGTKFLAPGT PARFSGSLLG GKAALTLSGV QPEDEAEYYC ALWYSNRWVF  240
GGGTKLTVL                                                          249

SEQ ID NO: 575          moltype = AA  length = 249
FEATURE                 Location/Qualifiers
REGION                  1..249
                        note = Synthetic Polypeptide
source                  1..249
                        mol_type = protein
                        organism = synthetic construct
SEQUENCE: 575
EVQLLESGGG LVQPGGSLKL SCAASGFTFN SYAMNWVRQA PGKGLEWVAR IRSKYNNYAT  60
YYADSVKGRF TISRDDSKNT AYLQMNNLKT EDTAVYYCVR HGNFGNSYVS WWAYWGQGTL  120
VTVSSGGGGS GGGGSGGGGS ELVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 576          moltype = AA  length = 249
FEATURE                 Location/Qualifiers
REGION                  1..249
                        note = Synthetic Polypeptide
source                  1..249
                        mol_type = protein
                        organism = synthetic construct
SEQUENCE: 576
EVQLLESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS ELVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 577          moltype = AA  length = 5
FEATURE                 Location/Qualifiers
REGION                  1..5
                        note = Synthetic
source                  1..5
                        mol_type = protein
                        organism = synthetic construct
SEQUENCE: 577
QDGNE                                                              5
```

The invention claimed is:

1. A bispecific antibody construct comprising a first binding domain which binds an epitope of human Delta-like Ligand 3 (DLL3) on the surface of a target cell within the amino acid sequence of SEQ ID NO: 269 and a second binding domain which binds human CD3 on the surface of a T cell, wherein the first binding domain comprises a VH region comprising CDR-H1, CDR-H2 and CDR-H3 and a VL region comprising CDR-L1, CDR-L2 and CDR-L3 selected from the group consisting of:

a) CDR-H1 comprising the amino acid sequence of SEQ ID NO: 171, CDR-H2 comprising the amino acid sequence of SEQ ID NO: 172, CDR-H3 comprising the amino acid sequence of SEQ ID NO: 173, CDR-L1 comprising the amino acid sequence of SEQ ID NO: 174, CDR-L2 comprising the amino acid sequence of SEQ ID NO: 175 and CDR-L3 comprising the amino acid sequence of SEQ ID NO: 176;

b) CDR-H1 comprising the amino acid sequence of SEQ ID NO: 181, CDR-H2 comprising the amino acid sequence of SEQ ID NO: 182, CDR-H3 comprising the amino acid sequence of SEQ ID NO: 183, CDR-L1 comprising the amino acid sequence of SEQ ID NO: 184, CDR-L2 comprising the amino acid sequence of SEQ ID NO: 185 and CDR-L3 comprising the amino acid sequence of SEQ ID NO: 186;

c) CDR-H1 comprising the amino acid sequence of SEQ ID NO: 191, CDR-H2 comprising the amino acid sequence of SEQ ID NO: 192, CDR-H3 comprising the amino acid sequence of SEQ ID NO: 193, CDR-L1 comprising the amino acid sequence of SEQ ID NO: 194, CDR-L2 comprising the amino acid sequence of SEQ ID NO: 195 and CDR-L3 comprising the amino acid sequence of SEQ ID NO: 196; and d) CDR-H1 comprising the amino acid sequence of SEQ ID NO: 201, CDR-H2 comprising the amino acid sequence of SEQ ID NO: 202, CDR-H3 comprising the amino acid sequence of SEQ ID NO: 203, CDR-L1 comprising the amino acid sequence of SEQ ID NO: 204, CDR-L2 comprising the amino acid sequence of SEQ ID NO: 205 and CDR-L3 comprising the amino acid sequence of SEQ ID NO: 206.

2. The antibody construct of claim 1, wherein the first binding domain comprises a VH region comprising an amino acid sequence comprising:

a) at least 85% identity to an amino acid sequence of SEQ ID NO: 177, SEQ ID NO: 187, SEQ ID NO: 197, or SEQ ID NO: 207; or b) the amino acid sequence of SEQ ID NO: 177, SEQ ID NO: 187, SEQ ID NO: 197, or SEQ ID NO: 207.

3. The antibody construct of claim 1, wherein the first binding domain comprises a VL region comprising an amino acid sequence comprising:

a) at least 85% identity to an amino acid sequence of SEQ ID NO: 178, SEQ ID NO: 188, SEQ ID NO: 198, or SEQ ID NO: 208; or b) the amino acid sequence of SEQ ID NO: 178, SEQ ID NO: 188, SEQ ID NO: 198, or SEQ ID NO: 208.

4. The antibody construct of claim 1, wherein the first binding domain comprises a VH region and VL region comprising a pair of amino acid sequences, respectively, comprising:

a) at least 85% identity to the amino acid sequences of SEQ ID NOs: 177 and 178, SEQ ID NOs: 187 and 188, SEQ ID NOs: 197 and 198, or SEQ ID NOs: 207 and 208; or b) the amino acid sequences of SEQ ID NOs: 177 and 178, SEQ ID NOs: 178 and 188, SEQ ID NOs: 197 and 198, or SEQ ID NOs: 207 and 208.

5. The antibody construct of claim 1, wherein the first binding domain comprises an amino acid sequence comprising:

a) at least 85% identity to an amino acid sequence of SEQ ID NO: 179, SEQ ID NO: 189, SEQ ID NO: 199, or SEQ ID NO: 209; or b) the amino acid sequence of SEQ ID NO: 179, SEQ ID NO: 189, SEQ ID NO:199, or SEQ ID NO: 209.

6. The antibody construct of claim 1, wherein the antibody construct comprises a polypeptide comprising the amino acid sequence of SEQ ID NO: 180, SEQ ID NO: 190, SEQ ID NO: 200, or SEQ ID NO: 210.

7. The antibody construct of claim 1, wherein antibody construct is in a format of $(scFv)_2$.

8. The antibody construct of claim 1, wherein antibody construct is in a format of scFv-single domain monoclonal antibody (mAb).

9. The antibody construct of claim 1, wherein the first binding domain, the second binding domain, or both is in a Fab format.

10. A composition comprising the antibody construct of claim 1 and an excipient or a combination of excipients.

11. A kit comprising the composition of claim 10.

12. The kit of claim 11 further comprising instructions for use in treating or ameliorating a tumor or cancer disease expressing Delta-like Ligand 3 (DLL3).

* * * * *